United States Patent
Zhang et al.

(10) Patent No.: US 9,556,191 B2
(45) Date of Patent: Jan. 31, 2017

(54) AMINOQUINAZOLINE DERIVATIVES AND THEIR SALTS AND METHODS OF USE THEREOF

(71) Applicant: SUNSHINE LAKE PHARMA CO., LTD, Dongguan, Guangdong (CN)

(72) Inventors: Yingjun Zhang, Dongguan (CN); Bing Liu, Dongguan (CN); Jinlei Liu, Dongguan (CN); Jiancun Zhang, Dongguan (CN); Changchung Cheng, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/774,702

(22) PCT Filed: Apr. 28, 2014

(86) PCT No.: PCT/CN2014/076377
§ 371 (c)(1),
(2) Date: Sep. 11, 2015

(87) PCT Pub. No.: WO2014/177038
PCT Pub. Date: Nov. 6, 2014

(65) Prior Publication Data
US 2016/0039838 A1    Feb. 11, 2016

(30) Foreign Application Priority Data

Apr. 28, 2013 (CN) .......................... 2013 1 0156470
Mar. 23, 2014 (CN) .......................... 2014 1 0108773

(51) Int. Cl.
| | |
|---|---|
| A01N 43/54 | (2006.01) |
| A61K 31/517 | (2006.01) |
| C07D 239/72 | (2006.01) |
| C07D 491/056 | (2006.01) |
| A61K 31/5415 | (2006.01) |
| A61K 31/553 | (2006.01) |
| C07D 413/12 | (2006.01) |

(Continued)

(52) U.S. Cl.
CPC ......... *C07D 491/056* (2013.01); *A61K 31/196* (2013.01); *A61K 31/198* (2013.01); *A61K 31/255* (2013.01); *A61K 31/282* (2013.01); *A61K 31/337* (2013.01); *A61K 31/4545* (2013.01); *A61K 31/475* (2013.01); *A61K 31/517* (2013.01); *A61K 31/538* (2013.01); *A61K 31/5377* (2013.01); *A61K 31/5383* (2013.01); *A61K 31/5415* (2013.01); *A61K 31/553* (2013.01); *A61K 31/573* (2013.01); *A61K 31/675* (2013.01); *A61K 31/704* (2013.01); *A61K 31/7008* (2013.01); *A61K 33/24* (2013.01); *A61K 38/12* (2013.01); *A61K 38/212* (2013.01); *A61K 39/39558* (2013.01); *C07D 401/12* (2013.01); *C07D 403/12* (2013.01); *C07D 413/12* (2013.01); *C07D 417/12* (2013.01); *C07D 491/044* (2013.01); *C07D 491/048* (2013.01); *C07D 495/04* (2013.01); *C07D 497/04* (2013.01); *C07D 498/04* (2013.01); *C07D 519/00* (2013.01); *A61K 2039/505* (2013.01)

(58) Field of Classification Search
None
See application file for complete search history.

(56) References Cited

U.S. PATENT DOCUMENTS

| | | |
|---|---|---|
| 6,627,634 B2 | 9/2003 | Himmelsbach et al. |
| 6,653,305 B2 | 11/2003 | Himmelsbach et al. |

(Continued)

FOREIGN PATENT DOCUMENTS

| | | |
|---|---|---|
| CN | 102146084 A | 8/2011 |
| CN | 102249997 A | 11/2011 |

(Continued)

OTHER PUBLICATIONS

Wolff et. al., "Burger's Medicinal Chemistry and Drug Discovery," 5th Ed. Part 1, pp. 975-977 (1995).*

(Continued)

*Primary Examiner* — Jeffrey H Murray
(74) *Attorney, Agent, or Firm* — Kam W. Law; Squire Patton Boggs (US) LLP

(57) ABSTRACT

Provided herein are aminoquinazoline compounds, salts and uses thereof. The compounds have Formula (I), or a stereoisomer, a geometric isomer, a tautomer, an N-oxide, a hydrate, a solvate, a metabolite, a pharmaceutically acceptable salt or a prodrug thereof. Also provided herein are pharmaceutical compositions containing the compounds disclosed herein, and uses of the compounds or the compositions for preventing, managing, treating or lessening the severity of a proliferative disorder in a patient and for modulating the protein tyrosine kinase activity.

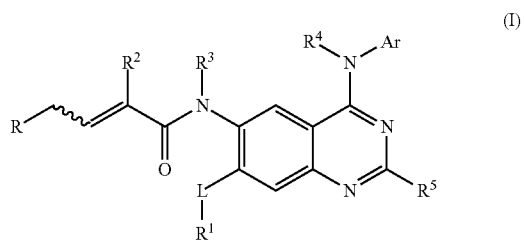

20 Claims, No Drawings

(51) Int. Cl.

| | | |
|---|---|---|
| *C07D 417/12* | (2006.01) | |
| *C07D 403/12* | (2006.01) | |
| *C07D 401/12* | (2006.01) | |
| *C07D 495/04* | (2006.01) | |
| *C07D 497/04* | (2006.01) | |
| *C07D 498/04* | (2006.01) | |
| *C07D 519/00* | (2006.01) | |
| *A61K 31/196* | (2006.01) | |
| *A61K 31/198* | (2006.01) | |
| *A61K 31/255* | (2006.01) | |
| *A61K 31/475* | (2006.01) | |
| *A61K 31/675* | (2006.01) | |
| *A61K 31/282* | (2006.01) | |
| *A61K 31/337* | (2006.01) | |
| *A61K 31/4545* | (2006.01) | |
| *A61K 31/5377* | (2006.01) | |
| *A61K 31/538* | (2006.01) | |
| *A61K 31/5383* | (2006.01) | |
| *A61K 31/573* | (2006.01) | |
| *A61K 31/7008* | (2006.01) | |
| *A61K 31/704* | (2006.01) | |
| *A61K 33/24* | (2006.01) | |
| *A61K 38/12* | (2006.01) | |
| *A61K 38/21* | (2006.01) | |
| *A61K 39/395* | (2006.01) | |
| *C07D 491/044* | (2006.01) | |
| *C07D 491/048* | (2006.01) | |
| *A61K 39/00* | (2006.01) | |

(56) References Cited

U.S. PATENT DOCUMENTS

| | | |
|---|---|---|
| 6,740,651 B2 | 5/2004 | Himmelsbach et al. |
| 6,972,288 B1 | 12/2005 | Himmelsbach et al. |
| 7,019,012 B2 | 3/2006 | Himmelsbach et al. |
| 7,220,750 B2 | 5/2007 | Himmelsbach et al. |
| 7,223,749 B2 | 5/2007 | Himmelsbach et al. |
| 7,294,629 B2 | 11/2007 | Kitano et al. |
| 7,772,243 B2 | 8/2010 | Fakhoury et al. |
| 7,863,281 B2 | 1/2011 | Himmelsbach et al. |
| 7,960,546 B2 | 6/2011 | Schroeder et al. |
| 8,044,063 B2 | 10/2011 | Guo et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 8,404,697 B2 | 3/2013 | Solca et al. |
| 8,466,165 B2 | 6/2013 | Fakhoury et al. |
| 8,586,608 B2 | 11/2013 | Himmelsbach et al. |
| 8,623,883 B2 | 1/2014 | Fakhoury et al. |
| 8,722,694 B2 | 5/2014 | Himmelsbach et al. |
| 8,735,409 B2 | 5/2014 | Zhang et al. |
| 8,846,699 B2 | 9/2014 | Ahn et al. |
| 8,901,140 B2 | 12/2014 | Tang et al. |
| 9,089,571 B2 | 7/2015 | Solca et al. |
| 9,090,588 B2 | 7/2015 | Shen et al. |
| 2004/0044014 A1 | 3/2004 | Himmelsbach et al. |
| 2005/0159436 A1 | 7/2005 | Himmelsbach et al. |
| 2006/0100223 A1 | 5/2006 | Himmelsbach et al. |
| 2006/0270670 A1 | 11/2006 | Chew et al. |
| 2007/0185081 A1 | 8/2007 | Himmelsbach et al. |
| 2007/0185091 A1 | 8/2007 | Himmelsbach et al. |
| 2007/0265260 A1 | 11/2007 | Kitano et al. |
| 2008/0200433 A1 | 8/2008 | Suzuki et al. |
| 2009/0306101 A1 | 12/2009 | Solca et al. |
| 2010/0069414 A1 | 3/2010 | Himmelsbach et al. |
| 2011/0046168 A1 | 2/2011 | Himmelsbach et al. |
| 2013/0184297 A1 | 7/2013 | Huang et al. |
| 2014/0161801 A1 | 6/2014 | Wu et al. |
| 2014/0199298 A1 | 7/2014 | Solca et al. |
| 2014/0206687 A1 | 7/2014 | Xia et al. |
| 2014/0221406 A1 | 8/2014 | Shen et al. |
| 2014/0235658 A1 | 8/2014 | Zhang |
| 2015/0126537 A1 | 5/2015 | Zhang |

FOREIGN PATENT DOCUMENTS

| | | | | |
|---|---|---|---|---|
| CN | 102382065 A | | 3/2012 | |
| CN | 102649778 A | | 8/2012 | |
| CN | WO2013/131424 | * | 12/2013 | ........... C07D 239/94 |
| CN | 103965120 A | | 8/2014 | |
| CN | 103965175 A | | 8/2014 | |
| WO | WO 2012136099 A1 | | 10/2012 | |
| WO | WO 2013131424 A1 | | 9/2013 | |

OTHER PUBLICATIONS

Banker, et. al., (1996), Modern Pharmaceuticals, p. 596.*
Eng. translation.
ISR of PCT/CN2014/076377.
Written Opinion of PCT/CN2014/076377.
Tsou Hwei-Ru et al., 6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity, J. Med. Chem., 2001, vol. 44, p. 2719-2734.

* cited by examiner

AMINOQUINAZOLINE DERIVATIVES AND THEIR SALTS AND METHODS OF USE THEREOF

CROSS-REFERENCE TO RELATED APPLICATIONS

This is a U.S. national stage application of the International Patent Application No. PCT/CN2014/076377, filed Apr. 28, 2014, which claims priorities to Chinese Patent Application No. 201310156470.2, filed Apr. 28, 2013, and No. 201410108773.1, filed Mar. 23, 2014, all of which are incorporated herein by reference in their entirety.

FIELD OF THE INVENTION

The present invention belongs to the field of pharmaceutical technology, more specifically relates to aminoquinazoline derivatives, salts thereof and methods of use thereof.

BACKGROUND OF THE INVENTION

Protein kinases (PKs) represent a large family of proteins, which play an important role in the regulation of a wide variety of cellular processes and maintaining control over cellular functions. There are two classes of protein kinases (PKs): the protein tyrosine kinases (PTKs) and the serine-threonine kinases (STKs). The protein tyrosine kinase is an enzyme that catalytically transfers the phosphate group from ATP to the tyrosine residue located at the protein substrate, and has a play in the normal cell growth. Many growth factor receptor proteins operate via the tyrosine kinase, and influence the conduction of signal passage and further regulate the cell growth by this process. However, in some circumstances, these receptors become abnormal due to either mutation or overexpression, which cause the uncontrolled cell multiplication, cause the tumor growth, and finally initiate the well-known disease, i.e., cancer. The growth factor receptor protein tyrosine kinase inhibitor, via the inhibition of the above phosphorylation process, may treat cancers and other diseases characterized by the uncontrolled or abnormal cell growth.

Epidermal growth factor receptor (EGFR), a kind of receptor tyrosine kinases, is a multifunction glycoprotein that is widely distributed on the cell membranes of the tissues of the human body, and is an oncogene analog of avian erythroblastic leukemia viral (v-erb-b). Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). They are single polypeptide chains, and each is encoded respectively by genes located on different chromosomes. EGFR and the like are expressed in the epithelia-derived tumors such as squamous cell carcinoma of head and neck, mammary cancer, rectal cancer, ovarian cancer, prostate carcinoma, non-small cell lung cancer, and the like, which are associated with cell proliferation, metastasis, and the like. Pan-HER tyrosine kinase inhibitor, via the competitive binding to the kinase catalytic sites in the intracellular region against ATP, blocks the autophosphorylation of intramolecular tyrosine, blocks the tyrosine kinase activation, inhibits HER-2 family activation, and therefore inhibits cell cycle progression, accelerates cell apoptosis, and exerts the therapeutic action.

EGFR, after binding to the ligand, forms a dimer with a subgroup of HER family, and then combines with ATP to activate the tyrosine kinase activity of the EGFR itself. Therefore, the autophosphorylation occurs in several tyrosine sites of the intracellular kinase region. Pan-HER tyrosine kinase inhibitor, via simultaneity acting on EGFR and HER2/4, inhibits the activation of HER family, and plays a good role in the tumor growth inhibition.

It is indicated in the study that Pan-HER tyrosine kinase irreversible inhibitor has an inhibition effect on HER2/4, besides it effectively inhibits EGFR. The pharmaceutical drugs of this kind, having an irreversible inhibition to both of HER/ErbB families, not only increase the drug activity, but also reduce the drug resistance, and have a substantial inhibition effect on H1975 cell lines which are resistant to erlotinib.

The pharmaceutical drugs that are now commercially available include selective EGFR tyrosine kinase inhibitor gefitinb (IRESSA®, ZD1839), erlotinib (TARCEVA®, OSI-774), double EGFR/HER2 inhibitor Lapatinib (TYKERB®, GW572016), and the like. These three drugs are all reversible EGF receptor tyrosine phosphorylation kinase inhibitor. It has been found in the study that they have good therapeutic response to some tumors initially. However, several months after the treatment, the disease progression appears again and therefore a natural or secondary drug resistance forms. For example, about half of the patients administered with gefitinib or erlotinib develop resistance to gefitinib or erlotinib, which can not lead to the desired therapeutic effect. And it has been indicated by study that the development of drug resistance to selective EGFR tyrosine kinase inhibitor relates to mutations in EGFR.

The mutations of EGFR gene mostly located in the tyrosing kinase coding domain (TK, exons 18-21) are mainly deletion mutation in exon 19 and point mutation in exon 21, both of which are drug-sensitive, and few are point mutation in exon 18 and insertion mutation in exon 20. T790M mutation recognized as one of the mechanism of drug resistance is a point mutation in exon 20 of EGFR. The presence of a second-site EGFR mutation leads to the substitution of methionine for threonine at position 790 (T790M) and changes in the structure of EGFR, which hinder the binding of EGFR inhibitors to EGFR or greatly increase the affinity between EGFR and ATP, so that ATP affinity back to the level of wild-type EGFR, thus resulting in drug resistance. Further studies shows that the pre-treatment tumor samples with mutations of EGFR contain T790M mutation, which indicates that T790M mutation is not just associated with drug resistance and it may have the carcinogenic potential itself.

Irreversible inhibitor can bind to EGFR tyrosine kinase by covalent bond. Thus, the drugs can act on the entire link of epidermal growth factor signal transduction pathway, and improve efficiency of drug blocking. Many clinical studies show that some irreversible inhibitors in current development can against T790M mutation, and overcome the drug resistance caused by T790M. Meanwhile, listed drug Afatinib (BIBW 2992) and some irreversible inhibitors in clinical development (e.g., Dacomitinib, PF00299804, etc.), can inhibit multiple members of EGFR receptor family, especially to the role of EGFR and HER-2, possibly by blocking collaborative signal pathway activated by homodimer and heterodimer to enhance inhibitory effect (*Oncologist*, 2009, 14 (11): 1116-1130).

Upon developing the drug having an excellent antineoplastic effect, being able to reduce the drug resistance and having a good tolerance, the present inventors discover a quinazoline derivatives as tyrosine kinase inhibitors having a Pan-HER irreversible inhibition function.

SUMMARY OF THE INVENTION

In one aspect, provided herein are quinazoline compounds having formula (I) as shown below:

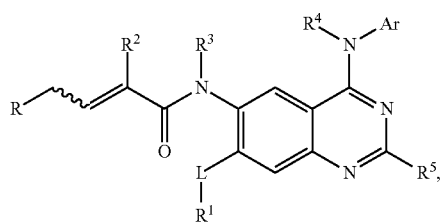

(I)

or a stereoisomer, a geometric isomer, a tautomer, an N-oxide, a hydrate, a solvate, a metabolite, a pharmaceutically acceptable salt or a prodrug thereof, wherein R is

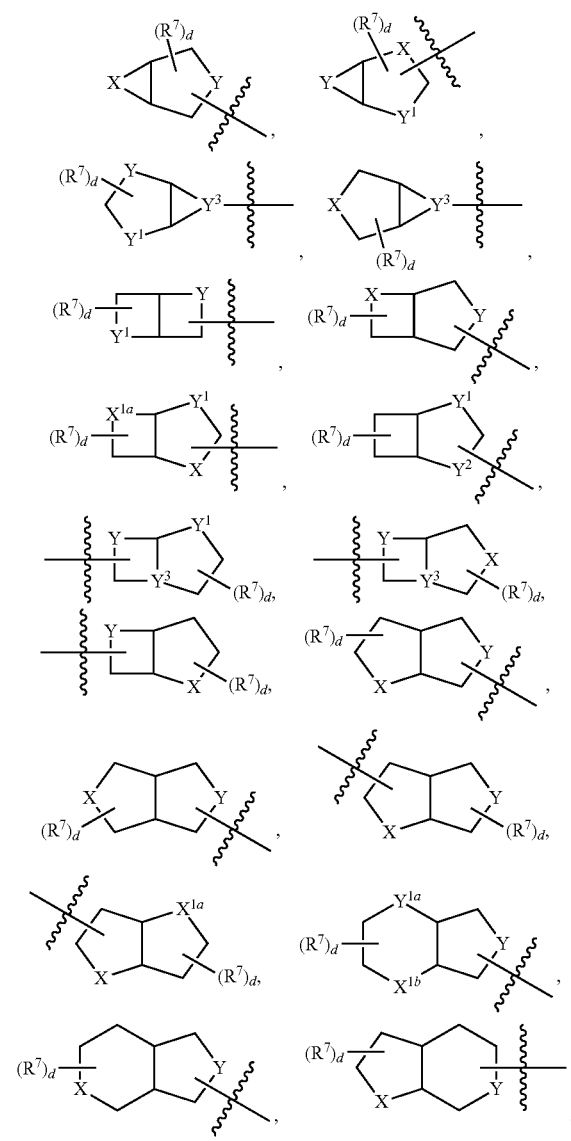

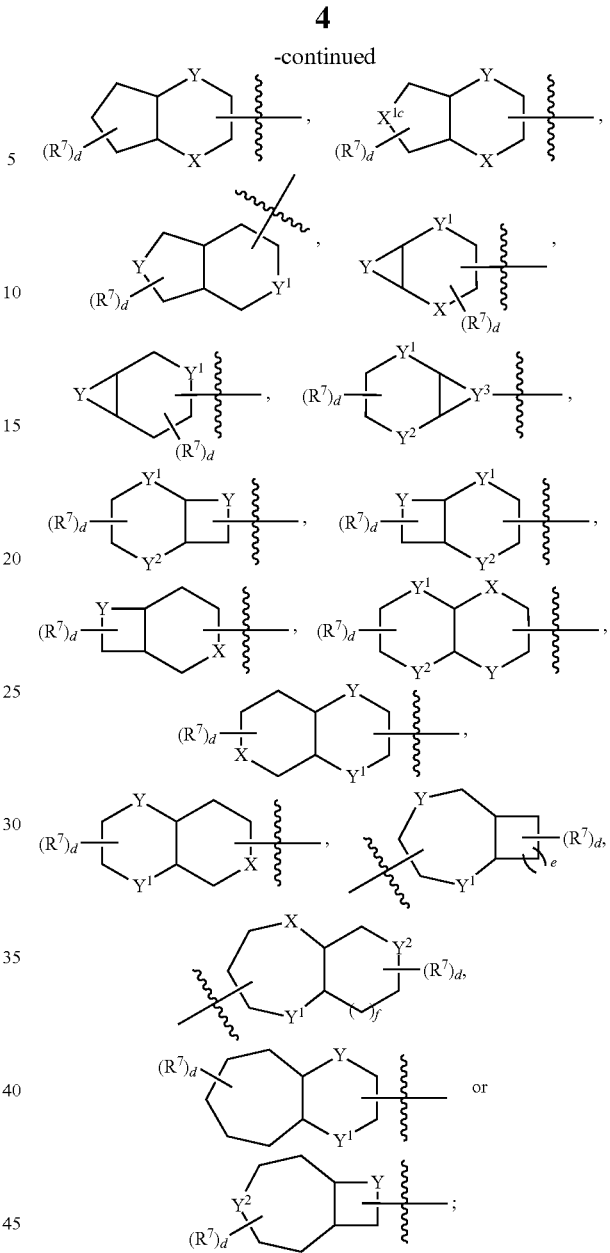

wherein each X and $X^{1a}$ is independently O, S, S(=O), S(=O)$_2$ or NR$^a$;
$X^{1b}$ is O, S, S(=O), S(=O)$_2$ or NR$^{a1}$;
$X^{1c}$ is S, S(=O) or S(=O)$_2$;
each Y, $Y^1$, and $Y^2$ is independently O, S, S(=O), S(=O)$_2$, NR$^a$ or CR$^b$R$^{b'}$;
$Y^{1a}$ is O, S, S(=O), S(=O)$_2$, NR$^{a1}$ or CR$^b$R$^{b'}$;
each $Y^3$ is independently CR$^{b''}$ or N;
wherein each R$^a$ is independently H, D or C$_{1-3}$ alkyl;
each R$^{a1}$ is independently D, ethyl, n-propyl or isopropyl;
each R$^b$, R$^{b'}$ and R$^{b''}$ is independently H, D, F, Cl, Br, I, —OH, —NO$_2$, —NH$_2$, —CN, C$_{1-3}$ alkyl, C$_{1-3}$ alkoxy or C$_{1-3}$ alkylamino;
each R$^7$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl, C$_{6-10}$ aryl, C$_{6-10}$ aryl-C$_{1-6}$-alkyl, C$_{6-10}$ aryloxy, C$_{6-10}$ aryl-C$_{1-6}$-alkoxy or C$_{1-9}$ heteroaryl;

each d is independently 0, 1, 2, 3, 4 or 5;
e is 0, 1, 2, or 3;
f is 0 or 1;
L is a bond, O, NR$^a$, S, S(=O), S(=O)$_2$ or C(=O);
R$^1$ is H, D, F, Cl, Br, I, —OH, —NO$_2$, —NH$_2$, —CN, C$_{1-6}$ alkyl, C$_{1-6}$ haloalkyl, C$_{1-6}$ alkoxy-C$_{1-6}$-alkyl, C$_{2-6}$ alkenyl, C$_{2-6}$ alkynyl, C$_{1-6}$ alkylamino-C$_{1-6}$-alkyl, C$_{3-8}$ cycloalkyl, C$_{3-8}$ cycloalkyl-C$_{1-6}$-alkyl, C$_{3-8}$ cycloalkyl-C$_{2-6}$-alkenyl, C$_{3-8}$ cycloalkyl-C$_{2-6}$-alkynyl, C$_{3-8}$ cycloalkyloxy-C$_{2-6}$-alkynyl, C$_{2-10}$ heterocyclyl, C$_{2-10}$ heterocyclyl-C$_{1-6}$-alkyl, C$_{2-10}$ heterocyclyl-C$_{2-6}$-alkenyl, C$_{2-10}$ heterocyclyl-C$_{2-6}$-alkynyl, C$_{5-12}$ fused bicyclyl, C$_{5-12}$ fused bicyclyl-C$_{1-6}$-alkyl, C$_{5-12}$ fused bicyclyl-C$_{2-6}$-alkenyl, C$_{5-12}$ fused bicyclyl-C$_{2-6}$-alkynyl, C$_{5-12}$ fused heterobicyclyl, C$_{5-12}$ fused heterobicyclyl-C$_{1-6}$-alkyl, C$_{5-12}$ fused heterobicyclyl-C$_{2-6}$-alkenyl, C$_{5-12}$ fused heterobicyclyl-C$_{2-6}$-alkynyl, C$_{5-12}$ spiro bicyclyl, C$_{5-12}$ spiro bicyclyl-C$_{1-6}$-alkyl, C$_{5-12}$ spiro bicyclyl C$_{2-6}$ alkenyl, C$_{5-12}$ spiro bicyclyl C$_{2-6}$ alkynyl, C$_{5-12}$ spiro heterobicyclyl, C$_{5-12}$ spiro heterobicyclyl-C$_{1-6}$-alkyl, C$_{5-12}$ spiro heterobicyclyl-C$_{2-6}$-alkenyl, C$_{5-12}$ spiro heterobicyclyl-C$_{2-6}$-alkynyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl;
R$^2$ is H, F, Cl, Br, I, —NH$_2$, —NO$_2$, —CN or C$_{1-6}$ alkyl;
each of R$^3$ and R$^4$ is independently H, D or C$_{1-4}$ alkyl;
R$^5$ is H, D, F, Cl, Br, I, C$_{1-6}$ alkyl, C$_{1-6}$ alkoxy, C$_{1-6}$ alkylamino or C$_{3-8}$ cycloalkyl;
Ar is

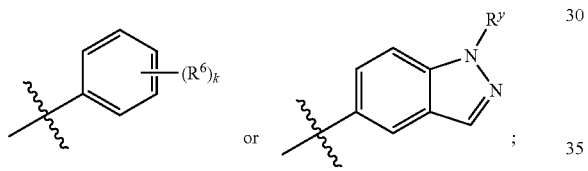

wherein each R$^6$ is independently H, D, F, Cl, Br, I, —OH, —NO$_2$, —NH$_2$, —CN, C$_{1-6}$ alkyl, C$_{2-6}$ alkenyl, C$_{2-6}$ alkynyl, C$_{1-6}$ alkoxy, C$_{6-10}$ aryloxy, C$_{1-9}$ heteroaryloxy, C$_{6-10}$ aryl-C$_{1-6}$-alkyl, C$_{6-10}$ aryl-C$_{1-6}$-alkoxy, C$_{1-9}$ heteroaryl-C$_{1-6}$-alkyl, C$_{1-9}$ heteroaryl-C$_{1-6}$-alkoxy, C$_{1-6}$ alkylthio, C$_{1-6}$ alkylamino, C$_{6-10}$ arylamino, C$_{1-6}$ alkylcarbonyl, C$_{1-6}$ alkylacylamino, C$_{1-6}$ alkylsulfonyl or C$_{1-6}$ alkylsulfinyl;
k is 0, 1, 2, 3, 4 or 5; and
R$^y$ is H, C$_{1-6}$ alkyl, C$_{2-6}$ alkenyl, C$_{2-6}$ alkynyl, C$_{3-8}$ cycloalkyl, C$_{3-8}$ cycloalkyl-C$_{1-6}$-alkyl, C$_{6-10}$ aryl-C$_{1-6}$-alkyl or C$_{1-9}$ heteroaryl-C$_{1-6}$-alkyl;
wherein optionally each of alkyl, alkoxy, alkoxyalkyl, alkylamino, alkylaminoalkyl, heteroalkyl, alkenyl, alkynyl, cycloalkyl, cycloalkylalkyl, cycloalkylalkenyl, cycloalkylalkynyl, cycloalkyloxyalkynyl, heterocyclyl, heterocyclylalkyl, heterocyclylalkenyl, heterocyclylalkynyl, fused bicyclyl, fused bicyclylalkyl, fused bicyclylalkenyl, fused bicyclylalkynyl, fused heterobicyclyl, fused heterobicyclylalkyl, fused heterobicyclylalkenyl, fused heterobicyclylalkynyl, spiro bicyclyl, spiro bicyclylalkyl, spiro bicyclylalkenyl, spiro bicyclylalkynyl, spiro heterobicyclyl, spiro heterobicyclylalkyl, spiro heterobicyclylalkenyl, spiro heterobicyclylalkynyl, aryl, aryloxy, arylalkyl, arylalkoxy, arylamino, heteroaryl, heteroarylalkyl, heteroarylalkoxy, heteroaryloxy, alkylthio, alkylcarbonyl, alkylacylamino, alkylsulfonyl, haloalkyl and alkylsulfinyl is independently substituted with one or more substituents selected from D, F, Cl, Br, I, —OH, —NO$_2$, —NH$_2$, —CN, —COOH, C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl, and wherein optionally each of C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl and hydroxy-substituted C$_{1-3}$ alkyl.

In some embodiments, R is

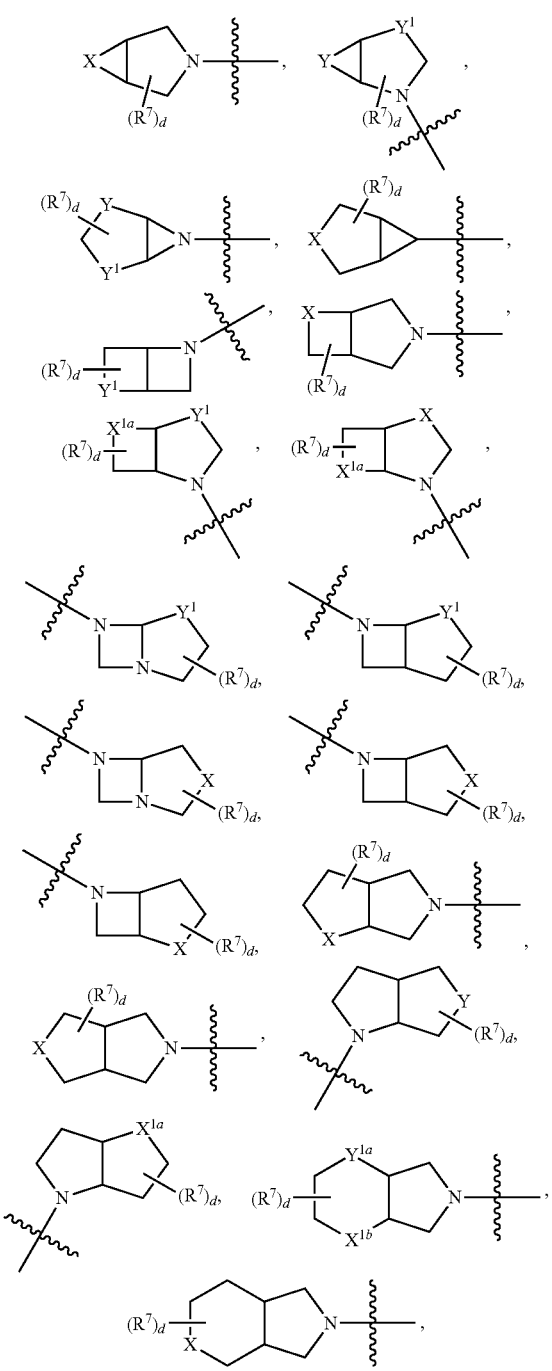

-continued
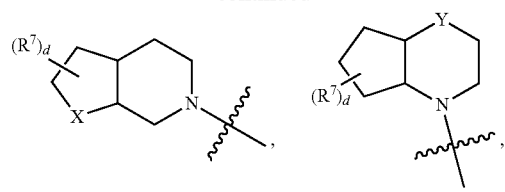
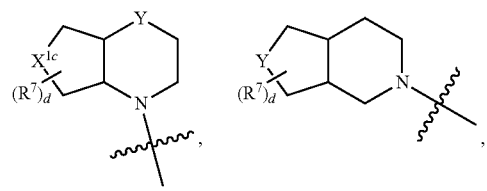
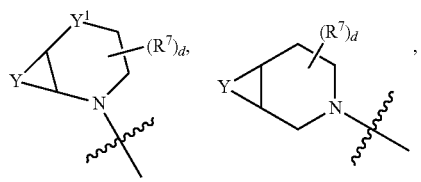
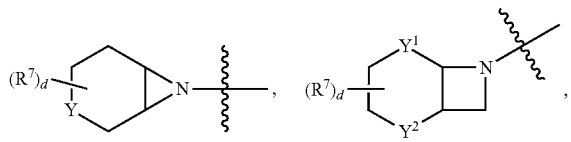
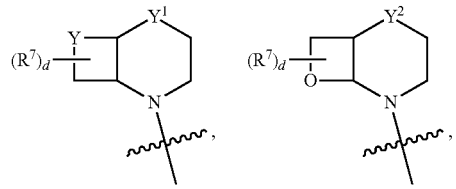
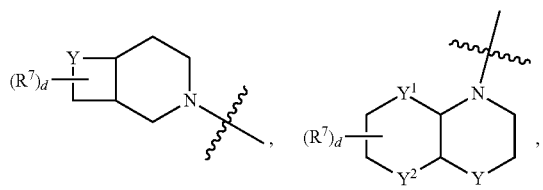
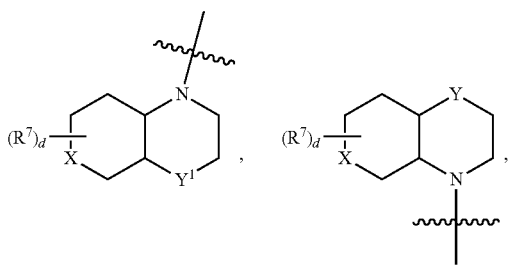
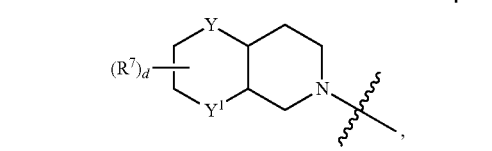
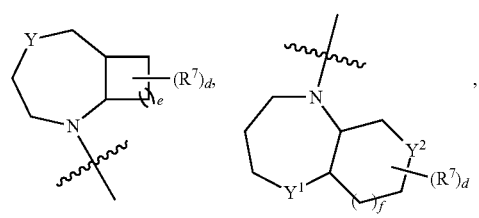
-continued
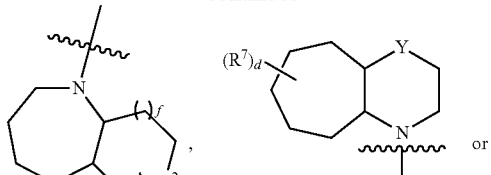
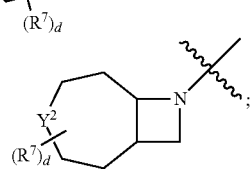
and
each X, $X^{1a}$, $X^{1b}$, $X^{1c}$, Y, $Y^1$, $Y^{1a}$, $Y^2$, $R^7$, d, e and f is independently as defined herein.
In other embodiments, R is
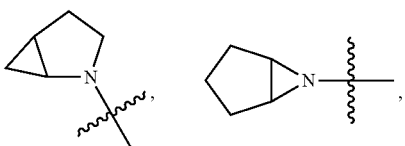
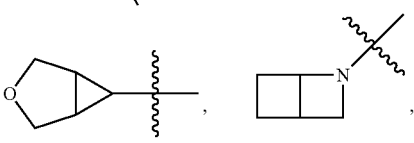
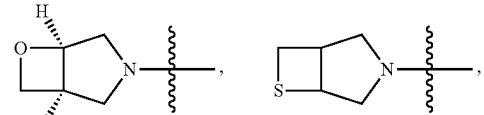
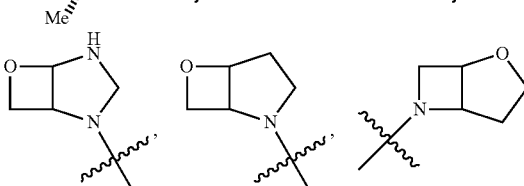
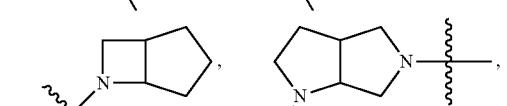
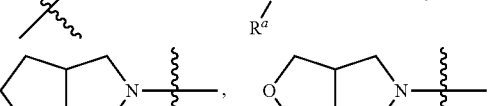
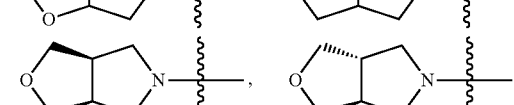
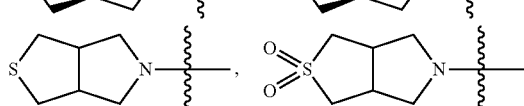
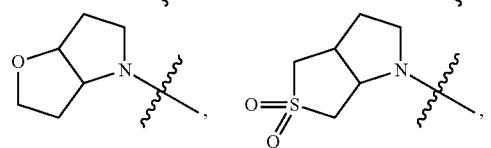

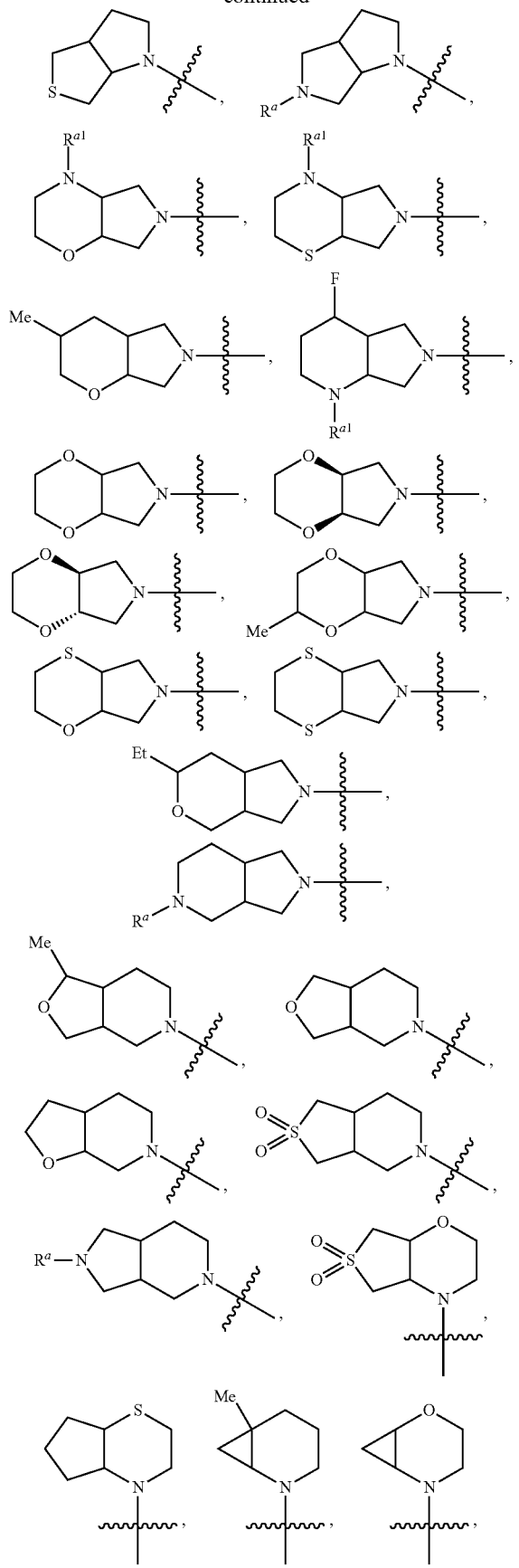

-continued

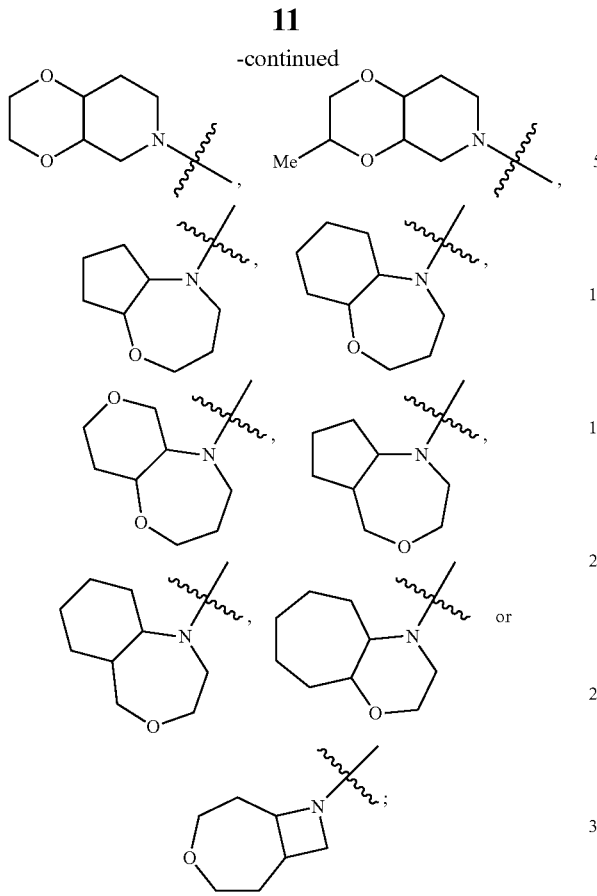

and each $R^a$ and $R^{a1}$ is independently as defined herein.

In some embodiments, $R^1$ is H, D, F, Cl, Br, I, —OH, —NO$_2$, —NH$_2$, —CN, C$_{1-6}$ alkyl, C$_{2-6}$ alkynyl or C$_{1-6}$ alkoxy-C$_{1-6}$-alkyl, wherein optionally each of C$_{1-6}$ alkyl, C$_{2-6}$ alkynyl and C$_{1-6}$ alkoxy-C$_{1-6}$-alkyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl, C$_{1-3}$ alkylamino, deuterated C$_{1-3}$ alkylamino, C$_{1-3}$ alkoxy, deuterated C$_{1-3}$ alkoxy, C$_{6-10}$ aryl, C$_{1-9}$ heteroaryl, C$_{3-8}$ cycloalkyl, C$_{3-8}$ cycloalkyloxy and C$_{2-10}$ heterocyclyl, or $R^1$ is

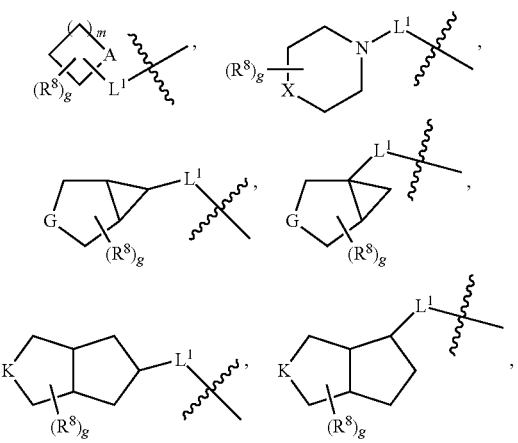

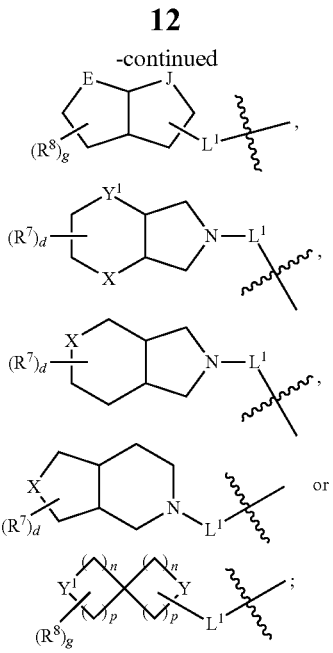

wherein each A, G, E and J is independently CR$^b$R$^{b'}$, NR$^a$, O, S, S(=O) or S(=O)$_2$;

each K is independently NR$^a$, O, S, S(=O) or S(=O)$_2$;

each L$^1$ is independently a bond, C$_{1-4}$ alkylene, C$_{2-4}$ alkenylene or C$_{2-4}$ alkynylene, wherein optionally each of C$_{1-4}$ alkylene, C$_{2-4}$ alkenylene and C$_{2-4}$ alkynylene is independently substituted with one or more substituents independently selected from D, F, Cl, Br, I, —OH, —NO$_2$, —NH$_2$, —CN, —COOH and C$_{1-3}$ alkyl;

each R$^8$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl or C$_{5-12}$ fused heterobicyclyl, wherein optionally each of C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl and C$_{5-12}$ fused heterobicyclyl is independently substituted with one or more substituents independently selected from D, F, Cl, Br, I, —OH, —SH, —NO$_2$, —NH$_2$, —CN, —COOH, C$_{1-3}$ alkyl and C$_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2; and each X, Y, Y$^1$, R$^a$, R$^b$, R$^{b'}$, R$^7$ and d is independently as defined herein.

In other embodiments, $R^1$ is H, D, F, Cl, Br, I, —OH, —NO$_2$, —NH$_2$, —CN, C$_{1-3}$ alkyl, C$_{2-3}$ alkynyl or C$_{1-3}$ alkoxy-C$_{1-3}$-alkyl, wherein optionally each of C$_{1-3}$ alkyl, C$_{2-3}$ alkynyl and C$_{1-3}$ alkoxy-C$_{1-3}$-alkyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl, C$_{1-3}$ alkylamino, deuterated C$_{1-3}$ alkylamino, C$_{1-3}$ alkoxy, deuterated C$_{1-3}$ alkoxy and C$_{3-8}$ cycloalkyloxy, or $R^1$ is

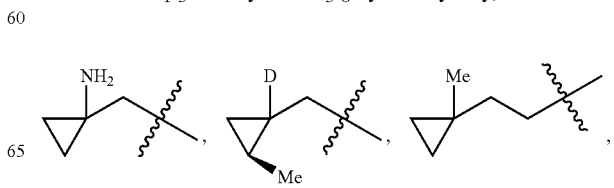

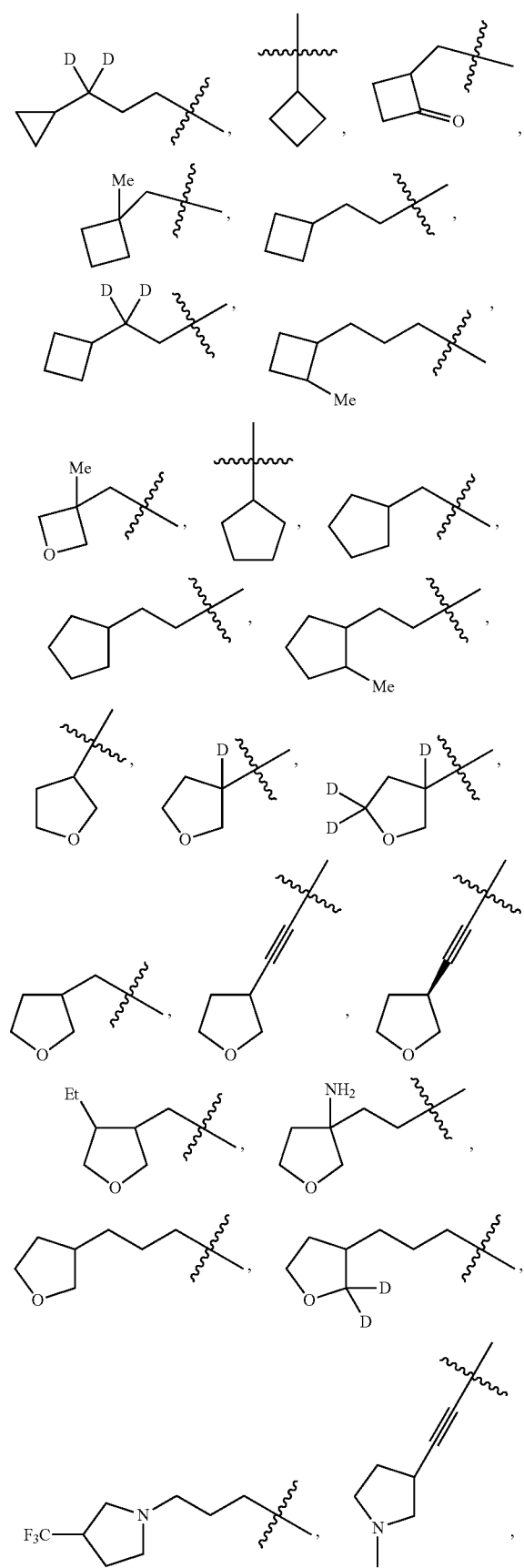
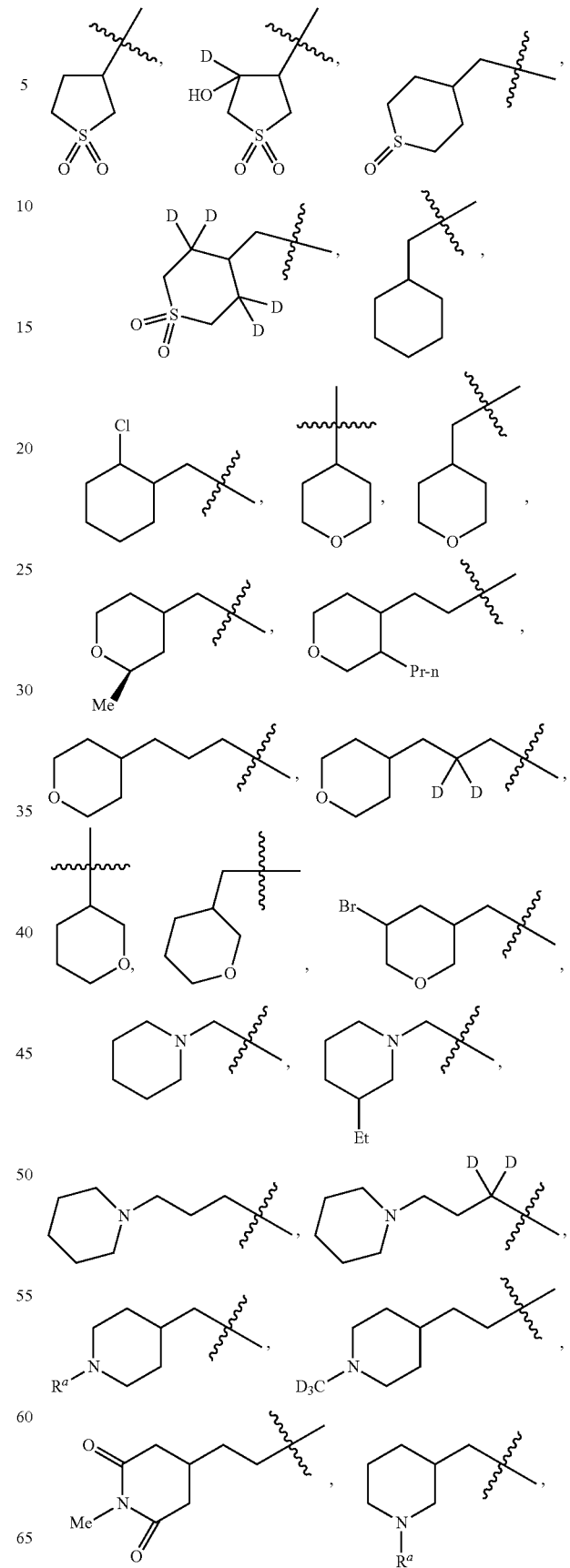

-continued
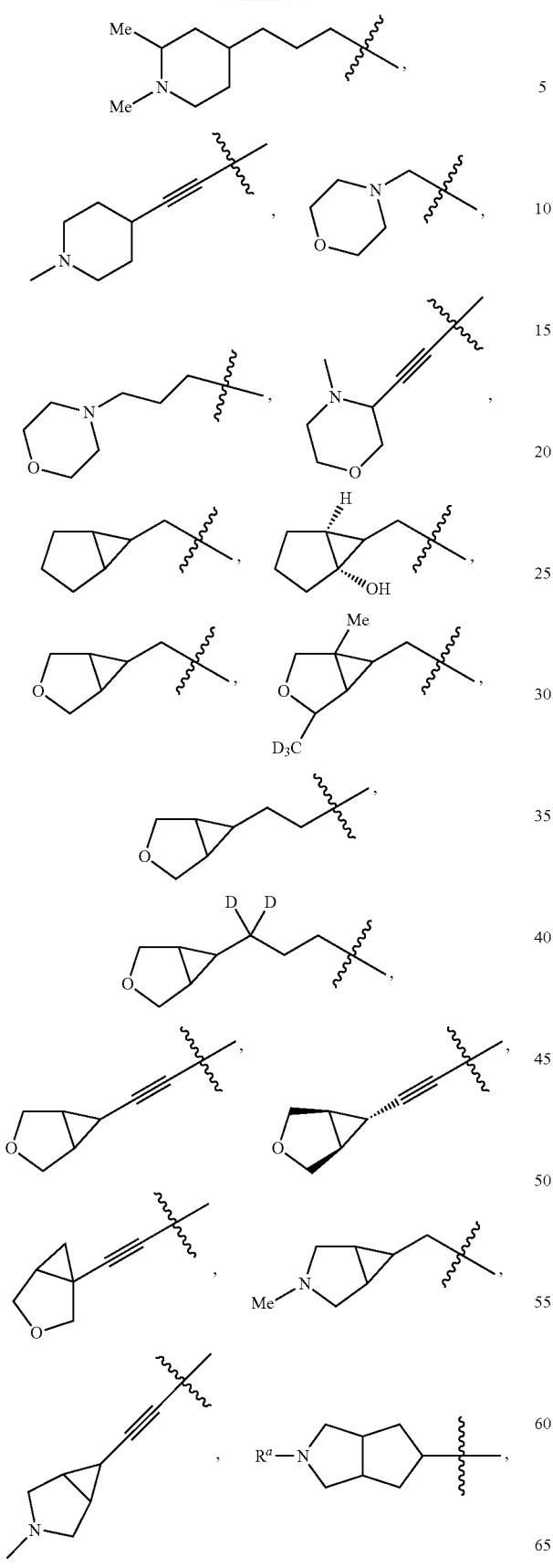
-continued
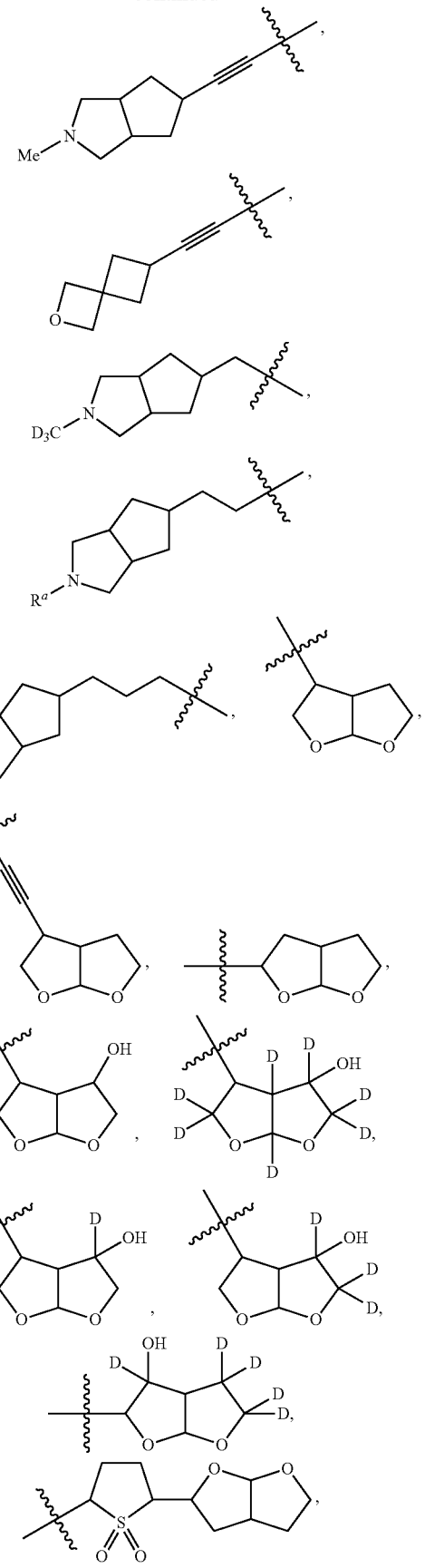

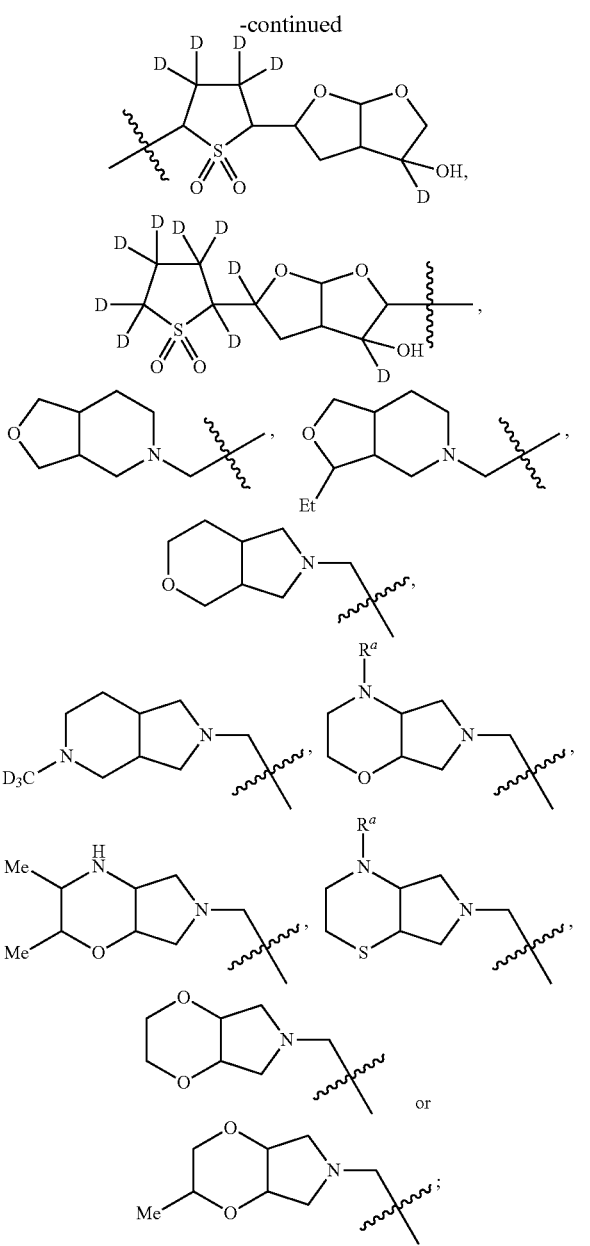

wherein each $R^a$ is independently H, D or $C_{1-3}$ alkyl.

In some embodiments, each $R^6$ is independently H, D, F, Cl, Br, I, —OH, —NO$_2$, —NH$_2$, —CN, $C_{1-3}$ alkyl, $C_{2-4}$ alkynyl, $C_{1-3}$ alkoxy, $C_{6-10}$ aryloxy, $C_{6-10}$ aryl-$C_{1-3}$-alkyl, $C_{6-10}$ aryl-$C_{1-3}$-alkoxy, $C_{2-5}$ heteroaryloxy, $C_{2-5}$ heteroaryl-$C_{1-3}$-alkyl or $C_{2-5}$ heteroaryl-$C_{1-3}$-alkoxy; and $R^y$ is H, $C_{1-3}$ alkyl, $C_{6-10}$ aryl-$C_{1-3}$-alkyl or $C_{2-5}$ heteroaryl-$C_{1-3}$-alkyl, wherein optionally each of $C_{1-3}$ alkyl, $C_{2-4}$ alkynyl, $C_{1-3}$ alkoxy, $C_{6-10}$ aryloxy, $C_{6-10}$ aryl-$C_{1-3}$-alkyl, $C_{6-10}$ aryl-$C_{1-3}$-alkoxy, $C_{2-5}$ heteroaryloxy, $C_{2-5}$ heteroaryl-$C_{1-3}$-alkyl and $C_{2-5}$ heteroaryl-$C_{1-3}$-alkoxy is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy and $C_{3-8}$ cycloalkyloxy.

In some embodiments, provided herein are compounds having Formula (Ia) as shown below:

(Ia)

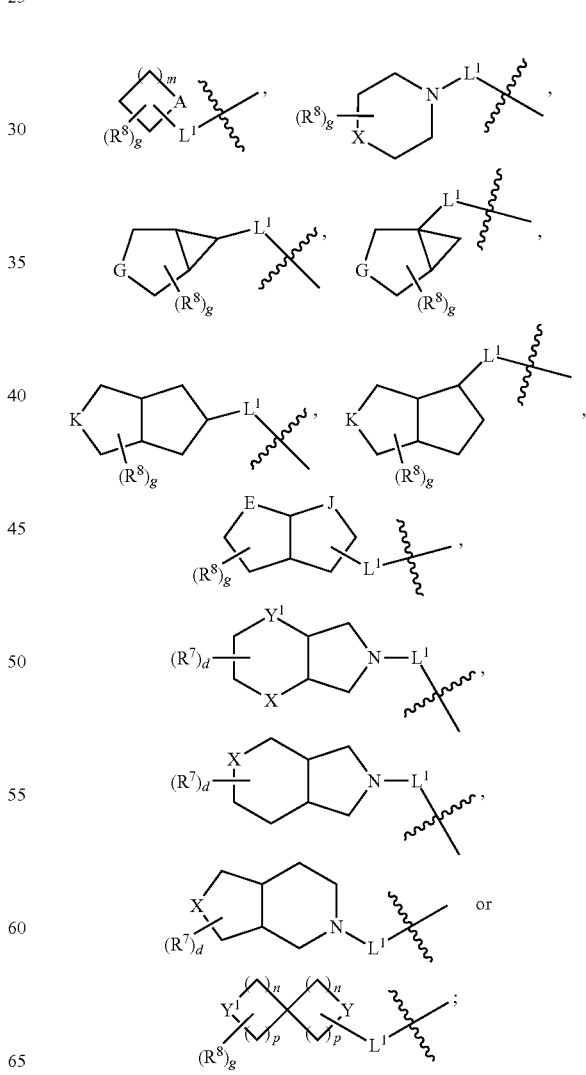

or a stereoisomer, a geometric isomer, a tautomer, an N-oxide, a hydrate, a solvate, a metabolite, a pharmaceutically acceptable salt or a prodrug thereof, wherein:

$R^1$ is H, D, F, Cl, Br, I, —OH, —NO$_2$, —NH$_2$, —CN, $C_{1-6}$ alkyl, $C_{2-6}$ alkynyl or $C_{1-6}$ alkoxy-$C_{1-6}$-alkyl, wherein optionally each of $C_{1-6}$ alkyl, $C_{2-6}$ alkynyl and $C_{1-6}$ alkoxy-$C_{1-6}$-alkyl is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy, $C_{6-10}$ aryl, $C_{1-9}$ heteroaryl, $C_{3-8}$ cycloalkyl, $C_{3-8}$ cycloalkyloxy and $C_{2-10}$ heterocyclyl, or $R^1$ is wherein each A, G, E and J is independently CR$^b$R$^{b'}$, NR$^a$, O, S, S(=O) or S(=O)$_2$;

each K is independently NR$^a$, O, S, S(=O) or S(=O)$_2$;

each L$^1$ is independently a bond, C$_{1-4}$ alkylene, C$_{2-4}$ alkenylene or C$_{2-4}$ alkynylene, wherein optionally each of C$_{1-4}$ alkylene, C$_{2-4}$ alkenylene and C$_{2-4}$ alkynylene is independently substituted with one or more substituents independently selected from D, F, Cl, Br, I, —OH, —NO$_2$, —NH$_2$, —CN, —COOH and C$_{1-3}$ alkyl;

each R$^8$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl or C$_{5-12}$ fused heterobicyclyl, wherein optionally each of C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl and C$_{5-12}$ fused heterobicyclyl is independently substituted with one or more substituents independently selected from D, F, Cl, Br, I, —OH, —SH, —NO$_2$, —NH$_2$, —CN, —COOH, C$_{1-3}$ alkyl and C$_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2;

Ar is

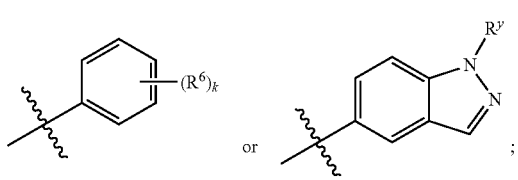

wherein each R$^6$ is independently H, D, F, Cl, Br, I, —OH, —NO$_2$, —NH$_2$, —CN, C$_{1-3}$ alkyl, C$_{2-4}$ alkynyl, C$_{1-3}$ alkoxy, C$_{6-10}$ aryloxy, C$_{6-10}$ aryl-C$_{1-3}$-alkoxy, C$_{2-5}$ heteroaryloxy or C$_{2-5}$ heteroaryl-C$_{1-3}$-alkoxy, wherein optionally each of C$_{1-3}$ alkyl, C$_{2-4}$ alkynyl, C$_{1-3}$ alkoxy, C$_{6-10}$ aryloxy, C$_{6-10}$ aryl-C$_{1-3}$-alkoxy, C$_{2-5}$ heteroaryloxy and C$_{2-5}$ heteroaryl-C$_{1-3}$-alkoxy is independently substituted with one or more substituents independently selected from D, F, Cl, Br, I, —OH, —NO$_2$, —NH$_2$, —CN, —COOH, C$_{1-3}$ alkyl, C$_{1-3}$ haloalkyl, C$_{1-3}$ alkylamino and C$_{1-3}$ alkoxy;

k is 0, 1, 2, 3, 4 or 5;

R$^y$ is H, C$_{1-3}$ alkyl or halobenzyl;

each of R$^2$, R$^3$, R$^4$, R$^5$ and L is independently as defined herein; and each X, Y, Y$^1$, R$^a$, R$^b$, R$^{b'}$, R$^7$ and d is independently as defined herein.

In other embodiments, R$^1$ is H, D, C$_{1-3}$ alkyl, C$_{2-3}$ alkynyl or C$_{1-3}$ alkoxy-C$_{1-3}$-alkyl, wherein optionally each of C$_{1-3}$ alkyl, C$_{2-3}$ alkynyl and C$_{1-3}$ alkoxy-C$_{1-3}$-alkyl is independently substituted with one or more substituents independently selected from D, F, Cl, Br, I, —OH, —NO$_2$, —NH$_2$, —CN, —COOH, C$_{1-3}$ alkoxy and C$_{3-8}$ cycloalkyloxy, or R$^1$ is

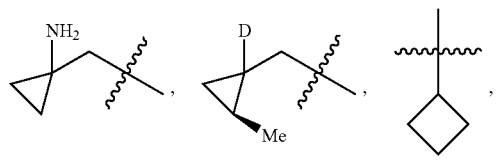

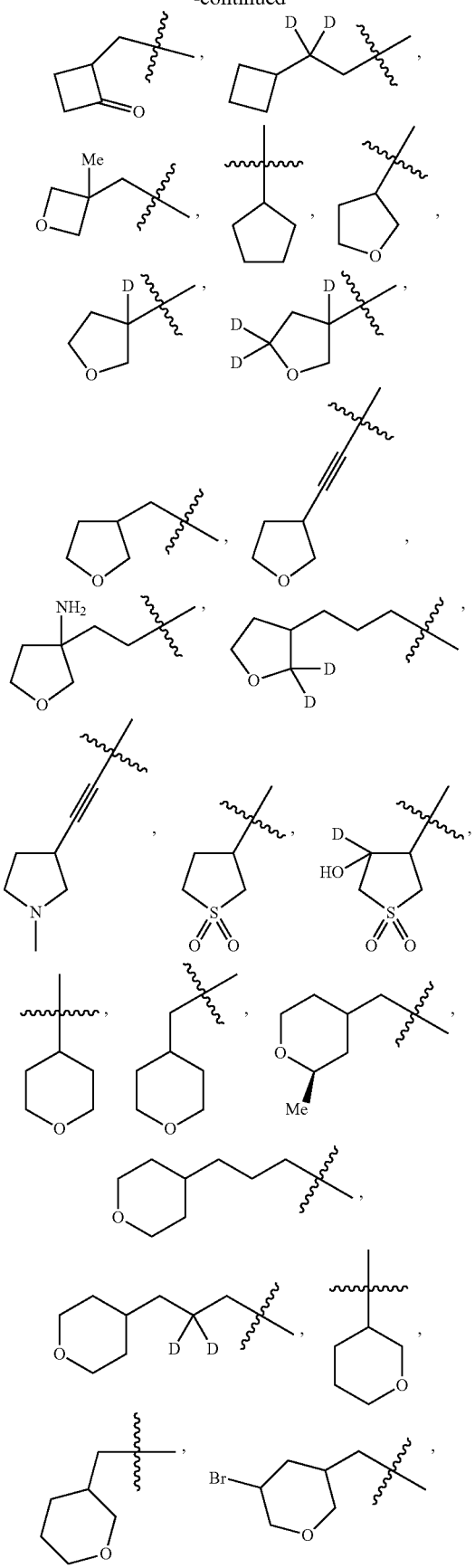

-continued
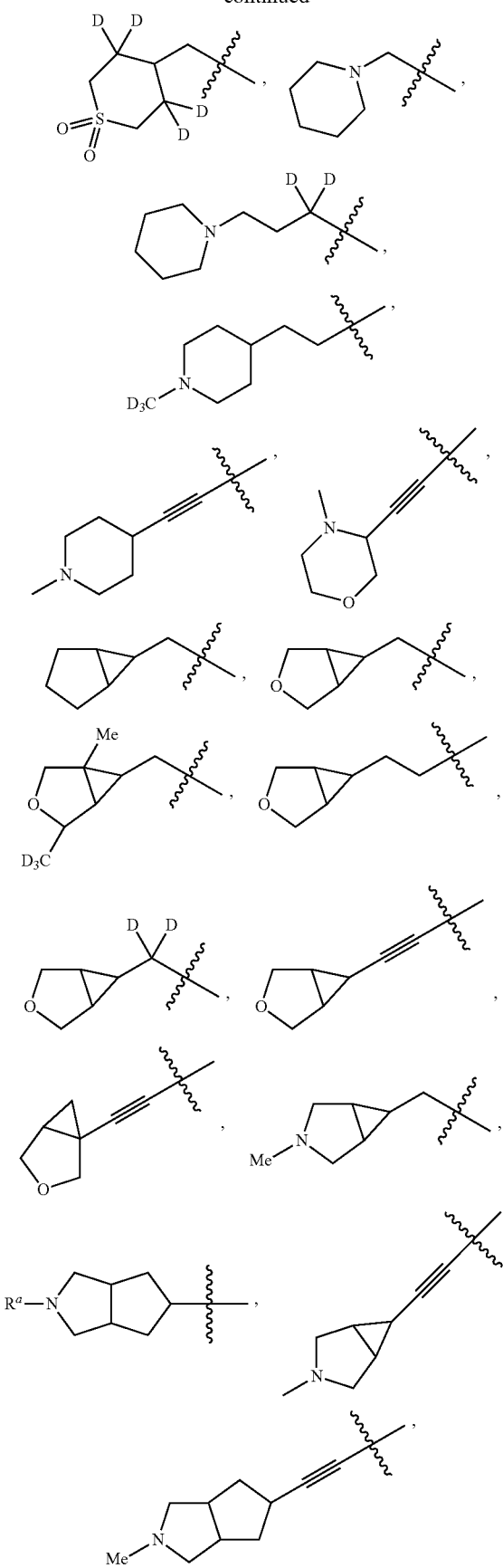
-continued
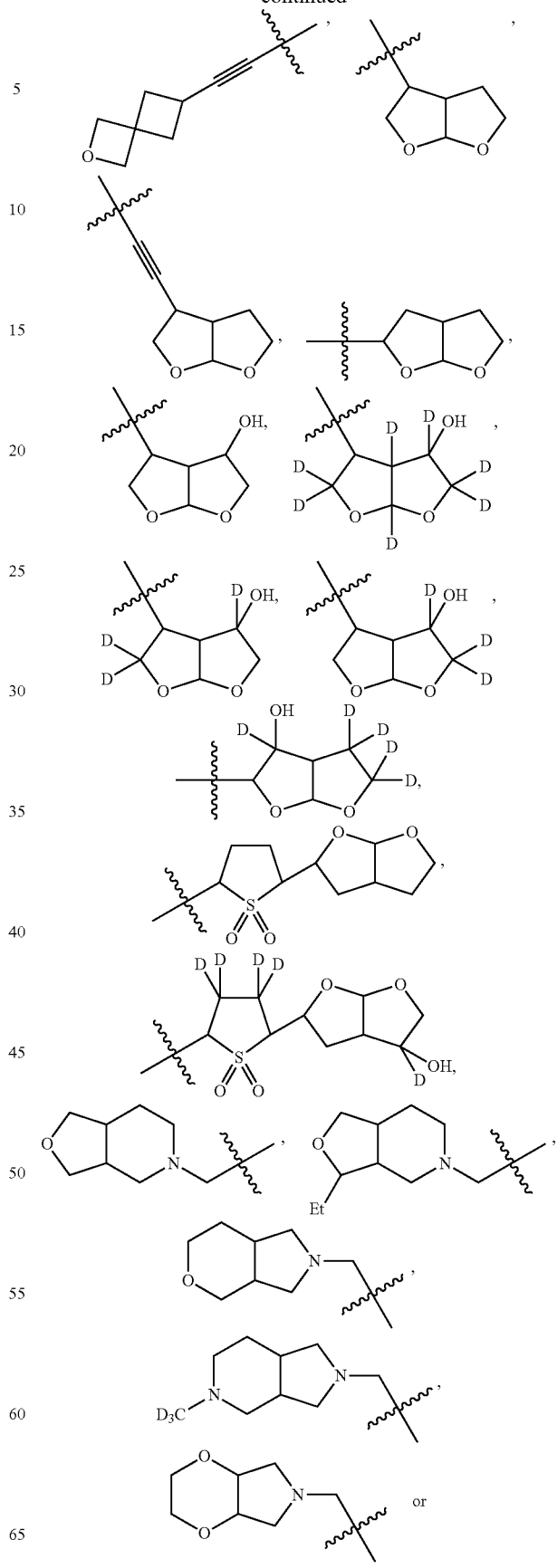

-continued

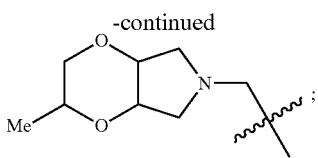

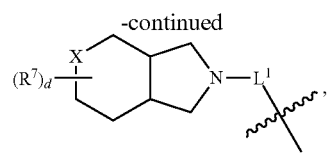

wherein $R^a$ is H, D or $C_{1-3}$ alkyl.

In some embodiments, provided herein are compounds having Formula (Ib) as shown below:

(Ib)

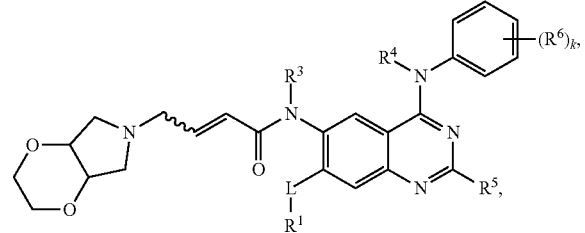

or a stereoisomer, a geometric isomer, a tautomer, an N-oxide, a hydrate, a solvate, a metabolite, a pharmaceutically acceptable salt or a prodrug thereof, wherein:

$R^1$ is H, D, $C_{1-3}$ alkyl, $C_{2-3}$ alkynyl or $C_{1-3}$ alkoxy-$C_{1-3}$-alkyl, wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy, $C_{3-8}$ cycloalkyl, $C_{3-8}$ cycloalkyloxy and $C_{2-10}$ heterocyclyl, or $R^1$ is

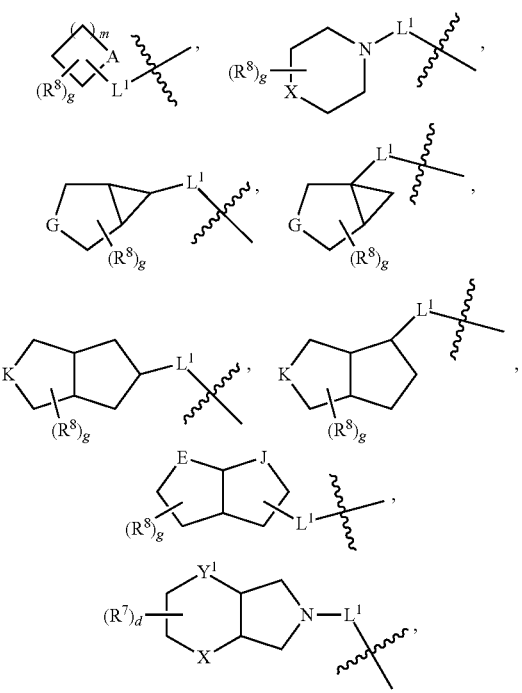

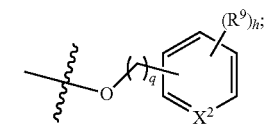

wherein each A, G, E and J is independently $CR^bR^{b'}$, $NR^a$, O, S, S(=O) or S(=O)$_2$;

each K is independently $NR^a$, O, S, S(=O) or S(=O)$_2$;

each $L^1$ is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —NO$_2$, —NH$_2$, —CN, —COOH and $C_{1-3}$ alkyl;

each $R^8$ is independently H, D, F, Cl, Br, I, —OH, —SH, —NO$_2$, —NH$_2$, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —NO$_2$, —NH$_2$, —CN, —COOH, $C_{1-3}$ alkyl and $C_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2;

each $R^6$ is independently H, D, F, Cl, Br, I, —OH, —NO$_2$, —NH$_2$, —CN, $C_{1-3}$ alkyl, $C_{2-4}$ alkynyl, $C_{1-3}$ alkoxy or each $R^6$ is

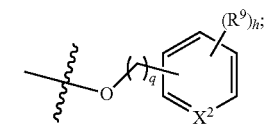

wherein $X^2$ is $CR^{10}$ or N, and wherein $R^{10}$ is H or $C_{1-3}$ alkyl;

q is 0, 1, 2 or 3;

each $R^9$ is independently H, D, F, Cl, Br, I, —OH, —NO$_2$, —NH$_2$, —CN, $C_{1-3}$ alkyl, $C_{2-4}$ alkynyl or $C_{1-3}$ alkoxy;

h is 0, 1, 2, 3, 4 or 5;

each of $R^3$, $R^4$, $R^5$ and L is independently as defined herein; and each X, Y, $Y^1$, $R^a$, $R^b$, $R^{b'}$, $R^7$ and d is independently as defined herein.

In other embodiments, $R^1$ is H, D, —CH$_3$, —CD$_3$, —CH$_2$CH$_3$, —CH$_2$CF$_3$, —CD$_2$CH$_3$, —CD$_2$CD$_3$, —CH$_2$CH$_2$OCH$_3$, —CH$_2$CD$_2$OCH$_3$, —CH$_2$CH$_2$OCD$_3$, —CH$_2$CH$_2$OCD$_2$CH$_3$, —C≡CCH$_2$OCH$_2$CH$_3$,

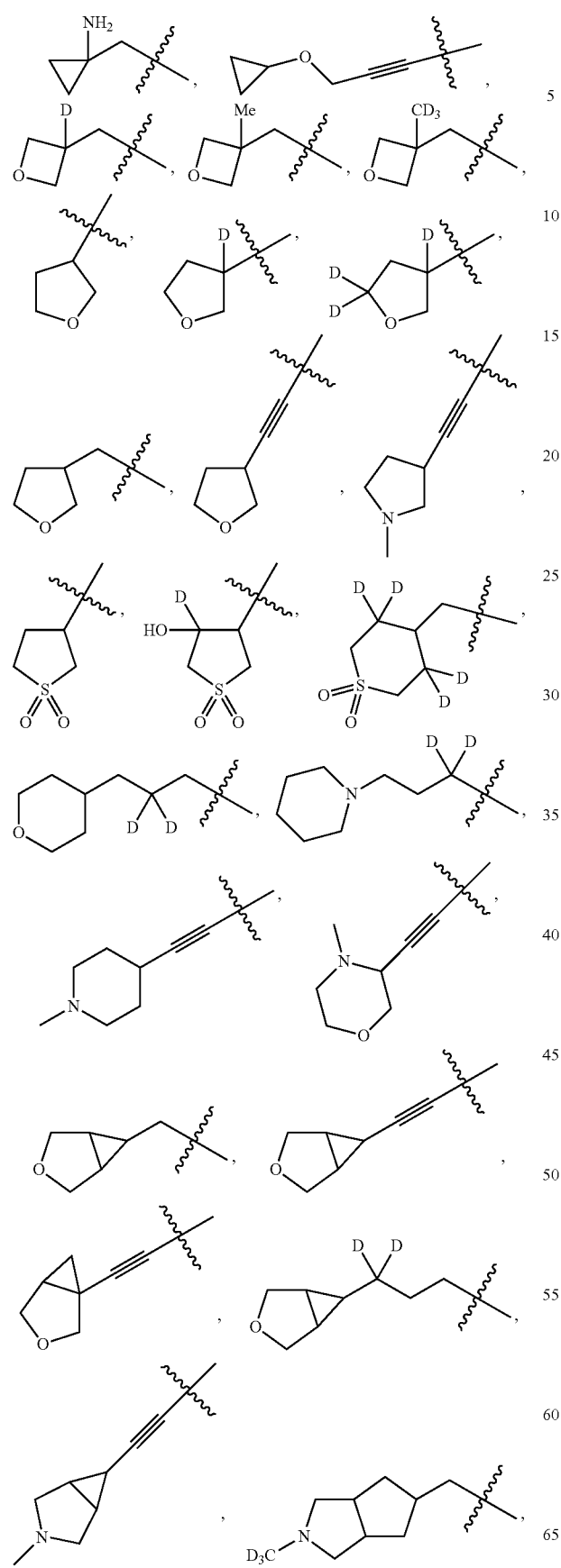
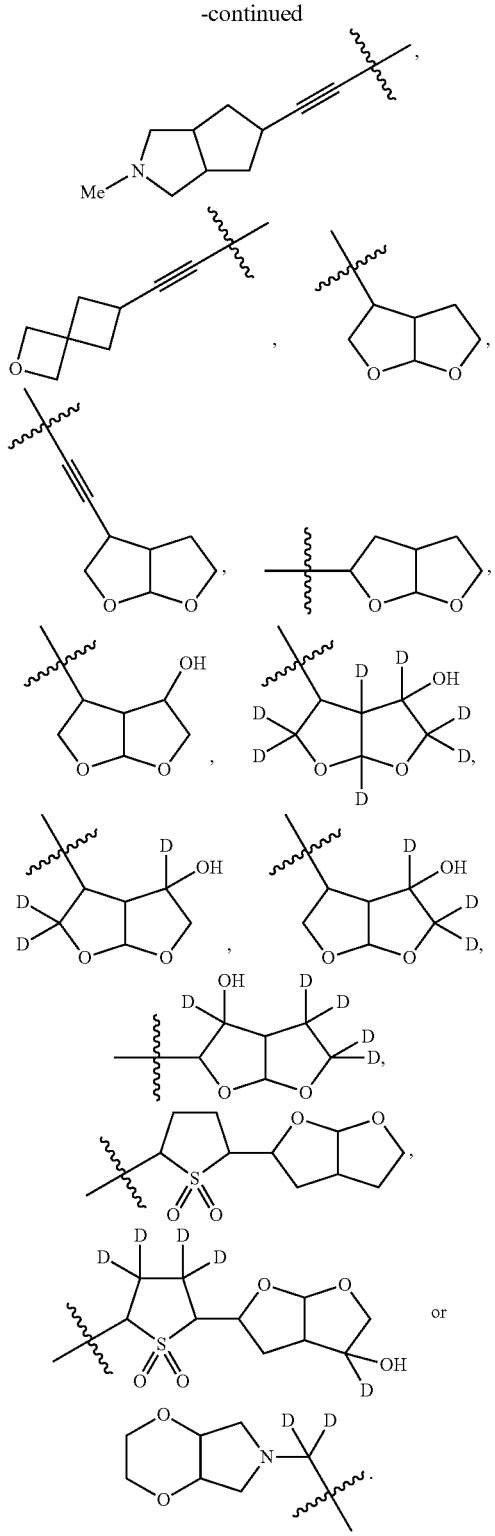

In one aspect, provided herein are pharmaceutical compositions comprising the compound disclosed herein, or a stereoisomer, a geometric isomer, a tautomer, an N-oxide, a hydrate, a solvate, a metabolite, a pharmaceutically acceptable salt or a prodrug thereof, and an optionally pharmaceutically acceptable carrier, excipient, diluent, adjuvant, vehicle or a combination thereof.

In some embodiments, the pharmaceutical composition disclosed herein further comprises at least one additional therapeutic agent selected from a chemotherapeutic agent, an anti-proliferative agent, an agent for treating non-small cell lung cancer and epidermal carcinoma, or a combination thereof.

In other embodiments, the additional therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab or a combination thereof.

In another aspect, provided herein is use of the compound or the pharmaceutical composition containing the compound disclosed herein in the manufacture of a medicament for preventing, managing, treating or lessening the severity of a proliferative disorder, atherosclerosis or lung fibrosis in a patient.

In another aspect, provided herein is a method of preventing, managing, treating or lessening the severity of a proliferative disorder, atherosclerosis or lung fibrosis in a patient comprising administering to the patient a therapeutically effective amount of the compound or the pharmaceutical composition containing the compound disclosed herein.

In another aspect, provided herein is the compound or the pharmaceutical composition containing the compound disclosed herein for use in preventing, managing, treating or lessening the severity of a proliferative disorder, atherosclerosis or lung fibrosis in a patient.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, thyroid cancer, head and neck cancer, prostate cancer, pancreatic cancer, CNS (central nervous system) cancer, glioblastoma or a myeloproliferative disorder.

In another aspect, provided herein is use of the compound or the pharmaceutical composition containing the compound disclosed herein in the manufacture of a medicament for modulating protein kinase activity.

In another aspect, provided herein is a method of modulating protein kinase activity with the compound or the pharmaceutical composition containing the compound disclosed herein.

In another aspect, provided herein is the compound or the pharmaceutical composition containing the compound disclosed herein for use in modulating protein kinase activity.

In some embodiments, the protein kinase is receptor tyrosine kinase.

In other embodiments, the receptor tyrosine kinase is at least one of EGFR and HER-2.

In another aspect, provided herein is a pharmaceutical combination comprising the compound disclosed herein and at least one additional therapeutic agent selected from a chemotherapeutic agent, an anti-proliferative agent, an agent for treating non-small cell lung cancer and an agent for treating epidermal carcinoma, wherein the additional therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab or a combination thereof.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope of the invention as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the*

Handbook of Chemistry and Physics, 75th Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen groups in a given structure with the group of a specified substituent. Unless otherwise indicated, an optionally substituted group may have a substituent at each substitutable position of the group. When more than one position in a given structure may be substituted with more than one substituent selected from a specified group, the substituent may be either the same or different at each position. Wherein the substituents include, but are not limited to, deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

The term "optional" or "optionally" means that the subsequently described event or circumstances may or may not occur. The description includes instances where the event or circumstance occurs, and instances where it does not occur.

The term "alkyl" refers to a saturated linear or branched chain monovalent hydrocarbon group of 1-20 carbon atoms, wherein the alkyl group may be optionally substituted independently with one or more substituents described herein. In some embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms and in yet other embodiments, the alkyl group contains 1-3 carbon atoms. Some non-limiting examples of the alkyl group include methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, and the like. The term "alkyl" or the prefix "alk-" is inclusive of both straight chain and branched saturated carbon chain.

The term "haloalkyl" refers to an alkyl group substituted with one or more identical or different halogen atoms, wherein the alkyl group is as defined herein and the halogen atom refers to F, Cl, Br or I. Some non-limiting examples of the haloalkyl group include trifluoromethyl, trifluoroethyl, and the like.

The term "hydroxy-substituted alkyl" or "hydroxyalkyl" as used interchangeably herein refers to an alkyl group substituted with one or more hydroxy groups, wherein the alkyl group is as defined herein. Some non-limiting examples of the hydroxy-substituted alkyl group include hydroxymethyl, (R)-hydroxyethyl, (S)-hydroxyethyl, (R)-hydroxypropyl, (S)-hydroxypropyl, 2-hydroxypropyl, 2-hydroxy-2-propyl, 3-hydroxy-3-pentyl, and the like.

The term "divalent group" refers to a group obtained by removing two hydrogen atoms from a molecule. In some embodiments, two hydrogen atoms are removed from the same atom of a molecule. In other embodiments, two hydrogen atoms are removed from the different atom of a molecule.

The term "alkylene" refers to a saturated divalent hydrocarbon group derived from a straight or branched chain saturated hydrocarbon by the removal of two hydrogen atoms. Some non-limiting examples of the alkylene group include methylene, ethylene, isopropylidene, 1,1-ethylidene, 1,3-propylene, 2-methoxy-1,1-propylidene, 2-hydroxy-1,1-propylidene, 2-methyl-2-hydroxy-1,1-propylidene, and the like.

The term "alkenyl" refers to a linear or branched chain monovalent hydrocarbon group of 2-12 carbon atoms with at least one site of unsaturation, i.e., a carbon-carbon, sp² double bond, wherein the alkenyl group may be optionally substituted independently with one or more substituents described herein, and includes groups having "cis" and "trans" orientations, or alternatively, "E" and "Z" orientations. Some non-limiting examples of the alkenyl group include ethenyl or vinyl (—CH=$CH_2$), allyl (—$CH_2$CH=$CH_2$), propenyl ($CH_3$CH=CH—), and the like.

As described herein,

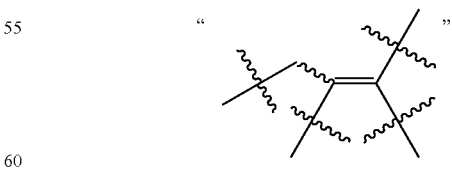

means that a compound containing double bond may be Z-configuration, E-configuration or a mixture of Z configuration and E configuration.

The term "alkenylene" refers to an unsaturated divalent group derived from a straight or branched chain unsaturated hydrocarbon alkenyl by the removal of two hydrogen atoms.

Some non-limiting examples of the alkenylene group include ethenylene (—CH═CH—), and the like.

The term "alkynyl" refers to a linear or branched chain monovalent hydrocarbon group of 2-12 carbon atoms with at least one site of unsaturation, i.e., a carbon-carbon, sp triple bond, wherein the alkynyl group may be optionally substituted independently with one or more substituents described herein. Some non-limiting examples of the alkynyl group include ethynyl (—C≡CH), propargyl (—CH$_2$C≡CH), and the like.

The term "alkynylene" refers to an unsaturated divalent group derived from a straight or branched chain unsaturated hydrocarbon alkynyl by the removal of two hydrogen atoms. Some non-limiting examples of the alkynylene group include ethynylene (—C≡C—), propynylene (—CH$_2$C≡C—), and the like.

The term "carbocyclyl" or "cycloalkyl" refers to a monovalent or multivalent, non-aromatic, saturated or partially unsaturated ring including 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of the carbocyclyl group include cycloalkyl, cycloalkenyl and cycloalkynyl. Further examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The term "carbocyclyl" or "cycloalkyl" described herein may be substituted or unsubstituted, wherein the substituents include, but are not limited to, deuterium, fluoro, chloro, bromo, iodo, hydroxy, mercapto, nitro, amino, cyano, carboxy, oxo (═O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (═O), $C_{1-3}$ alkyl, deuterated $C_{1-3}$ alkyl, $C_{1-3}$ haloalkyl and hydroxy-substituted $C_{1-3}$ alkyl.

The term "cycloalkylalkyl" refers to an alkyl group substituted with one or more cycloalkyl groups, wherein the alkyl group and cycloalkyl group are as defined herein. Some non-limiting examples of the cycloalkylalkyl group include cyclopropylmethyl, cyclobutylethyl, cyclopentylmethyl, and the like.

The term "cycloalkylalkenyl" refers to an alkenyl group substituted with one or more cycloalkyl groups, wherein the alkenyl group and cycloalkyl group are as defined herein. Some non-limiting examples of the cycloalkylalkenyl group include cyclopropylvinyl, and the like.

The term "cycloalkylalkynyl" refers to an alkynyl group substituted with one or more cycloalkyl groups, wherein the alkynyl group and cycloalkyl group are as defined herein. Some non-limiting examples of the cycloalkylalkynyl group include cyclopropylethynyl, and the like.

The term "cycloalkyloxy" refers to optionally substituted cycloalkyl groups, as defined herein, attached to an oxygen atom, wherein the oxygen atom serves as the attaching point to the rest of the molecule. Some non-limiting examples of the cycloalkyloxy group include cyclopropyloxy, cyclobutyloxy, cyclopentyloxy, and the like.

The term "cycloalkyloxyalkynyl" refers to an alkynyl group substituted with one or more cycloalkyloxy groups, wherein the alkynyl group and cycloalkyloxy group are as defined herein. Some non-limiting examples of the cycloalkyloxyalkynyl group include 3-cyclopropyloxyprop-1-yn-1-yl, cyclobutyloxyethynyl, and the like.

The term "alkoxy" refers to optionally substituted alkyl groups, as defined herein, attached to an oxygen atom, wherein the oxygen atom serves as the attaching point to the rest of the molecule. Some non-limiting examples of the alkoxy group include methoxy, ethoxy, propoxy, and the like.

The term "alkoxyalkyl" refers to an alkyl group substituted with one or more alkoxy groups, wherein the alkyl group and alkoxy group are as defined herein. Some non-limiting examples of the alkoxyalkyl group include methoxymethyl, methoxyethyl, ethoxyethyl, and the like.

The term "alkylamino" refers to "N-alkylamino" and "N,N-dialkylamino", wherein the amino groups are independently substituted with one or two alkyl groups, respectively, and wherein the alkyl group is as defined herein. In some embodiments, the alkylamino group is lower alkylamino groups having one or two alkyl groups of 1 to 6 carbon atoms, attached to nitrogen atom. In other embodiments, the alkylamino group is lower alkylamino groups having 1 to 3 carbon atoms. Some non-limiting examples of the alkylamino group include monoalkylamino or dialkylamino such as N-methylamino, N-ethylamino, N,N-dimethylamino, N,N-diethylamino, and the like.

The term "alkylaminoalkyl" refers to an alkyl group substituted with one or more alkylamino groups, wherein the alkyl group and alkylamino group are as defined herein. Some non-limiting examples of the alkylaminoalkyl group include N-methylaminomethyl, N-ethylaminomethyl, N,N-dimethylaminoethyl, N,N-diethylaminoethyl, and the like.

The term "alkylthio" refers to a linear or branched alkyl group of 1 to 10 carbon atoms attached to a divalent sulfur atom, wherein the alkyl group is as defined herein. Some non-limiting examples of the alkylthio group include methylthio (CH$_3$S—), ethylthio, and the like.

The term "heteroalkyl" refers to an alkyl group in which one or more carbon atoms are an independently selected heteroatom, wherein the alkyl group is as defined herein, and the carbon atom serves as the attaching point to the rest of the molecule. In some embodiments, the heteroalkyl is a linear or branched chain having 1 to 10 atoms (e.g., 1 to 9 carbon atoms and 1 to 3 heteroatoms selected from N, O, P and S, wherein the S or P is optionally substituted with one or more oxo to provide the group SO or SO$_2$, or PO or PO$_2$). In other embodiments, the heteroalkyl group is a linear or branched chain having 1 to 8 atoms (e.g., 1 to 7 carbon atoms and 1 to 3 heteroatoms selected from N, O, P and S, wherein the S or P is optionally substituted with one or more oxo to provide the group SO or SO$_2$, or PO or PO$_2$). In still other embodiments, the heteroalkyl group is a linear or branched chain having 1 to 6 atoms (e.g., 1 to 5 carbon atoms and 1 to 3 heteroatoms selected from N, O, P and S, wherein the S or P is optionally substituted with one or more oxo to provide the group SO or SO$_2$, or PO or PO$_2$), a linear or branched chain having 1 to 4 atoms (e.g., 1 to 3 carbon atoms and 1 to 3 heteroatoms selected from N, O, P and S, wherein the S or P is optionally substituted with one or more oxo to provide the group SO or SO$_2$, or PO or PO$_2$) or a linear or branched chain having 1 to 3 atoms (e.g., 1 to 2 carbon atoms and 1 to 2 heteroatoms selected from N, O, P and S, wherein the S or P is optionally substituted with one or more oxo to provide the group SO or SO$_2$, or PO or PO$_2$). Some non-limiting examples of the heteroalkyl group include aminomethyl, methoxyethyl, and the like.

The term "deuterium" refers to D, which is a stable isotope of hydrogen and also is called heavy hydrogen.

The term "deuterated alkyl", "deuterated alkoxy" or "deuterated alkylamino" refers to alkyl groups, alkoxy groups or alkylamino groups which are substituted respectively with one or more D atoms.

The term "carboxy" or "carboxyl", whether used alone or with other terms such as "carboxyalkyl", refers to —CO$_2$H.

The term "carbonyl", whether used alone or with other terms such as "alkylcarbonyl" or "carbonyloxy", refers to —(C=O)—.

The term "acylamino", whether used alone or with other terms such as "alkylacylamino", refers to —C(=O)—NH—.

The term "sulfonyl", whether used alone or with other terms such as "alkylsulfonyl", refers to a bivalent group —S(=O)$_2$— respectively. The term "alkylsulfonyl" refers to a sulfonyl group substituted with alkyl groups, forming a alkylsulfonyl (—S(=O)$_2$CH$_3$).

The term "sulfinyl", whether used alone or with other terms such as "alkylsulfinyl", refers to a bivalent group —S(=O)— respectively. The term "alkylsulfinyl" refers to a sulfinyl group substituted with alkyl groups, forming a alkylsulfinyl (—S(=O)CH$_3$).

The term "heterocycle" or "heterocyclyl" as used interchangeably herein refers to a monocyclic, bicyclic, or tricyclic ring system in which one or more ring members are an independently selected heteroatom and that is completely saturated or that contains one or more units of unsaturation, but not aromatic, having one or more points of attachment to the rest of the molecule. One or more ring hydrogen atoms are optionally substituted independently with one or more substituents described herein. In some embodiments, the "heterocycle" or "heterocyclyl" group is a monocycle having 3 to 7 ring members (e.g., 1 to 6 carbon atoms and 1 to 3 heteroatoms selected from N, O, P and S, wherein the S or P is optionally substituted with one or more oxo to provide the group SO or SO$_2$, or PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P and S, wherein the S or P is optionally substituted with one or more oxo to provide the group SO or SO$_2$, or PO or PO$_2$).

The heterocyclyl may be a carbon group or heteroatom group. "Heterocyclyl" also includes groups where heterocycle groups are fused with a saturated, partially unsaturated carboatomic or heterocyclic ring. Some non-limiting examples of the heterocyclic ring include pyrrolidinyl, tetrahydrofuranyl, dihydrofuranyl, tetrahydrothienyl, tetrahydropyranyl, dihydropyranyl, tetrahydrothiopyranyl, morpholinyl, thiomorpholinyl, thioxanyl, piperazinyl, homopiperazinyl, azetidinyl, oxetanyl, thietanyl, azacyclohexyl, 1,1-dioxo-tetrahydrothiophen-3-yl, homopiperidinyl, epoxypropyl, azepanyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 3-oxabicyclo[3.1.0]hexyl, 3-azabicyclo[3.1.0]hexyl, 3-azabicyclo[4.1.0]heptyl, 3-azabicyclo[3.3.0]octyl, azabicyclo[2.2.2]hexyl, 3H-indolyl quinolizinyl and N-pyridyl urea. The heterocyclyl described herein may be substituted or unsubstituted, wherein the substituents include, but are not limited to, deuterium, fluoro, chloro, bromo, iodo, hydroxy, mercapto, nitro, amino, cyano, carboxy, oxo (=O), C$_{1-3}$ alkyl, deuterated C$_{1-3}$ alkyl, C$_{1-3}$ haloalkyl, hydroxy-substituted C$_{1-3}$ alkyl, C$_{2-3}$ alkenyl, C$_{2-3}$ alkynyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ aryl-C$_{1-3}$-alkyl, C$_{6-10}$ aryl-C$_{1-3}$-alkoxy, C$_{6-10}$ arylamino, C$_{1-9}$ heteroaryl, C$_{1-9}$ heteroaryl-C$_{1-3}$-alkyl, C$_{1-9}$ heteroaryloxy, C$_{3-8}$ cycloalkyl, C$_{3-8}$ cycloalkyloxy, C$_{2-10}$ heterocyclyl or C$_{5-12}$ fused heterobicyclyl, and the like, and wherein optionally each of C$_{1-3}$ alkyl, C$_{2-3}$ alkenyl, C$_{2-3}$ alkynyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ aryl-C$_{1-3}$-alkyl, C$_{6-10}$ aryl-C$_{1-3}$-alkoxy, C$_{6-10}$ arylamino, C$_{1-9}$ heteroaryl, C$_{1-9}$ heteroaryl-C$_{1-3}$-alkyl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), C$_{1-3}$ alkyl, deuterated C$_{1-3}$ alkyl, C$_{1-3}$ haloalkyl and hydroxy-substituted C$_{1-3}$ alkyl.

The term "heterocyclylalkyl" refers to a heterocyclyl-substituted alkyl group, wherein the heterocyclyl group and alkyl group are as defined herein. Some non-limiting examples of the heterocyclylalkyl group include (tetrahydrofuran-3-yl)methyl, (oxetan-3-yl)methyl, (pyrrol-2-yl)methyl, (morpholin-4-yl)methyl, and the like.

The term "heterocyclylalkenyl" refers to a heterocyclyl-substituted alkenyl group, wherein the heterocyclyl group and alkenyl group are as defined herein. Some non-limiting examples of the heterocyclylalkenyl group include (pyrrol-2-yl)vinyl, (morpholin-3-yl)vinyl, (piperidin-4-yl)vinyl, and the like.

The term "heterocyclylalkynyl" refers to a heterocyclyl-substituted alkynyl group, wherein the heterocyclyl group and alkynyl group are as defined herein. Some non-limiting examples of the heterocyclylalkynyl group include (tetrahydrofuran-3-yl)ethynyl, (pyrrolidin-3-yl)ethynyl, (morpholin-3-yl)ethynyl, (piperidin-4-yl)ethynyl, (tetrahydro-2H-pyran-4-yl)ethynyl, (3-oxabicyclo[3.1.0]hex-1-yl)ethynyl, (3-oxabicyclo[3.1.0]hex-6-yl) ethynyl, (3-azabicyclo[3.1.0]hex-6-yl)ethynyl, and the like.

The term "fused bicyclic", "fused cyclic", "fused bicyclyl" or "fused cyclyl" refers to saturated fused ring system, which refers to a bicyclic ring system that is not aromatic. Such system may contain isolated or conjugated unsaturation, but not aromatic or heteroaromatic rings in its core structure (but may have aromatic substitution thereon). Each cyclic ring in the fused bicyclyl can be either a carbocyclic or a heteroalicyclic. Some non-limiting examples of the fused bicyclic ring system include hexahydro-furo[3,2-b]furan, 2,3,3a,4,7,7a-hexahydro-1H-indene, 7-azabicyclo[2.2.1]heptane, fused bicyclo[3.3.0]octane, fused bicyclo[3.1.0]hexane, 1,2,3,4,4a,5,8,8a-octahydro-naphthalene, and the like. And the fused bicyclyl group defined herein may be substituted or unsubstituted, wherein the substituents include, but are not limited to, deuterium, fluoro, chloro, bromo, iodo, hydroxy, mercapto, nitro, amino, cyano, carboxy, oxo (=O), C$_{1-3}$ alkyl, deuterated C$_{1-3}$ alkyl, C$_{1-3}$ haloalkyl, hydroxy-substituted C$_{1-3}$ alkyl, C$_{2-3}$ alkenyl, C$_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

The term "fused heterobicyclyl" refers to saturated or unsaturated fused ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, and wherein each ring in the system contains 3 to 7 ring members and that contains 1 to 6 carbon atoms and 1 to 3 heteroatoms selected from N, O, P, and S, wherein the S or P is optionally substituted with one or more oxo to provide the group SO or $SO_2$, or PO or $PO_2$. Some non-limiting examples of the fused heterobicyclyl group include hexahydro-furo[3,2-b]furan, 7-azabicyclo[2.2.1]heptane, 3-azabicyclo[3.3.0]octane, 3,5,8-trioxabicyclo[5,1,0]octane, 1-aza-4,6-dioxabicyclo[3.3.0]octane, and the like. And the fused heterobicyclyl group defined herein may be substituted or unsubstituted, wherein the substituents include, but are not limited to, deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

The term "fused bicyclylalkyl" refers to an alkyl group substituted with one or more fused bicyclyl groups, wherein the alkyl group and fused bicyclyl group are as defined herein. Some non-limiting examples of the fused bicyclylalkyl group include (1,2,3,4,4a,5,8,8a-octahydronaphthyl)ethyl, (1,2,3,4,4a,5,8,8a-octahydro-naphthyl)methyl, (1,2,3,4,4a,5,8,8a-octahydro-naphthyl)propyl, (7-azabicyclo[2.2.1]hept-7-yl)ethyl, (3-oxabicyclo[3.1.0]hexyl)ethyl, (fused bicyclo[3.3.0]octyl)methyl, (fused bicyclo[3.1.0]hexyl)ethyl, and the like.

The term "fused bicyclylalkenyl" refers to an alkenyl group substituted with one or more fused bicyclyl groups, wherein the alkenyl group and fused bicyclyl group are as defined herein. Some non-limiting examples of the fused bicyclylalkenyl group include (1,2,3,4,4a,5,8,8a-octahydro-naphthyl)ethenyl, (fused bicyclo[3.3.0]octyl) ethenyl, and the like.

The term "fused bicyclylalkynyl" refers to an alkynyl group substituted with one or more fused bicyclyl groups, wherein the alkynyl group and fused bicyclyl group are as defined herein. Some non-limiting examples of the fused bicyclylalkynyl group include (1,2,3,4,4a,5,8,8a-octahydro-naphthyl)ethynyl, (fused bicyclo[3.3.0]octyl)ethynyl, and the like.

The term "fused heterobicyclylalkyl" refers to an alkyl group substituted with one or more fused heterobicyclyl groups, wherein the alkyl group and fused heterobicyclyl group are as defined herein. Some non-limiting examples of the fused heterobicyclylalkyl group include (hexahydro-furo[3,2-b]furan-2-yl)ethyl, (hexahydro-furo[3,2-b]furan-2-yl)methyl, (7-azabicyclo[2.2.1]hept-2-yl)methyl, (7-azabicyclo[2.2.1]heptan-2-yl)ethyl, (7-azabicyclo[2.2.1]hept-4-yl)methyl, and the like.

The term "fused heterobicyclylalkenyl" refers to an alkenyl group substituted with one or more fused heterobicyclyl groups, wherein the alkenyl group and fused heterobicyclyl group are as defined herein. Some non-limiting examples of the fused heterobicyclylalkenyl group include (hexahydro-furo[3,2-b]furan-2-yl)vinyl, (3-oxabicyclo[3.1.0]hex-6-yl)vinyl, and the like.

The term "fused heterobicyclylalkynyl" refers to an alkynyl group substituted with one or more fused heterobicyclyl groups, wherein the alkynyl group and fused heterobicyclyl group are as defined herein. Some non-limiting examples of the fused heterobicyclylalkynyl group include (3-oxabicyclo[3.1.0]hex-1-yl)ethynyl, (3-oxabicyclo[3.1.0]hex-6-yl)ethynyl, (3-azabicyclo[3.1.0]hex-6-yl)ethynyl, (3-azabicyclo[3.3.0]oct-7-yl)ethynyl, (hexahydro-furo[2,3-b]furan-3-yl)ethynyl, and the like.

The term "spirocyclyl", "spirocyclic", "spiro bicyclyl" or "spiro bicyclic" refers to a ring originating from a particular annular carbon of another ring. For example (as shown in FIGURE b), ring A and ring B share a carbon atom between the two saturated ring systems, which terms as a "spirocyclyl" or "spiro bicyclyl". Each cyclic ring in the spirocyclyl or spiro bicyclyl can be either a carbocyclic or a heteroalicyclic. Some non-limiting examples of the spirocyclyl group include spiro[4.5]dec-3-yl, 2,7-diazaspiro[4.4]non-2-yl, 7-oxo-2-azaspiro[4.5]dec-2-yl, 4-azaspiro[2.4]hept-5-yl, 4-oxaspiro[2.4]hept-5-yl, 5-azaspiro[2.4]hept-5-yl, spiro[2.4]heptyl, spiro[4.4]nonyl, 7-hydroxy-5-azaspiro[2.4]hept-5-yl, 3-oxaspiro[5.5]undecyl, 2-oxa-5-azaspiro[3,4]oct-5-yl, 2-oxaspiro[3.3]heptyl, and the like. The spirocyclyl or spiro bicyclyl group defined herein may be substituted or unsubstituted, wherein the substituents include, but are not limited to, deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

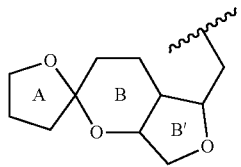

(b)

The term "spiro heterobicyclyl" refers to a ring originating from a particular annular carbon of another ring. For example, as depicted above, ring A and ring B share a carbon atom between the two saturated ring systems, which terms as a "spirocyclyl" or "spiro bicyclyl". Wherein at least one ring in the system contains one or more heteroatoms, and wherein each ring in the system contains 3 to 7 ring members and that contains 1 to 6 carbon atoms and 1 to 3 heteroatoms selected from N, O, P, and S, wherein the S or P is optionally substituted with one or more oxo to provide the group SO or $SO_2$, or PO or $PO_2$. Some non-limiting examples of the spiro heterobicyclyl group include 4-azaspiro[2.4]hept-5-yl, 4-oxaspiro[2.4]hept-5-yl, 5-azaspiro[2.4]hept-5-yl, 7-hydroxy-5-azaspiro[2.4]hept-5-yl, and the like. The spiro heterobicyclyl group defined herein may be substituted or unsubstituted, wherein the substituents include, but are not limited to, deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

The term "spiro bicyclylalkyl" refers to an alkyl group substituted with one or more spiro bicyclyl groups, wherein the alkyl group and spiro bicyclyl group are as defined herein. Some non-limiting examples of the spiro bicyclylalkyl group include (spiro[2.4]hept-1-yl)ethyl, (2,7-diazaspiro[4.4]non-2-yl)methyl, (4-azaspiro[2.4]hept-5-yl) ethyl, and the like.

The term "spiro bicyclylalkenyl" refers to an alkenyl group substituted with one or more spiro bicyclyl groups, wherein the alkenyl group and spiro bicyclyl group are as defined herein. Some non-limiting examples of the spiro bicyclylalkenyl group include (spiro[2.4]hept-1-yl)vinyl, (2,7-diazaspiro[4.4]non-2-yl)vinyl, (4-azaspiro[2.4]hept-5-yl)vinyl, and the like.

The term "spiro bicyclylalkynyl" refers to an alkynyl group substituted with one or more spiro bicyclyl groups, wherein the alkynyl group and spiro bicyclyl group are as defined herein. Some non-limiting examples of the spiro bicyclylalkynyl group include (spiro[2.4]hept-1-yl)ethynyl, (2,7-diazaspiro[4.4]non-2-yl)ethynyl, (4-azaspiro[2.4]hept-5-yl)ethynyl, and the like.

The term "spiro heterobicyclylalkyl" refers to an alkyl group substituted with one or more spiro heterobicyclyl groups, wherein the alkyl group and spiro heterobicyclyl group are as defined herein. Some non-limiting examples of the spiro heterobicyclylalkyl group include (4-azaspiro[2.4] hept-5-yl)ethyl, and the like.

The term "spiro heterobicyclylalkenyl" refers to an alkenyl group substituted with one or more spiro heterobicyclyl groups, wherein the alkenyl group and spiro heterobicyclyl group are as defined herein. Some non-limiting examples of the spiro heterobicyclylalkenyl group include (4-azaspiro [2.4]hept-5-yl)vinyl, and the like.

The term "spiro heterobicyclylalkynyl" refers to an alkynyl groups substituted with one or more spiro heterobicyclyl groups, wherein the alkynyl group and spiro heterobicyclyl group are as defined herein. Some non-limiting examples of the spiro heterobicyclylalkynyl group include (4-azaspiro [2.4]hept-5-yl)ethynyl, (2-oxaspiro[3.3]hept-6-yl)ethynyl, and the like.

The term "heteroatom" refers to one or more of oxygen, sulfur, nitrogen, phosphorus or silicon, including any oxidized form of nitrogen, sulfur or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "unsaturated" refers to a moiety having one or more units of unsaturation.

The term "aryl" used alone or as part of a larger moiety as in "arylalkyl", "arylalkoxy" or "aryloxyalkyl" refers to monocyclic, bicyclic or tricyclic carbocyclic ring systems having a total of 6 to 14 ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of the aryl group include phenyl, naphthyl and anthracene. The aryl group defined herein may be substituted or unsubstituted, wherein the substituents include, but are not limited to, deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl, hydroxy-substituted $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl or $C_{5-12}$ fused heterobicyclyl, and the like, and wherein optionally each of $C_{1-3}$ alkyl, $C_{2-3}$ alkenyl, $C_{2-3}$ alkynyl, $C_{1-3}$ alkoxy, $C_{1-3}$ alkylamino, $C_{1-3}$ alkylthio, $C_{6-10}$ aryl, $C_{6-10}$ aryloxy, $C_{6-10}$ aryl-$C_{1-3}$-alkyl, $C_{6-10}$ aryl-$C_{1-3}$-alkoxy, $C_{6-10}$ arylamino, $C_{1-9}$ heteroaryl, $C_{1-9}$ heteroaryl-$C_{1-3}$-alkyl, $C_{1-9}$ heteroaryloxy, $C_{3-8}$ cycloalkyl, $C_{3-8}$ cycloalkyloxy, $C_{2-10}$ heterocyclyl and $C_{5-12}$ fused heterobicyclyl is independently substituted with one or more substituents independently selected from deuterium, fluoro, chloro, bromo, iodo, hydroxy, mercapto, nitro, amino, cyano, carboxy, oxo (=O), $C_{1-3}$ alkyl, deuterated $C_{1-3}$ alkyl, $C_{1-3}$ haloalkyl and hydroxy-substituted $C_{1-3}$ alkyl.

The term "arylalkyl" refers to an alkyl group substituted with one or more aryl groups, wherein the alkyl group and aryl group are as defined herein. Some non-limiting examples of the arylalkyl group include phenylmethyl, phenylethyl, p-tolylethyl, styryl, and the like.

The term "aryloxy" refers to an optionally substituted aryl group, as defined herein, attached to an oxygen atom, wherein the oxygen atom serves as the attaching point to the rest of the molecule. Some non-limiting examples of the aryloxy group include phenyloxy, p-methylphenyloxy, p-ethylphenyloxy, and the like.

The term "arylamino" refers to an amino group substituted with one or two aryl groups, wherein the aryl group is as defined herein. Some non-limiting examples of the arylamino group include phenylamino, diphenylamino, ditolylamino, and the like.

The term "arylalkoxy" refers to an alkoxy group substituted with one or more aryl groups, wherein the aryl group and alkyloxy group are as defined herein. Some non-limiting examples of the arylalkoxy group include phenylmethoxy, p-tolylethoxy, p-ethylphenylmethoxy, and the like.

The term "heteroaryl" used alone or as part of a larger moiety as in "heteroarylalkyl" or "heteroarylalkoxy" refers to monocyclic, bicyclic or tricyclic ring systems having a total of 5 to 14 ring members, wherein at least one ring in the system is aromatic, and at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". And the heteroaryl group defined herein may be substituted or unsubstituted, wherein the substituents include, but are not limited to, hydroxy, amino, halogen, cyano, aryl, heteroaryl, alkoxy, alkyl, alkenyl, alkynyl, heterocyclyl, mercapto, nitro, aryloxy, and the like.

Some non-limiting examples of the heteroaryl group include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the like; and the following bicycles: benzimidazolyl, benzofuryl, benzothiophenyl, indolyl (e.g., 2-indolyl), purinyl, quinolinyl (e.g., 2-quinolinyl, 3-quinolinyl and 4-quinolinyl), or isoquinolinyl (e.g., 1-isoquinolinyl, 3-isoquinolinyl and 4-isoquinolinyl), and the like.

The term "heteroarylalkyl" refers to an alkyl group substituted with one or more heteroaryl groups, wherein the alkyl group and heteroaryl group are as defined herein. Some non-limiting examples of the heteroarylalkyl group include (pyrid-2-yl)ethyl, (thiazol-2-yl)methyl, (imidazol-2-yl)ethyl, (pyrimidin-2-yl)propyl, and the like.

The term "heteroaryloxy" refers to an optionally substituted heteroaryl group, as defined herein, attached to an oxygen atom, wherein the oxygen atom serves as the attaching point to the rest of the molecule. Some non-limiting examples of the heteroaryloxy group include (pyrid-2-yl)oxy, (thiazol-2-yl)oxy, (imidazol-2-yl)oxy, (pyrimidin-2-yl)oxy, and the like.

The term "heteroarylalkoxy" refers to an alkoxy group substituted with one or more heteroaryl groups, wherein the heteroaryl group and alkoxy group are as defined herein, in which the oxygen atom serves as the attaching point to the rest of the molecule. Some non-limiting examples of the heteroarylalkoxy group include pyridylmethoxy, thiazolethoxy, and the like.

As described herein, a bond drawn from a substituent to the center of one ring within a ring system (as shown in FIGURE a) represents substitution of one or more $R^7$ at any substitutable position on ring A or ring B. For example, FIGURE a represents possible substitution of one or more $R^7$ in any of the position on ring A or ring B.

A connecting bond drawn from the center of one ring within a ring system (as shown in FIGURE a) represents connection of the connecting bond attached to the rest of the molecule at any substitutable position on ring B. For example, FIGURE a represents possible connection attached to the rest of the molecule in any of the position on ring B.

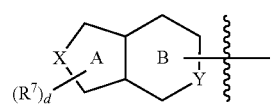

a

Unless otherwise stated, structures depicted herein are also meant to include all isomeric (e.g., enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope of the invention.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates such as those phosphates resulting from the phosphonation of an OH group on the parent compound. A thorough discussion of prodrugs is provided in Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al., Prodrugs of Phosphates and Phosphonates, *J Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66: 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form the solvate include water, isopropanol, ethanol, methanol, DMSO, ethyl acetate, acetic acid and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of the carboxy-protecting group include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., Protective Groups in Organic Synthesis, John Wiley & Sons, New York, 1991 and Kocienski et al., Protecting Groups, Thieme, Stuttgart, 2005.

DESCRIPTION OF COMPOUNDS OF THE INVENTION

Provided herein are quinazoline compounds and pharmaceutical compositions thereof, which are potentially useful in the treatment of diseases, conditions and/or disorders modulated by tyrosine kinase receptors, especially EGFR and HER-2. In one aspect, provided herein are compounds having Formula (I) as shown below:

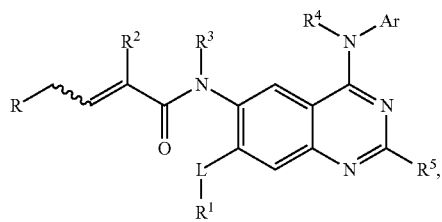

or a stereoisomer, a geometric isomer, a tautomer, an N-oxide, a hydrate, a solvate, a metabolite, a pharmaceutically acceptable salt or a prodrug thereof, wherein R is

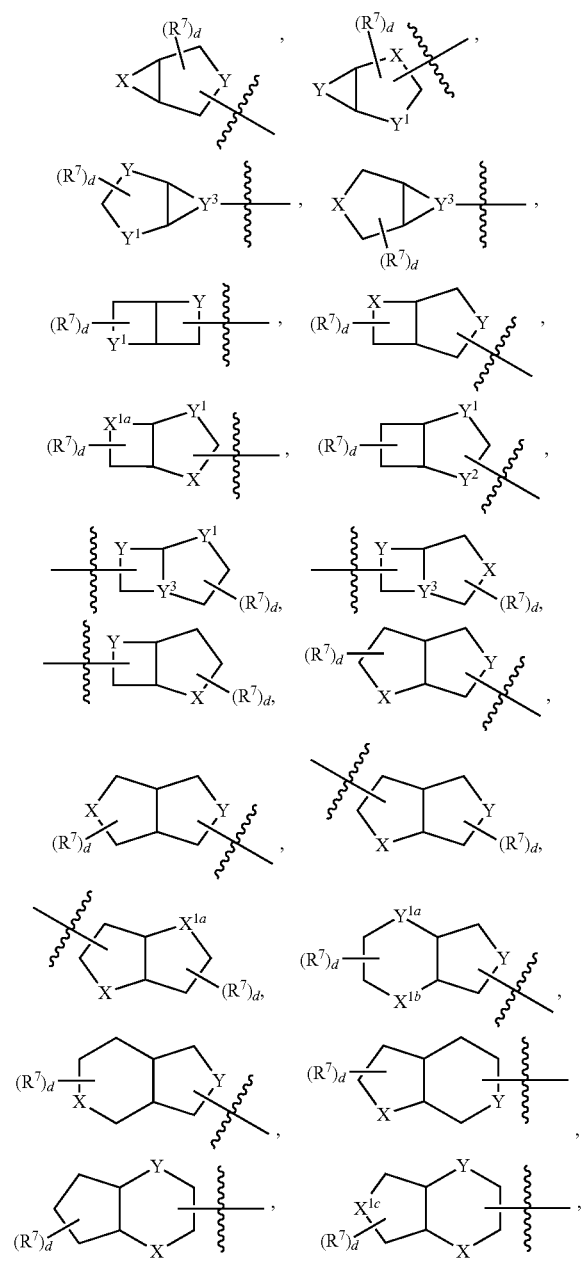

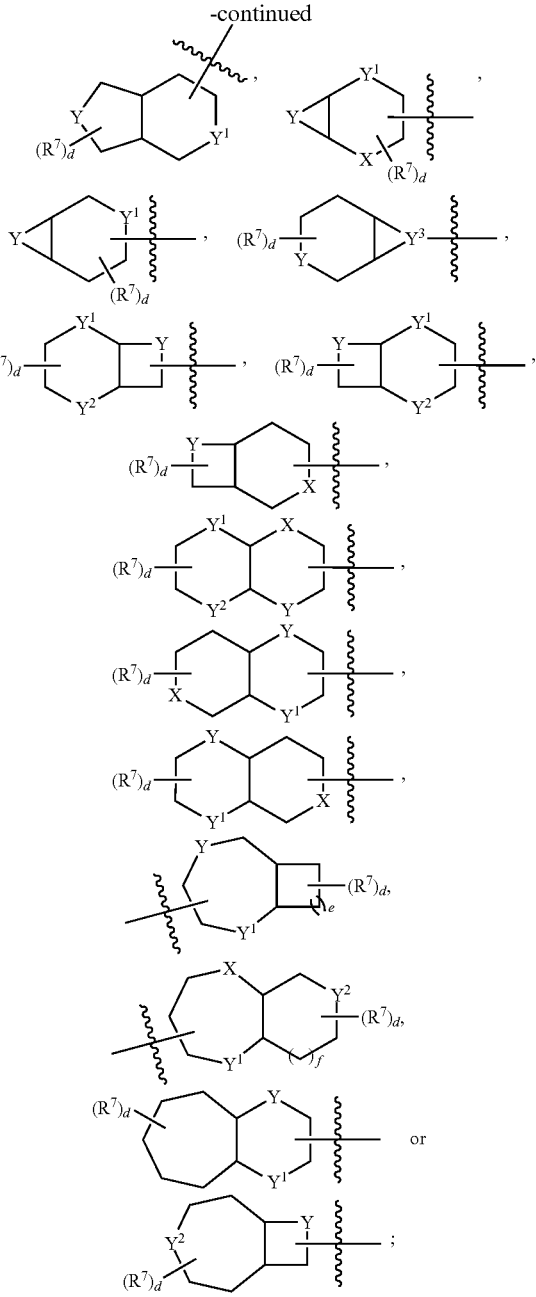

wherein each X and $X^{1a}$ is independently O, S, S(=O), S(=O)$_2$ or NR$^a$;

$X^{1b}$ is O, S, S(=O), S(=O)$_2$ or NR$^{a1}$;

$X^{1c}$ is S, S(=O) or S(=O)$_2$;

each Y, $Y^1$, and $Y^2$ is independently O, S, S(=O), S(=O)$_2$, NR$^a$ or CR$^b$R$^{b'}$;

$Y^{1a}$ is O, S, S(=O), S(=O)$_2$, NR$^{a1}$ or CR$^b$R$^b$;

each $Y^3$ is independently CR$^{b''}$ or N;

wherein each R$^a$ is independently H, D or C$_{1-3}$ alkyl;

each R$^{a1}$ is independently D, ethyl, n-propyl or isopropyl;

each R$^b$, R$^{b'}$ and R$^{b''}$ is independently H, D, F, Cl, Br, I, —OH, —NO$_2$, —NH$_2$, —CN, C$_{1-3}$ alkyl, C$_{1-3}$ alkoxy or C$_{1-3}$ alkylamino;

each R$^7$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl, C$_{6-10}$ aryl, C$_{6-10}$ aryl-C$_{1-6}$-alkyl, C$_{6-10}$ aryloxy, C$_{6-10}$ aryl-C$_{1-6}$-alkoxy or C$_{1-9}$ heteroaryl;

each d is independently 0, 1, 2, 3, 4 or 5;
e is 0, 1, 2, or 3;
f is 0 or 1;
L is a bond, O, NR$^a$, S, S(=O), S(=O)$_2$ or C(=O);
R$^1$ is H, D, F, Cl, Br, I, —OH, —NO$_2$, —NH$_2$, —CN, C$_{1-6}$ alkyl, C$_{1-6}$ haloalkyl, C$_{1-6}$ alkoxy-C$_{1-6}$-alkyl, C$_{2-6}$ alkenyl, C$_{2-6}$ alkynyl, C$_{1-6}$ alkylamino-C$_{1-6}$-alkyl, C$_{3-8}$ cycloalkyl, C$_{3-8}$ cycloalkyl-C$_{1-6}$-alkyl, C$_{3-8}$ cycloalkyl-C$_{2-6}$-alkenyl, C$_{3-8}$ cycloalkyl-C$_{2-6}$-alkynyl, C$_{3-8}$ cycloalkyloxy-C$_{2-6}$-alkynyl, C$_{2-10}$ heterocyclyl, C$_{2-10}$ heterocyclyl-C$_{1-6}$-alkyl, C$_{2-10}$ heterocyclyl-C$_{2-6}$-alkenyl, C$_{2-10}$ heterocyclyl-C$_{2-6}$-alkynyl, C$_{5-12}$ fused bicyclyl, C$_{5-12}$ fused bicyclyl-C$_{1-6}$-alkyl, C$_{5-12}$ fused bicyclyl-C$_{2-6}$-alkenyl, C$_{5-12}$ fused bicyclyl-C$_{2-6}$-alkynyl, C$_{5-12}$ fused heterobicyclyl, C$_{5-12}$ fused heterobicyclyl-C$_{1-6}$-alkyl, C$_{5-12}$ fused heterobicyclyl-C$_{2-6}$-alkenyl, C$_{5-12}$ fused heterobicyclyl-C$_{2-6}$-alkynyl, C$_{5-12}$ spiro bicyclyl, C$_{5-12}$ spiro bicyclyl-C$_{1-6}$-alkyl, C$_{5-12}$ spiro bicyclyl-C$_{2-6}$-alkenyl, C$_{5-12}$ spiro bicyclyl-C$_{2-6}$-alkynyl, C$_{5-12}$ spiro heterobicyclyl, C$_{5-12}$ spiro heterobicyclyl-C$_{1-6}$-alkyl, C$_{5-12}$ spiro heterobicyclyl-C$_{2-6}$-alkenyl, C$_{5-12}$ spiro heterobicyclyl-C$_{2-6}$-alkynyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl;
R$^2$ is H, F, Cl, Br, I, —NH$_2$, —NO$_2$, —CN or C$_{1-6}$ alkyl;
each of R$^3$ and R$^4$ is independently H, D or C$_{1-4}$ alkyl;
R$^5$ is H, D, F, Cl, Br, I, C$_{1-6}$ alkyl, C$_{1-6}$ alkoxy, C$_{1-6}$ alkylamino or C$_{3-8}$ cycloalkyl;
Ar is

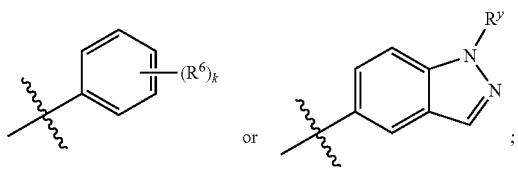

or wherein each R$^6$ is independently H, D, F, Cl, Br, I, —OH, —NO$_2$, —NH$_2$, —CN, C$_{1-6}$ alkyl, C$_{2-6}$ alkenyl, C$_{2-6}$ alkynyl, C$_{1-6}$ alkoxy, C$_{6-10}$ aryloxy, C$_{1-9}$ heteroaryloxy, C$_{6-10}$ aryl-C$_{1-6}$-alkyl, C$_{6-10}$ aryl-C$_{1-6}$-alkoxy, C$_{1-9}$ heteroaryl-C$_{1-6}$-alkyl, C$_{1-9}$ heteroaryl-C$_{1-6}$-alkoxy, C$_{1-6}$ alkylthio, C$_{1-6}$ alkylamino, C$_{6-10}$ arylamino, C$_{1-6}$ alkylcarbonyl, C$_{1-6}$ alkylacylamino, C$_{1-6}$ alkylsulfonyl or C$_{1-6}$ alkylsulfinyl;

k is 0, 1, 2, 3, 4 or 5; and
R$^y$ is H, C$_{1-6}$ alkyl, C$_{2-6}$ alkenyl, C$_{2-6}$ alkynyl, C$_{3-8}$ cycloalkyl, C$_{3-8}$ cycloalkyl-C$_{1-6}$-alkyl, C$_{6-10}$ aryl-C$_{1-6}$-alkyl or C$_{1-9}$ heteroaryl-C$_{1-6}$-alkyl, wherein optionally each of alkyl, alkoxy, alkoxyalkyl, alkylamino, alkylaminoalkyl, heteroalkyl, alkenyl, alkynyl, cycloalkyl, cycloalkylalkyl, cycloalkylalkenyl, cycloalkylalkynyl, cycloalkyloxyalkynyl, heterocyclyl, heterocyclylalkyl, heterocyclylalkenyl, heterocyclylalkynyl, fused bicyclyl, fused bicyclylalkyl, fused bicyclylalkenyl, fused bicyclylalkynyl, fused heterobicyclyl, fused heterobicyclylalkyl, fused heterobicyclylalkenyl, fused heterobicyclylalkynyl, spiro bicyclyl, spiro bicyclylalkyl, spiro bicyclylalkenyl, spiro bicyclylalkynyl, spiro heterobicyclyl, spiro heterobicyclylalkyl, spiro heterobicyclylalkenyl, spiro heterobicyclylalkynyl, aryl, aryloxy, arylalkyl, arylalkoxy, arylamino, heteroaryl, heteroarylalkyl, heteroarylalkoxy, heteroaryloxy, alkylthio, alkylcarbonyl, alkylacylamino, alkylsulfonyl, haloalkyl and alkylsulfinyl is independently substituted with one or more substituents independently selected from D, F, Cl, Br, I, —OH, —NO$_2$, —NH$_2$, —CN, —COOH, C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl, and wherein optionally each of C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl and hydroxy-substituted C$_{1-3}$ alkyl.

In some embodiments, R is

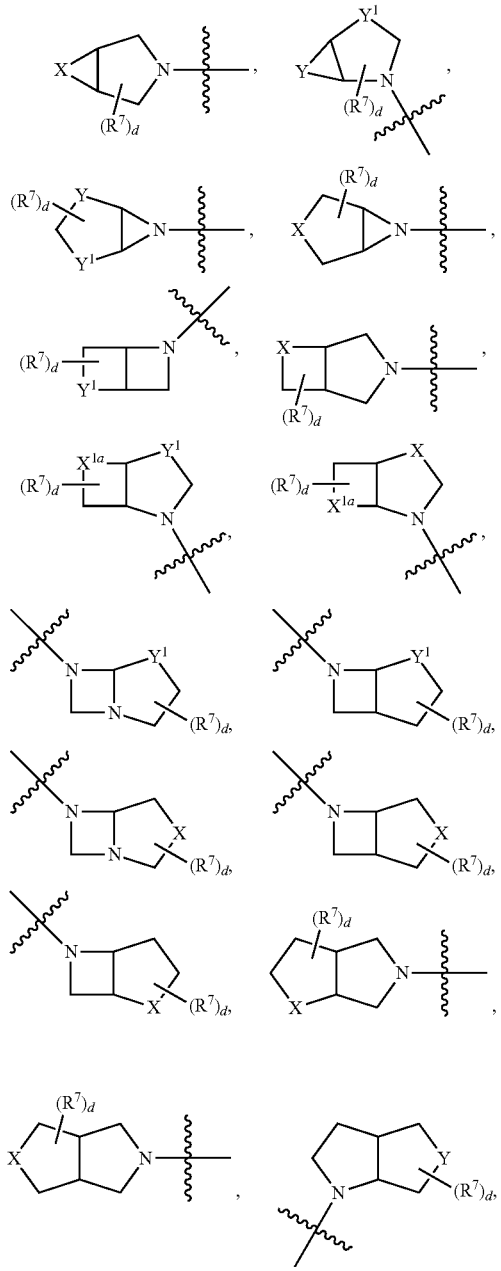

-continued
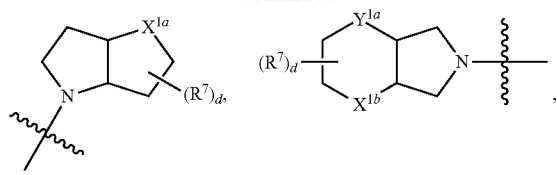
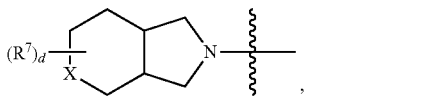
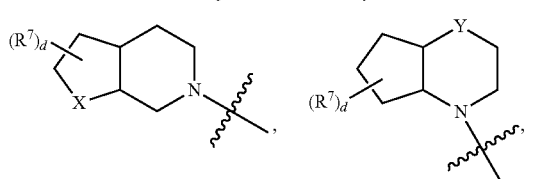
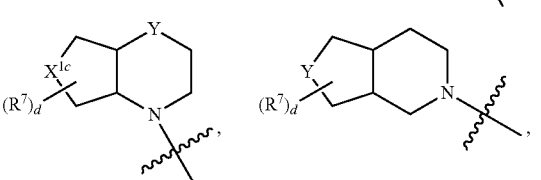
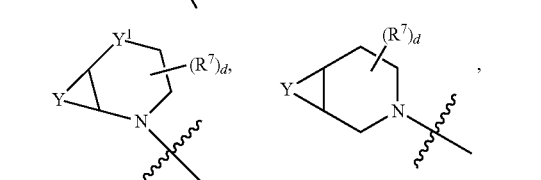
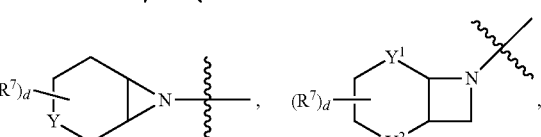
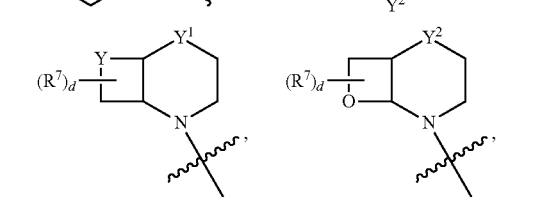
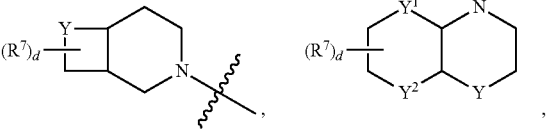
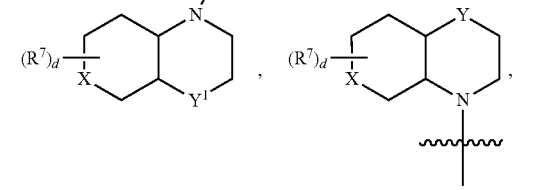
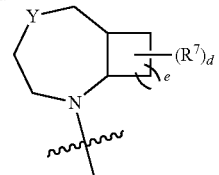
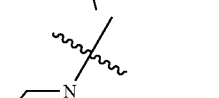
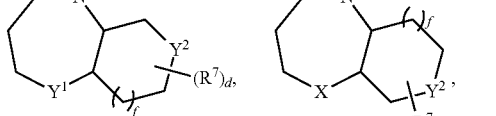
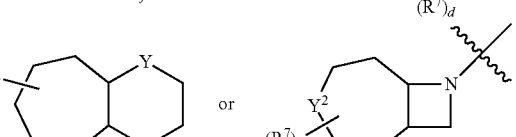
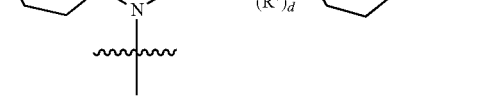
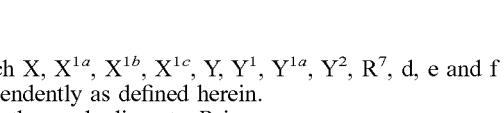
and
each X, $X^{1a}$, $X^{1b}$, $X^{1c}$, Y, $Y^1$, $Y^{1a}$, $Y^2$, $R^7$, d, e and f is independently as defined herein.
In other embodiments, R is
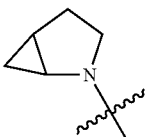
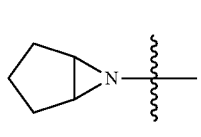
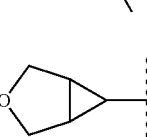
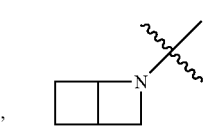
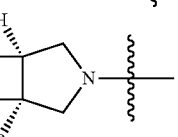
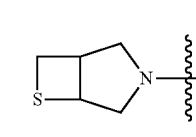
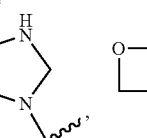
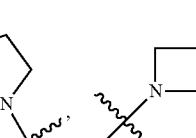
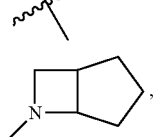
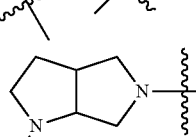
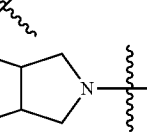
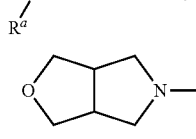
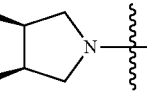
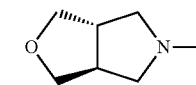

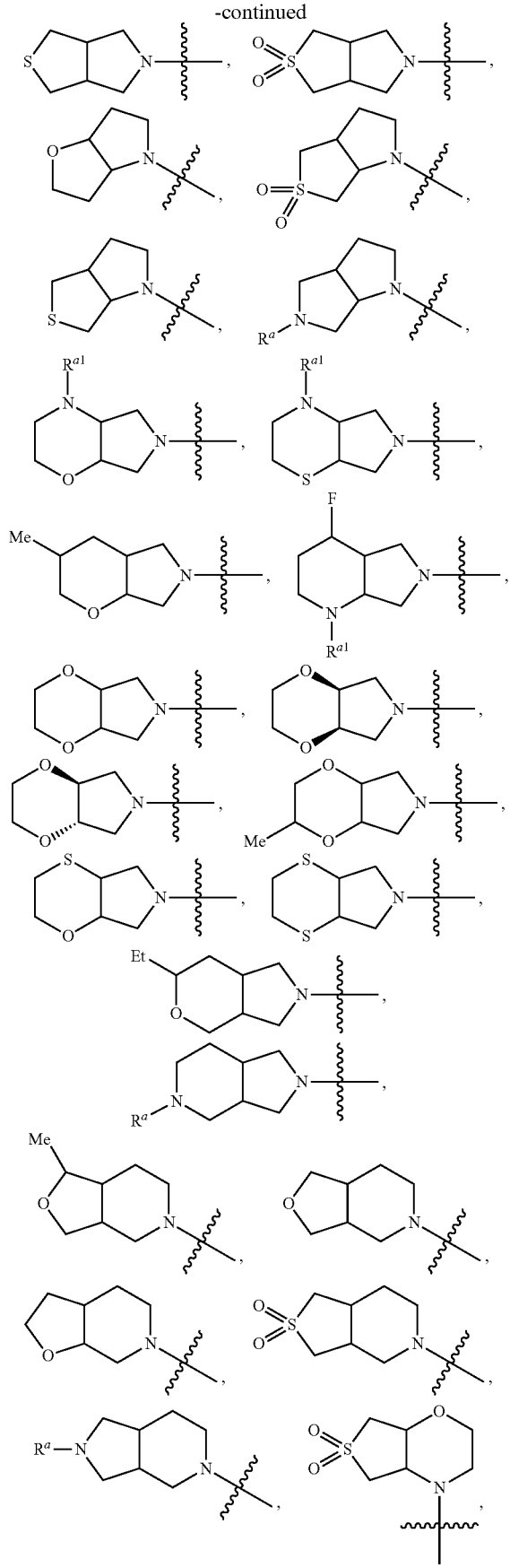
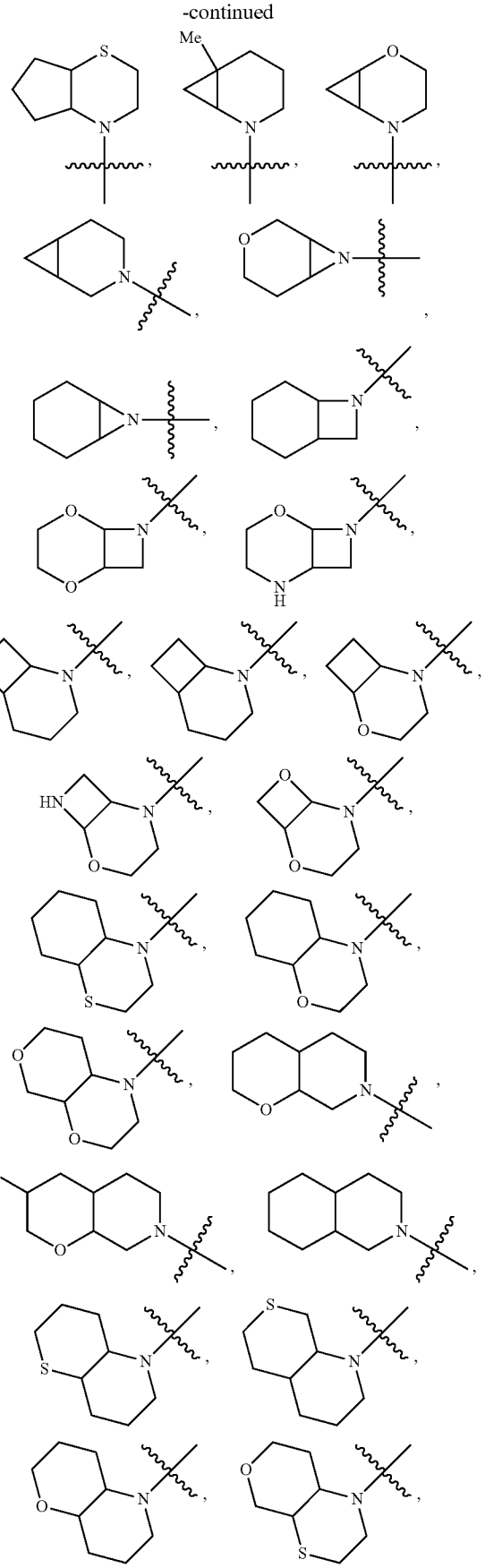

-continued

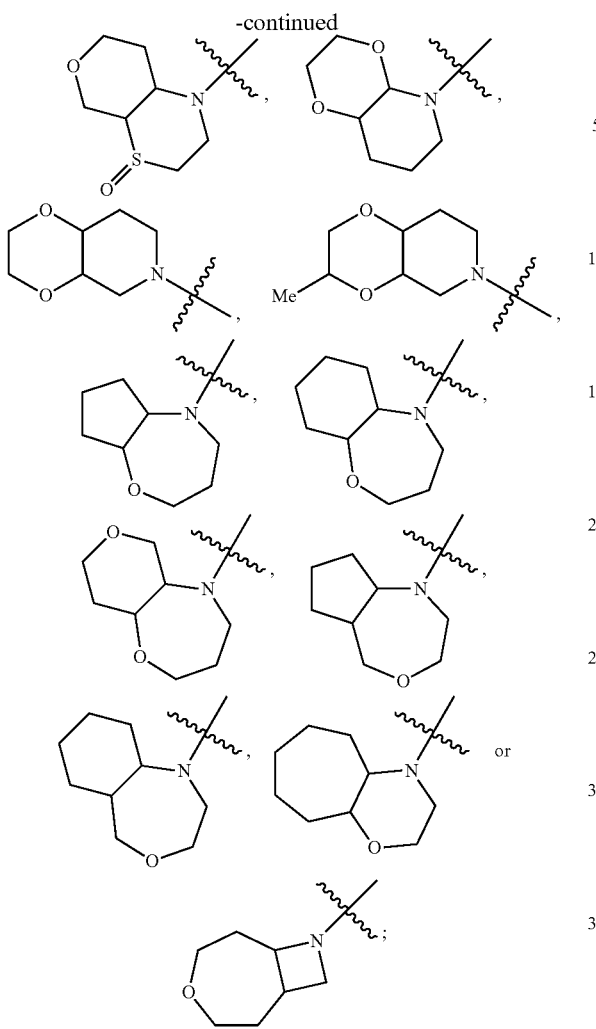

and each $R^a$ and $R^{a1}$ is independently as defined herein.

In some embodiments, $R^1$ is H, D, F, Cl, Br, I, —OH, —NO$_2$, —NH$_2$, —CN, C$_{1-6}$ alkyl, C$_{2-6}$ alkynyl or C$_{1-6}$ alkoxy-C$_{1-6}$-alkyl, wherein optionally each of C$_{1-6}$ alkyl, C$_{2-6}$ alkynyl and C$_{1-6}$ alkoxy-C$_{1-6}$-alkyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl, C$_{1-3}$ alkylamino, deuterated C$_{1-3}$ alkylamino, C$_{1-3}$ alkoxy, deuterated C$_{1-3}$ alkoxy, C$_{6-10}$ aryl, C$_{1-9}$ heteroaryl, C$_{3-8}$ cycloalkyl, C$_{3-8}$ cycloalkyloxy and C$_{2-10}$ heterocyclyl, or $R^1$ is

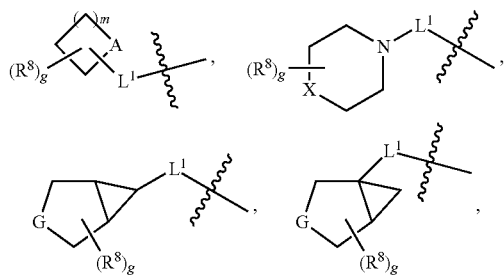

-continued

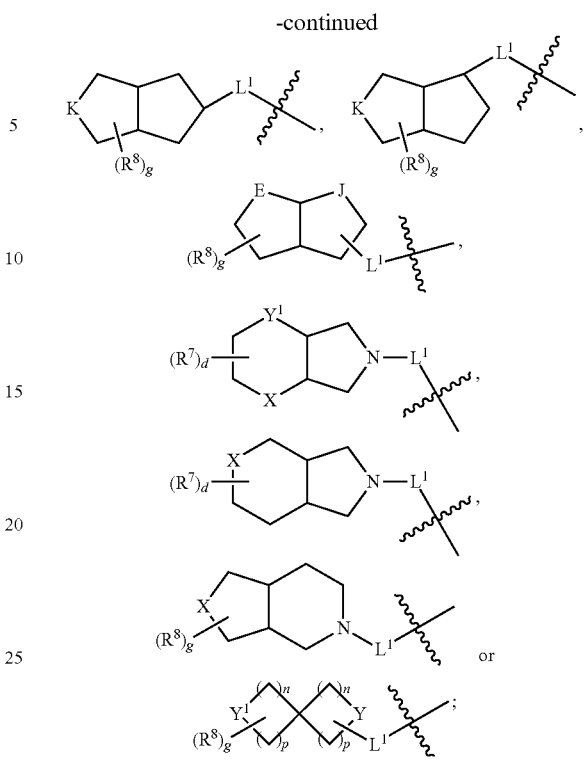

wherein each A, G, E and J is independently CR$^b$R$^{b'}$, NR$^a$, O, S, S(=O) or S(=O)$_2$;

each K is independently NR$^a$, O, S, S(=O) or S(=O)$_2$;

each L$^1$ is independently a bond, C$_{1-4}$ alkylene, C$_{2-4}$ alkenylene or C$_{2-4}$ alkynylene, wherein optionally each of C$_{1-4}$ alkylene, C$_{2-4}$ alkenylene and C$_{2-4}$ alkynylene is independently substituted with one or more substituents independently selected from D, F, Cl, Br, I, —OH, —NO$_2$, —NH$_2$, —CN, —COOH and C$_{1-3}$ alkyl;

each R$^8$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl or C$_{5-12}$ fused heterobicyclyl, wherein optionally each of C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl and C$_{5-12}$ fused heterobicyclyl is independently substituted with one or more substituents independently selected from D, F, Cl, Br, I, —OH, —SH, —NO$_2$, —NH$_2$, —CN, —COOH, C$_{1-3}$ alkyl and C$_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2; and each X, Y, Y$^1$, R$^a$, R$^b$, R$^{b'}$, R$^7$ and d is independently as defined herein.

In other embodiments, $R^1$ is H, D, F, Cl, Br, I, —OH, —NO$_2$, —NH$_2$, —CN, C$_{1-3}$ alkyl, C$_{2-3}$ alkynyl or C$_{1-3}$ alkoxy-C$_{1-3}$-alkyl, wherein optionally each of C$_{1-3}$ alkyl, C$_{2-3}$ alkynyl and C$_{1-3}$ alkoxy-C$_{1-3}$-alkyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl, C$_{1-3}$ alkylamino, deuterated C$_{1-3}$ alkylamino, C$_{1-3}$ alkoxy, deuterated C$_{1-3}$ alkoxy and C$_{3-8}$ cycloalkyloxy, or $R^1$ is

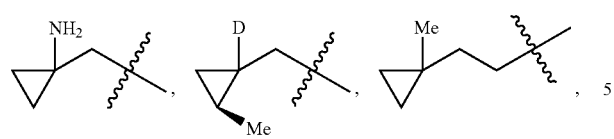
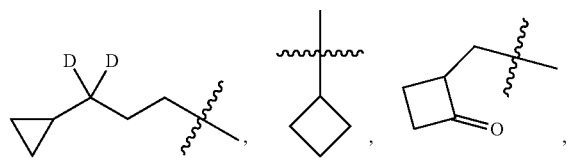
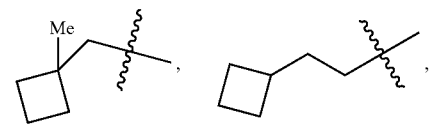
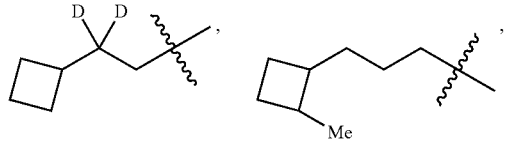
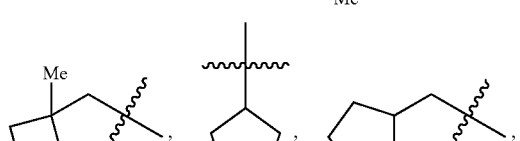
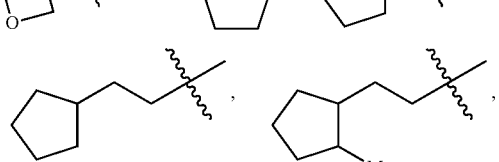
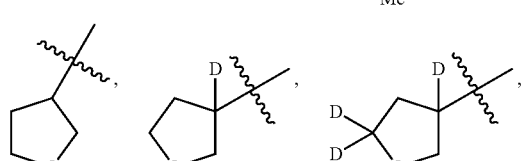

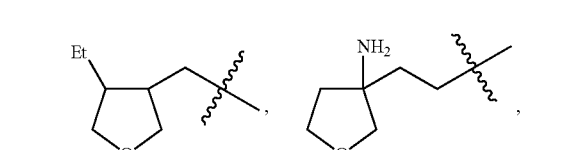
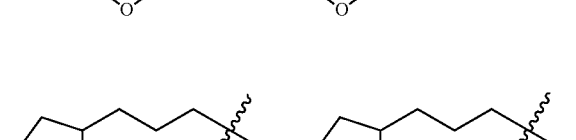
-continued
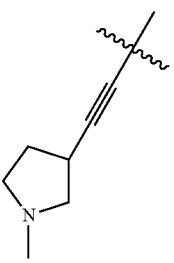
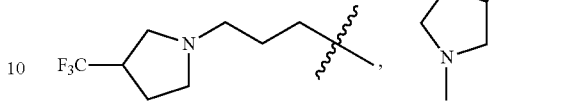
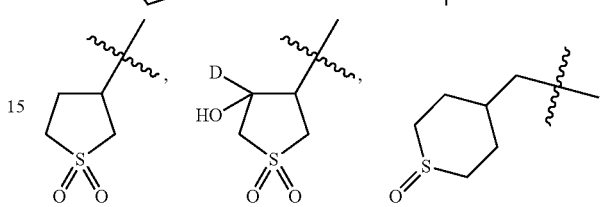
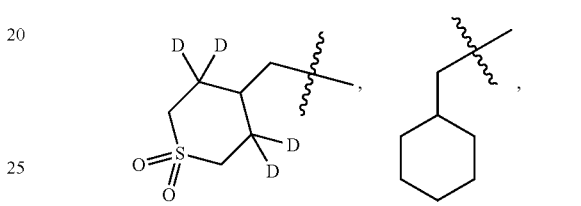
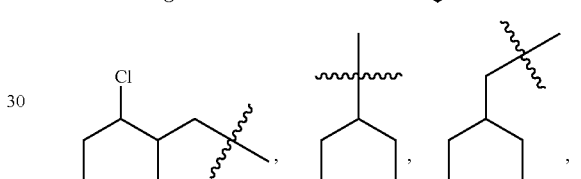
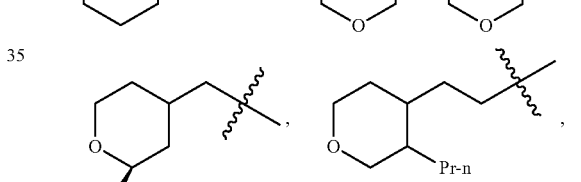
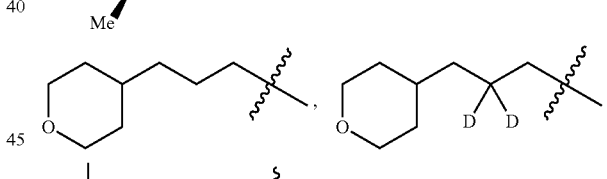
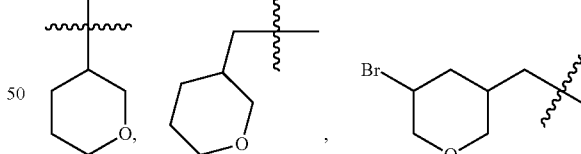
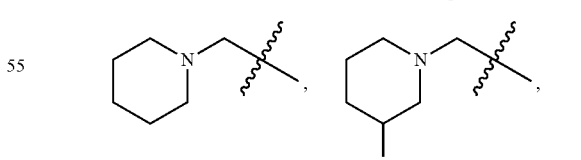
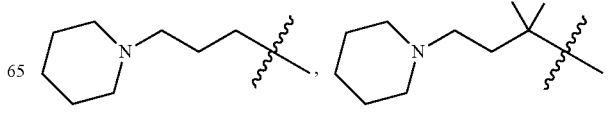

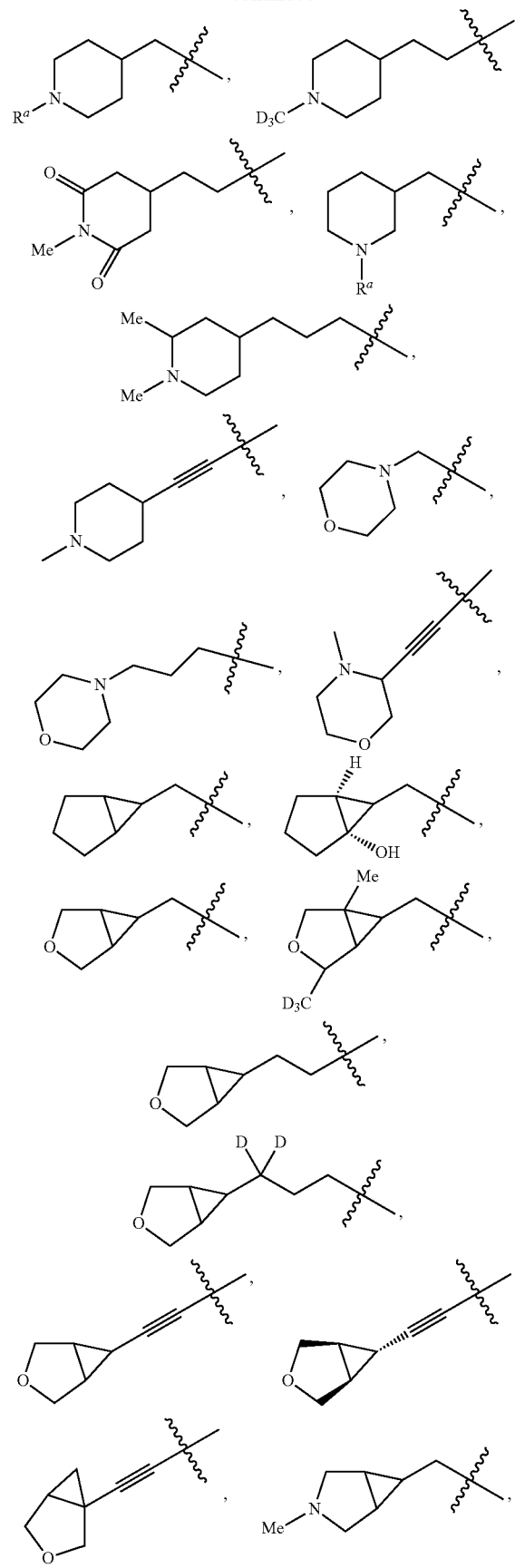
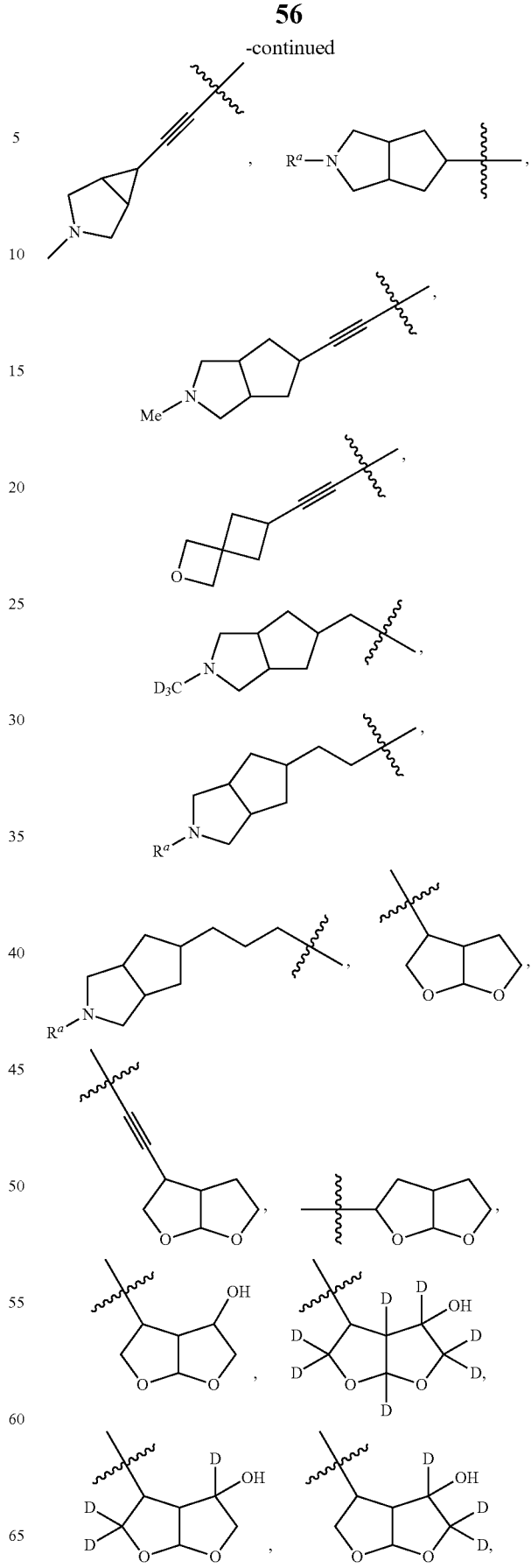

-continued

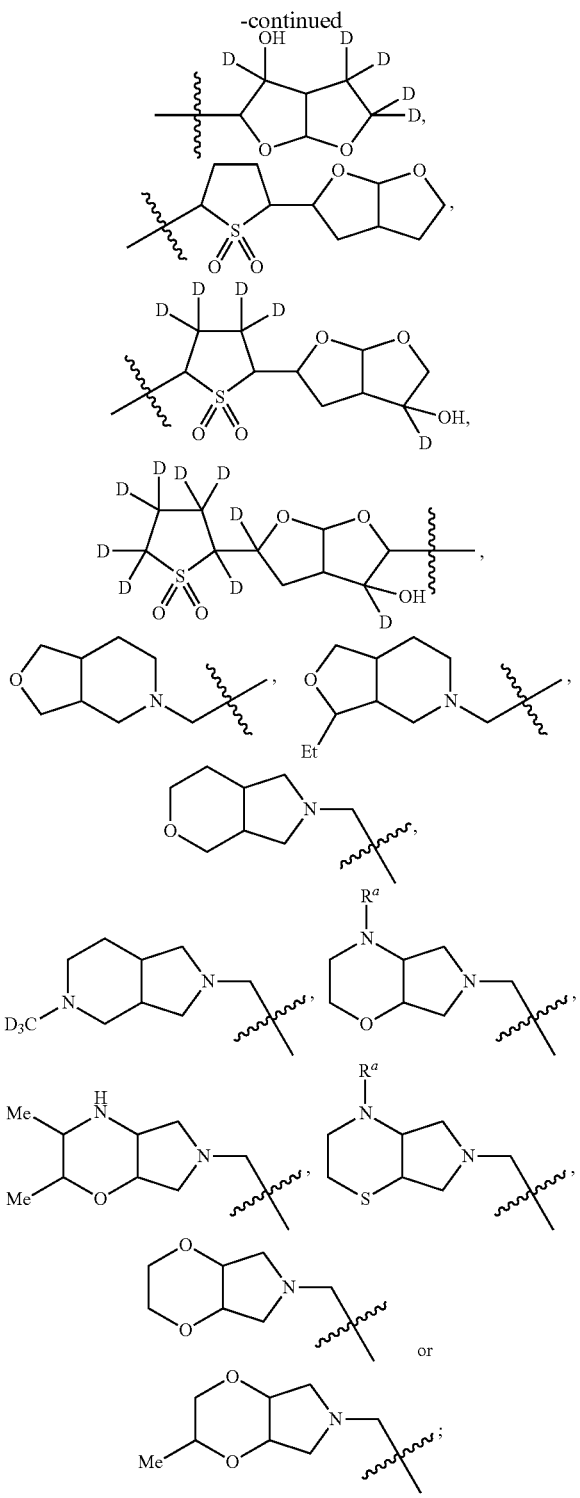

wherein each $R^a$ is independently H, D or $C_{1-3}$ alkyl.

In some embodiments, each $R^6$ is independently H, D, F, Cl, Br, I, —OH, —NO$_2$, —NH$_2$, —CN, $C_{1-3}$ alkyl, $C_{2-4}$ alkynyl, $C_{1-3}$ alkoxy, $C_{6-10}$ aryloxy, $C_{6-10}$ aryl-$C_{1-3}$-alkyl, $C_{6-10}$ aryl-$C_{1-3}$-alkoxy, $C_{2-5}$ heteroaryloxy, $C_{2-5}$ heteroaryl-$C_{1-3}$-alkyl or $C_{2-5}$ heteroaryl-$C_{1-3}$-alkoxy; and $R^y$ is H, $C_{1-3}$ alkyl, $C_{6-10}$ aryl-$C_{1-3}$-alkyl or $C_{2-5}$ heteroaryl-$C_{1-3}$-alkyl, wherein optionally each of $C_{1-3}$ alkyl, $C_{2-4}$ alkynyl, $C_{1-3}$ alkoxy, $C_{6-10}$ aryloxy, $C_{6-10}$ aryl-$C_{1-3}$-alkyl, $C_{6-10}$ aryl-$C_{1-3}$-alkoxy, $C_{2-5}$ heteroaryloxy, $C_{2-5}$ heteroaryl-$C_{1-3}$-alkyl and $C_{2-5}$ heteroaryl-$C_{1-3}$-alkoxy is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy and $C_{3-8}$ cycloalkyloxy.

In some embodiments, provided herein are compounds having Formula (Ia) as shown below:

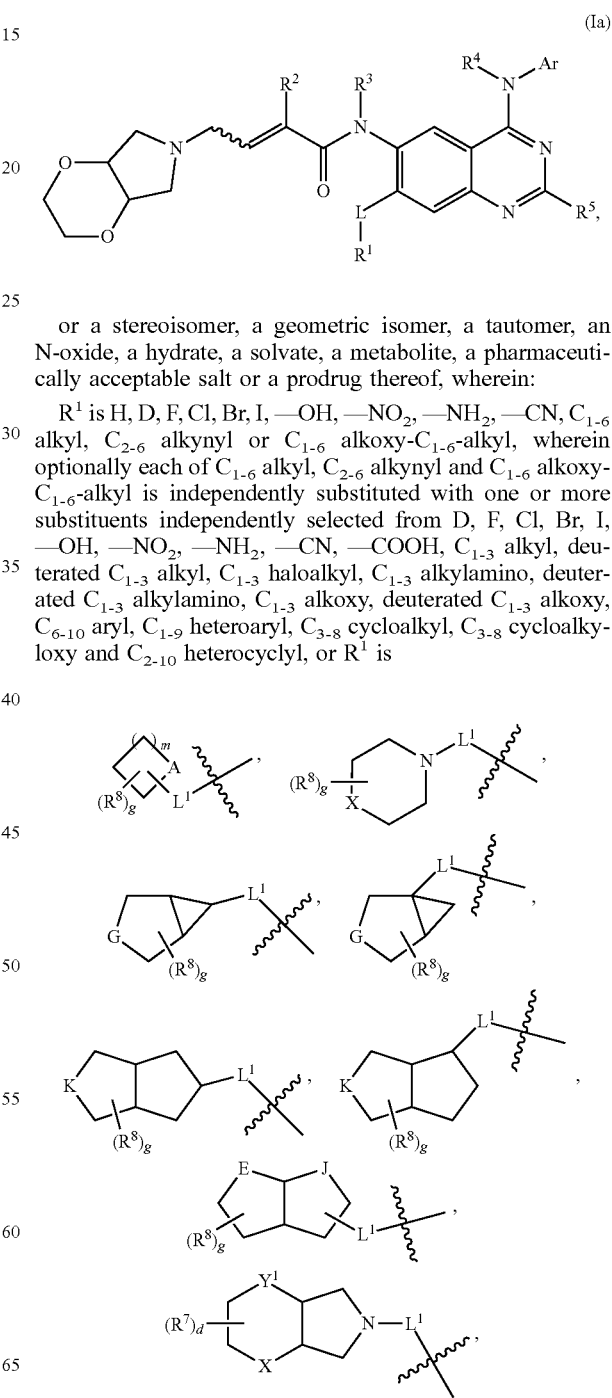

(Ia)

or a stereoisomer, a geometric isomer, a tautomer, an N-oxide, a hydrate, a solvate, a metabolite, a pharmaceutically acceptable salt or a prodrug thereof, wherein:

$R^1$ is H, D, F, Cl, Br, I, —OH, —NO$_2$, —NH$_2$, —CN, $C_{1-6}$ alkyl, $C_{2-6}$ alkynyl or $C_{1-6}$ alkoxy-$C_{1-6}$-alkyl, wherein optionally each of $C_{1-6}$ alkyl, $C_{2-6}$ alkynyl and $C_{1-6}$ alkoxy-$C_{1-6}$-alkyl is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy, $C_{6-10}$ aryl, $C_{1-9}$ heteroaryl, $C_{3-8}$ cycloalkyl, $C_{3-8}$ cycloalkyloxy and $C_{2-10}$ heterocyclyl, or $R^1$ is

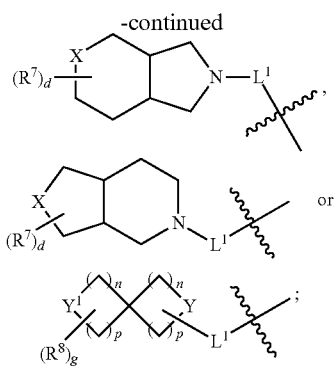

wherein each A, G, E and J is independently $CR^bR^{b'}$, $NR^a$, O, S, S(=O) or S(=O)$_2$;

each K is independently $NR^a$, O, S, S(=O) or S(=O)$_2$;

each $L^1$ is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —NO$_2$, —NH$_2$, —CN, —COOH and $C_{1-3}$ alkyl;

each $R^8$ is independently H, D, F, Cl, Br, I, —OH, —SH, —NO$_2$, —NH$_2$, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —NO$_2$, —NH$_2$, —CN, —COOH, $C_{1-3}$ alkyl and $C_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2;

Ar is

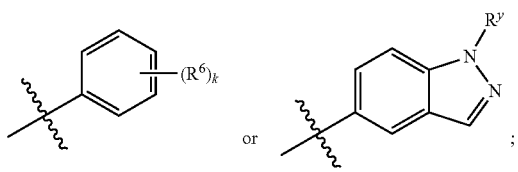

wherein each $R^6$ is independently H, D, F, Cl, Br, I, —OH, —NO$_2$, —NH$_2$, —CN, $C_{1-3}$ alkyl, $C_{2-4}$ alkynyl, $C_{1-3}$ alkoxy, $C_{6-10}$ aryloxy, $C_{6-10}$ aryl-$C_{1-3}$-alkoxy, $C_{2-5}$ heteroaryloxy or $C_{2-5}$ heteroaryl-$C_{1-3}$-alkoxy, wherein optionally each of $C_{1-3}$ alkyl, $C_{2-4}$ alkynyl, $C_{1-3}$ alkoxy, $C_{6-10}$ aryloxy, $C_{6-10}$ aryl-$C_{1-3}$-alkoxy, $C_{2-5}$ heteroaryloxy and $C_{2-5}$ heteroaryl-$C_{1-3}$-alkoxy is independently substituted with one or more substituents independently selected from D, F, Cl, Br, I, —OH, —NO$_2$, —NH$_2$, —CN, —COOH, $C_{1-3}$ alkyl, $C_{1-3}$ haloalkyl, $C_{1-3}$ alkylamino and $C_{1-3}$ alkoxy;

k is 0, 1, 2, 3, 4 or 5;

$R^y$ is H, $C_{1-3}$ alkyl or halobenzyl;

each of $R^2$, $R^3$, $R^4$, $R^5$ and L is independently as defined herein; and each X, Y, $Y^1$, $R^a$, $R^b$, $R^{b'}$, $R^7$ and d is independently as defined herein.

In other embodiments, $R^1$ is H, D, $C_{1-3}$ alkyl, $C_{2-3}$ alkynyl or $C_{1-3}$ alkoxy-$C_{1-3}$-alkyl, wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —NO$_2$, —NH$_2$, —CN, —COOH, $C_{1-3}$ alkoxy and $C_{3-8}$ cycloalkyloxy, or $R^1$ is

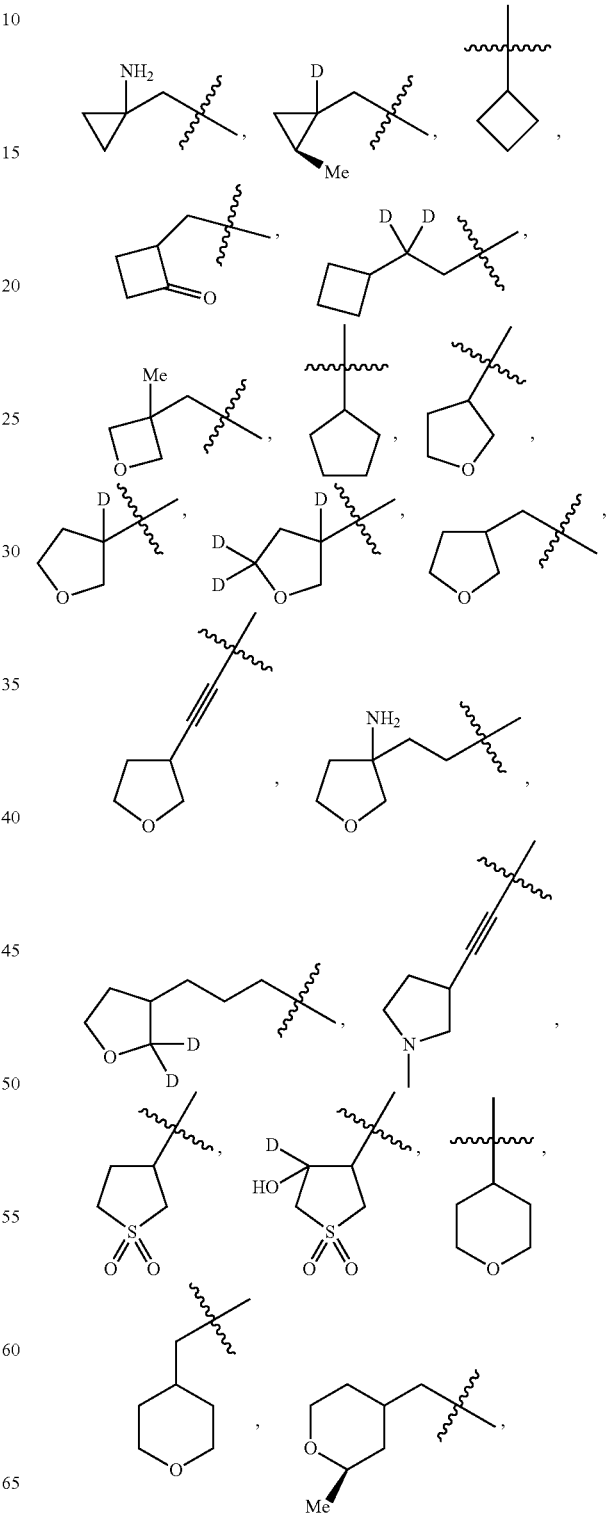

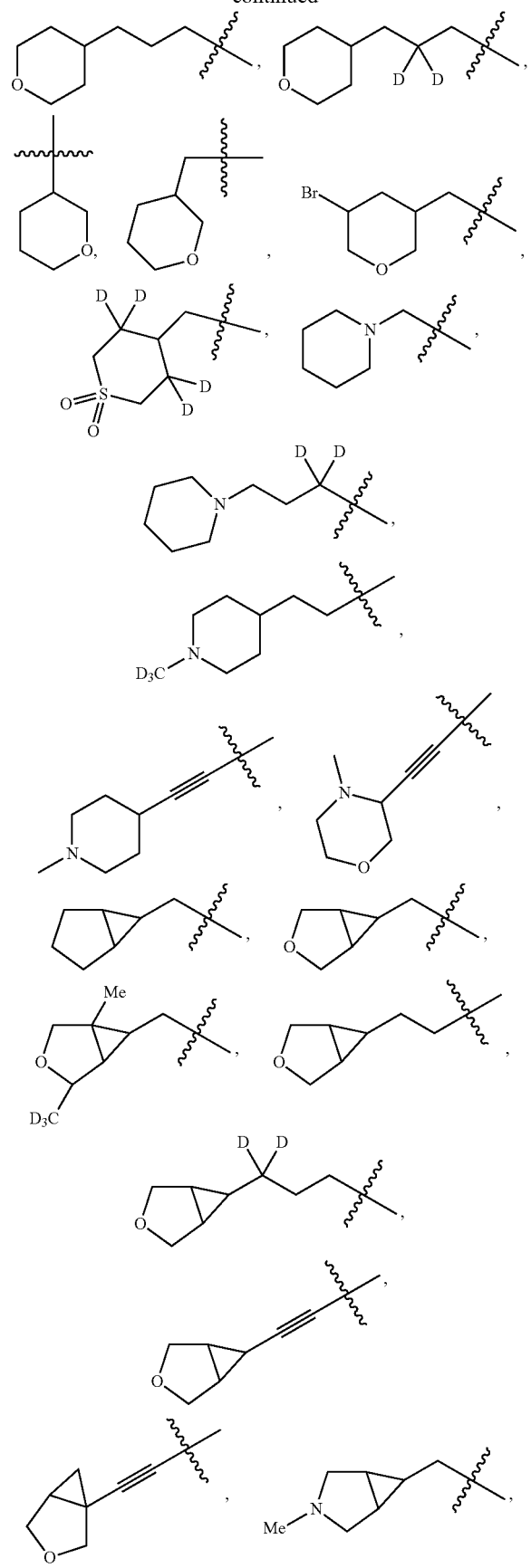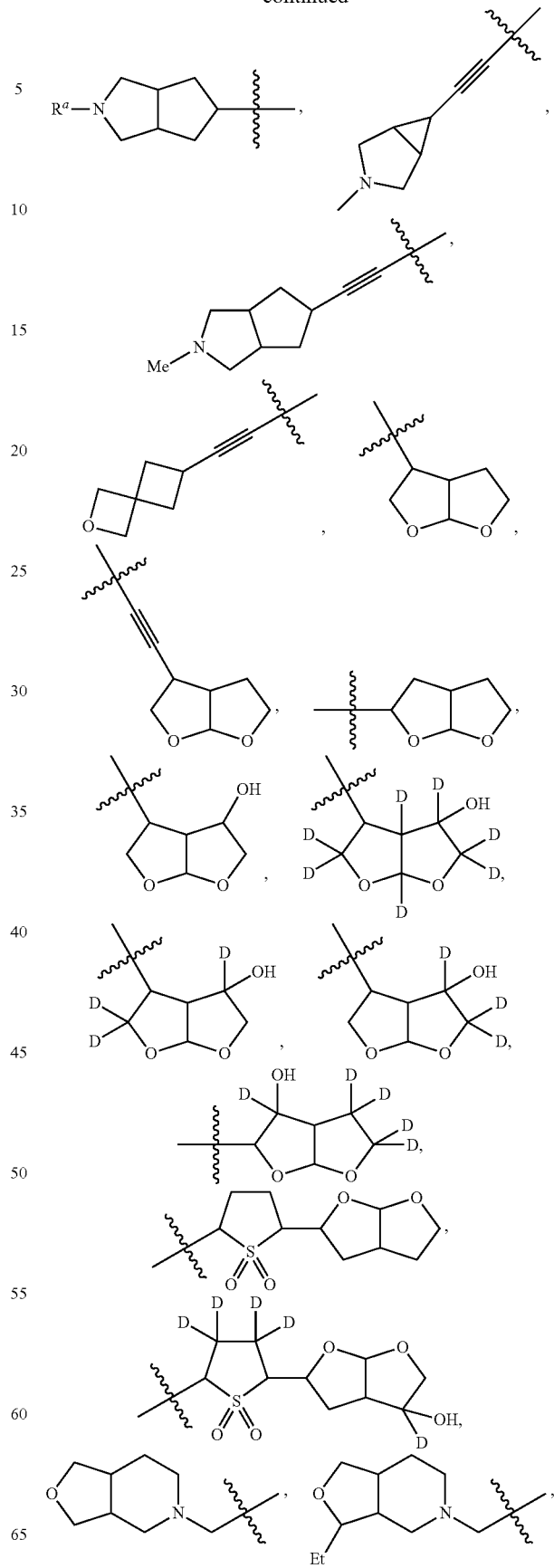

-continued

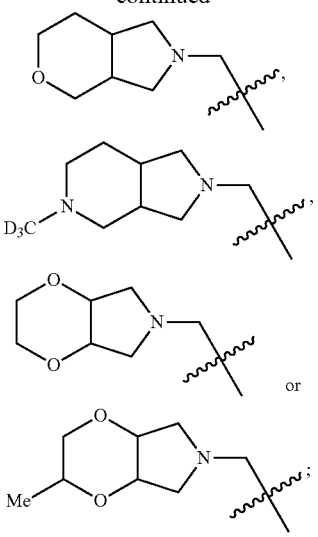

wherein $R^a$, is H, D or $C_{1-3}$ alkyl.

In some embodiments, provided herein are compounds having Formula (Ib) as shown below:

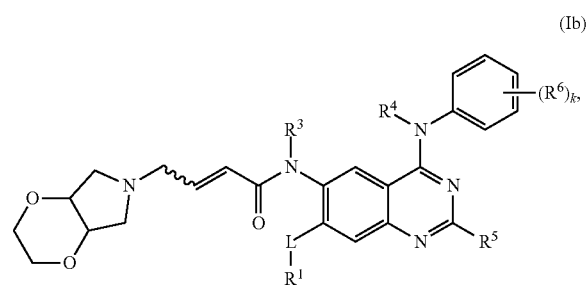

(Ib)

or a stereoisomer, a geometric isomer, a tautomer, an N-oxide, a hydrate, a solvate, a metabolite, a pharmaceutically acceptable salt or a prodrug thereof, wherein:

$R^1$ is H, D, $C_{1-3}$ alkyl, $C_{2-3}$ alkynyl or $C_{1-3}$ alkoxy-$C_{1-3}$-alkyl, wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —NO$_2$, —NH$_2$, —CN, —COOH, $C_{1-3}$ alkyl, deuterated $C_{1-3}$ alkyl, $C_{1-3}$ haloalkyl, $C_{1-3}$ alkylamino, deuterated $C_{1-3}$ alkylamino, $C_{1-3}$ alkoxy, deuterated $C_{1-3}$ alkoxy, $C_{3-8}$ cycloalkyl, $C_{3-8}$ cycloalkyloxy and $C_{2-10}$ heterocyclyl, or $R^1$ is

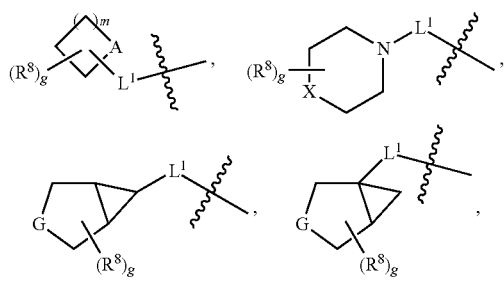

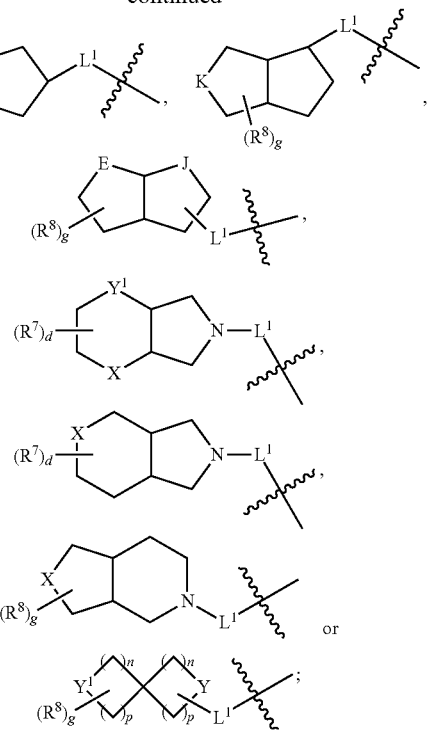

wherein each A, G, E and J is independently $CR^bR^{b'}$, $NR^a$, O, S, S(=O) or S(=O)$_2$;

each K is independently $NR^a$, O, S, S(=O) or S(=O)$_2$;

each $L^1$ is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —NO$_2$, —NH$_2$, —CN, —COOH and $C_{1-3}$ alkyl;

each $R^8$ is independently H, D, F, Cl, Br, I, —OH, —SH, —NO$_2$, —NH$_2$, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —NO$_2$, —NH$_2$, —CN, —COOH, $C_{1-3}$ alkyl and $C_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2;

each $R^6$ is independently H, D, F, Cl, Br, I, —OH, —NO$_2$, —NH$_2$, —CN, $C_{1-3}$ alkyl, $C_{2-4}$ alkynyl, $C_{1-3}$ alkoxy or each $R^6$ is

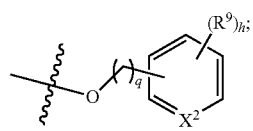

wherein $X^2$ is $CR^{10}$ or N, and wherein $R^{10}$ is H or $C_{1-3}$ alkyl;

q is 0, 1, 2 or 3;

each $R^9$ is independently H, D, F, Cl, Br, I, —OH, —$NO_2$, —$NH_2$, —CN, $C_{1-3}$ alkyl, $C_{2-4}$ alkynyl or $C_{1-3}$ alkoxy;

h is 0, 1, 2, 3, 4 or 5;

each of $R^3$, $R^4$, $R^5$ and L is independently as defined herein; and each X, Y, $Y^1$, $R^a$, $R^b$, $R^{b'}$, $R^7$ and d is independently as defined herein.

In other embodiments, $R^1$ is

H, D, —$CH_3$, —$CD_3$, —$CH_2CH_3$, —$CH_2CF_3$, —$CD_2CH_3$, —$CD_2CD_3$, —$CH_2CH_2OCH_3$, —$CH_2CD_2OCH_3$, —$CH_2CH_2OCD_3$, —$CH_2CH_2OCD_2CH_3$, —C≡C$CH_2OCH_2CH_3$,

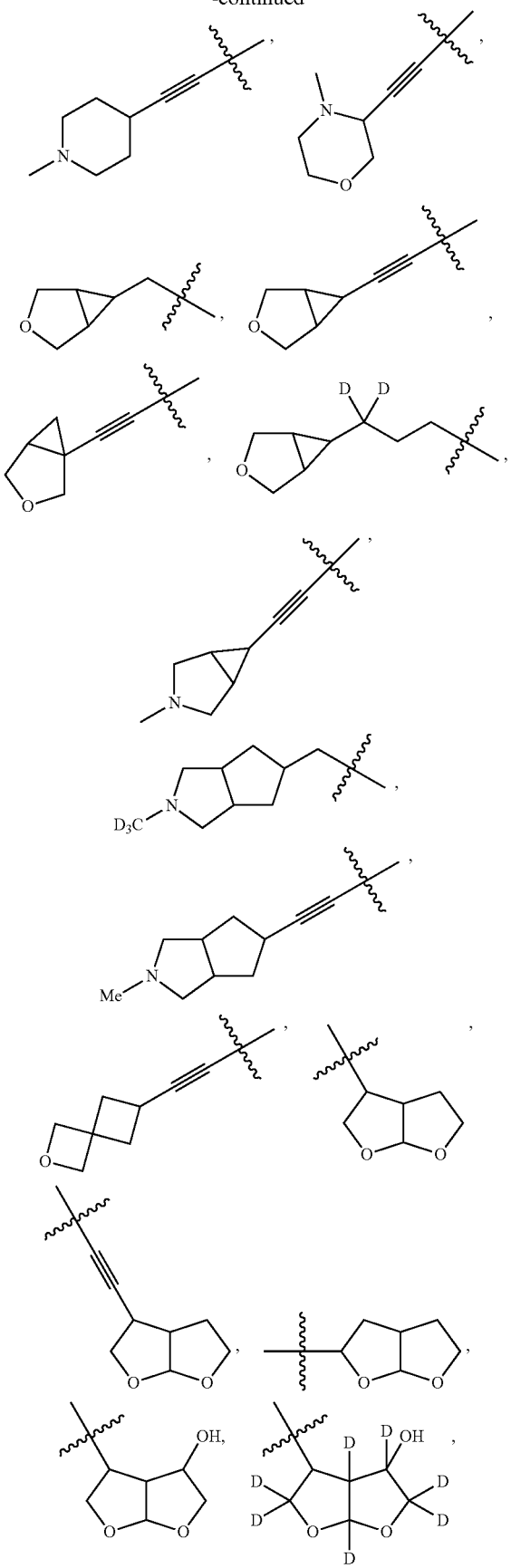

-continued

67
-continued
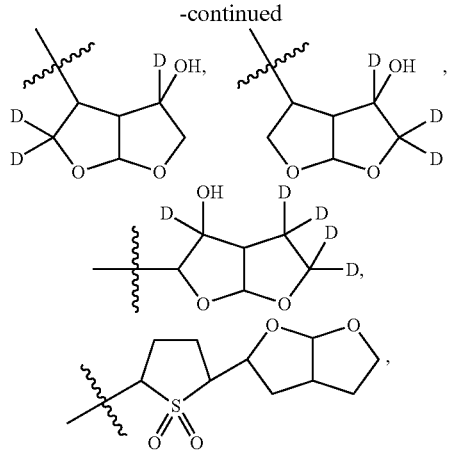
68
-continued
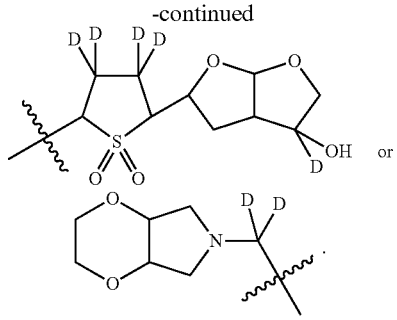
In other embodiments, non-limiting examples of the compounds disclosed herein, and the pharmaceutically acceptable salts and solvates thereof, include:
(1)
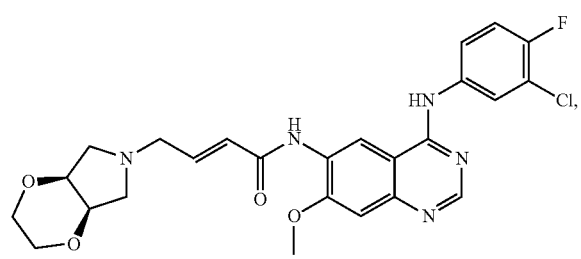
(2)
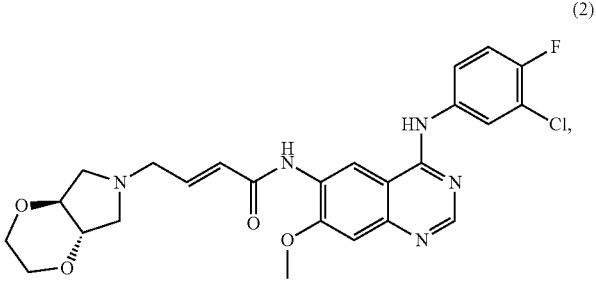
(3)
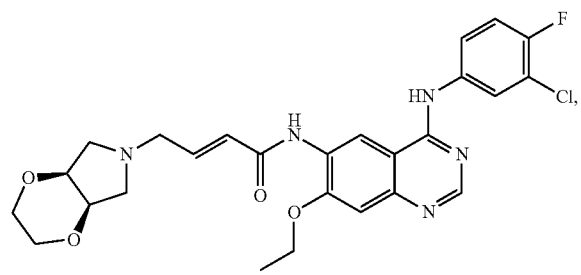
(4)
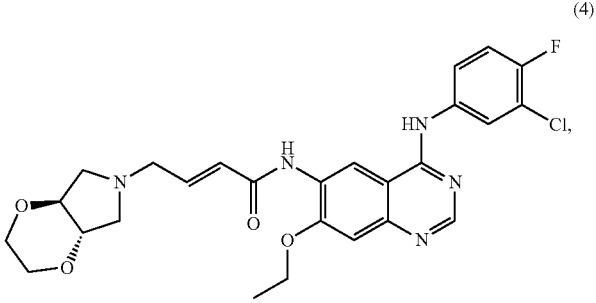
(5)
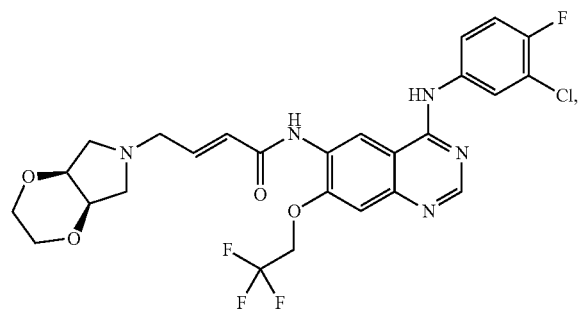
(6)
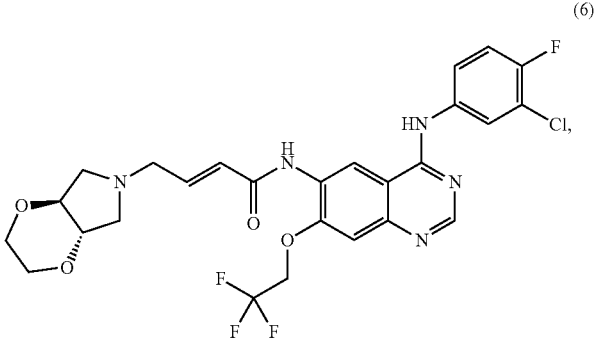

-continued
(7)
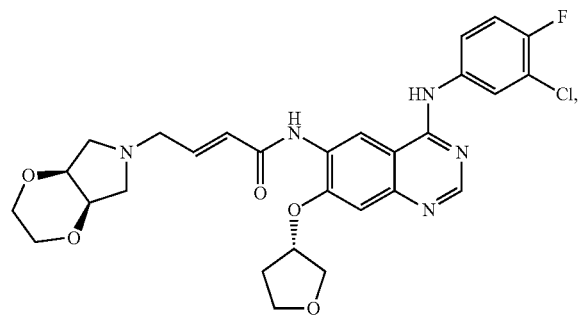
(8)
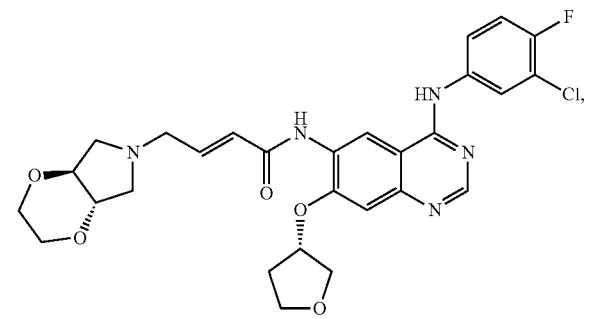
(9)
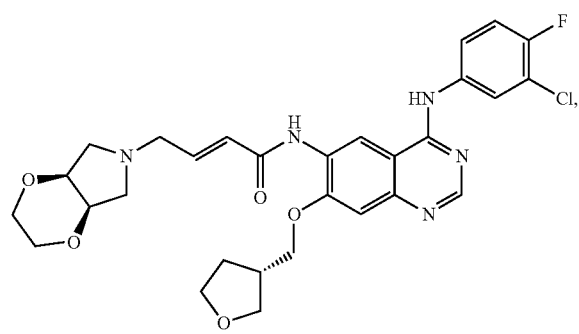
(10)
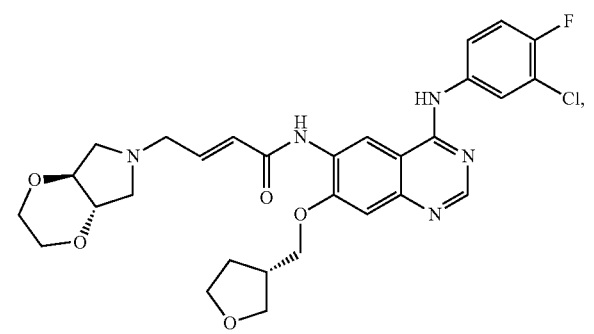
(11)
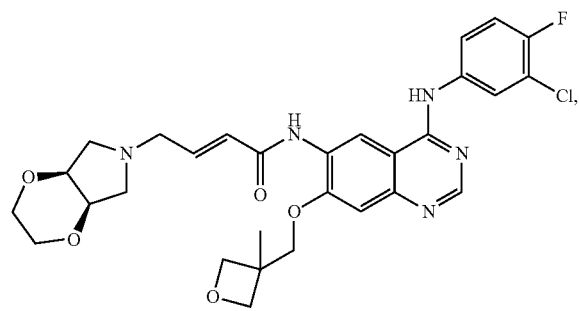
(12)
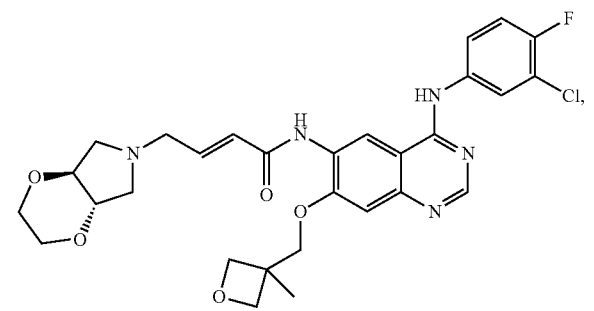
(13)
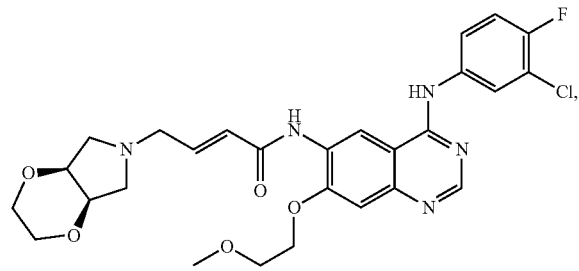
(14)
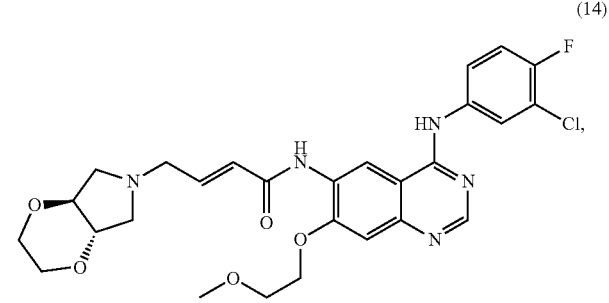
(15)
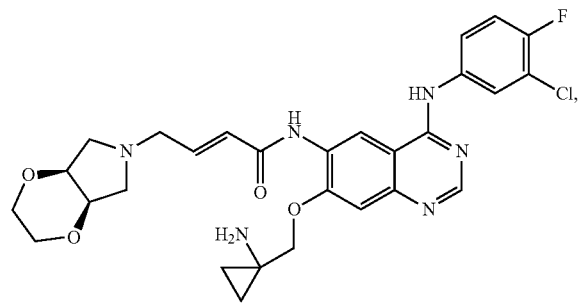
(16)
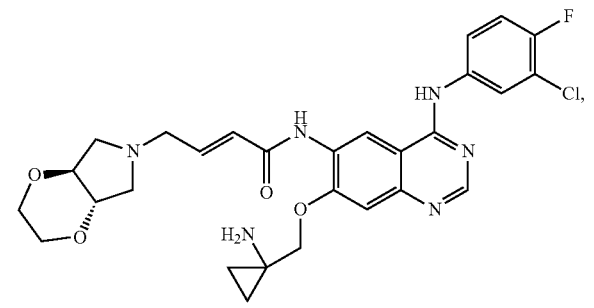

-continued
(17)
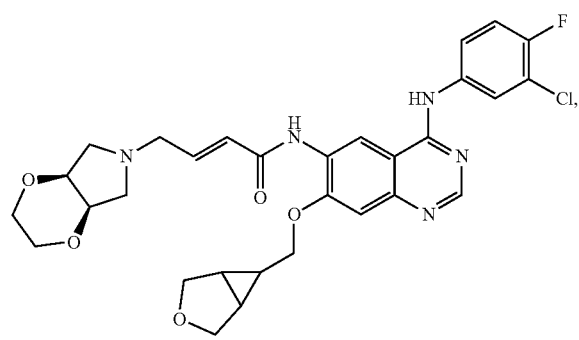
(18)
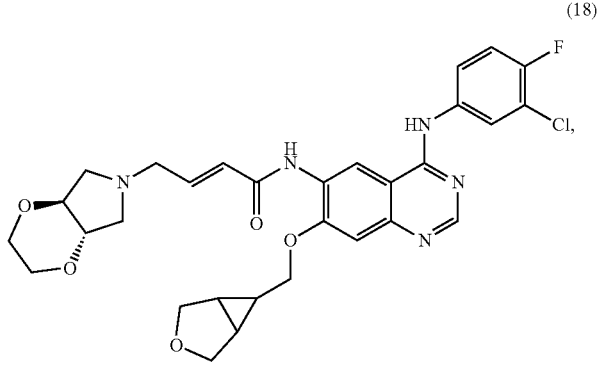
(19)
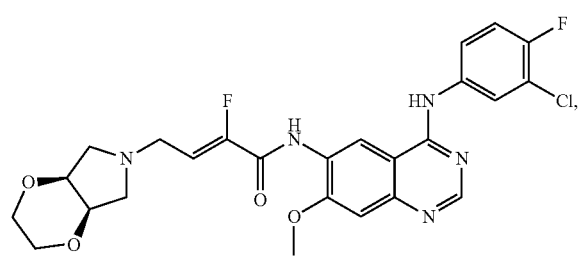
(20)
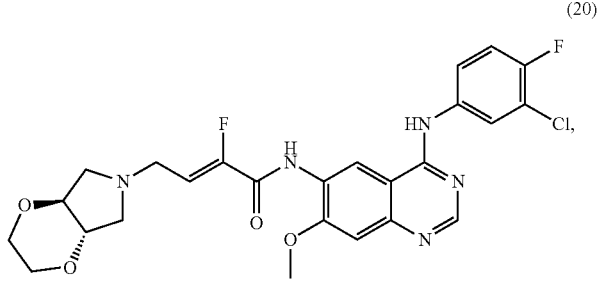
(21)
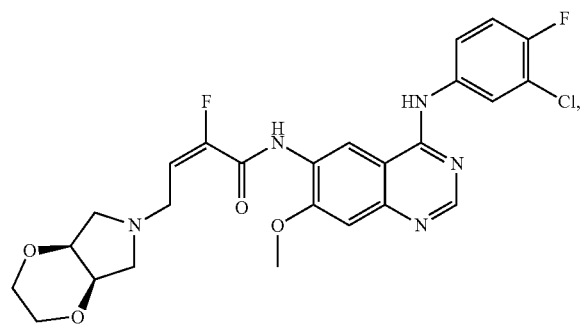
(22)
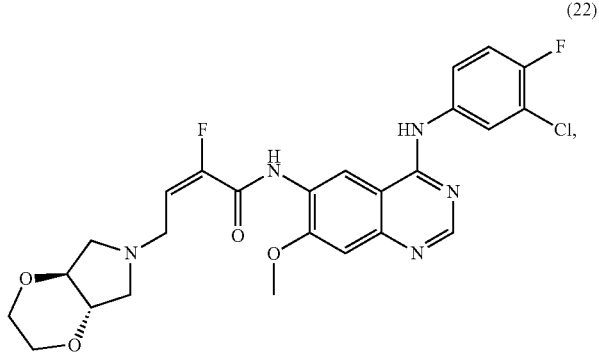
(23)
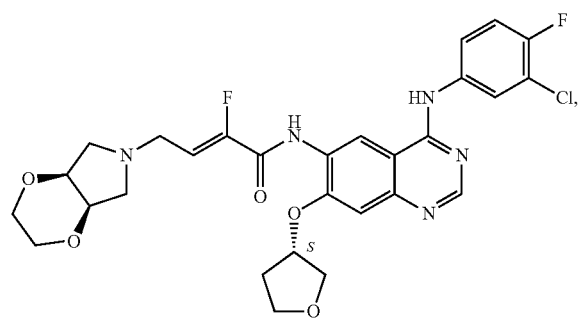
(24)
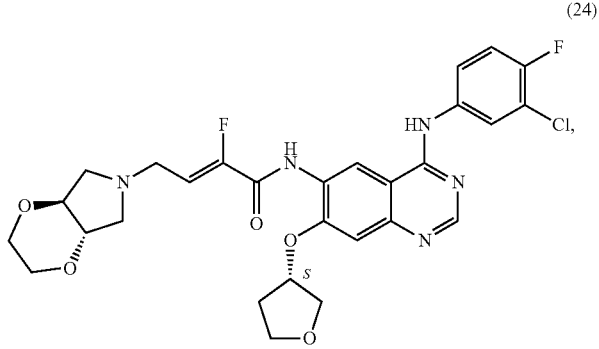

-continued
(25)
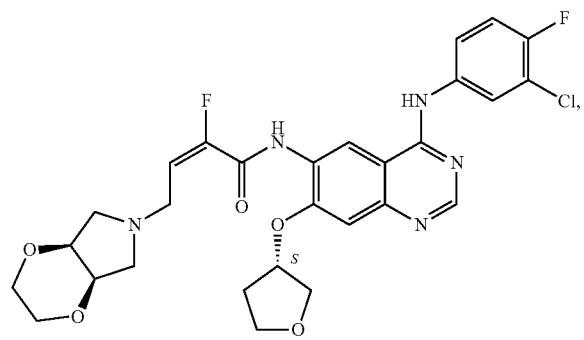
(26)
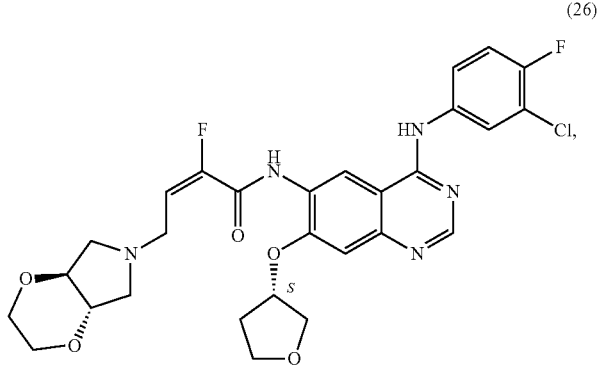
(27)
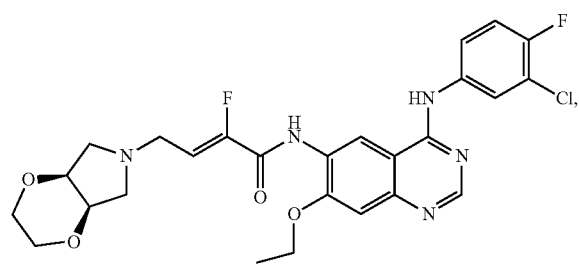
(28)
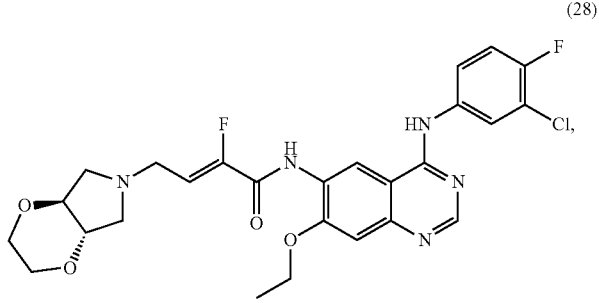
(29)
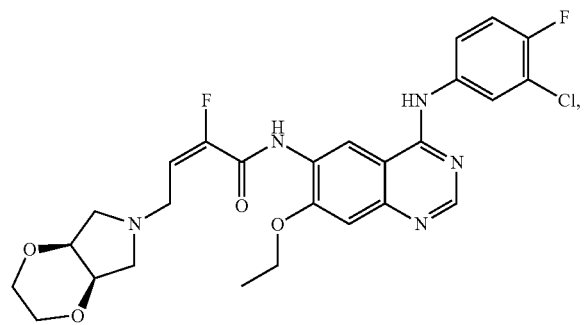
(30)
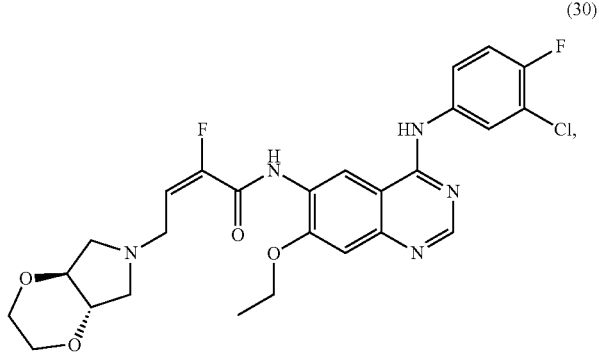
(31)
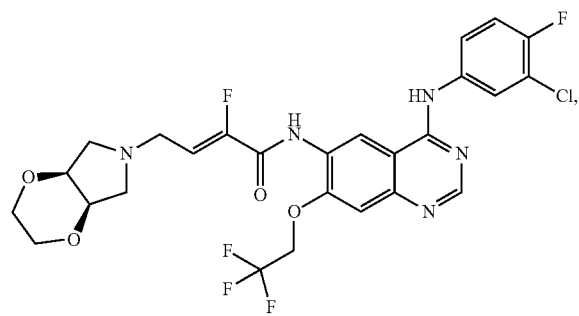
(32)
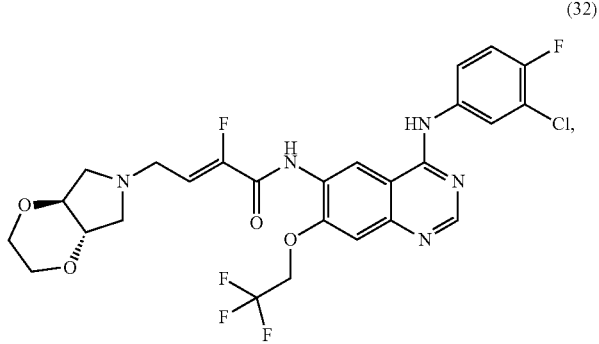

-continued
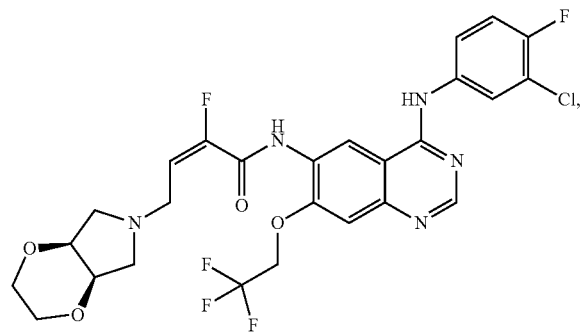
(33)
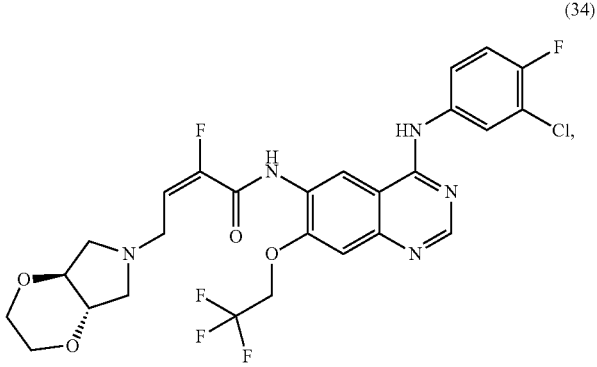
(34)
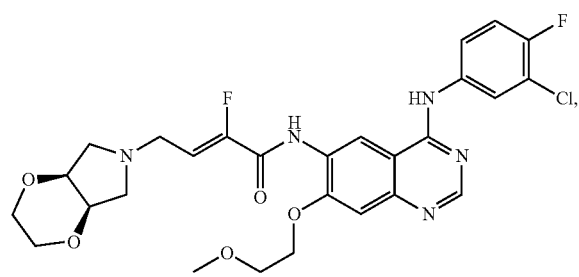
(35)
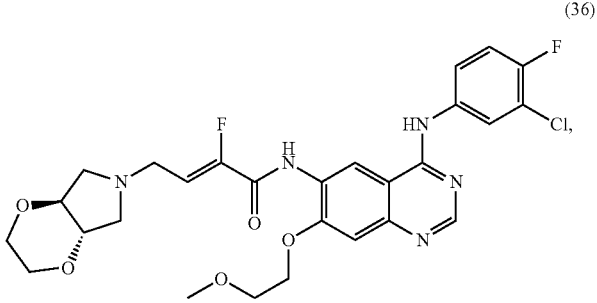
(36)
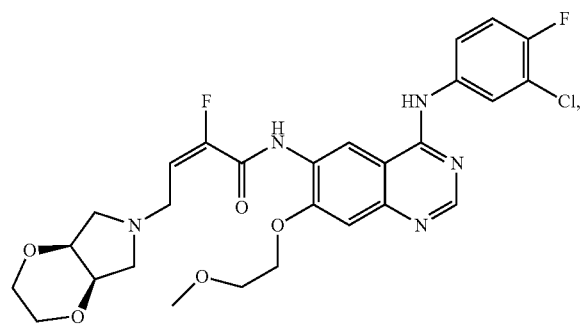
(37)
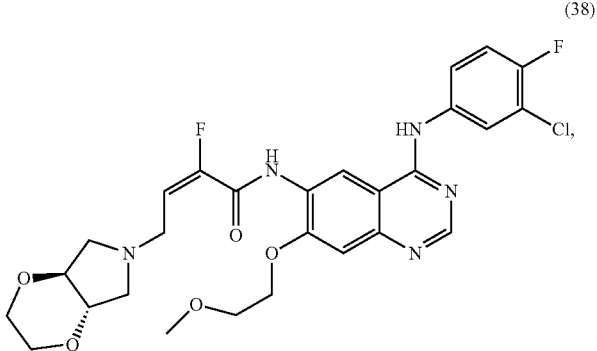
(38)
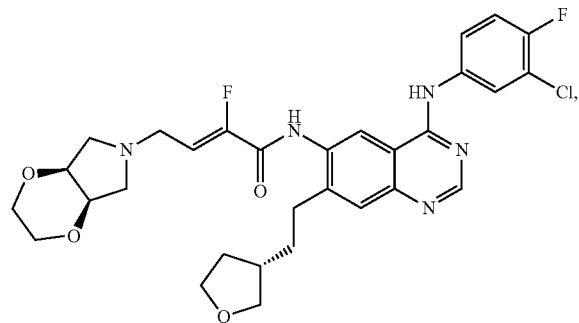
(39)
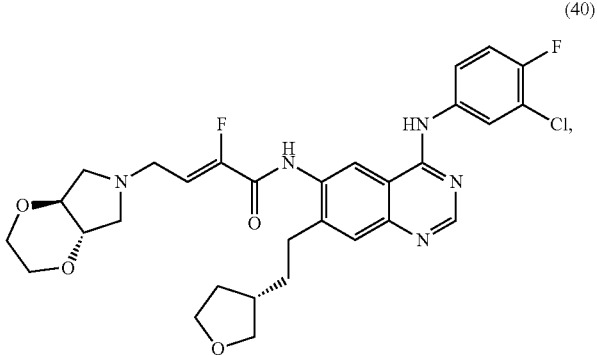
(40)

-continued
(41)
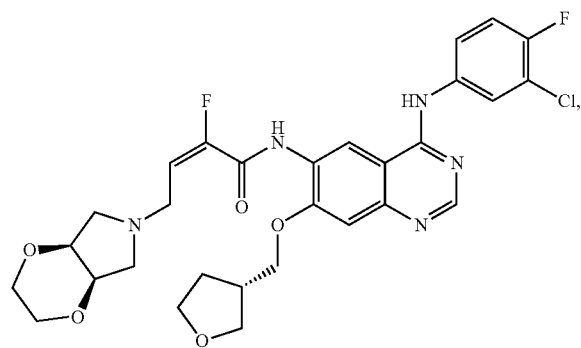
(42)
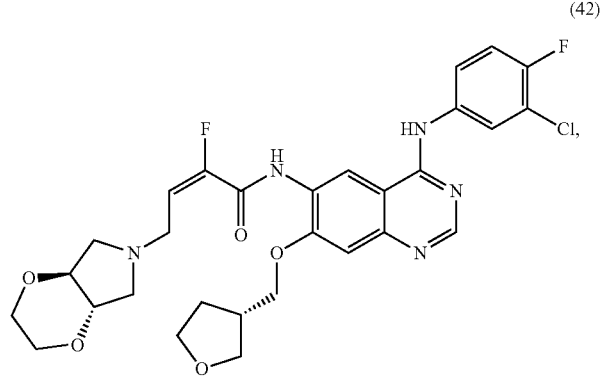
(43)
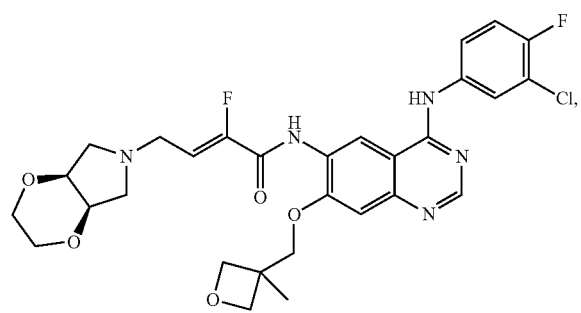
(44)
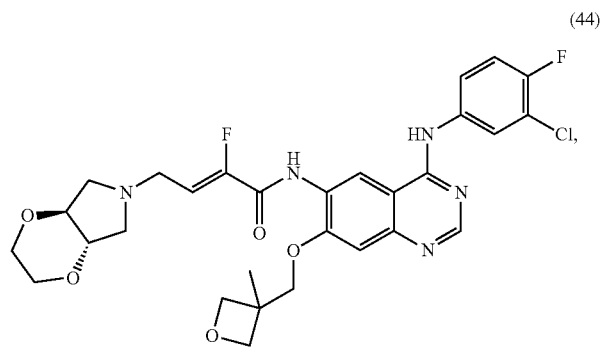
(45)
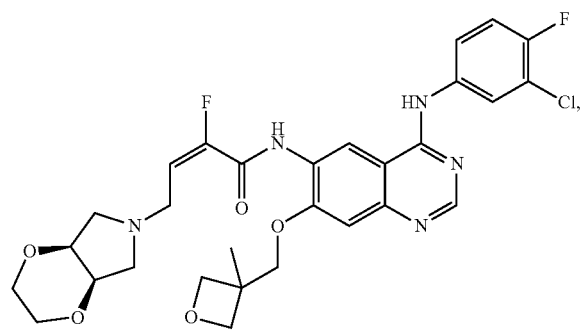
(46)
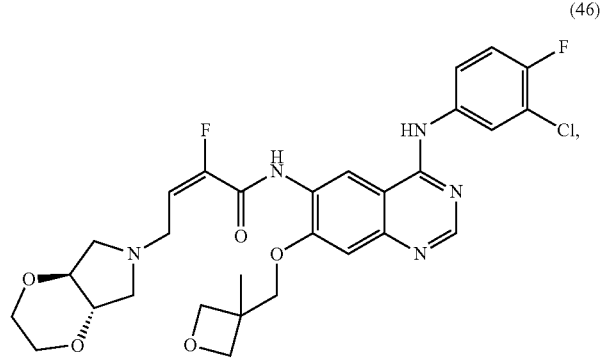
(47)
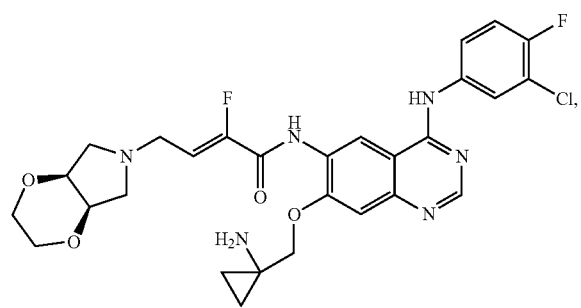
(48)
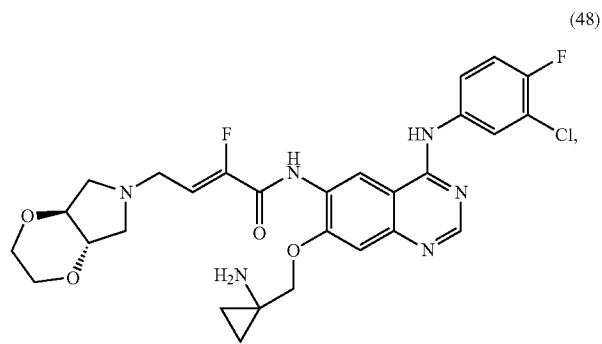

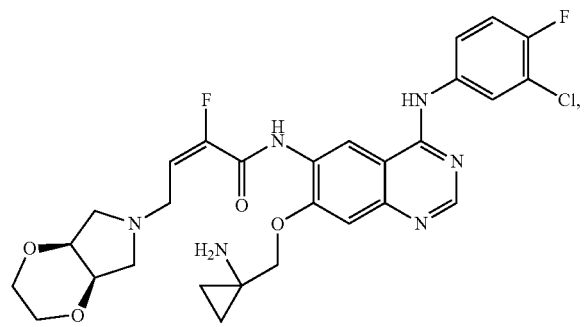
(49)
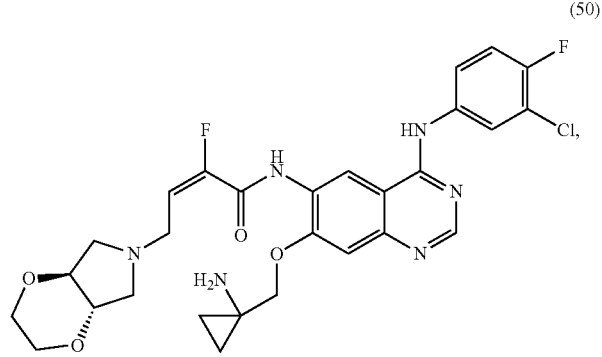
(50)
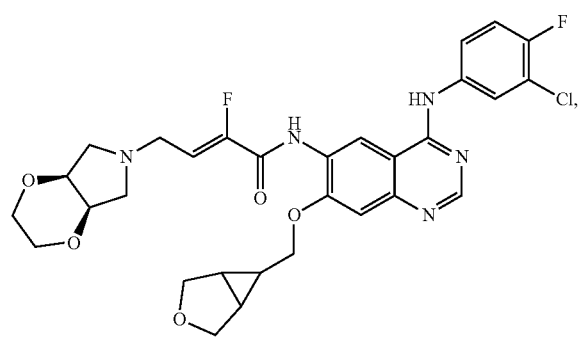
(51)
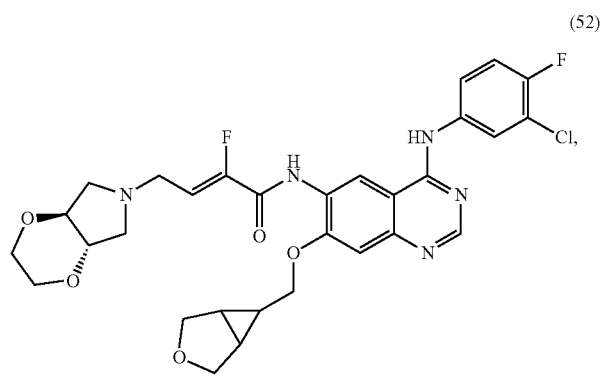
(52)
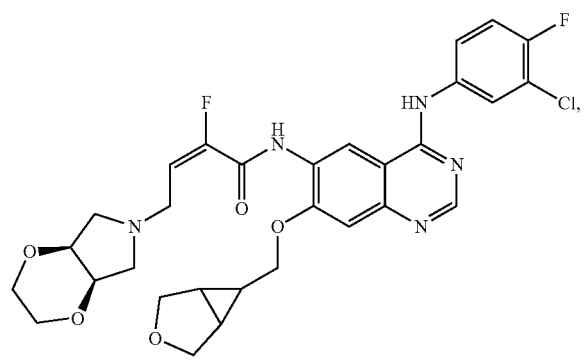
(53)
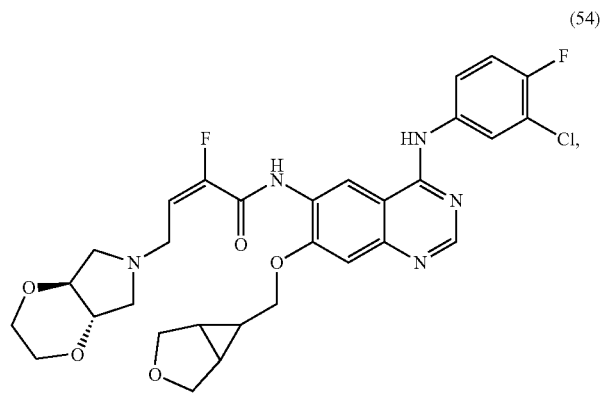
(54)
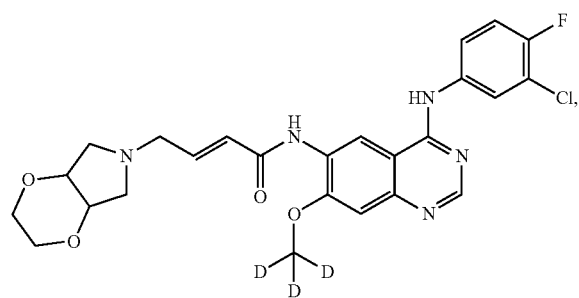
(55)

-continued
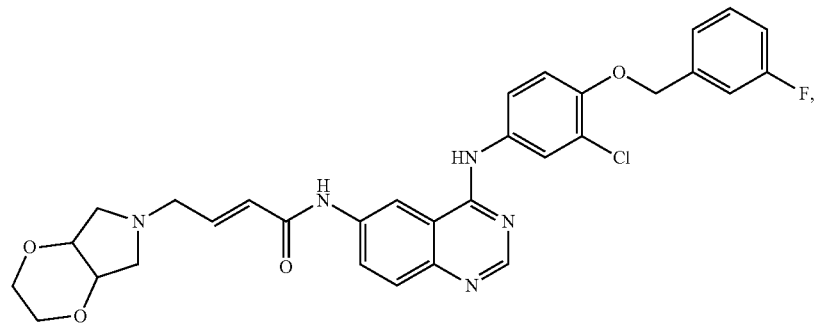
(56)
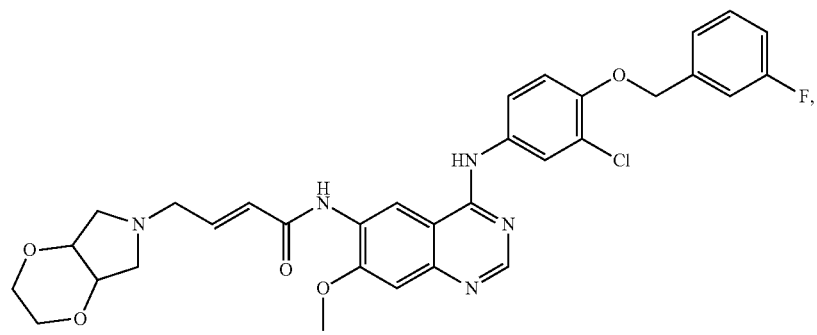
(57)
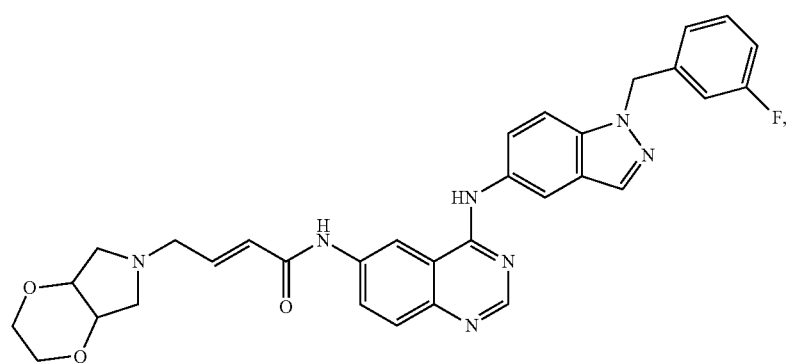
(58)
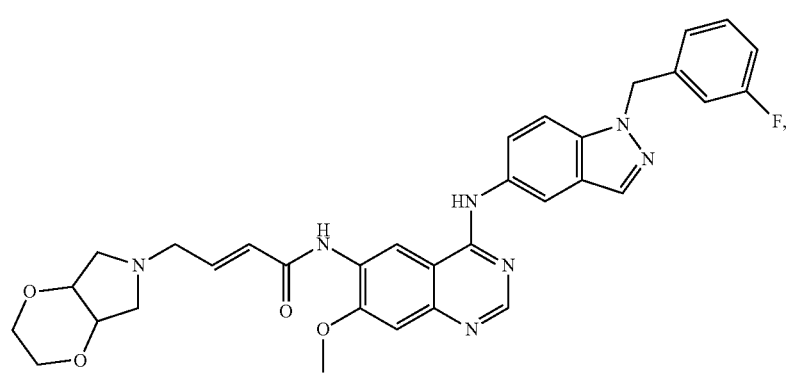
(59)

-continued
(60)
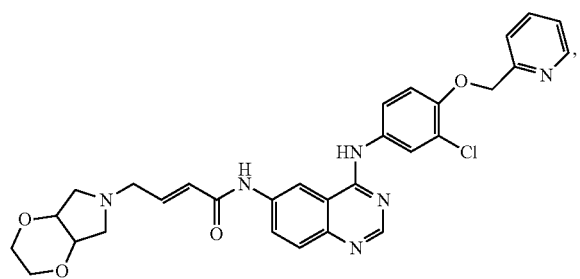
(61)
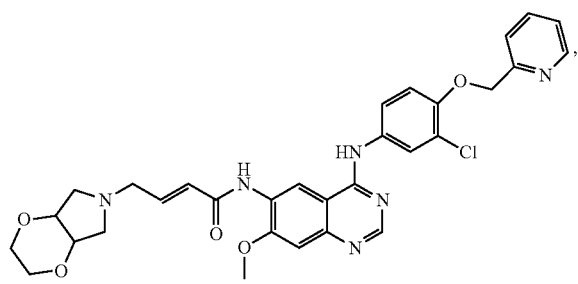
(62)
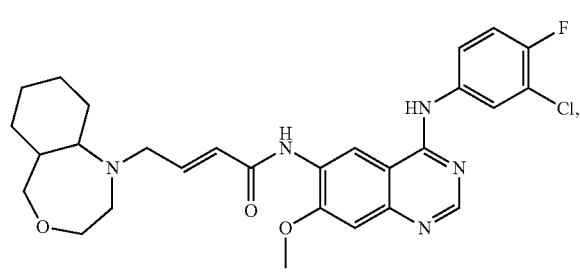
(63)
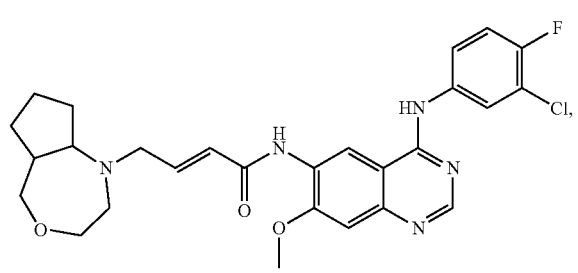
(64)
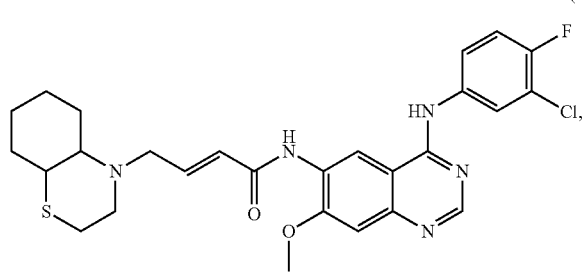
(65)
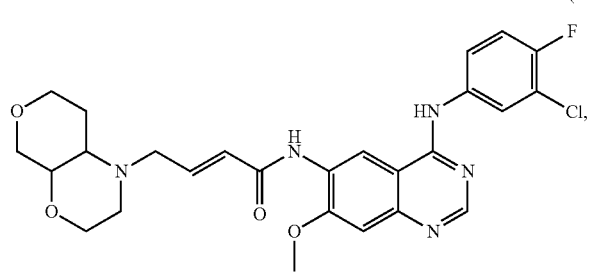
(66)
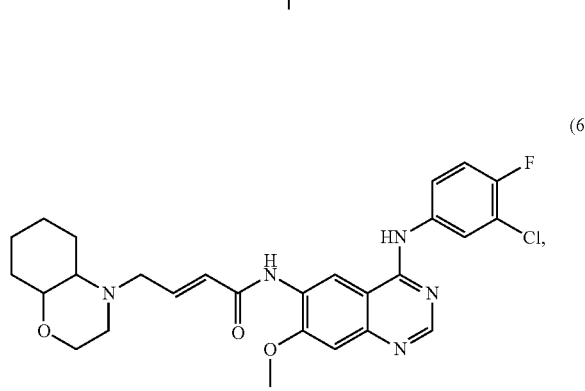
(67)
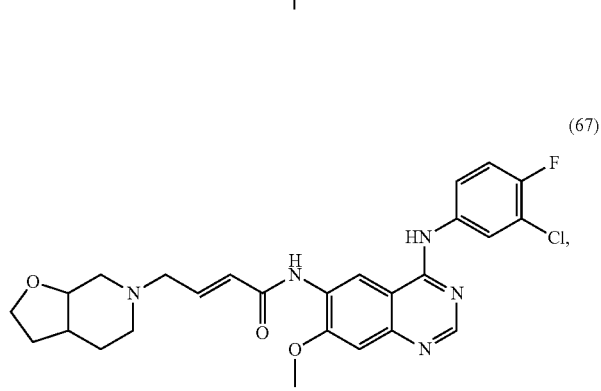
(68)
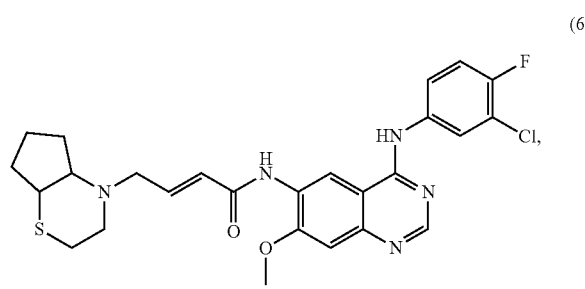
(69)
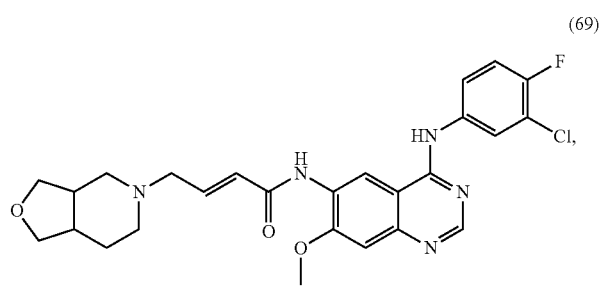

-continued
(70) 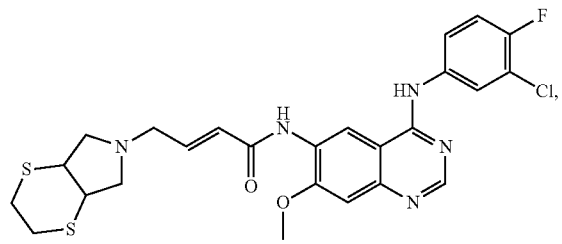
(71) 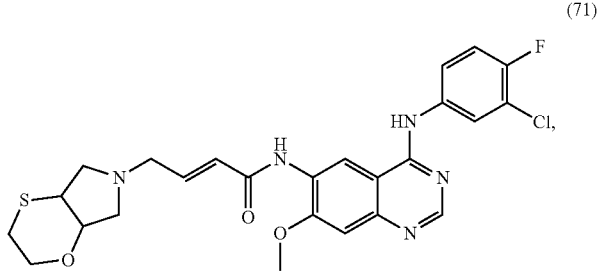
(72) 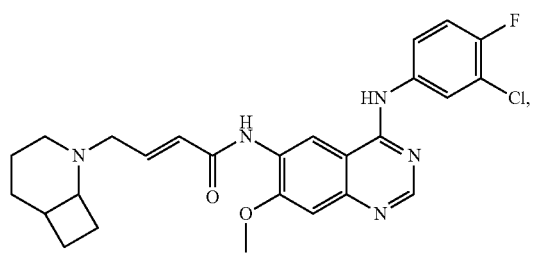
(73) 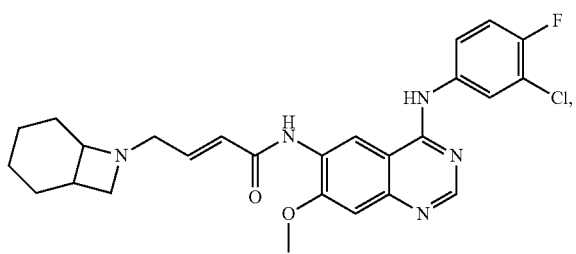
(74) 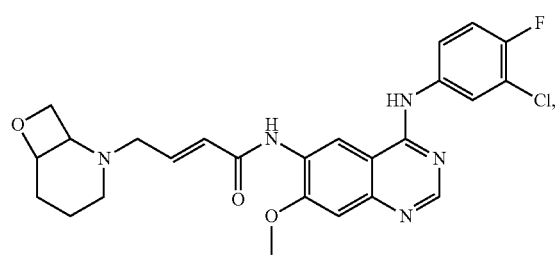
(75) 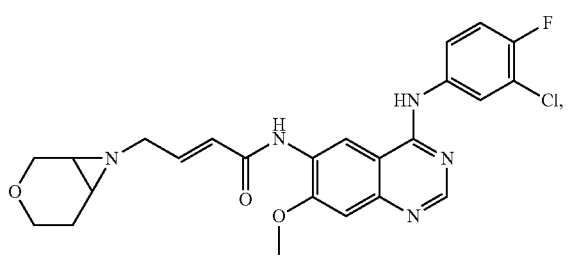
(76) 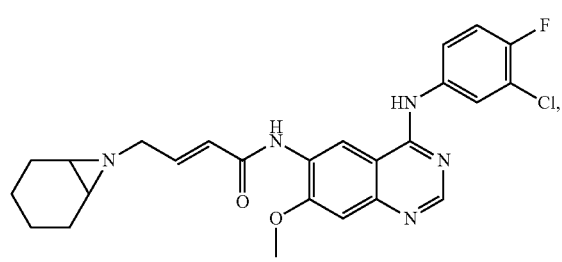
(77) 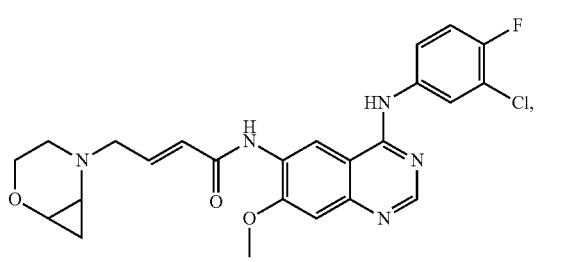
(78) 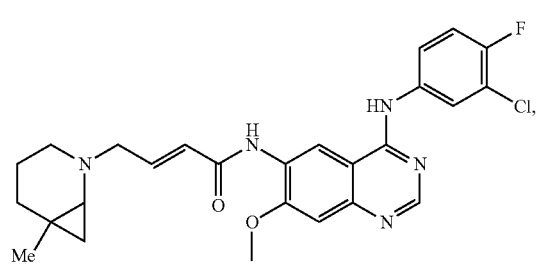
(79) 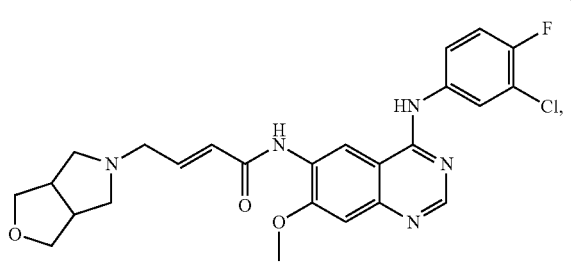
(80) 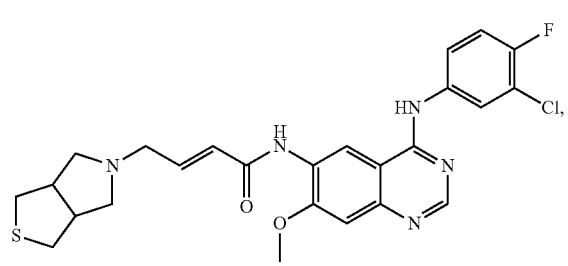
(81) 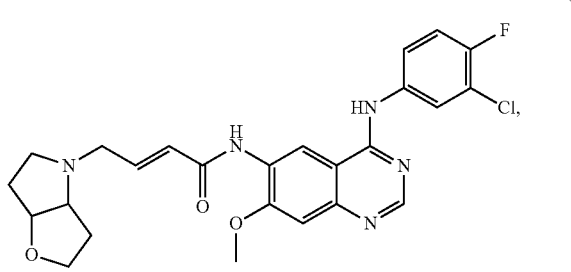

-continued
(82)
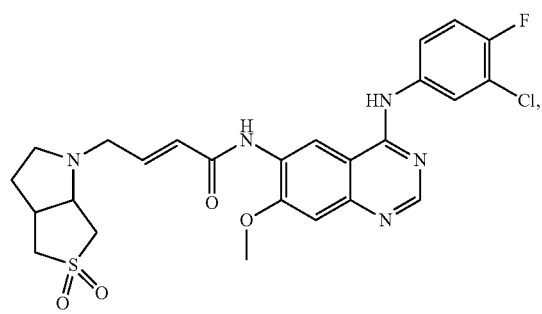
(83)
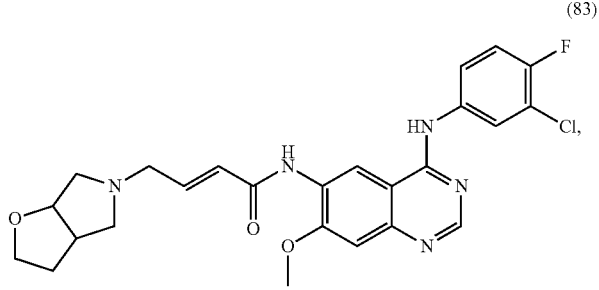
(84)
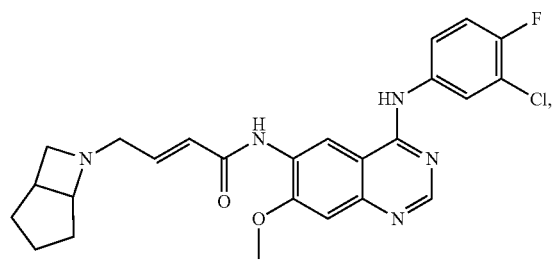
(85)
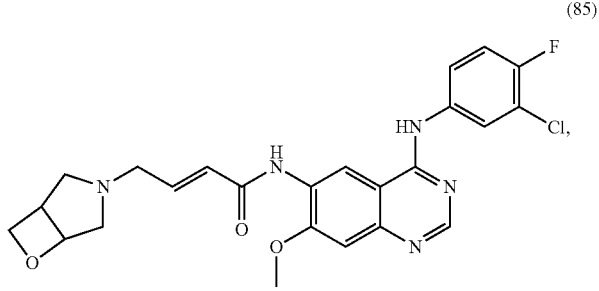
(86)
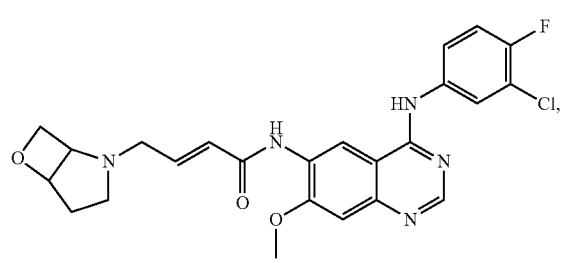
(87)
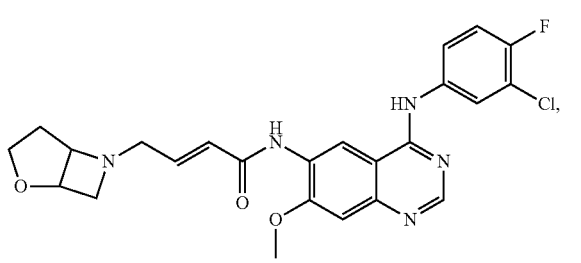
(88)
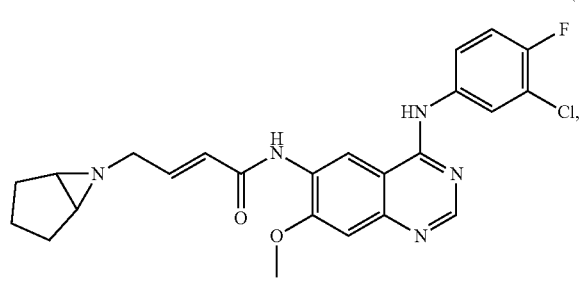
(89)
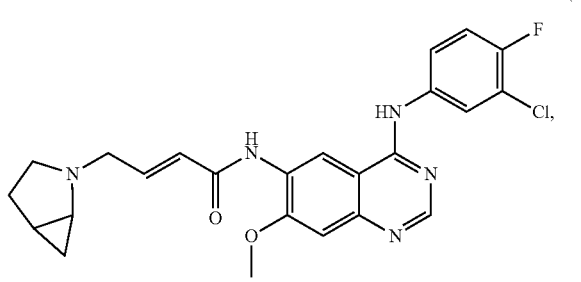
(90)
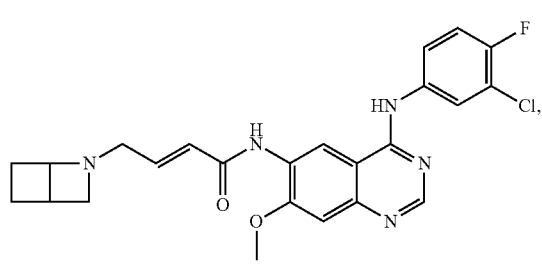
(91)
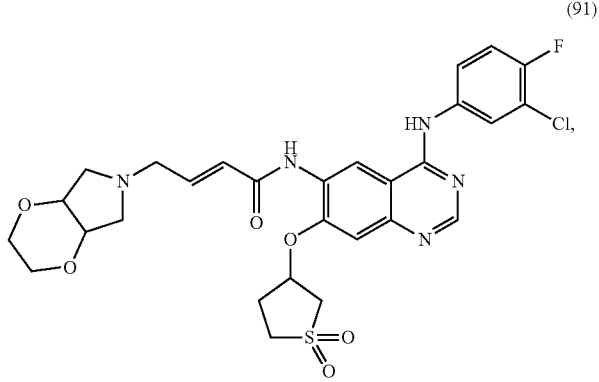

-continued
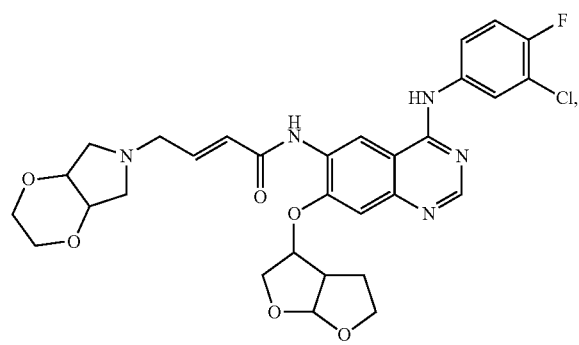
(92)
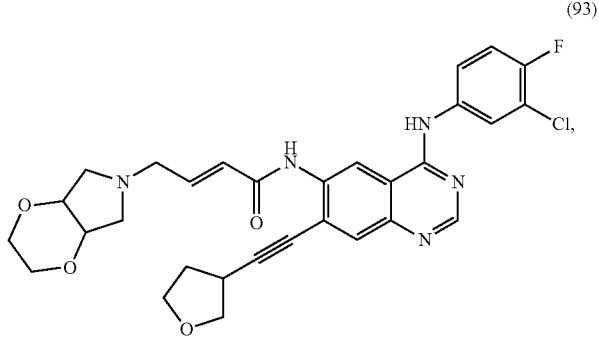
(93)
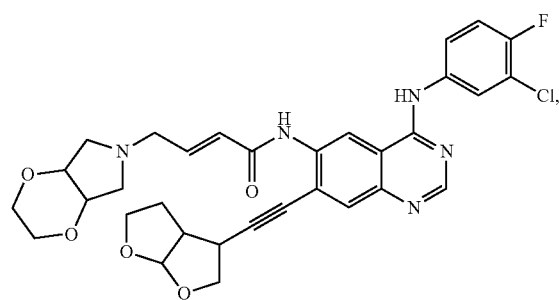
(94)
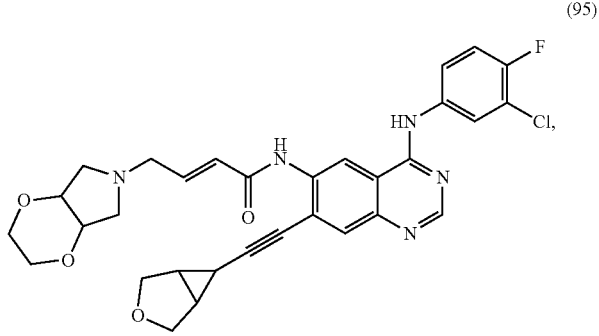
(95)
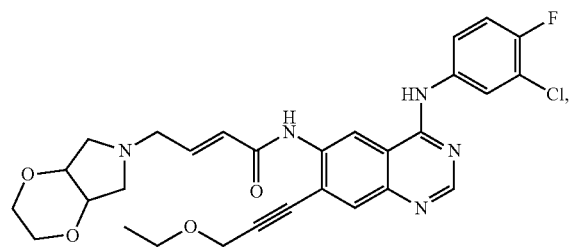
(96)
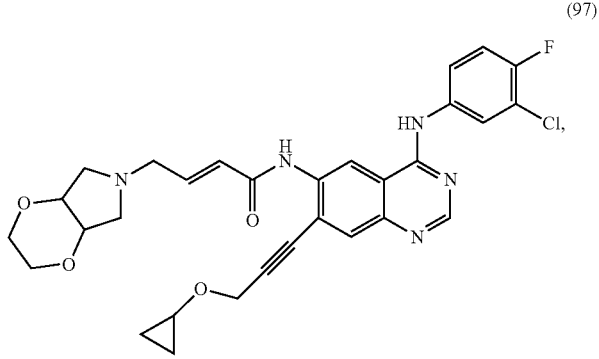
(97)
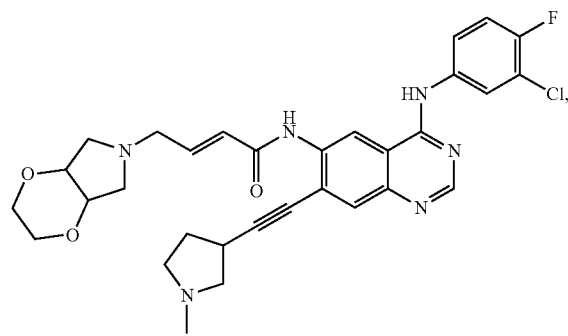
(98)
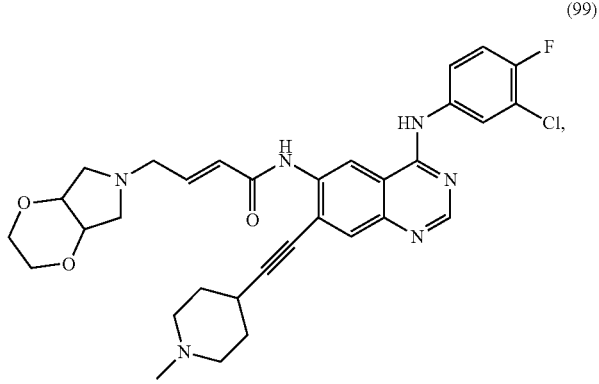
(99)

-continued
(100)
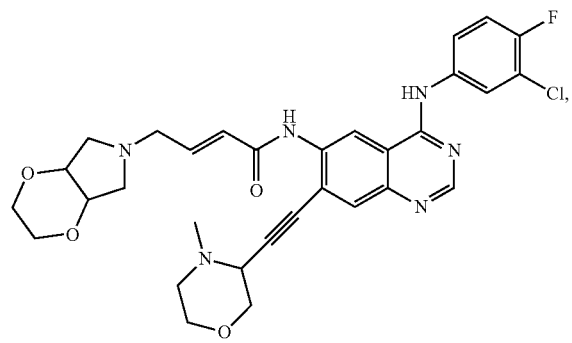
(101)
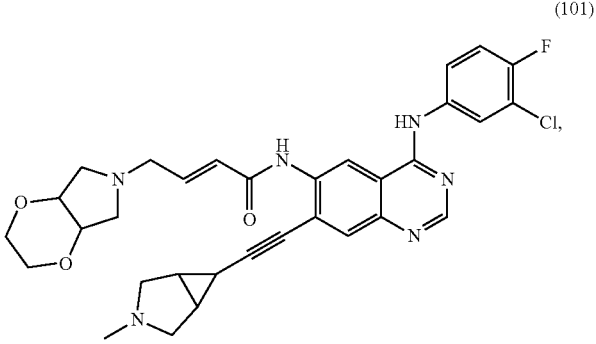
(102)
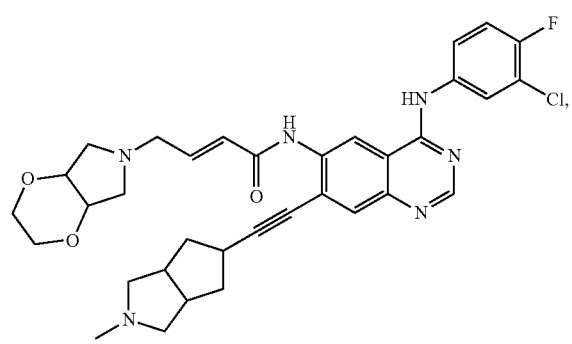
(103)
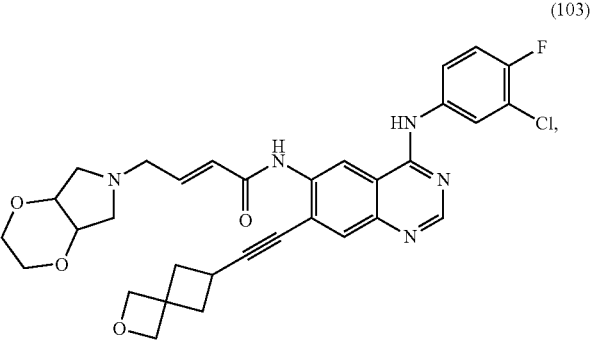
(104)
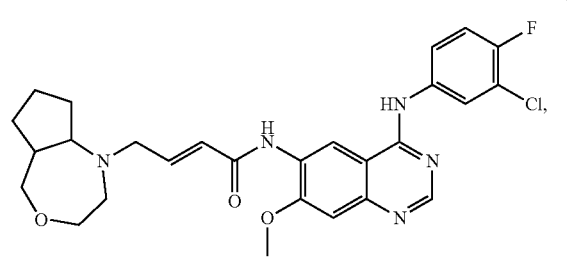
(105)
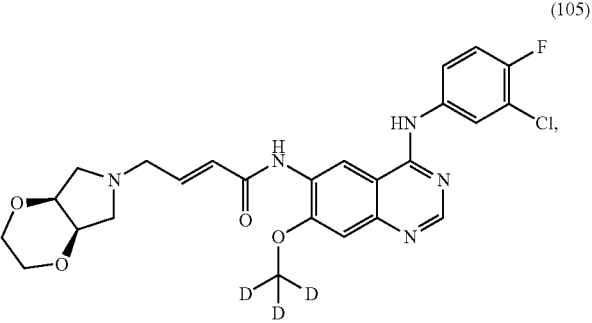
(106)
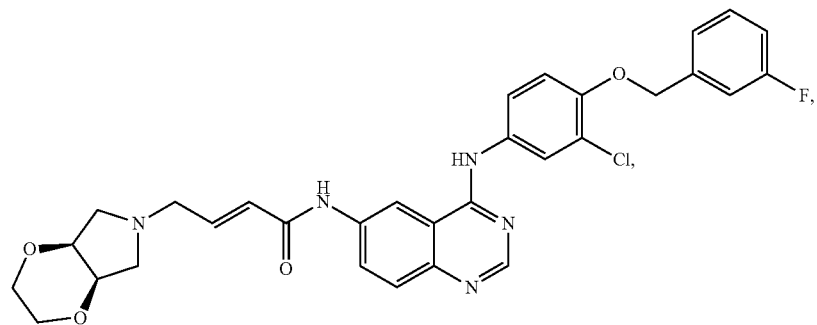

-continued
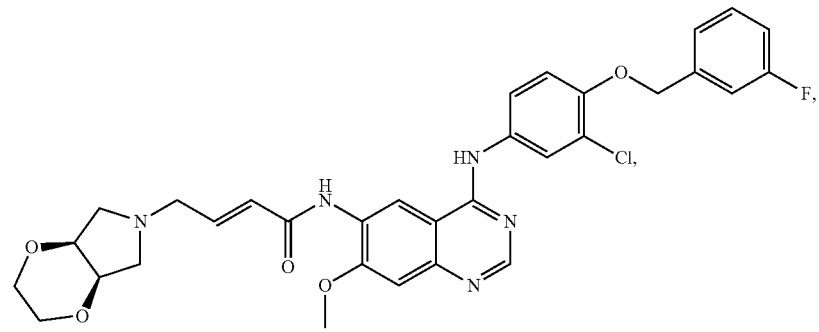
(107)
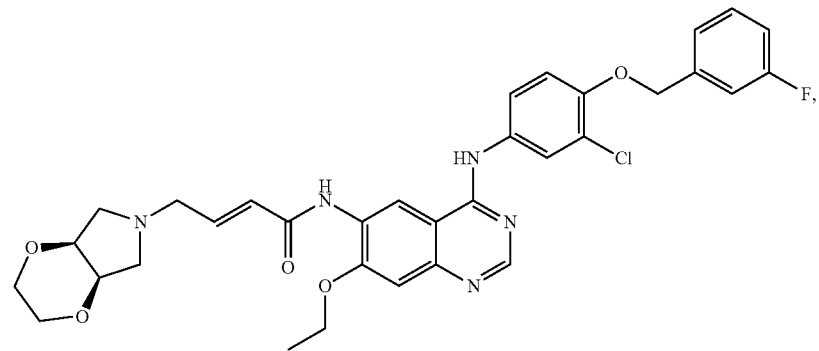
(108)
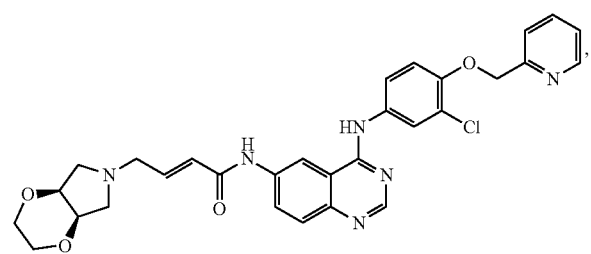
(109)
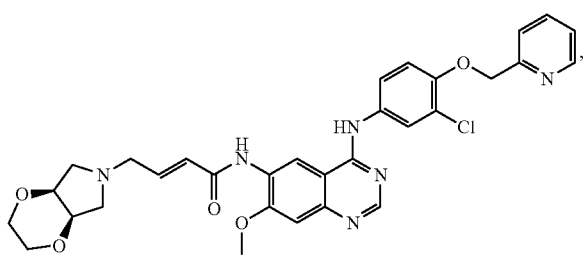
(110)
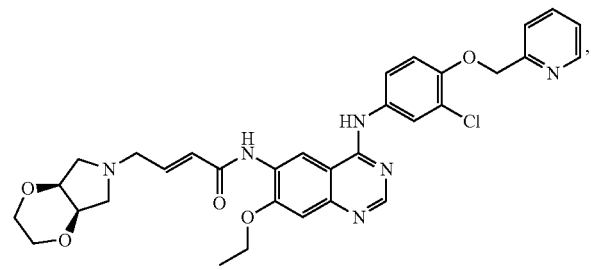
(111)
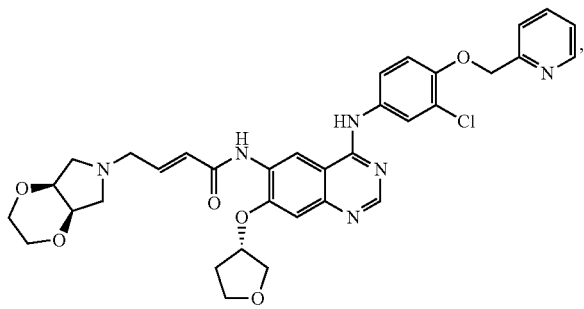
(112)

-continued
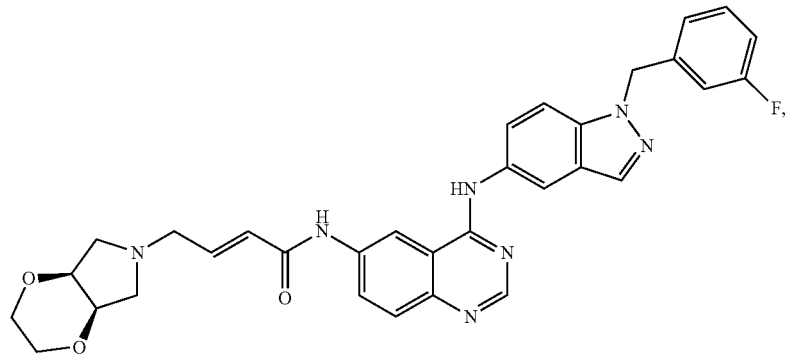
(113)
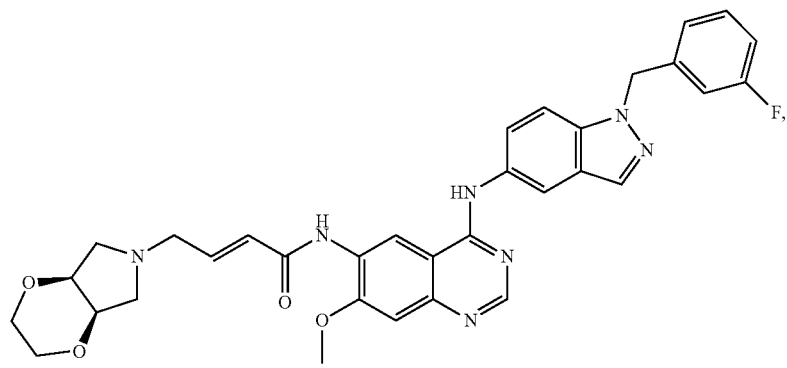
(114)
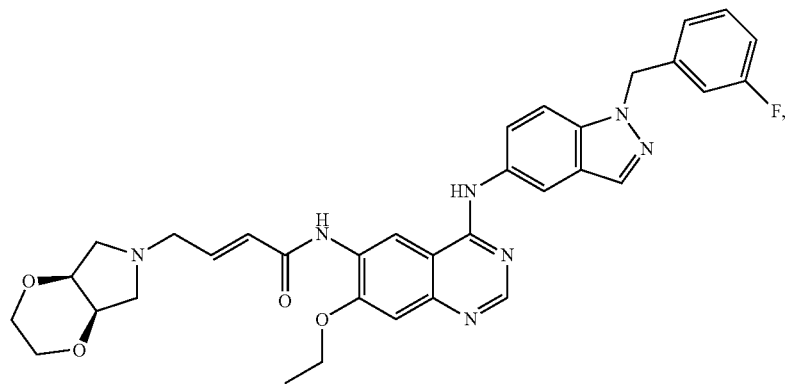
(115)
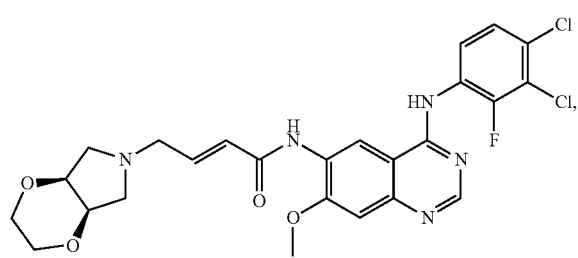
(116)
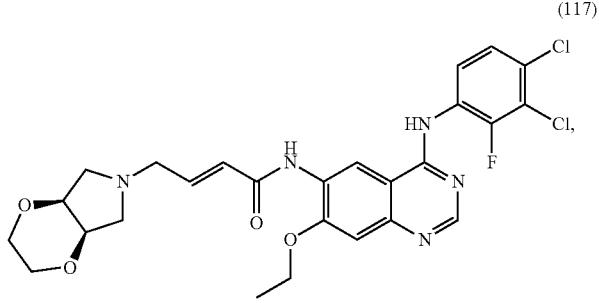
(117)

-continued (118)
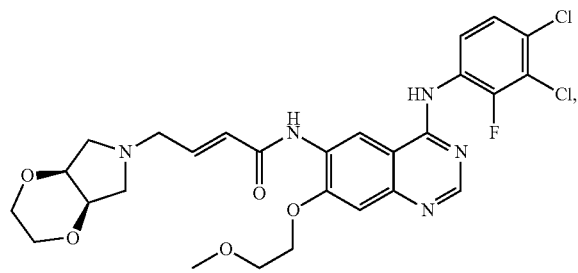

(119)
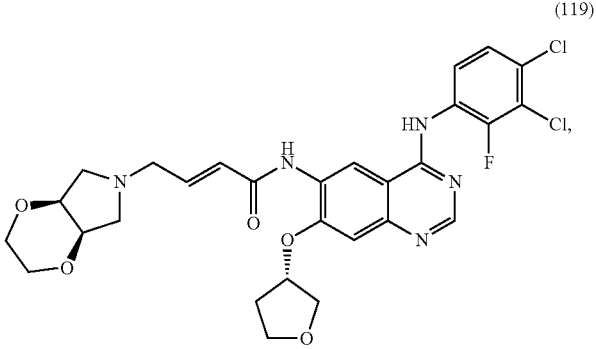

(120)
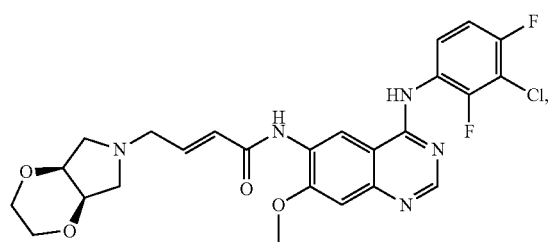

(121)
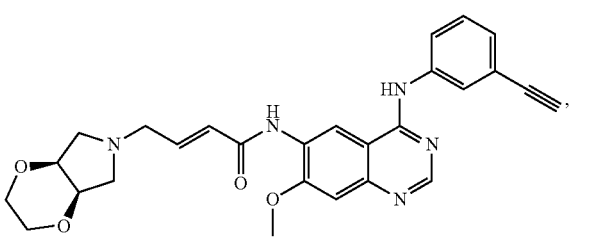

(122)
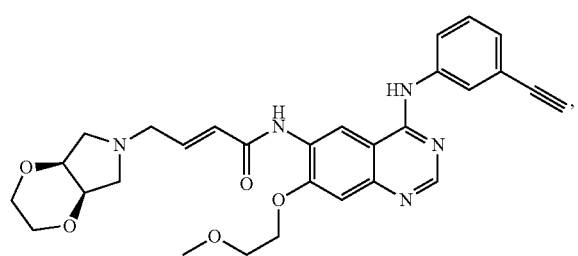

(123)
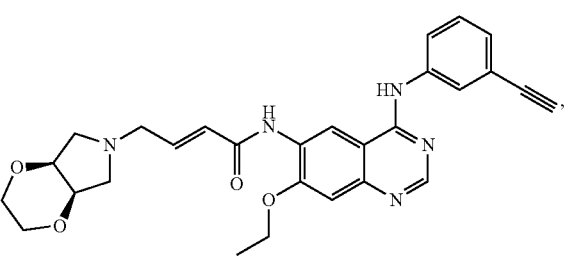

(124)
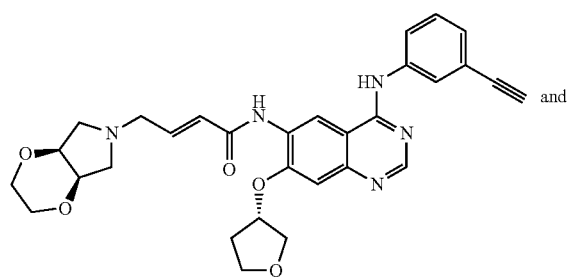

and (125)
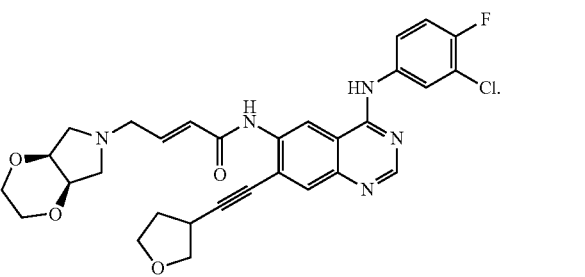

Provided herein includes the use of a compound disclosed herein, or the pharmaceutically acceptable salt thereof, in the manufacture of a medicament for the treatment of a proliferative disorder including those described herein. The compounds disclosed herein are useful in the manufacture of an anti-cancer medicament. The compounds disclosed herein are also useful in the manufacture of a medicament to attenuate, prevent, manage or treat disorders through inhibition of EGFR or HER-2. Also provided herein is a pharmaceutical composition comprising a therapeutically effective amount of a compound of Formula (I) in association with at least one pharmaceutically acceptable carrier, adjuvant or diluent.

Also provided herein is a method of treating proliferative disorder in a subject having or susceptible to such disorder. The method comprises treating the subject with a therapeutically effective amount of a compound of Formula (I).

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of Formula (I) and/or for separating enantiomers of compounds of Formula (I).

If the compound disclosed herein is a base, the desired salt may be prepared by any suitable method available in the art, for example, treatment of the free base with an inorganic acid such as hydrochloric acid, hydrobromic acid, sulfuric acid, nitric acid, phosphoric acid, and the like, or with an organic acid such as acetic acid, maleic acid, succinic acid, mandelic acid, fumaric acid, malonic acid, pyruvic acid, oxalic acid, glycolic acid and salicylic acid; a pyranosidyl acid such as glucuronic acid and galacturonic acid; an alpha-hydroxy acid such as citric acid and tartaric acid; an amino acid such as aspartic acid and glutamic acid; an aromatic acid such as benzoic acid and cinnamic acid; a sulfonic acid such as p-toluenesulfonic acid and ethanesulfonic acid; and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids such as glycine and arginine, ammonia, primary, secondary, and tertiary amines, and cyclic amines such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the invention features pharmaceutical compositions that include a compound of Formula (I), a compound listed herein, or a compound named in Examples 1-40, and a pharmaceutically acceptable carrier, adjuvant, or vehicle. The amount of the compound in the compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. Troy et al., Lippincott Williams & Wilkins, Philadelphia, and *Encyclopedia of Pharmaceutical Technology,* eds. Swarbrick et al., 1988-1999, Marcel Dekker, New York, both of which are herein incorporated by reference in their entireties, disclose various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchanger; aluminum; aluminum stearate; lecithin; serum protein such as human serum albumin; buffer substance such as phosphate; glycine; sorbic acid; potassium sorbate; partial glyceride mixture of saturated vegetable fatty acid; water; salt or electrolyte such as protamine sulfate, disodium hydrogen phosphate and potassium hydrogen phosphate, sodium chloride and zinc salt; colloidal silica; magnesium trisilicate; polyvinyl pyrrolidone; polyacrylate; waxe; polyethylene-polyoxypropylene-block polymer; wool fat; sugar such as lactose, glucose and sucrose; starch such as corn starch and potato starch; cellulose and its derivative such as sodium carboxymethyl cellulose, ethyl cellulose and cellulose acetate; powdered tragacanth; malt; gelatin; talc; excipients such as cocoa butter and suppository waxes; oil such as peanut oil, cottonseed oil, safflower oil, sesame oil, olive oil, corn oil and soybean oil; glycol such as propylene glycol and polyethylene glycol; ester such as ethyl oleate and ethyl laurate; agar; buffering agent such as magnesium hydroxide and aluminum hydroxide; alginic acid; pyrogen-free water; isotonic saline; Ringer's solution; ethyl alcohol and phosphate buffer solution, as well as other non-toxic compatible lubricant such as sodium lauryl sulfate and magnesium stearate, coloring agent, releasing agent, coating agent, sweetening, flavoring and perfuming agent, preservative and antioxidant.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. In some embodiments, the compositions are administered orally, intraperitoneally or intravenously. Sterile injectable forms of the compositions disclosed herein include aqueous or oleaginous suspension. These suspensions may be formulated according to techniques known in the art using suitable dispersing or wetting agents and suspending agents. The sterile injectable preparation may also be a sterile injectable solution or suspension is a non-toxic parenterally acceptable diluent or solvent, for example as a solution in 1,3-butanediol. Among the acceptable vehicles and solvents that include water, Ringer's solution and isotonic sodium chloride solution. In addition, sterile, non-volatile oil can be conventionally employed as a solvent or suspending medium.

For this purpose, any non-volatile oil includes synthetic mono- or di-glycosylated diglyceride. Fatty acids, such as oleic acid and its glyceride derivatives, which are useful in the preparation of injectable, can be used as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions disclosed herein include orally administered in any orally acceptable dosage form including, but not limited to, capsules, tablets, aqueous suspensions and solutions. In the case of tablets for oral use, carriers commonly include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions disclosed herein include administered in the form of suppositories for rectal administration. These can be prepared by mixing the agent with a suitable non-irrigating excipient that is solid at room temperature but liquid at rectal temperature and therefore will melt in the rectum to release the drug. Such materials include cocoa butter, beeswax and polyethylene glycols. The pharmaceutically acceptable compositions disclosed herein also include administered topically, especially when the target of treatment includes areas or organs readily accessible by topical application, including diseases of the eye, the skin, and the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds disclosed herein include, but are not limited to, mineral oil, liquid petrolatum, white petrolatum, propylene glycol, polyoxyethylene, polyoxypropylene compound, emulsifying wax and water. In addition, the pharmaceutically acceptable compositions can be formulated in a suitable lotion or cream containing the active components suspended or dissolved in one or more pharmaceutically acceptable carriers. Suitable carriers include, but are not limited to, mineral oil, Span 60 (sorbitan monostearate), Tween 60 (polysorbate 60), cetyl esters wax, cetearyl alcohol, 2-octyldodecanol, benzyl alcohol and water.

For ophthalmic uses, the pharmaceutically acceptable compositions may be formulated, e.g., as micronized suspension in isotonic, pH adjusted sterile saline or other aqueous solutions, or in other embodiments, as solution in isotonic, pH adjusted sterile saline or other aqueous solution, either with or without a preservative such as benzalkonium chloride. In addition, for ophthalmic uses, the pharmaceutically acceptable compositions may be formulated in an ointment such as petrolatum. The pharmaceutically acceptable compositions disclosed herein may also be administered by nasal aerosol or inhalation. Such compositions are prepared according to techniques well known in the art of pharmaceutical formulation and may be prepared as solutions in saline, employing benzyl alcohol or other suitable preservatives, absorption promoters, fluorocarbons, and/or other conventional solubilizing or dispersing agents to enhance bioavailability.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oil), glycerol, 2-tetrahydrofurfury alcohol, polyethylene glycols and fatty acid esters of sorbitan, and mixtures thereof. Besides inert diluents, the oral compositions can also include adjuvants such as wetting agents, emulsifying or suspending agents, sweetening, flavoring and perfuming agents.

Injectable preparations, for example, sterile injections or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P and isotonic sodium chloride solution. In addition, sterile, non-volatile oil can be conventionally employed as a solvent or suspending medium. For this purpose any non-volatile oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. In addition, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly (orthoesters) and poly (anhydrides). Depot injectable formulations are also prepared by entrapping the compound in liposomes or microemulsions that are compatible with body tissues.

Compositions for rectal or vaginal administration are preferably suppositories which can be prepared by mixing the compounds disclosed herein with suitable non-irrigating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders and granules. In such solid dosage forms, the active compound is mixed with at least one inert, pharmaceutically acceptable excipient or carrier such as sodium citrate or calcium phosphate and/or a) fillers or extenders such as starches, lactose, sucrose, glucose, mannitol, and silicic acid; b) binders such as carboxymethylcellulose, alginates, gelatin, polyvinyl pyrrolidone, sucrose and *acacia*; c) humectants such as glycerol; d)

disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft or hard-filled gelatin capsules using such excipients as lactose or milk sugar as well as high molecular polyethylene glycols and the like. The solid dosage forms of tablets, dragees, capsules, pills and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills and granules can be prepared with coatings and shells such as enteric coatings, release controlling coatings and other coatings well known in the pharmaceutical formulating art. In such solid dosage forms, the active compound may be mixed with at least one inert diluent such as sucrose, lactose or starch. Such dosage forms may also comprise, as is normal practice, addition substances other than inert diluents, e.g., tableting lubricants and other tableting aids such as magnesium stearate and microcrystalline cellulose. In the case of capsules, tablets and pills, the dosage forms may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active ingredient is admixed under sterile conditions with a pharmaceutically acceptable carrier and any needed preservatives or buffers as may be required. Ophthalmic formulation, eardrops, and eyedrops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The term "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration and the rate of excretion of the specific compound employed; the duration of treatment; drug used in combination or coincidental with the specific compound employed, and like factors well known in the medical art.

The amount of the compounds disclosed herein that may be combined with the carrier materials to produce a composition in a single dosage form will vary depending upon the host treated, the particular mode of administration. In some embodiments, the compositions should be formulated so that a dosage of between 0.01-200 mg/kg body weight/day of the inhibitor can be administered to a patient receiving these compositions.

Compounds disclosed herein can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compounds disclosed herein can be combined with known cytotoxic agents, single transduction inhibitors or other anti-cancer agents, as well as with admixtures and combinations thereof. As used herein, additional therapeutic agents that are normally administered to treat a particular diseases, or condition, are known as "appropriate for the disease, or condition, being treated". As used herein, "additional therapeutic agent" refers to include chemotherapeutic agents and other anti-proliferative agents. For example, chemotherapeutic agents and other anti-proliferative agents may be combined with compounds disclosed herein to treat proliferative diseases or cancer.

Examples of chemotherapeutic agents or other anti-proliferative agents include histone deacetylase (HDAC) inhibitors including, but not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO2005/030705, and WO 2005/092899, and demethylating agents including, but not limited to 5-aza-2'-deoxycytidine (5-aza-dC), azacitidine (Vidaza), decitabine (Decitabine) and those described in U.S. Pat. Nos. 6,268,137, 5,578,716, 5,919,772, 6,054,439, 6,184,211, 6,020,318, 6,066,625, 6,506,7356,221,849, 6,953,783, and U.S. Ser. No. 11/393,380.

In another embodiment disclosed herein, for example, chemotherapeutic agents or other anti-proliferative agents may be combined with the compounds disclosed herein to treat proliferative diseases and cancer. Examples of known chemotherapeutic agents include, but are not limited to, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere, etc.), platinum derivatives, biological response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (Mechlorethamine, Chlorambucil, Cyclophosphamide, Melphalan, Ifosfamide), antimetabolites (Methotrexate, Pemetrexed, etc.), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosourea (Carmustine, Lomustine), inorganic ions (Cisplatin, Carboplatin), cell cycle inhibitors (KSP mitotic kinesin inhibitors, CENP-E and CDK inhibitors), enzymes (Asparaginase), and hormones (Tamoxifen, Leuprolide, Flutamide and Megestrol), gleevec, adriamycin, dexamethasone, cyclophosphamide, antiangiogenic agents (Avastin and others), kinase inhibitors (Imatinib, SUTENT®, NEXAVAR®, ERBITUX®, HERCEPTIN®, TARCEVA®, IRESSA® and others), agents inhibiting or activating cancer pathways such as the mTOR, HIF (hypoxia inducible factor) pathways and others. For a more comprehensive discussion of updated cancer therapies see, http://www.nci.nih.gov/, a list of the FAD approved oncology drugs at http://www.fda.gov/cder/cancer/druglist-rame.htm, and The Merck Manual, Eighteenth Ed. 2006, the entire contents of which are hereby incorporated by reference.

In another embodiment, the compounds disclosed herein can be combined with cytotoxic anti-cancer agents. Examples of such agents can be found in the 13th edition of the Merck Index (2001). These agents include, but are not limited to, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozotocin, tamoxifen, thioguanine, topotecan, vinblastine, vincristine, and vindesine.

Other cytotoxic drugs suitable for use with the compounds disclosed herein include, but are not limited to, those compounds acknowledged to be used in the treatment of neoplastic diseases, such as those for example in Goodman et al., *The Pharmacological Basis of Therapeutics* (Ninth Edition, 1996, McGraw-Hill). These agents include, but are not limited to, aminoglutethimide, L-asparaginase, azathioprine, 5-azacytidine, cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-laspartate (PALA), plicamycin, semustine, teniposide, testosterone propionate, thiotepa, trimethylmelamine, uridine and vinorelbine.

Other cytotoxic anti-cancer agents suitable for use in combination with the compounds disclosed herein also include newly discovered cytotoxic principles. Some examples of cytotoxic principles include, but are not limited to, oxaliplatin, gemcitabine, capecitabine, macrolide and its natural or synthetic derivatives, temozolomide (Quinn et al., *J. Clin. Oncology*, 2003, 21(4), 646-651), tositumomab (BEXXAR®), trabedectin (Vidal et al., *Proceedings of the American Society for Clinical Oncology*, 2004, 23, abstract, 3181), and the inhibitors of the kinesin spindle protein Eg5 (Wood et al., *Curr. Opin. Pharmacol.* 2001, 1, 370-377).

In another embodiment, the compounds disclosed herein can be combined with other signal transduction inhibitors. Of particular interest are signal transduction inhibitors which target the EGFR family, such as EGFR, HER-2 and HER-4 (Raymond et al., *Drugs*, 2000, 60 (Suppl. 1), 15-23; Harari et al., *Oncogene*, 2000, 19 (53), 6102-6114), and their respective ligands. Examples of such agents include, but are not limited to, antibody therapies such as trastuzumab, Erbitux, and Pertuzumab. Examples of such therapies also include, but are not limited to, small-molecule kinase inhibitors such as Gefitinib, Erlotinib, Lapatinib, Canertinib (CI1033), and AEE788 (Traxler et al., *Cancer Research*, 2004, 64, 4931-4941).

In another embodiment, the compounds disclosed herein can be combined with other signal transduction inhibitors targeting receptor kinase of the split-kinase domain families (VEGFR, FGFR, PDGFR, flt-3, c-kit, c-fms, and the line), and their respective ligands. These agents include, but are not limited to, antibodies such as bevacizumab. These agents also include, but are not limited to, small-molecule inhibitors such as Imanitib, Dasatinib, Nilotinib, Vandetanib, Vatalanib (PTK787/ZK222584) (Wood et al., *Cancer Res.* 2000, 60(8), 2178-2189), Telatinib/BAY-57-9352, BMS-690514, BMS-540215, Axitinib/AG-013736, Motesanib/AMG706, SUTENT®/Sunitinib/SU-11248, ZD-6474 (Hennequin et al., *92nd AACR Meeting*, New Orleans, Mar. 24-28, 2001, abstract 3152), KRN-951 (Taguchi et al., *95th AACR Meeting*, Orlando, Fla., 2004, abstract 2575), CP-547, 632 (Beebe et al., *Cancer Res.* 2003, 63, 7301-7309), CP-673,451 (Roberts et al., *Proceedings of the American Association of Cancer Research*, 2004, 45, abstract 3989), CHIR-258 (Lee et al., *Proceedings of the American Association of Cancer Research*, 2004, 45, abstract 2130), and MLN-518 (Shen et al., *Blood*, 2003, 102, 11, abstract 476).

In another embodiment, the compounds disclosed herein can be combined with inhibitors of histone deacetylase. Examples of such reagents include, but are not limited to, suberoylanilide hydroxamic acid (SAHA), LAQ-824 (Ottmann et al., *Proceedings of the American Society for Clinical Oncology*, 2004, 23, abstract 3024), LBH-589 (Beck et al., *Proceedings of the American Society for Clinical Oncology*, 2004, 23, abstract 3025), MS-275 (Ryan et al., *Proceedings of the American Association of Cancer Research*, 2004, 45, abstract 2452), FR-901228 (Piekarz et al., *Proceedings of the American Society for Clinical Oncology*, 2004, 23, abstract 3028) and MGCDOI 03 (U.S. Pat. No. 6,897,220).

In another embodiment, the compounds disclosed herein can be combined with other anti-cancer agents such as proteasome inhibitors, and m-TOR inhibitors. These include, but are not limited to, bortezomib (Mackay et al., *Proceedings of the American Society for Clinical Oncology*, 2004, 23, Abstract 3109), and CCI-779 (Wu et al., *Proceedings of the American Association of Cancer Research*, 2004, 45, abstract 3849). The compounds disclosed herein can be combined with other anti-cancer agents such as topoisomerase inhibitors, including but not limited to camptothecin.

Those additional agents may be administered separately from the pharmaceutical composition comprising the compounds disclosed herein, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the pharmaceutical compositions disclosed herein will be no more than the amount that would normally be administered in a pharmaceutical composition comprising that therapeutic agent as the only active agent. In other embodiments, the amount of additional therapeutic agent in the presently disclosed pharmaceutical compositions will range from about 50% to 100% of the amount normally present in a composition comprising that agent as the only therapeutically active agent. In those pharmaceutical compositions which comprise an additional therapeutic agent, that additional therapeutic agent and the compound disclosed herein may act synergistically.

Uses of the Compounds and Compositions of the Invention

The invention features of the pharmaceutical compositions that include a compound of formula (I) or a compound listed herein, or a stereoisomer, a geometric isomer, a tautomer, an N-oxide, a hydrate, a solvate, a metabolite, a pharmaceutically acceptable salt or a prodrug thereof, and a pharmaceutically acceptable carrier, adjuvant or vehicle. The compound or the pharmaceutical composition containing the compound disclosed herein can be effectively used in the manufacture of a medicament for preventing, managing, treating or lessening the severity of a proliferative disorder, atherosclerosis or lung fibrosis in a patient. The amount of the compound in the medicament disclosed herein is effective to detectably inhibit a protein kinase, such as EGFR inhibitory activity. The compounds disclosed herein are useful in therapy as antineoplasia agents or to minimize deleterious effects of EGFR.

The compounds disclosed herein would be useful for, but not limited to, the prevention or treatment of proliferative diseases, conditions, or disorders in a patient by administering to the patient with a therapeutically effective amount of a compound or a pharmaceutical composition disclosed herein. Such diseases, conditions, or disorders include cancer, particularly metastatic cancer, non-small cell lung cancer and epidermoid carcinoma.

The compounds disclosed herein would be useful for the treatment of neoplasia including cancer and metastasis, further including, but not limited to, carcinoma such as cancer of the epidermis, bladder, breast, colon, kidney, liver, lung (including small cell lung cancer), esophageal, gallbladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell lymphoma, Hodgkin's lymphoma, non-Hodgkin's lymphoma, hairy cell leukemia and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection; diabetic retinopathy; retrolental fibroplasia and neovascular glaucoma; retinal ischemia; vitreous hemorrhage; ulcerative diseases such as gastric ulcer; pathological, but non-malignant, conditions such as hemangiomas, including infantile hemangioendothelioma, angiofibroma of the nasopharynx and avascular necrosis of bone; and disorders of the female reproductive system such as endometriosis. The compounds are also useful for the treatment of edema and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds herein are also useful in the reduction of metastasis of a tumor in a patient.

Besides being useful for human treatment, these compounds are also useful for veterinary treatment of companion animals, exotic animals and farm animals, including mammals, rodents, and the like. In other embodiments, animals include horses, dogs and cats. As used herein, the compounds disclosed herein include the pharmaceutically acceptable derivatives thereof.

Where the plural form is used for compounds, salts, and the like, this is taken to refer to also a single compound, salt, and the like.

The treatment method that includes administering a compound or pharmaceutical composition disclosed herein can further include administering to the patient an additional therapeutic agent (combination therapy) selected from a chemotherapeutic or anti-proliferative agent, and an anti-inflammatory agent, wherein the additional therapeutic agent is appropriate for the disease being treated and the additional therapeutic agent is administered together with a compound or pharmaceutical composition disclosed herein as a single dosage form or separately from the compound or pharmaceutical composition as part of a multiple dosage form. The additional therapeutic agent may be administered at the same time as the compound disclosed herein or at a different time.

The invention also features a method of inhibiting the growth of a cell that expresses EGFR, which includes contacting the cell with a compound or pharmaceutical composition disclosed herein, thereby causing inhibition of growth of the cell. Examples of a cell whose growth can be inhibited include a epidermoid carcinoma cell, a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell and a leukemia cell.

Provided herein is a method of inhibiting EGFR kinase activity in a biological sample that includes contacting the biological sample with a compound or pharmaceutical composition disclosed herein. The term "biological sample" refers to a sample outside a living organism and includes, without limitation, cell cultures or extracts thereof; biopsied materials obtained from a mammal or extracts thereof; and blood, saliva, urine, feces, semen, tears, or other body liquids or extracts thereof. Inhibition of kinase activity, particularly EGFR kinase activity, in a biological sample is useful for a variety of purposes known to one of skill in the art. Examples of such purposes include, but are not limited to, blood transfusion, organ-transplantation, biological specimen storage and biological assays.

In certain embodiments disclosed herein, an "effective amount" or "effective dose" of the compound or pharmaceutical composition is that amount effective for treating or lessening the severity of one or more of the aforementioned disorders. The compounds and pharmaceutical compositions, according to the method disclosed herein, may be administered using any amount and any route of administration effective for treating or lessening the severity of the disorder or disease. The exact amount required will vary from subject to subject, depending on the species, age, and the general condition of the subject, the severity of the infection, the particular agent, its mode of administration, and the like. A compound or pharmaceutical composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099,562, 5,886,026 and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene-vinyl acetate, and mixtures thereof. The coatings may optionally be further covered by a suitable topcoat of fluorodimethicone, polysaccharide enzymes, polyethylene glycol, phospholipids or pharmaceutical combinations thereof to impart controlled release characteristics into the composition. Implantable devices coated with a compound disclosed herein are another embodiment disclosed herein. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

Generally, the compounds disclosed herein may be prepared by methods described herein, wherein the substituents are as defined for Formulas (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope of the invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were obtained with $CDCl_3$, $d_6$-DMSO, $CD_3OD$ or $d_6$-acetone solution (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), and dt (doublet of triplets). Coupling constants, when given, are reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers described above were equipped with Agilent Zorbax SB-C18 (2.1×30 mm, 5 μm column). Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were shown in Table 1:

TABLE 1

| Time (min) | A (CH$_3$CN, 0.1% HCOOH) | B (H$_2$O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron). The run time was 10 min. The flow rate was 0.6 mL/min. The elution was performed with a gradient of 5 to 95% phase A (0.1% formic acid in CH$_3$CN) in phase B (0.1% formic acid in H$_2$O). Column was operated at 40° C.

The following abbreviations are used throughout the specification:
Me methyl
Et ethyl
n-Pr n-propyl
HPLC high performance liquid chromatography
H$_2$O water
MeOH, CH$_3$OH methanol
EtOH ethanol
HCOOH formic acid
CH$_3$CN, MeCN acetonitrile
Fe iron
Pd/C palladium on carbon
DCC dicyclohexylcarbodiimide
DIEA, DIPEA N,N-diisopropylethylamine
EDCI 1-(3-dimethylaminopropyl)-3-ethylcarbodiimide
HATU 2-(7-azabenzotriazole-1-yl)-N,N,N',N'-tetramethyluronium hexafluorophosphate
Et$_3$N, TEA, NEt$_3$ triethylamine
NaH sodium hydride
NaOH sodium hydroxide
KOH potassium hydroxide
HCl hydrogen chloride
H$_2$SO$_4$ sulfuric acid
TFA trifluoroacetic acid
THF tetrahydrofuran
DMF N,N-dimethylformamide
conc. HCl concentrated hydrochloric acid
g gram
mg milligram
mmol millimole
h hour
min minute
mL, ml milliliter
r.t, RT room temperature
Rt retention time
DCM, CH$_2$Cl$_2$ dichloromethane
CHCl$_3$ chloroform, trichloromethane
DMSO dimethyl sulfoxide
CDCl$_3$ deuterated chloroform
CD$_3$OD Methanol-d
DMAC dimethylacetamide

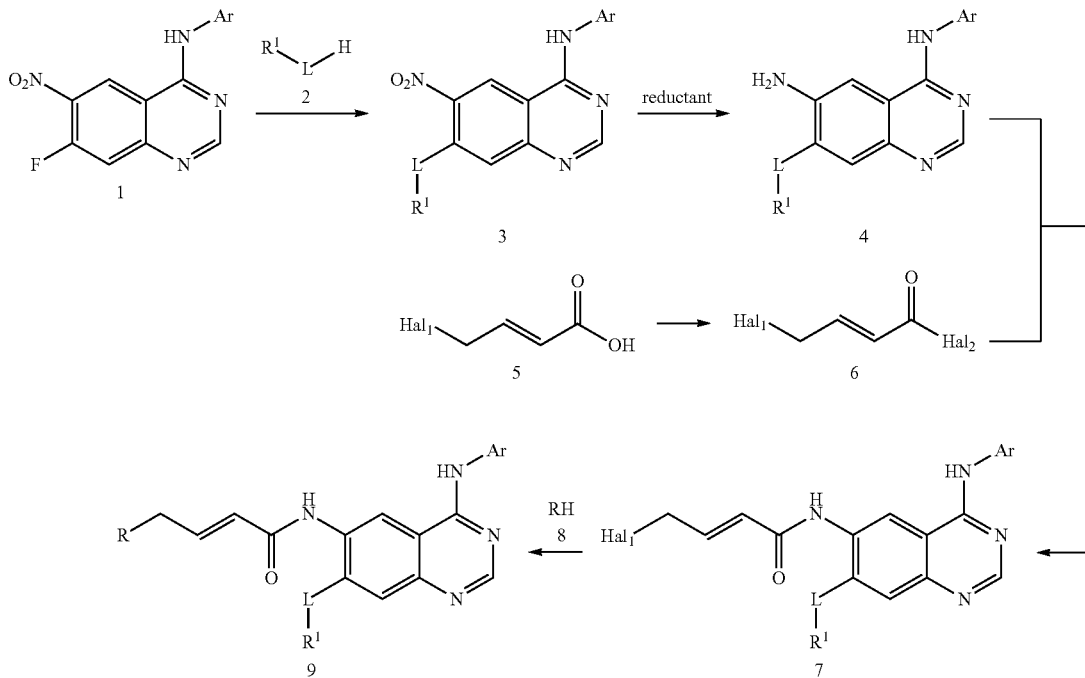

Scheme 1

Compound 9 can be prepared by the process illustrated in Scheme 1, wherein each Ar, R, R$^1$ and L is as defined herein. Each Hal$_1$ is Cl, Br or I, and Hal$_2$ is Cl or Br, wherein Hal$_1$ and Hal$_2$ may be same or different. Substitution reaction of compound 1 with compound 2 to afford compound 3 in the presence of a base (such as sodium hydride, sodium hydroxide or potassium hydroxide, etc.). Compound 3 can be reduced to give compound 4 with a reductant (such as iron powder, Raney Ni or Pd/C, etc.). Compound 5 can be converted to compound 6 by substitution reaction under a certain condition (for example, in the presence of oxalyl chloride, thionyl chloride, NBS or bromine, etc). Condensation reaction of compound 4 with compound 6 can yield compound 7 in the presence of a base (such as triethylamine or N,N-diisopropylethylamine, etc.). Then compound 7 can react with compound 8 to afford compound 9 by substitution reaction in the presence of a base (such as N,N-diisopropylethylamine or sodium hydride, etc.).

sodium hydroxide or potassium hydroxide, etc.). Condensation reaction of compound 4 with compound 11 can give compound 12 in the presence of a condensation agent (such as DCC, EDCI or HATU, etc.). Compound 8 can react with compound 13 to afford compound 14 by substitution reaction in the presence of base 1 (such as triethylamine, N,N-diisopropylethylamine, pyridine or 4-dimethylaminopyridine, etc.). Then the protecting group of compound 14

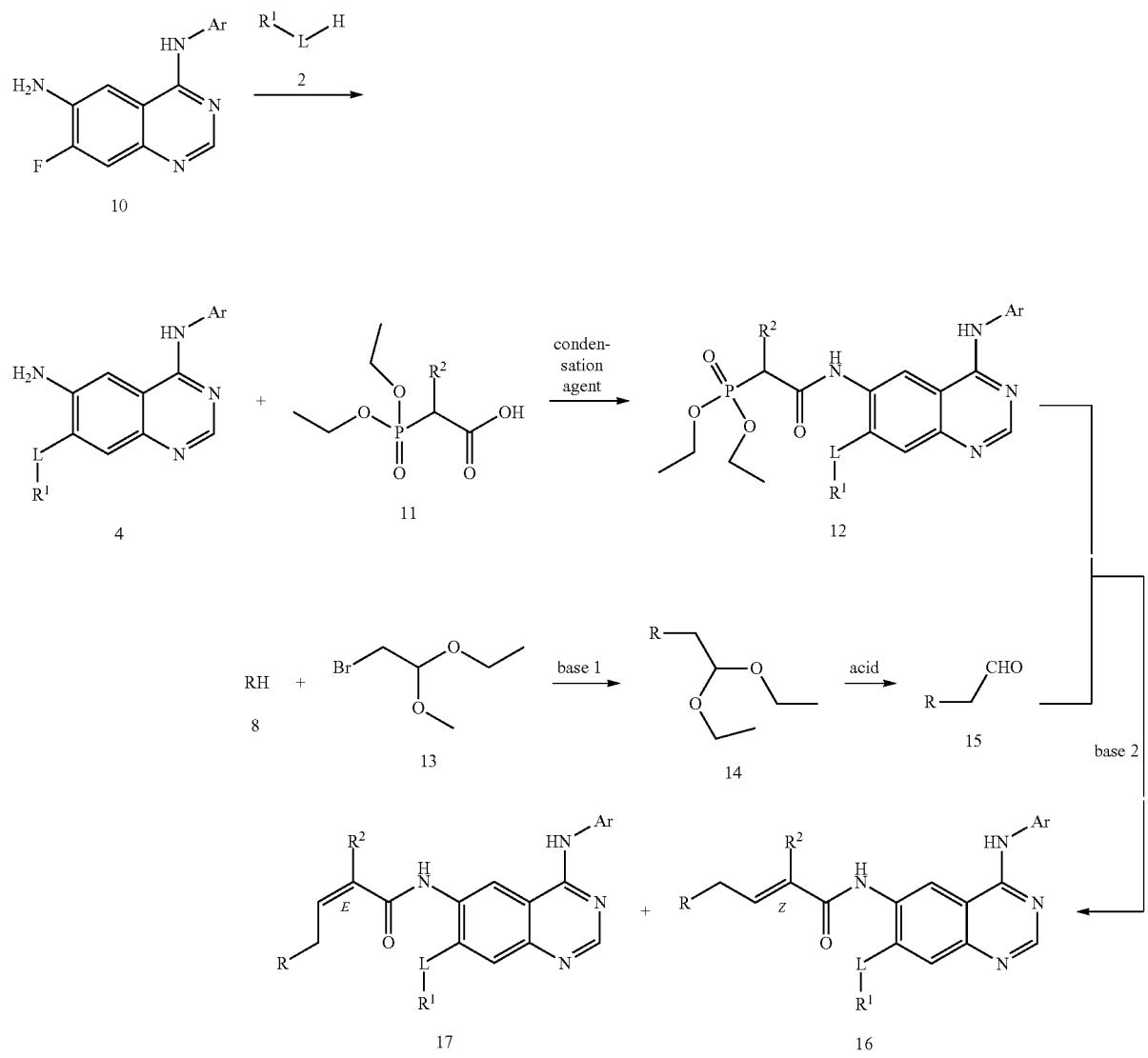

Scheme 2

Compound 16 and compound 17 can be prepared by the process illustrated in Scheme 2, wherein each Ar, R, $R^1$, $R^2$ and L is as defined herein. Compound 10 can be prepared according to the literature *J. Med. Chem.* 2009, 52: 6880-6888. Compound 10 can react with compound 2 to give compound 4 by substitution reaction in the presence of a base (such as potassium tert-butoxide, sodium hydride, can be removed to give compound 15 in the presence of an acid (such as hydrochloric acid, sulfuric acid or trifluoroacetic acid, etc.). Horner-Wadsworth-Emmons reaction of compound 12 with compound 15 can yield cis- and trans-isomers 16 and 17 in the presence of base 2 (such as potassium tert-butoxide, sodium hydride, sodium hydroxide or potassium hydroxide, etc.).

Scheme 3

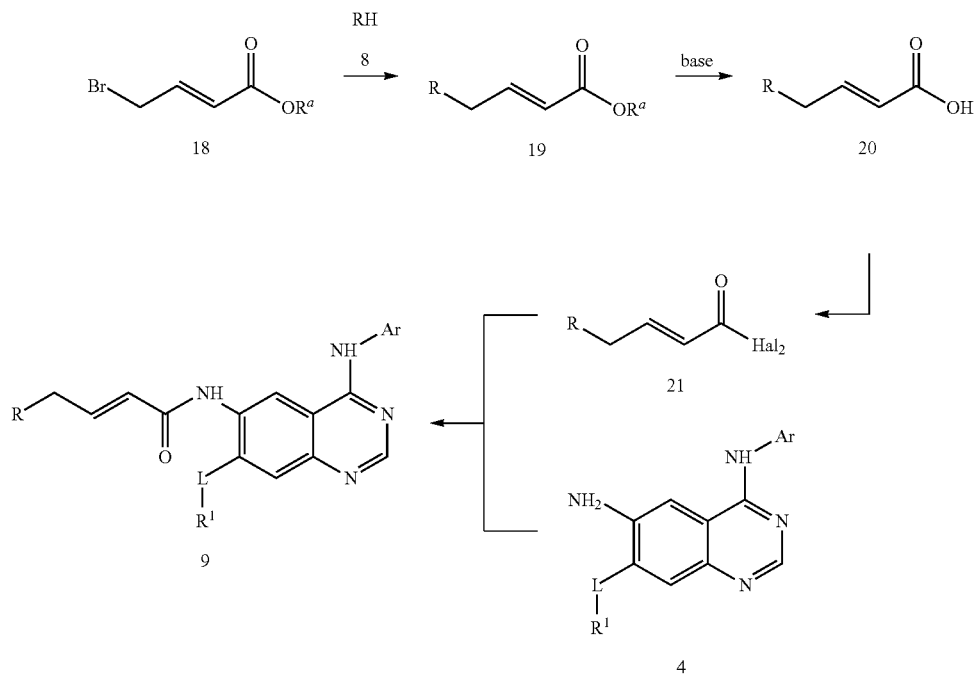

Compound 9 can be prepared by the process illustrated in Scheme 3, wherein each Ar, R, $R^1$ and L is as defined herein, $R^a$ is methyl or ethyl, and $Hal_2$ is Cl or Br. Compound 18 can be converted to compound 19 by reacting with compound 8 in the presence of a base (such as triethylamine and N,N-diisopropylethylamine, ect.). Compound 19 can be hydrolyzed to give compound 20 in the presence of a base (such as sodium hydroxide and potassium hydroxide, ect.). Compound 20 can be then converted to compound 21 under a certain condition (for example, in the presence of oxalyl chloride, thionyl chloride, NBS or bromine, etc). Reaction of compound 4 with compound 21 can afford compound 9 in the presence of a base (such as potassium carbonate or sodium carbonate, etc.).

Scheme 4

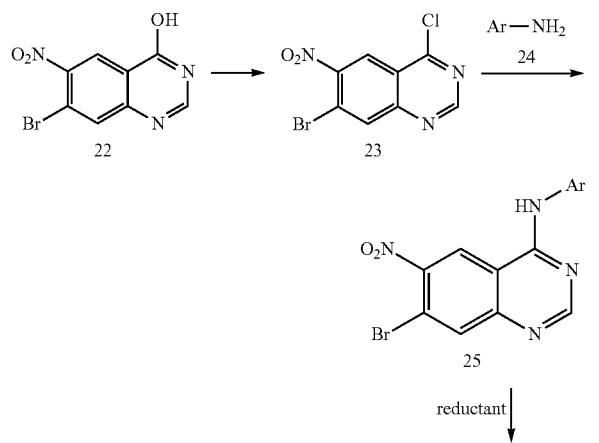

-continued

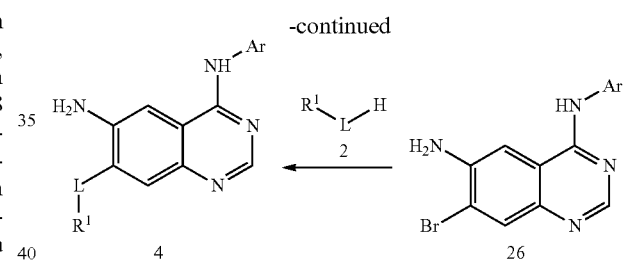

Compound 4 can be prepared by the process illustrated in Scheme 4, wherein each Ar, $R^1$ and L is as defined herein. Compound 22 can be converted to compound 23 under a certain condition (for example, in the presence of phosphorus oxychloride or thionyl chloride, etc). Compound 23 can react with compound 24 directly or in the presence of a base (such as triethylamine and N,N-diisopropylethylamine, ect.) to afford compound 25. Compound 25 can be then reduced to give compound 26 with a reductant (such as iron powder, Raney Ni or Pd/C, etc.). Coupling reaction of compound 26 with compound 2 can afford compound 4 in the presence of a catalyst (such as Pd(dppf)$Cl_2$, etc.) and a base (such as triethylamine, etc.).

The following examples disclosed herein are presented to further describe the invention. However, these examples should not be used to limit the scope of the invention.

EXAMPLES

Example 1

(E)-N-(4-((3-Chloro-4-fluorophenyl)amino)-7-methoxyquinazolin-6-yl)-4-((4aR,7aS)-tetrahydro-2H-[1,4]dioxin[2,3-c]pyrrol-6(3H)-yl)but-2-enamide

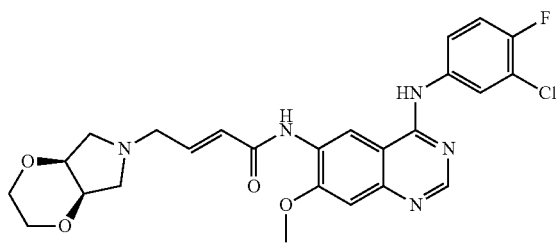 [SMILES: COc1cc2ncnc(Nc3ccc(F)c(Cl)c3)c2cc1NC(=O)/C=C/CN1C[C@@H]2OCCO[C@@H]2C1]

Step 1) N-(3-chloro-4-fluorophenyl)-7-methoxy-6-nitroquinazolin-4-amine

A solution of N-(3-chloro-4-fluorophenyl)-7-fluoro-6-nitroquinazolin-4-amine (10.00 g, 29.8 mmol) and sodium methanolate (2.80 g, 51.8 mmol) in methanol (150 mL) was heated to 70° C. and stirred for 4.0 hours. The reaction mixture was then cooled to 25° C. The resulting mixture was poured into ice water (500 mL), and a yellow solid precipitated out. The mixture was filtered and the filter cake was dried under vacuum to give the title compound as a yellow solid (9.00 g, 86.9%). The compound was characterized by the following spectroscopic data: MS (ESI, pos.ion) m/z: 349.1 [M+1]$^+$; and $^1$H NMR (400 MHz, DMSO-d$_6$) δ: 11.60 (s, 1H), 9.55 (s, 1H), 8.08 (dd, J$_1$=6.6 Hz, J$_2$=2.4 Hz, 1H), 7.90 (s, 1H), 7.76-7.71 (m, 1H), 7.58 (s, 1H), 7.55 (t, J=9.4 Hz, 1H), 4.10 (s, 3H).

Step 2) N$^4$-(3-chloro-4-fluorophenyl)-7-methoxyquinazoline-4,6-diamine

To a solution of N-(3-chloro-4-fluorophenyl)-7-methoxy-6-nitroquinazolin-4-amine (9.00 g, 25.9 mmol) in ethanol (100 mL) were added iron powder (14.50 g, 259.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethanol (50 mL) and filtered. The filter cake was dried under vacuum to give the title compound as a yellow solid (6.00 g, 73.0%). The compound was characterized by the following spectroscopic data: MS (ESI, pos.ion) m/z: 319.1 [M+1]$^+$.

Step 3) (E)-4-bromobut-2-enoyl chloride

To a solution of 4-bromocrotonic acid (2.47 g, 15.0 mmol) and DMF (0.05 mL) in DCM (60 mL) was added oxalyl chloride (4.19 g, 33.0 mmol) dropwise at 0° C. The reaction mixture was stirred at 0° C. for 3.0 hours, and then concentrated in vacuo. The residue was stored in a refrigerator for the next step.

Step 4) (E)-4-bromo-N-(4-((3-chloro-4-fluorophenyl)amino)-7-methoxyquinazolin-6-yl)but-2-enamide To a solution of N$^4$-(3-chloro-4-fluorophenyl)-7-methoxyquinazoline-4,6-diamine (4.00 g, 12.6 mmol) and TEA (6.0 mL, 37.8 mmol) in anhydrous tetrahydrofuran (80 mL) was added (E)-4-bromobut-2-enoyl chloride (2.74 g, 15.1 mmol) slowly at 0° C. The reaction mixture was then heated to 25° C. and stirred for 2.0 hours. The resulting mixture was poured into water (100 mL) and extracted with DCM (50 mL×3). The combined organic phases were dried over anhydrous Na$_2$SO$_4$, filtered and concentrated in vacuo. The residue was triturated with DCM (30 mL) and filtered. The filter cake was dried under vacuum to give the title compound as a brownish yellow solid (2.00 g, 34.5%). The compound was characterized by the following spectroscopic data: MS (ESI, pos.ion) m/z: 465.1 [M+1]$^+$.

Step 5) (E)-N-(4-((3-chloro-4-fluorophenyl)amino)-7-methoxyquinazolin-6-yl)-4-((4aR,7aS)-tetrahydro-2H-[1,4]dioxin[2,3-c]pyrrol-6(3H)-yl)but-2-enamide To a solution of (E)-4-bromo-N-(4-((3-chloro-4-fluorophenyl)amino)-7-methoxyquinazolin-6-yl)but-2-enamide (0.50 g, 1.1 mmol) and diisopropylethylamine (0.6 mL, 3.2 mmol) in N,N-dimethylacetamide (10 mL) was added (4aR,7aS)-hexahydro-2H-[1,4]dioxino[2,3-c]pyrrole (0.42 g, 3.2 mmol) at 25° C., and the reaction mixture was then stirred at 25° C. for 5.0 hours. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.30 g, 54.5%). The compound was characterized by the following spectroscopic data: MS (ESI, pos.ion) m/z: 514.1 [M+1]$^+$; and $^1$H NMR (400 MHz, DMSO-d$_6$) δ: 10.60 (s, 1H), 9.35 (s, 1H), 8.90 (s, 1H), 8.08 (dd, J$_1$=6.6 Hz, J$_2$=2.4 Hz, 1H), 7.76-7.70 (m, 1H), 7.58 (s, 1H), 7.55 (t, J=8.4 Hz, 1H), 6.75-6.65 (m, 1H), 6.63 (d, J=16.2 Hz, 1H), 4.10 (s, 3H), 3.78 (t, J=6.2 Hz, 4H), 3.26 (t, J=4.4 Hz, 2H), 3.20 (dd, J$_1$=7.8 Hz, J$_2$=2.6 Hz, 2H), 2.20 (d, J=4.6 Hz, 4H).

Example 2

(E)-N-(4-((3-Chloro-4-fluorophenyl)amino)-7-methoxyquinazolin-6-yl)-4-((4aS,7aS)-tetrahydro-2H-[1,4]dioxino[2,3-c]pyrrol-6(3H)-yl)but-2-enamide

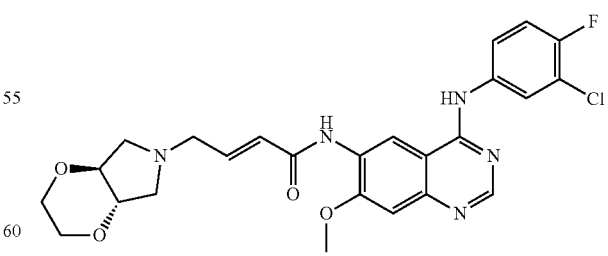

To a solution of (E)-4-bromo-N-(4-((3-chloro-4-fluorophenyl)amino)-7-methoxyquinazolin-6-yl)but-2-enamide (0.50 g, 1.1 mmol) and diisopropylethylamine (0.6 mL, 3.2 mmol) in N,N-dimethylacetamide (10 mL) was added (4aS,7aS)-hexahydro-2H-[1,4]dioxino[2,3-c]pyrrole (0.42 g, 3.2 mmol) at 25° C., and the reaction mixture was then stirred at 25° C. for 5.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a brownish yellow solid (0.35 g, 63.6%). The compound was characterized by the following spectroscopic data: MS (ESI, pos.ion) m/z: 514.1 [M+1]$^+$; and $^1$H NMR (400 MHz, DMSO-$d_6$) δ: 10.30 (s, 1H), 9.37 (s, 1H), 8.91 (s, 1H), 8.09 (dd, $J_1$=6.6 Hz, $J_2$=2.4 Hz, 1H), 7.78-7.72 (m, 1H), 7.59 (s, 1H), 7.56 (t, J=8.4 Hz, 1H), 6.75-6.67 (m, 1H), 6.64 (d, J=18.4 Hz, 1H), 4.10 (s, 3H), 3.78 (t, J=6.2 Hz, 4H), 3.26 (t, J=4.4 Hz, 2H), 3.20-3.12 (m, 2H), 2.20-2.12 (m, 4H).

Example 3

(E)-N-(4-((3-Chloro-4-fluorophenyl)amino)-7-ethoxyquinazolin-6-yl)-4-((4aR,7aS)-tetrahydro-2H-[1,4]dioxin[2,3-c]pyrrol-6(3H)-yl)but-2-enamide

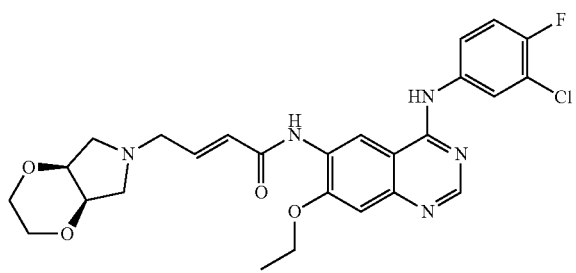 [SMILES: CCOc1cc2ncnc(Nc3ccc(F)c(Cl)c3)c2cc1NC(=O)/C=C/CN1C[C@@H]2OCCO[C@@H]2C1]

Step 1) N-(3-chloro-4-fluorophenyl)-7-ethoxy-6-nitroquinazolin-4-amine

A mixture of N-(3-chloro-4-fluorophenyl)-7-fluoro-6-nitroquinazolin-4-amine (10.00 g, 29.8 mmol) and sodium ethanolate (5.00 g, 73.5 mmol) in methanol (150 mL) was heated to 70° C. and stirred for 4.0 hours. The reaction mixture was then cooled to 25° C. The resulting mixture was poured into ice water (500 mL), and a yellow solid precipitated out. The mixture was filtered, and the filter cake was dried under vacuum to give the title compound as a yellow solid (9.20 g, 85.4%). The compound was characterized by the following spectroscopic data: MS (ESI, pos.ion) m/z: 363.1 [M+1]$^+$; and $^1$H NMR (400 MHz, DMSO-$d_6$) δ: 9.02 (s, 1H), 8.89 (d, J=4.6 Hz, 1H), 8.82 (s, 1H), 7.84 (dd, $J_1$=6.8 Hz, $J_2$=2.6 Hz, 1H), 7.65-7.57 (m, 1H), 7.44 (s, 1H), 7.09 (t, J=8.8 Hz, 1H), 4.31 (q, J=6.8 Hz, 2H), 1.56 (t, J=7.2 Hz, 3H).

Step 2) $N^4$-(3-chloro-4-fluorophenyl)-7-ethoxyquinazoline-4,6-diamine

To a solution of N-(3-chloro-4-fluorophenyl)-7-ethoxy-6-nitroquinazolin-4-amine (9.00 g, 24.8 mmol) in ethanol (100 mL) were added iron powder (14.50 g, 259.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethanol (50 mL) and filtered. The filter cake was dried under vacuum to give the title compound as a yellow solid (7.00 g, 84.8%). The compound was characterized by the following spectroscopic data: MS (ESI, pos.ion) m/z: 333.1 [M+1]$^+$.

Step 3) (E)-4-bromo-N-(4-((3-chloro-4-fluorophenyl)amino)-7-ethoxyquinazolin-6-yl)but-2-enamide To a solution of $N^4$-(3-chloro-4-fluorophenyl)-7-ethoxyquinazoline-4,6-diamine (2.00 g, 6.0 mmol) and TEA (3.0 mL, 18.9 mmol) in anhydrous tetrahydrofuran (40 mL) was added (E)-4-bromobut-2-enoyl chloride (1.21 g, 6.6 mmol) slowly at 0° C. The reaction mixture was then heated to 25° C. and stirred for 2.0 hours. The resulting mixture was poured into water (100 mL) and extracted with DCM (50 mL×3). The combined organic phases were dried over anhydrous $Na_2SO_4$, filtered and concentrated in vacuo. The residue was triturated with DCM (30 mL) and filtered. The filter cake was dried under vacuum to give the title compound as a brownish yellow solid (1.00 g, 33.7%). The compound was characterized by the following spectroscopic data: MS (ESI, pos.ion) m/z: 479.1 [M+1]$^+$.

Step 4) (E)-N-(4-((3-chloro-4-fluorophenyl)amino)-7-ethoxyquinazolin-6-yl)-4-((4aR,7aS)-tetrahydro 2H-[1,4]dioxino[2,3-c]pyrrol-6(3H)-yl)but-2-enamide To a solution of (E)-4-bromo-N-(4-((3-chloro-4-fluorophenyl)amino)-7-ethoxyquinazolin-6-yl)but-2-enamide (0.50 g, 1.0 mmol) and diisopropylethylamine (0.6 mL, 3.2 mmol) in N,N-dimethylacetamide (10 mL) was added (4aR,7aS)-hexahydro-2H-[1,4]dioxino[2,3-c]pyrrole (0.42 g, 3.2 mmol). The reaction mixture was then stirred at 25° C. for 5.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give a brownish yellow solid (0.26 g, 47.3%). The compound was characterized by the following spectroscopic data: MS (ESI, pos.ion) m/z: 528.2 [M+1]$^+$; and $^1$H NMR (400 MHz, DMSO-$d_6$) δ: 9.02 (s, 1H), 8.89 (d, J=4.6 Hz, 1H), 8.82 (s, 1H), 7.84 (dd, $J_1$=6.8 Hz, $J_2$=2.6 Hz, 1H), 7.65-7.57 (m, 1H), 7.44 (s, 1H), 7.09 (t, J=8.8 Hz, 1H), 6.72-6.68 (m, 1H), 6.58 (d, J=16.4 Hz, 1H), 4.31 (q, J=6.8 Hz, 2H), 3.78 (t, J=6.2 Hz, 4H), 3.26 (t, J=4.4 Hz, 2H), 3.20 (dd, $J_1$=7.8 Hz, $J_2$=2.6 Hz, 2H), 2.26-2.12 (m, 4H), 1.56 (t, J=7.2 Hz, 3H).

Example 4

(E)-N-(4-((3-Chloro-4-fluorophenyl)amino)-7-ethoxyquinazolin-6-yl)-4-((4aS,7aS)-tetrahydro-2H-[1,4]dioxino[2,3-c]pyrrol-6(3H)-yl)but-2-enamide

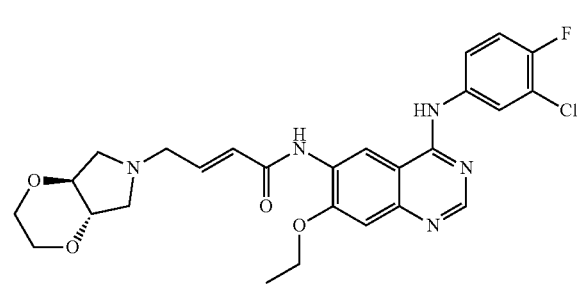 [SMILES: CCOc1cc2ncnc(Nc3ccc(F)c(Cl)c3)c2cc1NC(=O)/C=C/CN1C[C@@H]2OCCO[C@H]2C1]

To a solution of (E)-4-bromo-N-(4-((3-chloro-4-fluorophenyl)amino)-7-ethoxyquinazolin-6-yl)but-2-enamide (0.50 g, 1.0 mmol) and diisopropylethylamine (0.6 mL, 3.2 mmol) in DMAC (10 mL) was added (4aS,7aS)-hexahydro-2H-[1,4]dioxino[2,3-c]pyrrole (0.42 g, 3.2 mmol). The reaction mixture was then stirred at 25° C. for 5.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a brownish yellow solid (0.20 g, 36.3%). The compound was characterized by the following spectroscopic data: MS (ESI, pos.ion) m/z: 528.2 $[M+1]^+$; and $^1H$ NMR (400 MHz, DMSO-$d_6$) δ: 9.05 (s, 1H), 8.89 (d, J=4.6 Hz, 1H), 8.82 (s, 1H), 7.84 (dd, $J_1$=6.8 Hz, $J_2$=2.6 Hz, 1H), 7.65-7.57 (m, 1H), 7.44 (s, 1H), 7.11 (t, J=8.8 Hz, 1H), 6.75-6.67 (m, 1H), 6.64 (d, J=14.8 Hz, 1H), 4.24 (q, J=6.8 Hz, 2H), 3.68 (t, J=6.2 Hz, 4H), 3.36 (t, J=4.6 Hz, 2H), 3.20 (d, J=2.8 Hz, 2H), 2.21-2.09 (m, 4H), 1.56 (t, J=7.2 Hz, 3H).

Example 5

(E)-N-(4-((3-Chloro-4-fluorophenyl)amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide

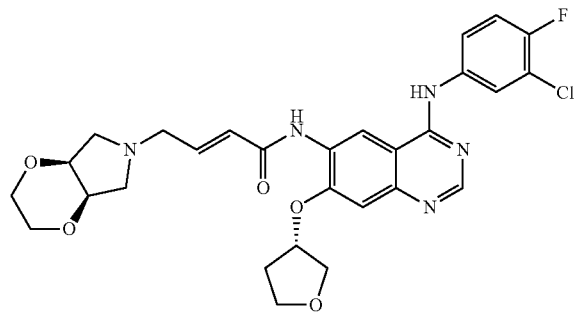 [SMILES: O=C(/C=C/CN1C[C@@H]2OCCO[C@@H]2C1)Nc1cc2c(Nc3ccc(F)c(Cl)c3)ncnc2cc1O[C@H]1CCOC1]

Step 1) (S)—N-(3-chloro-4-fluorophenyl)-6-nitro-7-((tetrahydrofuran-3-yl)oxy)quinazolin-4-amine To a solution of N-(3-chloro-4-fluorophenyl)-7-fluoro-6-nitroquinazolin-4-amine (10.00 g, 30.0 mmol) in anhydrous DMF (70 mL) was added potassium trimethylsilanolate (9.00 g, 60.0 mmol). After the mixture was stirred at 25° C. for 1.0 hour, to the mixture was added (S)-tetrahydrofuran-3-ol (5.00 g, 45.0 mmol). The reaction mixture was then stirred at 25° C. for 12.0 hours. The resulting mixture was poured into ice water (400 mL), and a brownish red solid precipitated out. The mixture was filtered, and the filter cake was dried under vacuum to give the title compound as a brownish red solid (6.00 g, 50.1%). The compound was characterized by the following spectroscopic data: MS (ESI, pos.ion) m/z: 405.1 $[M+1]^+$; and $^1H$ NMR (400 MHz, DMSO-$d_6$) δ: 9.04 (s, 1H), 8.89 (d, J=4.6 Hz, 1H), 8.62 (s, 1H), 7.86 (dd, $J_1$=8.2 Hz, $J_2$=2.4 Hz, 1H), 7.62-7.58 (m, 1H), 7.11 (t, J=8.2 Hz, 1H), 6.75-6.67 (m, 1H), 6.64 (d, J=16.8 Hz, 1H), 4.12-4.02 (m, 4H), 4.00-3.89 (m, 1H), 3.76-3.64 (m, 6H).

Step 2) (S)—$N^4$-(3-chloro-4-fluorophenyl)-7-((tetrahydrofuran-3-yl)oxy)quinazoline-4,6-diamine To a solution of (S)—N-(3-chloro-4-fluorophenyl)-6-nitro-7-((tetrahydrofuran-3-yl)oxy)quinazolin-4-amine (5.00 g, 12.4 mmol) in ethanol (150 mL) were added iron powder (13.80 g, 248.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethyl acetate (60 mL) and filtered. The filter cake was dried under vacuum to give the title compound as a yellow solid (3.50 g, 75.8%). The compound was characterized by the following spectroscopic data: MS (ESI, pos.ion) m/z: 375.2 $[M+1]^+$.

Step 3) (S,E)-4-bromo-N-(4-((3-chloro-4-fluorophenyl)amino)-7-((tetrahydrofuran-3-yl)oxy)quinazolin-6-yl)but-2-enamide To a solution of (S)—$N^4$-(3-chloro-4-fluorophenyl)-7-((tetrahydrofuran-3-yl)oxy)quinazoline-4,6-diamine (2.00 g, 5.3 mmol) and TEA (2.3 mL, 16.0 mmol) in anhydrous tetrahydrofuran (40 mL) was added (E)-4-bromobut-2-enoyl chloride (1.08 g, 5.9 mmol) slowly at 0° C. The reaction mixture was then heated to 25° C. and stirred for 2.0 hours. The resulting mixture was poured into water (100 mL) and extracted with DCM (50 mL×3). The combined organic phases were dried over anhydrous $Na_2SO_4$, filtered and concentrated in vacuo. The residue was triturated with DCM (30 mL) and filtered. The filter cake was dried under vacuum to give the title compound as a brownish yellow solid (1.00 g, 35.9%). The compound was characterized by the following spectroscopic data: MS (ESI, pos.ion) m/z: 521.1 $[M+1]^+$.

Step 4) (E)-N-(4-((3-chloro-4-fluorophenyl)amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide To a solution of (S,E)-4-bromo-N-(4-((3-chloro-4-fluorophenyl)amino)-7-((tetrahydrofuran-3-yl)oxy)quinazolin-6-yl)but-2-enamide (0.50 g, 1.0 mmol) and diisopropylethylamine (0.51 mL, 2.9 mmol) in N,N-dimethylacetamide (10 mL) was added (4aR,7aS)-hexahydro-2H-[1,4]dioxino[2,3-c]pyrrole (0.25 g, 1.9 mmol), and the reaction mixture was then stirred at 25° C. for 5.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a brownish yellow solid (0.17 g, 30.9%). The compound was characterized by the following spectroscopic data: MS (ESI, pos.ion) m/z: 570.2 $[M+1]^+$; and $^1H$ NMR (400 MHz, DMSO-$d_6$) δ: 9.06 (s, 1H), 8.92 (d, J=4.4 Hz, 1H), 8.69 (s, 1H), 7.86 (dd, $J_1$=6.4 Hz, $J_2$=2.8 Hz, 1H), 7.68-7.59 (m, 1H), 7.09 (t, J=8.8 Hz, 1H), 6.77-6.69 (m, 1H), 6.34 (d, J=16.2 Hz, 1H), 4.12-4.02 (m, 4H), 4.01-3.89 (m, 1H), 3.76-3.64 (m, 6H), 3.26 (t, J=4.4 Hz, 2H), 3.20 (dd, $J_1$=7.8 Hz, $J_2$=2.6 Hz, 2H), 2.26-2.12 (m, 4H).

Example 6

(E)-N-(4-((3-Chloro-4-fluorophenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide

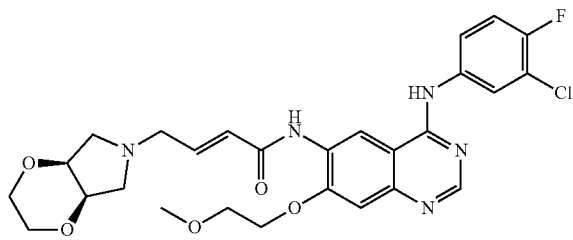 [SMILES: COCCOc1cc2ncnc(Nc3ccc(F)c(Cl)c3)c2cc1NC(=O)/C=C/CN1C[C@@H]2OCCO[C@@H]2C1]

Step 1) N-(3-chloro-4-fluorophenyl)-7-(2-methoxyethoxy)-6-nitroquinazolin-4-amine Sodium hydride (2.40 g, 60.0 mmol, 60% dispersion in mineral oil) was added into 2-methoxyethanol (80 mL) at 0° C. The mixture was heated to 30° C., and to the mixture was then added N-(3-chloro-4-fluorophenyl)-7-fluoro-6-nitroquinazolin-4-amine (10.00 g, 30.0 mmol). The reaction mixture was stirred at 30° C. for 7.0 hours. The resulting mixture was poured into ice water (200 mL), and a yellow solid precipitated out. The mixture was filtered. The filter cake was washed with water and dried under vacuum to give the title compound as a yellow solid (8.20 g, 70.2%). The compound was characterized by the following spectroscopic data: MS (ESI, pos.ion) m/z: 393.2 [M+1]$^+$; and $^1$H NMR (400 MHz, DMSO-d$_6$) δ: 10.30 (brs, 1H), 9.08 (s, 1H), 8.40 (s, 1H), 7.45-7.37 (m, 3H), 7.20 (t, J=8.4 Hz, 1H), 4.38-4.29 (m, 2H), 3.69-3.55 (m, 2H), 3.28 (s, 3H).

Step 2) N$^4$-(3-chloro-4-fluorophenyl)-7-(2-methoxyethoxy)quinazoline-4,6-diamine To a solution of N-(3-chloro-4-fluorophenyl)-7-(2-methoxyethoxy)-6-nitroquinazolin-4-amine (5.00 g, 12.8 mmol) in ethanol (150 mL) were added iron powder (14.34 g, 256.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethyl acetate (90 mL) and filtered. The filter cake was dried under vacuum to give the title compound as a yellow solid (4.00 g, 86.9%). The compound was characterized by the following spectroscopic data: MS (ESI, pos.ion) m/z: 363.1 [M+1]$^+$.

Step 3) (E)-4-bromo-N-(4-((3-chloro-4-fluorophenyl)amino)-7-(2-methoxyethoxy)quinazolin-6-yl)but-2-enamide To a solution of N$^4$-(3-chloro-4-fluorophenyl)-7-(2-methoxyethoxy)quinazoline-4,6-diamine (2.00 g, 5.5 mmol) and TEA (2.4 mL, 16.6 mmol) in anhydrous tetrahydrofuran (40 mL) was added (E)-4-bromobut-2-enoyl chloride (0.79 g, 6.1 mmol) slowly at 0° C. The reaction mixture was then heated to 25° C. and stirred for 2.0 hours. The resulting mixture was poured into water (100 mL) and extracted with DCM (70 mL×3). The combined organic phases were dried over anhydrous Na$_2$SO$_4$, filtered and concentrated in vacuo. The residue was triturated with DCM (20 mL) and filtered. The filter cake was dried under vacuum to give the title compound as a brownish yellow solid (1.20 g, 42.9%). The compound was characterized by the following spectroscopic data: MS (ESI, pos.ion) m/z: 509.1 [M+1]$^+$.

Step 4) (E)-N-(4-((3-chloro-4-fluorophenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-fluorophenyl)amino)-7-(2-methoxyethoxy)quinazolin-6-yl)but-2-enamide (0.50 g, 1.0 mmol) and diisopropylethylamine (0.55 mL, 2.9 mmol) in DMAC (10 mL) was added (4aR,7aS)-hexahydro-2H-[1,4]dioxino[2,3-c]pyrrole (0.26 g, 2.0 mmol). The reaction mixture was then stirred at 25° C. for 5.0 hours. The resulting mixture was poured into water (70 mL) and extracted with DCM (50 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.15 g, 27.8%). The compound was characterized by the following spectroscopic data: MS (ESI, pos.ion) m/z: 558.2 [M+1]$^+$; and $^1$H NMR (400 MHz, DMSO-d$_6$) δ: 9.30 (brs, 1H), 9.08 (s, 1H), 8.40 (s, 1H), 7.45-7.37 (m, 3H), 7.20 (t, J=8.4 Hz, 1H), 6.67-6.59 (m, 1H), 6.32 (d, J=18.2 Hz, 1H), 4.38-4.29 (m, 2H), 3.79-3.55 (m, 6H), 3.28 (s, 3H), 3.26-3.21 (m, 4H), 3.20 (dd, J$_1$=7.8 Hz, J$_2$=2.6 Hz, 2H), 3.12-3.06 (m, 2H).

Example 7

(E)-N-(4-((3-Chloro-4-fluorophenyl)amino)-7-(2,2,2-trifluoroethoxy)quinazolin-6-yl)-4-((4aR,7aS)-tetrahydro-2H-[1,4]dioxino[2,3-c]pyrrol-6(3H)-yl)but-2-enamide

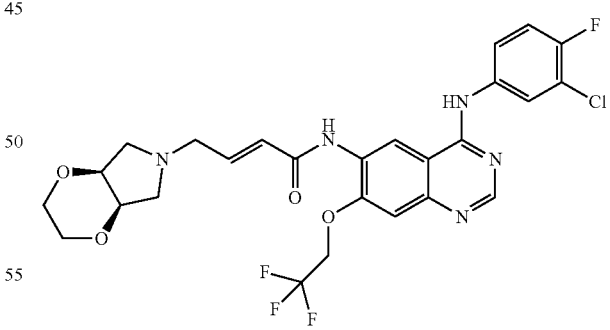

Step 1) N-(3-chloro-4-fluorophenyl)-6-nitro-7-(2,2,2-trifluoroethoxy)quinazolin-4-amine Sodium hydride (0.50 g, 2.5 mmol, 60% dispersion in mineral oil) was added into 2,2,2-trifluoroethanol (80 mL) in portions at 0° C. The mixture was heated to 30° C., and to the mixture was then added N-(3-chloro-4-fluorophenyl)-7-fluoro-6-nitroquinazolin-4-amine (5.00 g, 15.0 mmol). The reaction mixture was stirred at 30° C. for 7.0 hours. The resulting mixture was poured into ice water (200 mL), and a yellow solid precipitated out. The mixture was filtered. The filter cake was washed with water and dried under vacuum to give the title compound as a yellow solid (3.70 g, 59.8%). The compound was characterized by the following spectroscopic data: MS (ESI, pos.ion) m/z: 417.1 [M+1]$^+$; and $^1$H NMR (400 MHz, DMSO-d$_6$) δ: 9.06 (s, 1H), 8.91 (d, J=6.2 Hz, 1H), 8.85 (s, 1H), 7.86 (dd, J$_1$=6.2 Hz, J$_2$=2.4 Hz, 1H), 7.61-7.59 (m, 1H), 7.34 (s, 1H), 7.09 (t, J=8.2 Hz, 1H), 4.46-4.41 (m, 2H).

Step 2) N$^4$-(3-chloro-4-fluorophenyl)-7-(2,2,2-trifluoroethoxy)quinazoline-4,6-diamine To a solution of N-(3-chloro-4-fluorophenyl)-6-nitro-7-(2,2,2-trifluoroethoxy)quinazolin-4-amine (3.00 g, 7.2 mmol) in ethanol (150 mL) were added iron powder (8.10 g, 143.9 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethyl acetate (90 mL) and filtered. The filter cake was dried under vacuum to give the title compound as a yellow solid (2.50 g, 89.9%). The compound was characterized by the following spectroscopic data: MS (ESI, pos.ion) m/z: 387.1 [M+1]$^+$.

Step 3) (E)-4-bromo-N-(4-((3-chloro-4-fluorophenyl)amino)-7-(2,2,2-trifluoroethoxy)quinazolin-6-yl)but-2-enamide To a solution of N$^4$-(3-chloro-4-fluorophenyl)-7-(2,2,2-trifluoroethoxy)quinazoline-4,6-diamine (2.00 g, 5.2 mmol) and TEA (2.3 mL, 15.5 mmol) in anhydrous tetrahydrofuran (40 mL) was added (E)-4-bromobut-2-enoyl chloride (1.04 g, 5.7 mmol) slowly at 0° C. The reaction mixture was then heated to 25° C. and stirred for 2.0 hours. The resulting mixture was poured into water (100 mL) and extracted with DCM (70 mL×3). The combined organic phases were dried over anhydrous Na$_2$SO$_4$, filtered and concentrated in vacuo. The residue was triturated with DCM (40 mL) and filtered. The filter cake was dried under vacuum to give the title compound as a brownish yellow solid (1.30 g, 47.9%). The compound was characterized by the following spectroscopic data: MS (ESI, pos.ion) m/z: 533.0 [M+1]$^+$.

Step 4) (E)-N-(4-((3-chloro-4-fluorophenyl)amino)-7-(2,2,2-trifluoroethoxy)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-fluorophenyl)amino)-7-(2,2,2-trifluoroethoxy)quinazolin-6-yl)but-2-enamide (0.50 g, 0.9 mmol) and diisopropylethylamine (0.5 mL, 2.8 mmol) in DMAC (10 mL) was added (4aR,7aS)-hexahydro-2H-[1,4]dioxino[2,3-c]pyrrole (0.24 g, 1.9 mmol). The reaction mixture was then stirred at 25° C. for 5.0 hours. The resulting mixture was poured into water (70 mL) and extracted with DCM (50 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.17 g, 30.9%). The compound was characterized by the following spectroscopic data: MS (ESI, pos.ion) m/z: 582.1 [M+1]$^+$; and $^1$H NMR (400 MHz, DMSO-d$_6$) δ: 9.02 (s, 1H), 8.89 (d, J=6.4 Hz, 1H), 8.87 (s, 1H), 7.82 (dd, J$_1$=8.2 Hz, J$_2$=4.6 Hz, 1H), 7.63-7.59 (m, 1H), 7.37 (s, 1H), 7.11 (t, J=8.4 Hz, 1H), 6.68-6.59 (m, 1H), 6.34 (d, J=16.8 Hz, 1H), 4.46-4.41 (m, 2H), 3.72 (t, J=6.4 Hz, 4H), 3.36 (t, J=4.8 Hz, 2H), 3.26 (dd, J$_1$=8.2 Hz, J$_2$=2.4 Hz, 2H), 2.21-2.18 (m, 4H).

Example 8

(E)-N-(4-((3-Chloro-4-fluorophenyl)amino)-7-((3-methyloxetan-3-yl)methoxy)quinazolin-6-yl)-4-((4aR,7aS)-tetrahydro-2H-[1,4]dioxino[2,3-c]pyrrol-6(3H)-yl)but-2-enamide

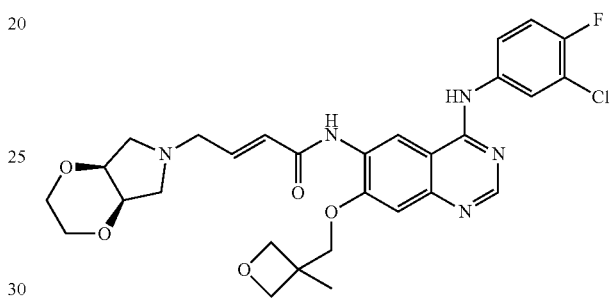

Step 1) N-(3-chloro-4-fluorophenyl)-7-((3-methyloxetan-3-yl)methoxy)-6-nitroquinazolin-4-amine To a solution of N-(3-chloro-4-fluorophenyl)-7-fluoro-6-nitroquinazolin-4-amine (10.00 g, 30.0 mmol) in anhydrous DMF (70 mL) was added potassium trimethylsilanolate (9.00 g, 60.0 mmol) at 25° C. After the mixture was stirred at 25° C. for 1.0 hour, to the mixture was added (3-methyloxetan-3-yl)methanol (4.50 g, 45.0 mmol). The reaction mixture was then stirred at 25° C. for further 12.0 hours. The resulting mixture was poured into ice water (400 mL), and a brownish red solid precipitated out. The mixture was filtered, and the filter cake was dried under vacuum to give the title compound as a brownish red solid (6.50 g, 52.8%). The compound was characterized by the following spectroscopic data: MS (ESI, pos.ion) m/z: 419.1 [M+1]$^+$.

Step 2) N$^4$-(3-chloro-4-fluorophenyl)-7-((3-methyloxetan-3-yl)methoxy)quinazoline-4,6-diamine To a solution of N-(3-chloro-4-fluorophenyl)-7-((3-methyloxetan-3-yl)methoxy)-6-nitroquinazolin-4-amine (5.00 g, 12.0 mmol) in ethanol (150 mL) were added iron powder (13.40 g, 239.8 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with ethyl acetate (70 mL), filtered, and the filter cake was dried under vacuum to give the title compound as a yellow solid (3.90 g, 84.7%). The compound was characterized by the following spectroscopic data: MS (ESI, pos.ion) m/z: 389.1 [M+1]$^+$.

Step 3) (E)-4-bromo-N-(4-((3-chloro-4-fluorophenyl)amino)-7-((3-methyloxetan-3-yl)methoxy)quinazolin-6-yl)but-2-enamide To a solution of $N^4$-(3-chloro-4-fluorophenyl)-7-((3-methyloxetan-3-yl)methoxy)quinazoline-4,6-diamine (2.00 g, 5.2 mmol) and TEA (2.25 mL, 15.5 mmol) in anhydrous tetrahydrofuran (40 mL) was added (E)-4-bromobut-2-enoyl chloride (1.04 g, 5.7 mmol) slowly at 0° C. The reaction mixture was then heated to 25° C. and stirred for 2.0 hours. The resulting mixture was poured into water (100 mL) and extracted with DCM (70 mL×3). The combined organic phases were dried over anhydrous $Na_2SO_4$, filtered and concentrated in vacuo. The residue was triturated with DCM (20 mL) and filtered. The filter cake was dried under vacuum to give the title compound as a brownish yellow solid (1.20 g, 43.6%). The compound was characterized by the following spectroscopic data: MS (ESI, pos.ion) m/z: 535.0 $[M+1]^+$.

Step 4) (E)-N-(4-((3-chloro-4-fluorophenyl)amino)-7-((3-methyloxetan-3-yl)methoxy)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-fluorophenyl)amino)-7-((3-methyloxetan-3-yl)methoxy)quinazolin-6-yl)but-2-enamide (0.50 g, 0.9 mmol) and diisopropylethylamine (0.50 mL, 2.8 mmol) in DMAC (15 mL) was added (4aR,7aS)-hexahydro-2H-[1,4]dioxino[2,3-c]pyrrole (0.24 g, 1.9 mmol). The reaction mixture was then stirred at 25° C. for 5.0 hours. The resulting mixture was poured into water (70 mL) and extracted with DCM (50 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a brownish yellow solid (0.15 g, 27.3%). The compound was characterized by the following spectroscopic data: MS (ESI, pos.ion) m/z: 584.1 $[M+1]^+$; and $^1H$ NMR (400 MHz, DMSO-$d_6$) δ: 9.30 (s, 1H), 8.89 (s, 1H), 8.76 (s, 1H), 7.67 (dd, $J_1$=6.2 Hz, $J_2$=2.8 Hz, 1H), 7.62-7.51 (m, 1H), 7.48 (s, 1H), 7.45 (t, J=8.6 Hz, 1H), 6.77-6.69 (m, 1H), 6.65 (d, J=16.8 Hz, 1H), 4.39-4.32 (m, 4H), 3.82 (s, 2H), 3.78 (t, J=6.2 Hz, 4H), 3.26 (t, J=4.4 Hz, 2H), 3.20 (dd, $J_1$=7.8 Hz, $J_2$=2.6 Hz, 2H), 2.23-2.12 (m, 4H), 1.04 (s, 3H).

Example 9

(Z)—N-(4-((3-Chloro-4-fluorophenyl)amino)-7-methoxyquinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-Chloro-4-fluorophenyl)amino)-7-methoxyquinazolin-6-yl)-2-fluoro-4-((4aR,7aS)-tetrahydro-2H-[1,4]dioxin[2,3-c]pyrrol-6(3H)-yl)but-2-enamide

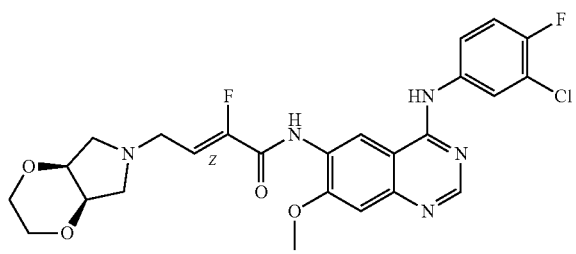

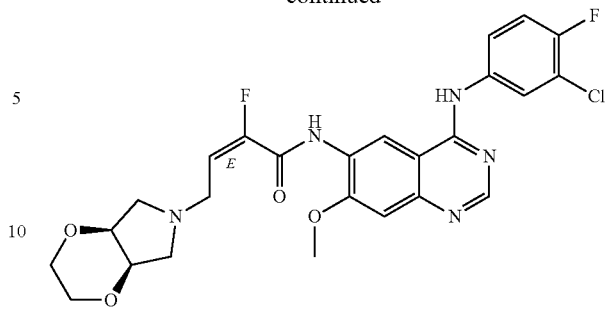

Step 1) diethyl(2-((4-((3-chloro-4-fluorophenyl)amino)-7-methoxyquinazolin-6-yl)amino)-1-fluoro-2-oxoethyl)phosphonate A mixture of 2-(diethoxyphosphoryl)-2-fluoroacetic acid (4.10 g, 18.8 mmol), HATU (7.20 g, 18.8 mmol) and $N^4$-(3-chloro-4-fluorophenyl)-7-methoxyquinazoline-4,6-diamine (5.00 g, 15.7 mmol) in DMF (60 mL) was stirred at 25° C. for 2.0 hours. The reaction mixture was then quenched with ice water (10 mL). The resulting mixture was poured into water (200 mL), and a yellow solid precipitated out. The mixture was filtered, and the filter cake was triturated with ethyl acetate (50 mL) to give the title compound as a yellow solid (3.50 g, 43.4%). The compound was characterized by the following spectroscopic data: MS (ESI, pos.ion) m/z: 515.1 $[M+1]^+$.

Step 2) (4aR,7aS)-6-(2,2-diethoxyethyl)hexahydro-2H-[1,4]dioxino[2,3-c]pyrrole A mixture of (4aR,7aS)-hexahydro-2H-[1,4]dioxino[2,3-c]pyrrole (10.00 g, 77.4 mmol), 2-bromo-1,1-diethoxyethane (18.0 mL, 116.0 mmol) and diisopropylethylamine (27.1 mL, 154.7 mmol) in DMF (100 mL) was heated to 80° C. and stirred for 8.0 hours. The reaction mixture was then cooled to 25° C. The resulting mixture was poured into water (200 mL) and extracted with DCM (60 mL×4). The combined organic phases were dried over anhydrous $Na_2SO_4$, filtered and concentrated in vacuo. The residue was purified by silica gel column chromatography ($CH_2Cl_2$/MeOH (v/v)=35/1) to give brown oil (7.00 g, 37.1%). The compound was characterized by the following spectroscopic data: MS (ESI, pos.ion) m/z: 246.2 $[M+1]^+$.

Step 3) 2-((4aR,7aS)-tetrahydro-2H-[1,4]dioxino[2,3-c]pyrrol-6(3H)-yl)acetaldehyde A mixture of (4aR,7aS)-6-(2,2-diethoxyethyl)hexahydro-2H-[1,4]dioxino[2,3-c]pyrrole (3.00 g, 12.2 mmol) in concentrated hydrochloric acid (10 mL) was heated to 80° C. and stirred for 5.0 hours. The reaction mixture was then cooled to 25° C. The resulting mixture was concentrated in vacuo. The residue was poured into saturated aqueous sodium carbonate solution (70 mL) and extracted with DCM (50 mL×5). The combined organic phases were dried over anhydrous $Na_2SO_4$, filtered and concentrated in vacuo to give the title compound as brown oil (2.00 g, 95.2%) without further purification. The compound was characterized by the following spectroscopic data: MS (ESI, pos.ion) m/z: 172.2 $[M+1]^+$.

Step 4) (Z)—N-(4-((3-chloro-4-fluorophenyl)amino)-7-methoxyquinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-chloro-4-fluorophenyl)amino)-7-methoxyquinazolin-6-yl)-2-fluoro-4-((4aR,7aS)-tetrahydro-2H-[1,4]dioxino[2,3-c]pyrrol-6(3H)-yl)but-2-enamide To a solution of diethyl(2-((4-((3-chloro-4-fluorophenyl)amino)-7-methoxyquinazolin-6-yl)amino)-1-fluoro-2-oxoethyl)phosphonate (0.50 g, 1.0 mmol) in anhydrous tetrahydrofuran (10 mL) was added sodium hydride (0.06 g, 1.5 mmol, 60% dispersion in mineral oil) at −65° C. After the mixture was stirred at −65° C. for 1.0 hour, to the mixture was added 2-((4aR,7aS)-tetrahydro-2H-[1,4]dioxino[2,3-c]pyrrol-6(3H)-yl)acetaldehyde (0.50 g, 2.9 mmol). The reaction mixture was then heated to 25° C. and stirred for 7.0 hours. The resulting mixture was quenched with ice water (5 mL), and then concentrated in vacuo. The residue was poured into water (30 mL) and extracted with DCM (30 mL×3). The combined organic phases were dried over anhydrous $Na_2SO_4$, filtered and concentrated in vacuo. The residue was purified by silica gel column chromatography ($CH_2Cl_2$/MeOH (v/v)=25/1) to give a brown solid (0.07 g) as a mixture of cis- and trans-isomers.

The mixture of cis- and trans-isomers obtained above was separated by preparative chromatography to give the title compounds: (Z)-isomer (10 mg, 1.94%) and (E)-isomer (20 mg, 3.87%). The compounds were characterized by the following spectroscopic data:

(Z)-isomer: MS (ESI, pos.ion) m/z: 532.1 $[M+1]^+$; and $^1H$ NMR (400 MHz, $CDCl_3$) δ: 9.02 (s, 1H), 8.92 (d, J=4.4 Hz, 1H), 8.70 (s, 1H), 7.88 (dd, $J_1$=6.2 Hz, $J_2$=2.4 Hz, 1H), 7.66-7.56 (m, 1H), 7.39 (s, 1H), 7.09 (t, J=8.8 Hz, 1H), 6.28 (dt, $J_1$=38.8 Hz, $J_2$=6.2 Hz, 1H), 4.02 (s, 3H), 3.78 (t, J=6.2 Hz, 4H), 3.26 (t, J=4.4 Hz, 2H), 3.20 (dd, $J_1$=7.8 Hz, $J_2$=2.6 Hz, 2H), 2.25 (d, J=4.6 Hz, 4H).

(E)-isomer: MS (ESI, pos.ion) m/z: 532.1 $[M+1]^+$; and $^1H$ NMR (400 MHz, $CDCl_3$) δ: 9.03 (s, 1H), 8.90 (d, J=4.4 Hz, 1H), 8.72 (s, 1H), 7.86 (dd, $J_1$=6.2 Hz, $J_2$=2.6 Hz, 1H), 7.65-7.54 (m, 1H), 7.41 (s, 1H), 7.07 (t, J=8.6 Hz, 1H), 6.25 (dt, $J_1$=24.8 Hz, $J_2$=4.2 Hz, 1H), 4.08 (s, 3H), 3.69 (t, J=6.4 Hz, 4H), 3.30 (t, J=4.1 Hz, 2H), 3.28 (dd, $J_1$=7.8 Hz, $J_2$=2.6 Hz, 2H), 2.29 (d, J=4.6 Hz, 4H).

Example 10

(Z)—N-(4-((3-Chloro-4-fluorophenyl)amino)-7-(((S)-tetrahydrofuran-3-yl)oxy)quinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-Chloro-4-fluorophenyl)amino)-7-(((S)-tetrahydrofuran-3-yl)oxy)quinazolin-6-yl)-2-fluoro-4-((4aR,7aS)-tetrahydro-2H-[1,4]dioxin[2,3-c]pyrrol-6(3H)-yl)but-2-enamide

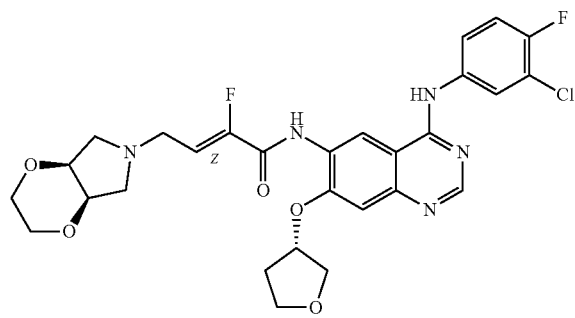

-continued

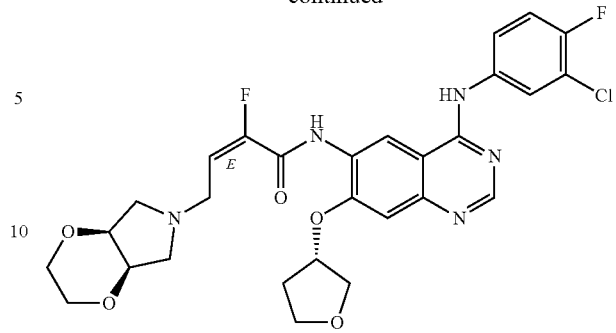

Step 1) diethyl(2-((4-((3-chloro-4-fluorophenyl)amino)-7-(((S)-tetrahydrofuran-3-yl)oxy)quinazolin-6-yl)amino)-1-fluoro-2-oxoethyl)phosphonate A mixture of (S)—$N^4$-(3-chloro-4-fluorophenyl)-7-((tetrahydrofuran-3-yl)oxy)quinazoline-4,6-diamine (3.00 g, 8.0 mmol), HATU (6.10 g, 16.0 mmol), 2-(diethoxyphosphoryl)-2-fluoroacetic acid (2.58 g, 12.0 mmol) and diisopropylethylamine (3.2 mL, 16.8 mmol) in anhydrous DMF (60 mL) was stirred at 25° C. for 7.0 hours. The resulting mixture was then poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give the title compound as a brown solid (1.50 g, 33.3%). The compound was characterized by the following spectroscopic data: MS (ESI, pos.ion) m/z: 571.1 $[M+1]^+$.

Step 2) (Z)—N-(4-((3-chloro-4-fluorophenyl)amino)-7-(((S)-tetrahydrofuran-3-yl)oxy)quinazolin-6-yl)-2-fluoro-4-((4aR,7aS)-tetrahydro-2H-[1,4]dioxin[2,3-c]pyrrol-6(3H)-yl)but-2-enamide (E)-N-(4-((3-chloro-4-fluorophenyl)amino)-7-(((S)-tetrahydrofuran-3-yl)oxy)quinazolin-6-yl)-2-fluoro-4-((4aR,7aS)-tetrahydro-2H-[1,4]dioxino[2,3-c]pyrrol-6(3H)-yl)but-2-enamide To a solution of diethyl(2-((4-((3-chloro-4-fluorophenyl)amino)-7-(((S)-tetrahydrofuran-3-yl)oxy)quinazolin-6-yl)amino)-1-fluoro-2-oxoethyl)phosphonate (0.50 g, 0.9 mmol) in anhydrous tetrahydrofuran (10 mL) was added sodium hydride (0.06 g, 1.5 mmol, 60% dispersion in mineral oil) at −65° C. After the mixture was stirred at −65° C. for 1.0 hour, to the mixture was added 2-((4aR,7aS)-tetrahydro-2H-[1,4]dioxino[2,3-c]pyrrol-6(3H)-yl)acetaldehyde (0.50 g, 2.9 mmol). The reaction mixture was then heated to 25° C. and stirred for 7.0 hours. The resulting mixture was quenched with ice water (5 mL), and then concentrated in vacuo. The residue was poured into water (30 mL) and extracted with DCM (30 mL×3). The combined organic phases were dried over anhydrous $Na_2SO_4$, filtered and concentrated in vacuo. The residue was purified by silica gel column chromatography ($CH_2Cl_2$/MeOH (v/v)=25/1) to give a brown solid (0.05 g) as a mixture of cis- and trans-isomers.

The mixture of cis- and trans-isomers obtained above was separated by preparative chromatography to give the title compounds: (Z)-isomer (0.015 g, 2.91%) and (E)-isomer (0.035 g, 6.80%). The compounds were characterized by the following spectroscopic data:

(Z)-isomer: MS (ESI, pos.ion) m/z: 588.2 [M+1]$^+$; and $^1$H NMR (400 MHz, CDCl$_3$) δ: 9.06 (s, 1H), 8.92 (d, J=4.4 Hz, 1H), 8.69 (s, 1H), 7.86 (dd, J$_1$=6.4 Hz, J$_2$=2.8 Hz, 1H), 7.68-7.59 (m, 1H), 7.32 (s, 1H), 7.09 (t, J=8.8 Hz, 1H), 6.38 (dt, J$_1$=38.4 Hz, J$_2$=6.8 Hz, 1H), 5.02 (s, 2H), 4.12-4.02 (m, 4H), 4.02-3.89 (m, 1H), 3.76-3.64 (m, 6H), 3.29 (dd, J$_1$=6.2 Hz, J$_2$=2.8 Hz, 2H), 2.45-2.35 (m, 4H).

(E)-isomer: MS (ESI, pos.ion) m/z: 588.2 [M+1]$^+$; and $^1$H NMR (400 MHz, CDCl$_3$) δ: 9.02 (s, 1H), 8.92 (d, J=4.4 Hz, 1H), 8.71 (s, 1H), 7.84 (dd, J$_1$=6.4 Hz, J$_2$=2.8 Hz, 1H), 7.62-7.57 (m, 1H), 7.35 (s, 1H), 7.04 (t, J=8.8 Hz, 1H), 6.41 (dt, J$_1$=21.6 Hz, J$_2$=6.2 Hz, 1H), 5.02 (s, 2H), 4.22-4.12 (m, 4H), 4.01-3.86 (m, 1H), 3.79-3.66 (m, 6H), 3.31 (dd, J$_1$=6.2 Hz, J$_2$=2.8 Hz, 2H), 2.41-2.29 (m, 4H).

Example 11

(Z)—N-(4-((3-Chloro-4-fluorophenyl)amino)-7-ethoxyquinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-Chloro-4-fluorophenyl)amino)-7-ethoxyquinazolin-6-yl)-2-fluoro-4-((4aR,7aS)-tetrahydro-2H-[1,4]dioxino[2,3-c]pyrrol-6(3H)-yl)but-2-enamide

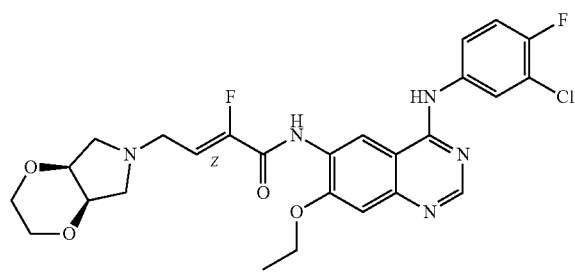

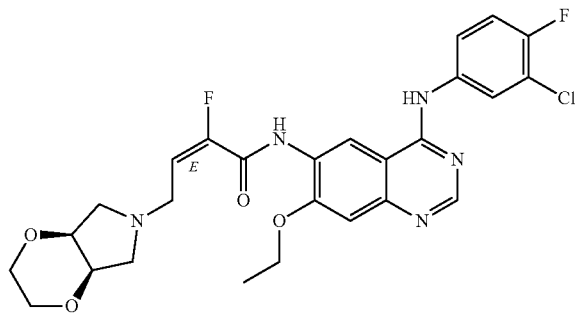

Step 1) diethyl(2-((4-((3-chloro-4-fluorophenyl)amino)-7-ethoxyquinazolin-6-yl)amino)-1-fluoro-2-oxoethyl)phosphonate A mixture of N$^4$-(3-chloro-4-fluorophenyl)-7-ethoxyquinazoline-4,6-diamine (3.00 g, 9.1 mmol), HATU (6.89 g, 18.1 mmol), 2-(diethoxyphosphoryl)-2-fluoroacetic acid (3.88 g, 18.1 mmol) and diisopropylethylamine (4.8 mL, 27.2 mmol) in anhydrous DMF (60 mL) was stirred at 25° C. for 8.0 hours. The resulting mixture was then poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=30/1) to give the title compound as a brown solid (1.60 g, 32.1%). The compound was characterized by the following spectroscopic data: MS (ESI, pos.ion) m/z: 529.1 [M+1]$^+$.

Step 2) (Z)—N-(4-((3-chloro-4-fluorophenyl)amino)-7-ethoxyquinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-chloro-4-fluorophenyl)amino)-7-ethoxyquinazolin-6-yl)-2-fluoro-4-((4aR,7aS)-tetrahydro-2H-[1,4]dioxin[2,3-c]pyrrol-6(3H)-yl)but-2-enamide To a solution of diethyl(2-((4-((3-chloro-4-fluorophenyl)amino)-7-ethoxyquinazolin-6-yl)amino)-1-fluoro 2-oxoethyl)phosphonate (0.50 g, 0.9 mmol) in anhydrous tetrahydrofuran (10 mL) was added sodium hydride (0.05 g, 1.1 mmol, 60% dispersion in mineral oil) at −65° C. After the mixture was stirred at −65° C. for 1.0 hour, to the mixture was added 2-((4aR,7aS)-tetrahydro-2H-[1,4]dioxino[2,3-c]pyrrol-6(3H)-yl)acetaldehyde (0.32 g, 1.9 mmol). The reaction mixture was then heated to 25° C. and stirred for 7.0 hours. The resulting mixture was quenched with ice water (5 mL), and then concentrated in vacuo. The residue was poured into water (30 mL) and extracted with DCM (30 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=25/1) to give a brown solid (0.07 g) as a mixture of cis- and trans-isomers.

The mixture of cis- and trans-isomers obtained above was separated by preparative chromatography to give the title compounds: (Z)-isomer (0.02 g, 3.87%) and (E)-isomer (0.03 g, 5.81%). The compounds were characterized by the following spectroscopic data:

(Z)-isomer: MS (ESI, pos.ion) m/z: 546.1 [M+1]$^+$; and $^1$H NMR (400 MHz, CDCl$_3$) δ: 9.00 (s, 1H), 8.92 (d, J=4.6 Hz, 1H), 8.80 (s, 1H), 7.82 (dd, J$_1$=6.8 Hz, J$_2$=2.6 Hz, 1H), 7.62-7.56 (m, 1H), 7.44 (s, 1H), 7.09 (t, J=8.8 Hz, 1H), 6.21 (dt, J$_1$=34.8 Hz, J$_2$=6.2 Hz, 1H), 4.31 (q, J=6.8 Hz, 2H), 3.66 (t, J=6.2 Hz, 4H), 3.36 (t, J=4.2 Hz, 2H), 3.28 (dd, J$_1$=7.6 Hz, J$_2$=2.4 Hz, 2H), 2.29 (d, J=4.6 Hz, 4H), 1.56 (t, J=7.2 Hz, 3H).

(E)-isomer: MS (ESI, pos.ion) m/z: 546.1 [M+1]$^+$; and $^1$H NMR (400 MHz, CDCl$_3$) δ: 9.12 (s, 1H), 8.91 (d, J=4.8 Hz, 1H), 8.81 (s, 1H), 7.84 (dd, J$_1$=6.2 Hz, J$_2$=2.4 Hz, 1H), 7.62-7.56 (m, 1H), 7.47 (s, 1H), 7.11 (t, J=8.2 Hz, 1H), 6.23-6.19 (m, 1H), 4.35 (q, J=6.8 Hz, 2H), 3.66 (t, J=6.2 Hz, 4H), 3.36 (t, J=4.2 Hz, 2H), 3.24 (dd, J$_1$=7.6 Hz, J$_2$=2.8 Hz, 2H), 2.21 (d, J=4.6 Hz, 4H), 1.46 (t, J=7.2 Hz, 3H).

Example 12

(Z)—N-(4-((3-Chloro-4-fluorophenyl)amino)-7-(2-methoxyethoxy)quinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-Chloro-4-fluorophenyl)amino)-7-(2-methoxyethoxy)quinazolin-6-yl)-2-fluoro-4-((4aR,7aS)-tetrahydro-2H-[1,4]dioxino[2,3-c]pyrrol-6(3H)-yl)but-2-enamide

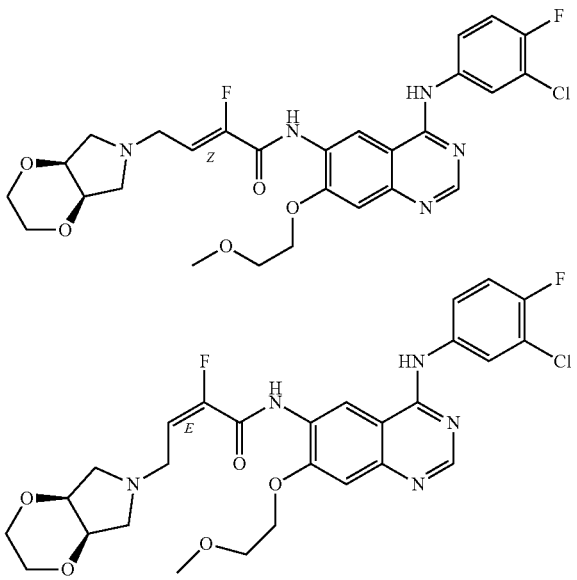

Step 1) diethyl(2-((4-((3-chloro-4-fluorophenyl)amino)-7-(2-methoxyethoxy)quinazolin-6-yl)amino)-1-fluoro-2-oxoethyl)phosphonate A mixture of N⁴-(3-chloro-4-fluorophenyl)-7-(2-methoxyethoxy)quinazoline-4,6-diamine (3.00 g, 8.3 mmol), HATU (6.30 g, 16.6 mmol), 2-(diethoxyphosphoryl)-2-fluoroacetic acid (3.60 g, 16.6 mmol) and diisopropylethylamine (4.6 mL, 24.8 mmol) in anhydrous DMF (60 mL) was stirred at 30° C. for 8.0 hours. The resulting mixture was then poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give a brown solid (2.00 g, 43.2%). The compound was characterized by the following spectroscopic data: MS (ESI, pos.ion) m/z: 559.1 [M+1]⁺.

Step 2) (Z)—N-(4-((3-chloro-4-fluorophenyl)amino)-7-(2-methoxyethoxy)quinazolin-6-yl)-2-fluoro-4-((4aR,7aS)-tetrahydro-2H-[1,4]dioxino[2,3-c]pyrrol-6(3H)-yl)but-2-enamide (E)-N-(4-((3-chloro-4-fluorophenyl)amino)-7-(2-methoxyethoxy)quinazolin-6-yl)-2-fluoro-4-((4aR,7aS)-tetrahydro-2H-[1,4]dioxino[2,3-c]pyrrol-6(3H)-yl)but-2-enamide To a solution of diethyl(2-((4-((3-chloro-4-fluorophenyl)amino)-7-(2-methoxyethoxy)quinazolin-6-yl)amino)-1-fluoro-2-oxoethyl)phosphonate (0.50 g, 0.9 mmol) in anhydrous tetrahydrofuran (10 mL) was added sodium hydride (0.04 g, 1.1 mmol, 60% dispersion in mineral oil) at −65° C. After the mixture was stirred at −65° C. for 1.0 hour, to the mixture was added 2-((4aR,7aS)-tetrahydro-2H-[1,4]dioxino[2,3-c]pyrrol-6(3H)-yl)acetaldehyde (0.32 g, 1.9 mmol). The reaction mixture was then heated to 25° C. and stirred for 7.0 hours. The resulting mixture was quenched with ice water (5 mL), and then concentrated in vacuo. The residue was poured into water (30 mL) and extracted with DCM (30 mL×3). The combined organic phases were dried over anhydrous $Na_2SO_4$, filtered and concentrated in vacuo. The residue was purified by silica gel column chromatography ($CH_2Cl_2$/MeOH (v/v)=25/1) to give a brown solid (0.07 g) as a mixture of cis- and trans-isomers.

The mixture of cis- and trans-isomers obtained above was separated by preparative chromatography to give the title compounds: (Z)-isomer (0.03 g, 5.82%) and (E)-isomer (0.03 g, 5.82%). The compounds were characterized by the following spectroscopic data:

(Z)-isomer: MS (ESI, pos.ion) m/z: 576.1 [M+1]⁺; and ¹H NMR (400 MHz, DMSO-$d_6$) δ: 9.30 (brs, 1H), 9.08 (s, 1H), 8.40 (s, 1H), 7.45-7.37 (m, 3H), 7.20 (t, J=8.2 Hz, 1H), 6.25 (dt, $J_1$=34.2 Hz, $J_2$=6.2 Hz, 1H), 4.12 (s, 3H), 3.71-3.66 (m, 2H), 3.56 (t, J=6.2 Hz, 4H), 3.36 (t, J=4.2 Hz, 2H), 3.28 (m, 4H), 2.29 (d, J=4.6 Hz, 4H).

(E)-isomer: MS (ESI, pos.ion) m/z: 576.1 [M+1]⁺; and ¹H NMR (400 MHz, DMSO-$d_6$) δ: 9.31 (brs, 1H), 9.10 (s, 1H), 8.50 (s, 1H), 7.50-7.41 (m, 3H), 7.20 (t, J=8.6 Hz, 1H), 6.23-6.20 (m, 1H), 4.08 (s, 3H), 3.72-3.67 (m, 2H), 3.66 (t, J=6.2 Hz, 4H), 3.36 (t, J=4.2 Hz, 2H), 3.30-3.26 (m, 4H), 2.29 (d, J=4.6 Hz, 4H).

Example 13

(E)-N-(4-((3-Chloro-4-fluorophenyl)amino)-7-methoxyquinazolin-6-yl)-4-(octahydro-1H-cyclopenta[e][1,4]oxazepin-1-yl)but-2-enamide

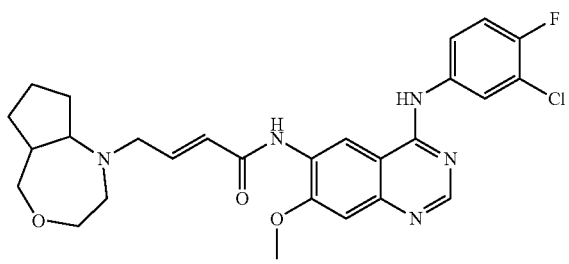 [SMILES: COc1cc2ncnc(Nc3ccc(F)c(Cl)c3)c2cc1NC(=O)/C=C/CN1CCOCC2CCCC21]

To a solution of (E)-4-bromo-N-(4-((3-chloro-4-fluorophenyl)amino)-7-methoxyquinazolin-6-yl)but-2-enamide (0.56 g, 1.2 mmol) and octahydro-1H-cyclopenta[e][1,4]oxazepine (0.25 g, 1.8 mmol) in DMAC (10 mL) was added DIPEA (0.5 mL, 3.0 mmol). The reaction mixture was then stirred at 25° C. for 5.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a white solid (0.24 g, 38.0%). The compound was characterized by the following spectroscopic data: MS (ESI, pos.ion) m/z: 526.0 [M+H]⁺; and ¹H NMR (400 MHz, CDCl₃) δ: 10.21 (s, 1H), 8.52 (s, 1H), 8.14 (s, 1H), 7.56 (d, J=0.8 Hz, 1H), 7.34 (d, J=14.2 Hz, 1H), 7.30 (d, J=12.8 Hz, 1H), 6.78 (s, 1H), 6.55-6.45 (m, 1H), 6.32 (d, J=12.0 Hz, 1H), 3.88 (s, 3H), 3.52 (d, J=6.8 Hz, 2H), 3.47-3.39 (m, 4H), 3.01 (s, 2H), 2.61-2.32 (m, 4H), 2.05-1.79 (m, 4H).

Example 14

(E)-N-(4-((3-Chloro-4-fluorophenyl)amino)-7-methoxyquinazolin-6-yl)-4-(hexahydro-2H-benzo[b][1,4]thiazin-4(3H)-yl)but-2-enamide

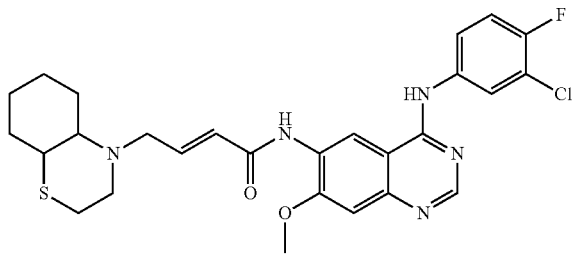 [SMILES: COc1cc2ncnc(Nc3ccc(F)c(Cl)c3)c2cc1NC(=O)/C=C/CN1CCSC2CCCCC21]

To a solution of (E)-4-bromo-N-(4-((3-chloro-4-fluorophenyl)amino)-7-methoxyquinazolin-6-yl)but-2-enamide (0.56 g, 1.2 mmol) and octahydro-2H-benzo[b][1,4]thiazine (0.28 g, 1.8 mmol) in DMAC (10 mL) was added DIPEA (0.5 mL, 3.0 mmol). The reaction mixture was then stirred at 25° C. for 5.0 hours. The resulting mixture was poured into water (70 mL) and extracted with DCM (40 mL×3). The combined organic phases were dried over anhydrous Na$_2$SO$_4$, filtered and concentrated in vacuo. The residue was purified by silica column chromatography (CH$_2$Cl$_2$/MeOH (v/v)=30/1) to give the title compound as a white solid (0.29 g, 44.6%). The compound was characterized by the following spectroscopic data: MS (ESI, pos.ion) m/z: 542.0 [M+H]$^+$; and $^1$H NMR (400 MHz, DMSO-d$_6$) δ: 10.30 (s, 1H), 9.37 (s, 1H), 8.91 (s, 1H), 8.09 (dd, J$_1$=6.6 Hz, J$_2$=2.4 Hz, 1H), 7.81-7.76 (m, 1H), 7.59 (s, 1H), 7.56 (t, J=8.4 Hz, 1H), 6.75-6.67 (m, 1H), 6.64 (d, J=18.4 Hz, 1H), 4.10 (s, 3H), 3.03 (d, J=4.6 Hz, 2H), 2.84-2.59 (m, 6H), 1.90-1.21 (m, 8H).

Example 15

(E)-N-(4-((3-Chloro-4-fluorophenyl)amino)-7-methoxyquinazolin-6-yl)-4-(hexahydro-2H-benzo[b][1,4]oxazin-4(3H)-yl)but-2-enamide

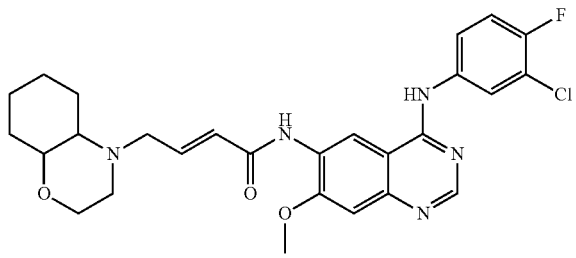 [SMILES: COc1cc2ncnc(Nc3ccc(F)c(Cl)c3)c2cc1NC(=O)/C=C/CN1CCOC2CCCCC21]

To a solution of (E)-4-bromo-N-(4-((3-chloro-4-fluorophenyl)amino)-7-methoxyquinazolin-6-yl)but-2-enamide (0.56 g, 1.2 mmol) and octahydro-2H-benzo[b][1,4]oxazine (0.25 g, 1.8 mmol) in DMAC (10 mL) was added DIPEA (0.5 mL, 3.0 mmol). The reaction mixture was then stirred at 25° C. for 5.0 hours. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=30/1) to give the title compound as a white solid (0.24 g, 38.0%). The compound was characterized by the following spectroscopic data: MS (ESI, pos.ion) m/z: 526.0 [M+H]$^+$; and $^1$H NMR (400 MHz, DMSO-d$_6$) δ: 10.28 (s, 1H), 9.27 (s, 1H), 8.89 (s, 1H), 8.19 (dd, J$_1$=6.6 Hz, J$_2$=2.8 Hz, 1H), 7.70-7.68 (m, 1H), 7.50 (s, 1H), 7.46 (t, J=8.4 Hz, 1H), 6.70-6.66 (m, 1H), 6.64 (d, J=18.4 Hz, 1H), 4.08 (s, 3H), 3.12 (d, J=4.6 Hz, 2H), 2.91-2.64 (m, 6H), 2.09-1.21 (m, 8H).

Example 16

(E)-N-(4-((3-Chloro-4-fluorophenyl)amino)-7-methoxyquinazolin-6-yl)-4-(hexahydrocyclopenta[b][1,4]thiazin-4(4aH)-yl)but-2-enamide

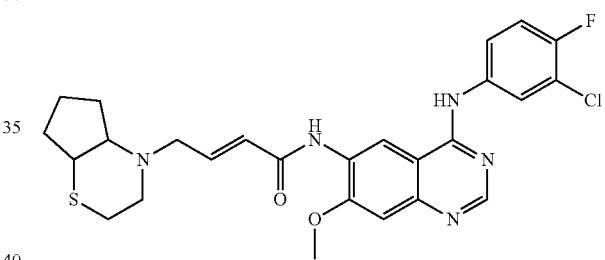

To a solution of (E)-4-bromo-N-(4-((3-chloro-4-fluorophenyl)amino)-7-methoxyquinazolin-6-yl)but-2-enamide (0.56 g, 1.2 mmol) and octahydrocyclopenta[b][1,4]thiazine (0.26 g, 1.8 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=30/1) to give the title compound as a white solid (0.29 g, 45.8%). The compound was characterized by the following spectroscopic data: MS (ESI, pos.ion) m/z: 528.0 [M+H]$^+$; and $^1$H NMR (400 MHz, DMSO-d$_6$) δ: 9.22 (s, 1H), 8.80 (d, J=4.2 Hz, 1H), 8.76 (s, 1H), 7.80 (dd, J$_1$=6.2 Hz, J$_2$=2.2 Hz, 1H), 7.66-7.54 (m, 1H), 7.46 (s, 1H), 7.10 (t, J=8.4 Hz, 1H), 6.62-6.59 (m, 1H), 6.28 (d, J=12.0 Hz, 1H), 3.89 (s, 3H), 3.01 (d, J=1.6 Hz, 2H), 2.91-2.49 (m, 6H), 1.97-1.45 (m, 6H).

Example 17

(E)-4-(2-Azabicyclo[4.2.0]octan-2-yl)-N-(4-((3-chloro-4-fluorophenyl)amino)-7-methoxyquinazolin-6-yl)but-2-enamide

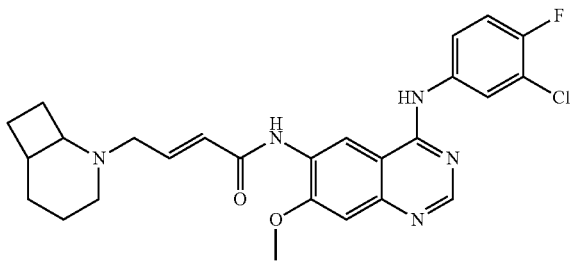 [SMILES: COc1cc2ncnc(Nc3ccc(F)c(Cl)c3)c2cc1NC(=O)/C=C/CN1CCCC2CCC21]

To a solution of (E)-4-bromo-N-(4-((3-chloro-4-fluorophenyl)amino)-7-methoxyquinazolin-6-yl)but-2-enamide (0.56 g, 1.2 mmol) and 2-azabicyclo[4.2.0]octane (0.20 g, 1.8 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give the title compound as a white solid (0.25 g, 42.0%). The compound was characterized by the following spectroscopic data: MS (ESI, pos.ion) m/z: 496.0 $[M+H]^+$; and $^1H$ NMR (400 MHz, $CDCl_3$) δ: 9.12 (s, 1H), 8.62 (s, 1H), 8.19 (d, J=28.6 Hz, 2H), 7.78 (s, 1H), 7.26 (d, J=8.6 Hz, 1H), 6.66-6.60 (m, 1H), 6.22 (d, J=12.0 Hz, 1H), 4.09 (s, 3H), 3.08-3.02 (m, 3H), 2.51 (t, J=2.4 Hz, 2H), 2.18-1.90 (m, 5H), 1.59-1.34 (m, 4H).

Example 18

(E)-N-(4-((3-Chloro-4-fluorophenyl)amino)-7-methoxyquinazolin-6-yl)-4-(tetrahydro-1H-furo[3,4-c]pyrrol-5(3H)-yl)but-2-enamide

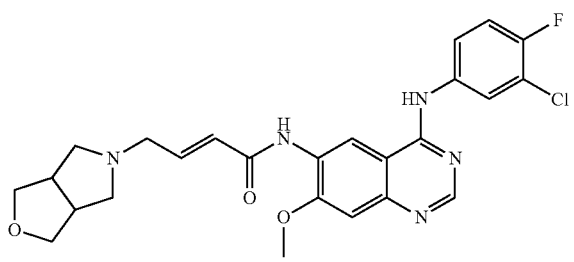 [SMILES: COc1cc2ncnc(Nc3ccc(F)c(Cl)c3)c2cc1NC(=O)/C=C/CN1CC2COCC2C1]

To a solution of (E)-4-bromo-N-(4-((3-chloro-4-fluorophenyl)amino)-7-methoxyquinazolin-6-yl)but-2-enamide (0.56 g, 1.2 mmol) and hexahydro-1H-furo[3,4-c]pyrrole (0.20 g, 1.8 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give the title compound as a white solid (0.16 g, 26.8%). The compound was characterized by the following spectroscopic data: MS (ESI, pos.ion) m/z: 498.0 $[M+H]^+$; and $^1H$ NMR (400 MHz, DMSO-$d_6$) δ: 10.91 (s, 1H), 9.45 (s, 1H), 8.92 (s, 1H), 8.12 (dd, $J_1$=6.8 Hz, $J_2$=2.6 Hz, 1H), 7.76 (s, 1H), 7.58 (s, 1H), 7.57 (t, J=8.4 Hz, 1H), 6.77-6.67 (m, 1H), 6.59 (d, J=12.0 Hz, 1H), 3.82 (s, 3H), 3.78 (t, J=6.2 Hz, 2H), 3.64-3.55 (m, 4H), 2.34-2.01 (m, 6H).

Example 19

(E)-N-(4-((3-Chloro-4-fluorophenyl)amino)-7-methoxyquinazolin-6-yl)-4-(tetrahydro-2H-furo[3,2-b]pyrrol-4(5H)-yl)but-2-enamide

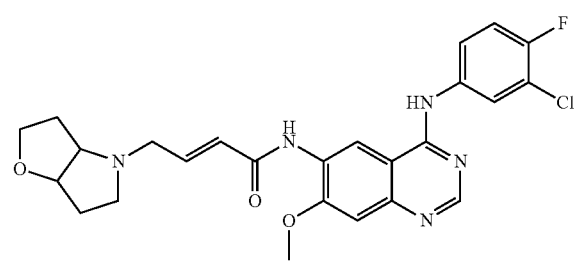 [SMILES: COc1cc2ncnc(Nc3ccc(F)c(Cl)c3)c2cc1NC(=O)/C=C/CN1CCC2OCCC21]

To a solution of (E)-4-bromo-N-(4-((3-chloro-4-fluorophenyl)amino)-7-methoxyquinazolin-6-yl)but-2-enamide (0.56 g, 1.2 mmol) and hexahydro-2H-furo[3,2-b]pyrrole (0.20 g, 1.8 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=30/1) to give the title compound as a white solid (0.14 g, 23.4%). The compound was characterized by the following spectroscopic data: MS (ESI, pos.ion) m/z: 498.0 $[M+H]^+$; and $^1H$ NMR (400 MHz, DMSO-$d_6$) δ: 10.60 (s, 1H), 9.35 (s, 1H), 8.90 (s, 1H), 8.08 (dd, $J_1$=6.6 Hz, $J_2$=2.4 Hz, 1H), 7.77-7.75 (m, 1H), 7.58 (s, 1H), 7.55 (t, J=8.4 Hz, 1H), 6.75-6.65 (m, 1H), 6.63 (d, J=16.2 Hz, 1H), 4.01-3.89 (m, 5H), 3.84 (t, J=4.8 Hz, 1H), 3.03 (d, J=1.8 Hz, 2H), 2.57-2.20 (m, 3H), 2.04-1.52 (m, 4H).

Example 20

(E)-N-(4-((3-Chloro-4-fluorophenyl)amino)-7-(methoxy-$D_3$)quinazolin-6-yl)-4-((4aR,7aS)-tetrahydro 2H-[1,4]dioxino[2,3-c]pyrrol-6(3H)-yl)but-2-enamide

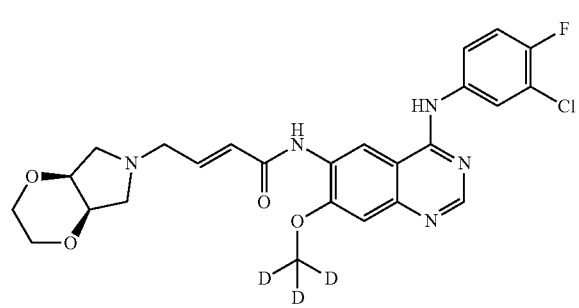 [SMILES: [2H]C([2H])([2H])Oc1cc2ncnc(Nc3ccc(F)c(Cl)c3)c2cc1NC(=O)/C=C/CN1C[C@@H]2OCCO[C@@H]2C1]

Step 1) N-(3-chloro-4-fluorophenyl)-7-(methoxy-D₃)-6-nitroquinazolin-4-amine To a solution of N-(3-chloro-4-fluorophenyl)-7-fluoro-6-nitroquinazolin-4-amine (10.00 g, 29.8 mmol) and potassium trimethylsilanolate (7.00 g, 54.0 mmol) in THF (150 mL) was added methanol-D₄ (2.00 g, 55.4 mmol) at 25° C. The reaction mixture was then heated to 50° C. and stirred for 4.0 hours. The resulting mixture was cooled to 25° C., and then poured into ice water (500 mL). A yellow solid precipitated out. The mixture was filtered, and the filter cake was dried under vacuum to give the title compound as a yellow solid (7.00 g, 67.5%). The compound was characterized by the following spectroscopic data: MS (ESI, pos.ion) m/z: 352.1 [M+1]$^+$; and $^1$H NMR (400 MHz, DMSO-d₆) δ: 10.90 (s, 1H), 9.57 (s, 1H), 8.90 (s, 1H), 8.08 (dd, J₁=6.8 Hz, J₂=2.4 Hz, 1H), 7.86-7.79 (m, 2H), 7.58 (s, 1H), 7.55 (t, J=9.4 Hz, 1H).

Step 2) N⁴-(3-chloro-4-fluorophenyl)-7-(methoxy-D₃)quinazoline-4,6-diamine

To a solution of N-(3-chloro-4-fluorophenyl)-7-(methoxy-D₃)-6-nitroquinazolin-4-amine (9.00 g, 25.9 mmol) in EtOH (100 mL) were added iron powder (14.50 g, 259.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (60 mL) and filtered. The filter cake was dried under vacuum to give the title compound as a yellow solid (5.00 g, 60.8%). The compound was characterized by the following spectroscopic data: MS (ESI, pos.ion) m/z: 322.2 [M+1]$^+$.

Step 3) (E)-4-bromo-N-(4-((3-chloro-4-fluorophenyl)amino)-7-(methoxy-D₃)quinazolin-6-yl)but-2-enamide To a solution of N⁴-(3-chloro-4-fluorophenyl)-7-(methoxy-D₃)quinazoline-4,6-diamine (4.00 g, 12.6 mmol) and TEA (6.0 mL, 37.8 mmol) in anhydrous THF (70 mL) was added (E)-4-bromobut-2-enoyl chloride (2.74 g, 15.1 mmol) slowly at 0° C. The reaction mixture was then heated to 25° C. and stirred for 2.0 hours. The resulting mixture was poured into water (100 mL) and extracted with DCM (50 mL×3). The combined organic phases were dried over anhydrous Na₂SO₄, filtered and concentrated in vacuo. The residue was triturated with DCM (30 mL) and filtered. The filter cake was dried under vacuum to give the title compound as a brownish yellow solid (2.20 g, 37.9%) The compound was characterized by the following spectroscopic data: MS (ESI, pos.ion) m/z: 468.1 [M+1]$^+$.

Step 4) (E)-N-(4-((3-chloro-4-fluorophenyl)amino)-7-(methoxy-D₃)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-fluorophenyl)amino)-7-(methoxy-D₃)quinazolin-6-yl) but-2-enamide (0.50 g, 1.1 mmol) and DIPEA (0.6 mL, 3.2 mmol) in DMAC (10 mL) was added (4aR,7aS)-hexahydro-2H-[1,4]dioxino[2,3-c]pyrrole (0.42 g, 3.2 mmol). The reaction mixture was then stirred at 25° C. for 5.0 hours. The resulting mixture was poured in water (70 mL) and extracted with DCM (40 mL×3). The combined organic phases were dried over anhydrous Na₂SO₄, filtered and concentrated in vacuo. The residue was purified by silica gel column chromatography (CH₂Cl₂/MeOH (v/v)=20/1) to give the title compound as a brownish yellow solid (0.15 g, 27.3%). The compound was characterized by the following spectroscopic data: MS (ESI, pos.ion) m/z: 517.9 [M+1]$^+$; and $^1$H NMR (400 MHz, DMSO-d₆) δ: 10.90 (s, 1H), 9.45 (s, 1H), 8.92 (s, 1H), 8.12 (dd, J₁=6.8 Hz, J₂=2.6 Hz, 1H), 7.76 (s, 1H), 7.58 (s, 1H), 7.57 (t, J=8.4 Hz, 1H), 6.77-6.67 (m, 1H), 6.59 (d, J=16.2 Hz, 1H), 3.78 (t, J=6.2 Hz, 4H), 3.26 (t, J=4.4 Hz, 2H), 3.20 (dd, J₁=7.8 Hz, J₂=2.6 Hz, 2H), 2.26 (d, J=4.6 Hz, 4H).

Example 21

(E)-N-(4-((3-Chloro-4-((3-fluorobenzyl)oxy)phenyl)amino)quinazolin-6-yl)-4-((4aR,7aS)-tetrahydro-2H-[1,4]dioxino[2,3-c]pyrrol-6(3H)-yl)but-2-enamide

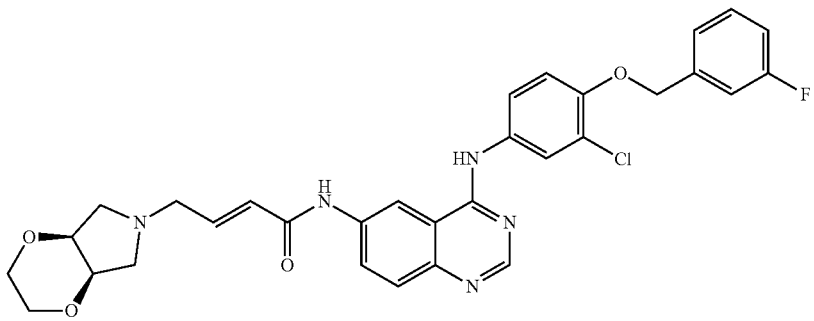 [SMILES: O=C(/C=C/CN1C[C@@H]2OCCO[C@@H]2C1)Nc1ccc2ncnc(Nc3ccc(OCc4cccc(F)c4)c(Cl)c3)c2c1]

Step 1) 4-chloro-6-nitroquinazoline

To a solution of 6-nitroquinazolin-4-ol (9.00 g, 47.1 mmol) and TEA (9.53 g, 94.2 mmol) in toluene (200 mL) was added POCl₃ (5.2 mL, 56.8 mmol) at 25° C. The reaction mixture was then heated to 80° C. and stirred for 3.0 hours. The resulting mixture was cooled to 25° C., and then to the mixture was added toluene (100 mL). The separated organic phase was washed with ice water (50 mL), dried over anhydrous Na₂SO₄, filtered and concentrated in vacuo to give the title compound as a yellow solid (7.00 g, 64.2%). The compound was characterized by the following spectroscopic data: $^1$H NMR (400 MHz, DMSO-d$_6$) δ: 8.78 (s, 1H), 8.54 (d, J=6.8 Hz, 1H), 8.39 (s, 1H), 7.87 (d, J=12.4 Hz, 1H).

Step 2) N-(3-chloro-4-((3-fluorobenzyl)oxy)phenyl)-6-nitroquinazolin-4-amine A mixture of 4-chloro-6-nitroquinazoline (7.50 g, 35.8 mmol) and 3-chloro-4-((3-fluorobenzyl)oxy)aniline (9.00 g, 35.8 mmol) in isopropanol (150 mL) was heated to 80° C. and stirred for 3.0 hours. The resulting mixture was then cooled to 20° C., and a yellow solid precipitated out. The mixture was filtered. The filter cake was washed with isopropanol (20 mL) and dried under vacuum to give the title compound as a yellow solid (8.50 g, 59.8%). The compound was characterized by the following spectroscopic data: MS (ESI, pos.ion) m/z: 425.8 [M+1]$^+$; and $^1$H NMR (400 MHz, CDCl$_3$) δ: 11.30 (brs, 1H), 9.54-9.48 (m, 1H), 8.45-8.41 (m, 1H), 8.31-8.25 (m, 1H), 7.98-7.89 (m, 1H), 7.50-7.47 (m, 1H), 7.35-7.26 (m, 1H), 7.05-6.96 (m, 1H), 6.90-6.80 (m, 2H), 7.74-7.60 (m, 2H), 4.84 (s, 2H).

Step 3) N$^4$-(3-chloro-4-((3-fluorobenzyl)oxy)phenyl)quinazoline-4,6-diamine To a solution of N-(3-chloro-4-((3-fluorobenzyl)oxy)phenyl)-6-nitroquinazolin-4-amine (6.20 g, 15.0 mmol) in EtOH (200 mL) were added iron powder (17.0 g, 304.0 mmol) and concentrated hydrochloric (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (50 mL) and filtered. The filter cake was dried under vacuum to give the title compound as a yellow solid (5.00 g, 86.8%). The compound was characterized by the following spectroscopic data: MS (ESI, pos.ion) m/z: 395.8 [M+1]$^+$.

Step 4) (E)-4-bromo-N-(4-((3-chloro-4-((3-fluorobenzyl)oxy)phenyl)amino)quinazolin-6-yl)but-2-enamide To a solution of N$^4$-(3-chloro-4-((3-fluorobenzyl)oxy)phenyl)quinazoline-4,6-diamine (0.90 g, 2.0 mmol) and TEA (0.60 g, 5.0 mmol) in anhydrous THF (10 mL) was added (E)-4-bromobut-2-enoyl chloride (0.30 g, 2.0 mmol) slowly at 0° C. The reaction mixture was then heated to 25° C. and stirred for 2.0 hours. The resulting mixture was then poured into water (50 mL) and extracted with DCM (30 mL×3). The combined organic phases were dried over anhydrous Na$_2$SO$_4$, filtered and concentrated in vacuo. The residue was triturated with DCM (7 mL) and filtered. The filter cake was dried under vacuum to give the title compound as a brownish yellow solid (0.70 g, 60.0%). The compound was characterized by the following spectroscopic data: MS (ESI, pos.ion) m/z: 542.8 [M+1]$^+$.

Step 5) (E)-N-(4-((3-chloro-4-((3-fluorobenzyl)oxy)phenyl)amino)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-((3-fluorobenzyl)oxy)phenyl)amino)quinazolin-6-yl)but-2-enamide (0.90 g, 1.1 mmol) and DIPEA (0.70 g, 3.1 mmol) in DMAC (10 mL) was added (4aR,7aS)-hexahydro-2H-[1,4]dioxino[2,3-c]pyrrole (0.50 g, 2.0 mmol) at 25° C. The reaction mixture was heated to 45° C. and stirred for 5.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.09 g, 9.0%). The compound was characterized by the following spectroscopic data: MS (ESI, pos.ion) m/z: 590.2 [M+1]$^+$; and $^1$H NMR (400 MHz, DMSO-d$_6$) δ: 10.40 (brs, 1H), 9.80 (s, 1H), 8.79 (s, 1H), 8.55 (s, 1H), 7.98 (d, J=2.4 Hz, 1H), 7.85 (dd, J=2.0, 9.2 Hz, 1H), 7.77 (d, J=9.2 Hz, 1H), 7.68 (dd, J=2.4, 8.8 HZ, 1H), 7.51-7.44 (m, 1H), 7.35-7.30 (m, 1H), 7.25 (d, J=8.8 Hz, 1H), 7.21-7.15 (m, 1H), 6.86-6.79 (m, 1H), 6.37 (d, J=15.2 Hz, 1H), 5.26 (s, 2H), 4.03 (t, J=4.0 Hz, 2H), 3.75-3.68 (m, 2H), 3.52-3.44 (m, 3H), 2.86 (dd, J=6.0, 9.6 Hz, 2H), 2.77 (dd, J=9.6, 4.0 Hz, 2H).

Example 22

(E)-N-(4-((3-Chloro-4-(pyridin-2-ylmethoxy)phenyl)amino)quinazolin-6-yl)-4-((4aR,7aS)-tetrahydro-2H-[1,4]dioxino[2,3-c]pyrrol-6(3H)-yl)but-2-enamide

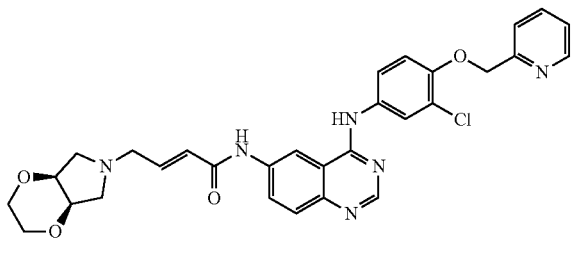 [SMILES: O=C(/C=C/CN1C[C@@H]2OCCO[C@@H]2C1)Nc1ccc2ncnc(Nc3ccc(OCc4ccccn4)c(Cl)c3)c2c1]

Step 1) N-(3-chloro-4-(pyridin-2-ylmethoxy)phenyl)-6-nitroquinazolin-4-amine A mixture of 4-chloro-6-nitroquinazoline (7.50 g, 35.8 mmol) and 3-chloro-4-(pyridin-2-ylmethoxy) aniline (8.79 g, 35.8 mmol) in isopropanol (150 mL) was heated to 80° C. and stirred for 3.0 hours. The resulting mixture was then cooled to 20° C., and a yellow solid precipitated out. The mixture was filtered. The filter cake was washed with isopropanol (20 mL) and dried under vacuum to give the title compound as a yellow solid (9.70 g, 66.4%). The compound was characterized by the following spectroscopic data: MS (ESI, pos.ion) m/z: 408.2 [M+1]$^+$.

Step 2) N$^4$-(3-chloro-4-(pyridin-2-ylmethoxy)phenyl)quinazoline-4,6-diamine To a solution of N-(3-chloro-4-(pyridin-2-ylmethoxy) phenyl)-6-nitroquinazolin-4-amine (6.20 g, 15.2 mmol) in EtOH (200 mL) were added iron powder (17.00 g, 304.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (50 mL) and filtered. The filter cake was dried under vacuum to give the title compound as a yellow solid (5.00 g, 87.7%). The compound was characterized by the following spectroscopic data: MS (ESI, pos.ion) m/z: 378.8 [M+1]$^+$; and $^1$H NMR (400 MHz, DMSO-d$_6$) δ: 9.82 (d, J=2.4 Hz, 1H), 8.97 (d, J=4.6 Hz, 1H), 8.75 (d, J=6.8 Hz, 1H), 8.14 (d, J=12.4 Hz, 1H), 7.93 (d, J=4.6 Hz, 1H), 7.70 (dd, J$_1$=2.6 Hz, J$_2$=12.4 Hz, 1H), 7.48-7.45 (m, 1H), 7.36-7.29 (m, 3H), 7.18 (t, J=6.8 Hz, 1H), 5.29 (s, 2H).

Step 3) (E)-4-bromo-N-(4-((3-chloro-4-(pyridin-2-ylmethoxy)phenyl)amino)quinazolin-6-yl)but-2-enamide To a solution of N$^4$-(3-chloro-4-(pyridin-2-ylmethoxy)phenyl)quinazoline-4,6-diamine (0.90 g, 2.4 mmol) and TEA (0.60 g, 5.0 mmol) in anhydrous THF (10 mL) was added (E)-4-bromobut-2-enoyl chloride (0.30 g, 2.0 mmol) slowly at 0° C. The reaction mixture was then heated to 25° C. and stirred for 2.0 hours. The resulting mixture was poured into water (50 mL) and extracted with DCM (30 mL×3). The combined organic phases were dried over anhydrous Na$_2$SO$_4$, filtered and concentrated in vacuo. The residue was triturated with DCM (7 mL) and filtered. The filter cake was dried under vacuum to give the title compound as a brownish yellow solid (0.50 g, 40.1%). The compound was characterized by the following spectroscopic data: MS (ESI, pos.ion) m/z: 524.2 [M+1]$^+$.

Step 4) (E)-N-(4-((3-chloro-4-(pyridin-2-ylmethoxy)phenyl)amino)quinazolin-6-yl)-4-((4aR,7aS)-tetrahydro-2H-[1,4]dioxin[2,3-c]pyrrol-6(3H)-yl)but-2-enamide To a solution of (E)-4-bromo-N-(4-((3-chloro-4-(pyridin-2-ylmethoxy)phenyl)amino)quinazolin-6-yl) but-2-enamide (0.50 g, 1.3 mmol) and DIPEA (0.70 g, 3.0 mmol) in DMAC (10 mL) was added (4aR,7aS)-hexahydro-2H-[1,4]dioxino[2,3-c]pyrrole (0.50 g, 2.0 mmol) at 25° C. The reaction mixture was heated to 45° C. and stirred for 5.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.08 g, 10.0%). The compound was characterized by the following spectroscopic data: MS (ESI, pos.ion) m/z: 573.1 [M+1]$^+$; and $^1$H NMR (400 MHz, DMSO-d$_6$) δ: 9.67 (s, 1H), 9.52 (s, 1H), 8.89 (s, 1H), 8.60 (d, J=1.2 Hz, 1H), 8.48 (s, 1H), 7.98 (d, J=4.0 Hz, 1H), 7.89 (s, 1H), 7.69 (d, J=4.8 Hz, 1H), 7.60 (d, J=4.8 Hz, 1H), 7.37 (s, 1H), 7.26 (s, 1H), 7.24 (s, 1H), 6.80 (d, J=9.6 Hz, 1H), 6.59 (d, J=9.6 Hz, 1H), 5.29 (s, 2H), 4.02 (s, 5H), 3.71 (s, 2H), 3.48 (d, J=2.8 Hz, 2H), 2.86 (s, J=4.6 Hz, 2H), 2.76 (s, 2H).

Example 23

(E)-N-(4-((3-Chloro-4-(pyridin-2-ylmethoxy)phenyl)amino)-7-methoxyquinazolin-6-yl)-4-((4 aR,7aS) tetrahydro-2H-[1,4]dioxino[2,3-c]pyrrol-6(3H)-yl) but-2-enamide

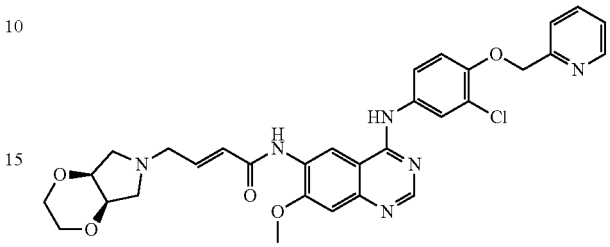

Step 1) N-(3-chloro-4-(pyridin-2-ylmethoxy)phenyl)-7-fluoro-6-nitroquinazolin-4-amine To a solution of 3-chloro-4-(pyridin-2-ylmethoxy)aniline (20.70 g, 88.1 mmol) in isopropanol (300 mL) was added 4-chloro-7-fluoro-6-nitroquinazoline (20.00 g, 88.1 mmol) at 25° C. The reaction mixture was then heated to 70° C. and stirred for 2.0 hours. Then a lot of yellow solid precipitated out. The resulting mixture was cooled to 25° C., and then filtered. The filter cake was dried under vacuum to give the title compound as a yellow solid (30.0 g, 80.8%). The compound was characterized by the following spectroscopic data: MS (ESI, pos.ion) m/z: 426.8 [M+1]$^+$.

Step 2) N-(3-chloro-4-(pyridin-2-ylmethoxy)phenyl)-7-methoxy-6-nitroquinazolin-4-amine To a solution of N-(3-chloro-4-(pyridin-2-ylmethoxy)phenyl)-7-fluoro-6-nitroquinazolin-4-amine (20.00 g, 46.9 mmol) in anhydrous methanol (300 mL) was added sodium methylate (14.60 g, 269.5 mmol) at 25° C. The reaction mixture was heated to 70° C. and stirred for 3.0 hours. Then the reaction mixture was cooled to 25° C. The resulting mixture was poured into water (2000 mL). Then a lot of solid precipitated out. The mixture was filtered, and the filter cake was dried under vacuum to give the title compound as a yellow solid (17.0 g, 82.5%). The compound was characterized by the following spectroscopic data: MS (ESI, pos.ion) m/z: 438.8 [M+1]$^+$.

Step 3) N$^4$-(3-chloro-4-(pyridin-2-ylmethoxy)phenyl)-7-methoxyquinazoline-4,6-diamine To a solution of N-(3-chloro-4-(pyridin-2-ylmethoxy)phenyl)-7-methoxy-6-nitroquinazolin-4-amine (10.00 g, 22.8 mmol) in EtOH (200 mL) were added iron powder (17.00 g, 304.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (50 mL) and filtered. The filter cake was dried under vacuum to give the title compound as a yellow solid (5.00 g, 54.3%). The compound was characterized by the following spectroscopic data: MS (ESI, pos.ion) m/z: 408.8 [M+1]$^+$.

Step 4) (E)-4-bromo-N-(4-((3-chloro-4-(pyridin-2-ylmethoxy)phenyl)amino)-7-methoxyquinazolin-6-yl)but-2-enamide To a solution of N$^4$-(3-chloro-4-(pyridin-2-ylmethoxy)phenyl)-7-methoxyquinazoline-4,6-diamine (1.00 g, 2.4 mmol) and TEA (0.60 g, 5.0 mmol) in anhydrous THF (10 mL) was added (E)-4-bromobut-2-enoyl chloride (0.30 g, 2.0 mmol) slowly at 0° C. The reaction mixture was then heated to 25° C. and stirred for 2.0 hours. The resulting mixture was poured into water (50 mL) and extracted with DCM (30 mL×3). The combined organic phases were dried over anhydrous Na$_2$SO$_4$, filtered and concentrated in vacuo. The residue was triturated with DCM (7 mL) and filtered. The filter cake was dried under vacuum to give the title compound as a brownish yellow solid (0.70 g, 51.4%). The compound was characterized by the following spectroscopic data: MS (ESI, pos.ion) m/z: 554.2 [M+1]$^+$.

Step 5) (E)-N-(4-((3-Chloro-4-(pyridin-2-ylmethoxy)phenyl)amino)-7-methoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-(pyridin-2-ylmethoxy)phenyl)amino)-7-methoxyquinazolin-6-yl)but-2-enamide (0.50 g, 0.9 mmol) and DIPEA (0.70 g, 3.0 mmol) in DMAC (10 mL) was added (4aR,7aS)-hexahydro-2H-[1,4]dioxino[2,3-c]pyrrole (0.50 g, 2.0 mmol) at 25° C. The reaction mixture was heated to 45° C. and stirred for 5.0 hours. Then the reaction mixture was cooled to 25° C. The resulting mixture was poured into water (70 mL) and extracted with DCM (50 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.08 g, 14.8%). The compound was characterized by the following spectroscopic data: MS (ESI, pos.ion) m/z: 603.2 [M+1]$^+$; and $^1$H NMR (400 MHz, DMSO-d$_6$) δ: 9.57 (s, 1H), 9.54 (s, 1H), 8.86 (s, 1H), 8.85-8.80 (m, 1H), 8.62 (d, J=1.2 Hz, 1H), 8.58 (s, 1H), 7.92 (d, J=4.0 Hz, 1H), 7.81-7.77 (m, 1H), 7.71-7.60 (m, 2H), 7.38-7.35 (m, 1H), 7.24 (s, 1H), 7.20 (s, 1H), 6.58 (d, J=12.0 Hz, 1H), 5.30 (s, 2H), 3.78 (s, 3H), 3.68 (t, J=6.2 Hz, 4H), 3.26 (t, J=4.4 Hz, 2H), 3.20 (dd, J$_1$=7.8 Hz, J$_2$=2.6 Hz, 2H), 2.26 (d, J=4.6 Hz, 4H).

Example 24

(E)-N-(4-((3-Chloro-4-(pyridin-2-ylmethoxy)phenyl)amino)-7-ethoxyquinazolin-6-yl)-4-((4aR,7aS)-tetrahydro-2H-[1,4]dioxino[2,3-c]pyrrol-6(3H)-yl)but-2-enamide

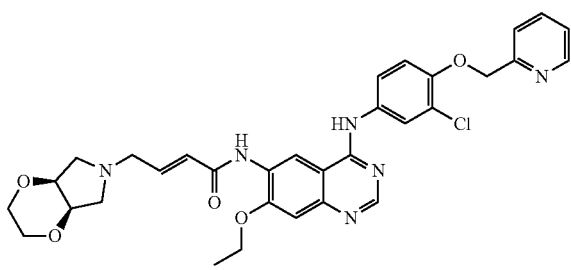 [SMILES: CCOc1cc2ncnc(Nc3ccc(OCc4ccccn4)c(Cl)c3)c2cc1NC(=O)/C=C/CN1C[C@@H]2OCCO[C@@H]2C1]

Step 1) N-(3-chloro-4-(pyridin-2-ylmethoxy)phenyl)-7-ethoxy-6-nitroquinazolin-4-amine To a solution of N-(3-chloro-4-(pyridin-2-ylmethoxy)phenyl)-7-fluoro-6-nitroquinazolin-4-amine (20.00 g, 46.9 mmol) in anhydrous ethanol (300 mL) was added sodium ethylate (14.60 g, 214.7 mmol) at 25° C. The reaction mixture was heated to 70° C. and stirred for 3.0 hours. Then the reaction mixture was cooled to 25° C. The resulting mixture was poured into water (2000 mL), and a lot of solid precipitated out. The mixture was filtered. The filter cake was dried under vacuum to give the title compound as a yellow solid (18.0 g, 84.9%). The compound was characterized by the following spectroscopic data: MS (ESI, pos.ion) m/z: 452.8 [M+1]$^+$.

Step 2) N$^4$-(3-chloro-4-(pyridin-2-ylmethoxy)phenyl)-7-ethoxyquinazoline-4,6-diamine To a solution of N-(3-chloro-4-(pyridin-2-ylmethoxy)phenyl)-7-ethoxy-6-nitroquinazolin-4-amine (10.00 g, 22.1 mmol) in EtOH (200 mL) were added iron powder (17.00 g, 304.0 mmol) and concentrated hydrochloric acid (4.0 mL) at 25° C. The reaction mixture was heated to 90° C. and stirred for 5.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (50 mL) and filtered. The filter cake was dried under vacuum to give the title compound as a yellow solid (5.20 g, 55.9%). The compound was characterized by the following spectroscopic data: MS (ESI, pos.ion) m/z: 422.8 [M+1]$^+$.

Step 3) (E)-4-bromo-N-(4-((3-chloro-4-(pyridin-2-ylmethoxy)phenyl)amino)-7-ethoxyquinazolin-6-yl)but-2-enamide To a solution of N$^4$-(3-chloro-4-(pyridin-2-ylmethoxy)phenyl)-7-ethoxyquinazoline-4,6-diamine (3.00 g, 7.1 mmol) and TEA (1.80 g, 15.0 mmol) in anhydrous THF (25 mL) was added (E)-4-bromobut-2-enoyl chloride (0.90 g, 6.0 mmol) slowly at 0° C. The reaction mixture was then heated to 25° C. and stirred for 2.0 hours. The resulting mixture was poured into water (90 mL) and extracted with DCM (50 mL×3). The combined organic phases were dried over anhydrous Na$_2$SO$_4$, filtered and concentrated in vacuo. The residue was triturated with DCM (17 mL) and filtered. The filter cake was dried under vacuum to give the title compound as a brownish yellow solid (2.55 g, 63.4%). The compound was characterized by the following spectroscopic data: MS (ESI, pos.ion) m/z: 568.1 [M+1]$^+$.

Step 4) (E)-N-(4-((3-chloro-4-(pyridin-2-ylmethoxy)phenyl)amino)-7-ethoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-(pyridin-2-ylmethoxy)phenyl)amino)-7-ethoxyquinazolin-6-yl)but-2-enamide (0.50 g, 0.9 mmol) and DIPEA (0.70 g, 3.0 mmol) in DMAC (10 mL) was added (4aR,7aS)-hexahydro-2H-[1,4]dioxino[2,3-c]pyrrole (0.50 g, 2.0 mmol) at 25° C. The reaction mixture was heated to 45° C. and stirred for 5.0 hours. Then the reaction mixture was cooled to 25° C. The resulting mixture was poured into water (70 mL) and extracted with DCM (50 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.10 g, 18.5%). The compound was characterized by the following spectroscopic data: MS (ESI, pos.ion) m/z: 617.2 [M+1]$^+$; and $^1$H NMR (400 MHz, DMSO-d$_6$) δ: 9.51 (s, 1H), 9.50 (s, 1H), 8.86 (s, 1H), 8.62 (d, J=1.2 Hz, 1H), 8.58 (s, 1H), 7.90 (d, J=4.0 Hz, 1H), 7.81-7.78 (m, 1H), 7.76-7.67 (m, 1H), 7.66 (d, J=4.2 Hz, 1H), 7.38-7.35 (m, 1H), 7.28 (s, 1H), 7.20 (s, 1H), 6.87-6.79 (m, 1H), 6.60 (d, J=12.0 Hz, 1H), 5.30 (s, 2H), 4.09 (q, J=4.2 Hz, 2H), 3.69 (t, J=6.2 Hz, 4H), 3.27 (t, J=4.4 Hz, 2H), 3.25 (dd, J$_1$=8.6 Hz, J$_2$=2.4 Hz, 2H), 2.26 (d, J=4.6 Hz, 4H), 1.32 (t, J=1.8 Hz, 3H).

Example 25

(E)-N-(4-((3-Chloro-4-(pyridin-2-ylmethoxy)phenyl) amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide

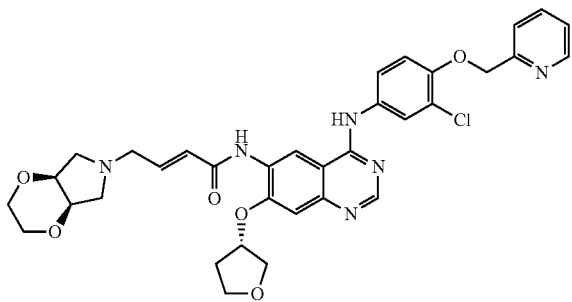 [SMILES: O=C(/C=C/CN1C[C@@H]2OCCO[C@@H]2C1)Nc1cc2c(Nc3ccc(OCc4ccccn4)c(Cl)c3)ncnc2cc1O[C@H]1CCOC1]

Step 1) (S)—N-(3-chloro-4-(pyridin-2-ylmethoxy) phenyl)-6-nitro-7-((tetrahydrofuran-3-yl)oxy) quinazolin-4-amine To a solution of N-(3-chloro-4-(pyridin-2-ylmethoxy) phenyl)-7-fluoro-6-nitroquinazolin-4-amine (20.00 g, 46.9 mmol) in DMF (300 mL) were added potassium trimethylsilanolate (18.20 g, 140.7 mmol) and (S)-tetrahydrofuran-3-ol (6.86 g, 78.0 mmol) at 25° C. The reaction mixture was heated to 50° C. and stirred for 3.0 hours. Then the reaction mixture was cooled to 25° C. The resulting mixture was poured into water (2000 mL), and a lot of solid precipitated out. The mixture was filtered. The filter cake was dried under vacuum to give the title compound as a yellow solid (19.0 g, 81.8%). The compound was characterized by the following spectroscopic data: MS (ESI, pos.ion) m/z: 494.1 [M+1]$^+$.

Step 2) (S)—N$^4$-(3-chloro-4-(pyridin-2-ylmethoxy) phenyl)-7-((tetrahydrofuran-3-yl)oxy)quinazoline-4,6-diamine To a solution of (S)—N-(3-chloro-4-(pyridin-2-ylmethoxy)phenyl)-6-nitro-7-((tetrahydrofuran-3-yl)oxy) quinazolin-4-amine (10.00 g, 20.2 mmol) in EtOH (200 mL) were added iron powder (17.00 g, 304.0 mmol) and concentrated hydrochloric acid (3.0 mL) at 25° C. The reaction mixture was heated to 90° C. and stirred for 5.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (70 mL) and filtered. The filter cake was dried under vacuum to give the title compound as a yellow solid (6.10 g, 65.5%). The compound was characterized by the following spectroscopic data: MS (ESI, pos.ion) m/z: 464.2 [M+1]$^+$.

Step 3) (S,E)-4-bromo-N-(4-((3-chloro-4-(pyridin-2-ylmethoxy)phenyl)amino)-7-((tetrahydrofuran-3-yl) oxy)quinazolin-6-yl)but-2-enamide To a solution of (S)—N$^4$-(3-chloro-4-(pyridin-2-ylmethoxy)phenyl)-7-((tetrahydrofuran-3-yl)oxy)quinazoline-4,6-diamine (1.00 g, 2.2 mmol) in THF (15 mL) were added TEA (0.28 g, 2.7 mmol) and (E)-4-bromobut-2-enoyl chloride (0.33 g, 1.8 mmol) at 0° C. The reaction mixture was then stirred at 0° C. for 1.0 hour. The resulting mixture was poured into water (50 mL) and extracted with DCM (50 mL×3). The combined organic phases were washed with saturated brine (20 mL), dried over anhydrous Na$_2$SO$_4$, filtered and concentrated in vacuo. The residue was purified by silica gel column chromatography (CH$_2$Cl$_2$/MeOH (v/v) =40/1) to give the title compound as a yellow solid (0.14 g, 10.6%). The compound was characterized by the following spectroscopic data: MS (ESI, pos.ion) m/z: 610.1 [M+1]$^+$.

Step 4) (E)-N-(4-((3-chloro-4-(pyridin-2-ylmethoxy) phenyl)amino)-7-(((S)-tetrahydrofuran-3-yl)oxy) quinazolin-6-yl)-4-((4aR,7aS)-tetrahydro-2H-[1,4] dioxino[2,3-c]pyrrol-6(3H)-yl)but-2-enamide To a solution of (S,E)-4-bromo-N-(4-((3-chloro-4-(pyridin-2-ylmethoxy)phenyl)amino)-7-((tetrahydrofuran-3-yl) oxy)quinazolin-6-yl)but-2-enamide (0.14 g, 0.2 mmol) in DMAC (2 mL) were added (4aR,7aS)-hexahydro-2H-[1,4] dioxino[2,3-c]pyrrole (0.40 g, 0.3 mmol) and DIPEA (0.09 g, 0.7 mmol) at 25° C. The reaction mixture was heated to 45° C. and stirred for 12.0 hours. Then the reaction mixture was cooled to 25° C. The resulting mixture was poured into water (50 mL) and extracted with DCM (50 mL×3). The combined organic phases were washed with saturated brine (150 mL), dried over anhydrous Na$_2$SO$_4$, filtered and concentrated in vacuo. The residue was purified by silica gel column chromatography (CH$_2$Cl$_2$/MeOH (v/v)=20/1) to give the title compound as a yellow solid (0.13 g, 87.4%). The compound was characterized by the following spectroscopic data: MS (ESI, pos.ion) m/z: 659.2 [M+1]$^+$; and $^1$H NMR (400 MHz, DMSO-d$_6$) δ: 9.69 (s, 1H), 9.45 (s, 1H), 8.92 (s, 1H), 8.61 (d, J=4.6 Hz, 1H), 8.48 (s, 1H), 7.99 (s, 1H), 7.89 (t, J=7.8 Hz, 1H), 7.70 (d, J=8.4 Hz, 1H), 7.60 (d, J=8.2 Hz, 1H), 7.42-7.35 (m, 1H), 7.31-7.18 (m, 2H), 6.81 (d, J=15.4 Hz, 1H), 6.58 (d, J=14.6 Hz, 1H), 5.29 (s, 2H), 4.02 (d, J=8.6 Hz, 2H), 3.85-3.65 (m, 3H), 3.53-3.43 (m, 2H), 2.80 (d, J=7.4 Hz, 3H), 2.35 (dd, J$_1$=13.2 Hz, J$_2$=6.4 Hz, 2H), 2.17 (s, 2H), 2.01 (d, J=7.6 Hz, 2H), 1.24 (s, 4H).

Example 26

(E)-N-(4-((1-(3-Fluorobenzyl)-1H-indazol-5-yl) amino)quinazolin-6-yl)-4-((4aR,7aS)-tetrahydro-2H-[1,4]dioxin[2,3-c]pyrrol-6(3H)-yl)but-2-enamide

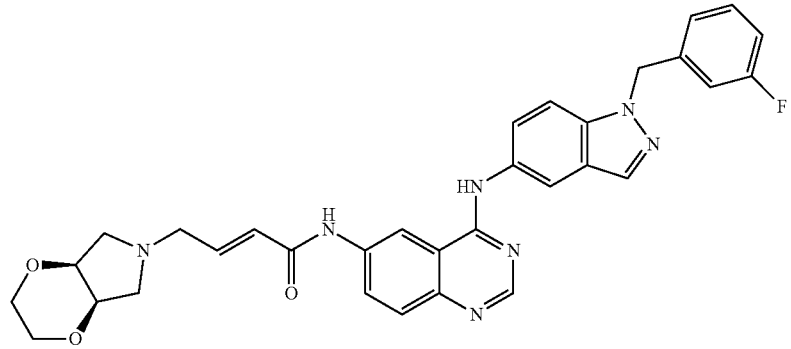 [SMILES: O=C(/C=C/CN1C[C@@H]2OCCO[C@@H]2C1)Nc1ccc2ncnc(Nc3ccc4c(cnn4Cc4cccc(F)c4)c3)c2c1]

Step 1) N-(1-(3-fluorobenzyl)-1H-indazol-5-yl)-6-nitroquinazolin-4-amine

A solution of 4-chloro-6-nitroquinazoline (8.00 g, 38.3 mmol) and 1-(3-fluorobenzyl)-1H-indazol-5-amine (9.22 g, 38.3 mmol) in isopropanol (150 mL) was heated to 80° C. and stirred for 3.0 hours. Then the reaction mixture was cooled to 20° C. A yellow solid precipitated out. The mixture was filtered. The filtered cake was washed with isopropanol (20 mL) and dried under vacuum to give the title compound as a yellow solid (10.0 g, 63.3%). The compound was characterized by the following spectroscopic data: MS (ESI, pos.ion) m/z: 415.3 [M+1]$^+$; and $^1$H NMR (400 MHz, DMSO-d$_6$) δ: 11.34 (s, 1H), 8.64 (s, 2H), 8.36 (s, 1H), 8.22 (s, 1H), 8.08 (s, 1H), 7.78 (d, J=1.6 Hz, 1H), 7.64-7.62 (m, 2H), 7.40-7.34 (m, 2H), 7.14-7.06 (m, 2H), 5.73 (s, 2H).

Step 2) N$^4$-(1-(3-fluorobenzyl)-1H-indazol-5-yl) quinazoline-4,6-diamine

To a solution of N-(1-(3-fluorobenzyl)-1H-indazol-5-yl)-6-nitroquinazolin-4-amine (7.20 g, 17.4 mmol) in EtOH (200 mL) were added iron powder (17.00 g, 304.0 mmol) and concentrated hydrochloric acid (3.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (50 mL) and filtered. The filter cake was dried under vacuum to give the title compound as a yellow solid (6.00 g, 89.9%). The compound was characterized by the following spectroscopic data: MS (ESI, pos.ion) m/z: 385.4 [M+1]$^+$.

Step 3) (E)-4-bromo-N-(4-((1-(3-fluorobenzyl)-1H-indazol-5-yl)amino)quinazolin-6-yl)but-2-enamide To a solution of N$^4$-(1-(3-fluorobenzyl)-1H-indazol-5-yl) quinazoline-4,6-diamine (0.90 g, 2.3 mmol) and TEA (0.60 g, 5.0 mmol) in anhydrous THF (10 mL) was added (E)-4-bromobut-2-enoyl chloride (0.35 g, 2.3 mmol) slowly at 0° C. The reaction mixture was then heated to 25° C. and stirred for 2.0 hours. The resulting mixture was poured into water (50 mL) and extracted with DCM (30 mL×3). The combined organic phases were dried over anhydrous Na$_2$SO$_4$, filtered and concentrated in vacuo. The residue was triturated with DCM (7 mL) and filtered. The filter cake was dried under vacuum to give the title compound as a brownish yellow solid (0.75 g, 61.4%). The compound was characterized by the following spectroscopic data: MS (ESI, pos.ion) m/z: 531.3 [M+1]$^+$.

Step 4) (E)-N-(4-((1-(3-fluorobenzyl)-1H-indazol-5-yl)amino)quinazolin-6-yl)-4-((4aR,7aS)-tetrahydro-2H-[1,4]dioxin[2,3-c]pyrrol-6(3H)-yl)but-2-enamide To a solution of (E)-4-bromo-N-(4-((1-(3-fluorobenzyl)-1H-indazol-5-yl)amino)quinazolin-6-yl)but-2-enamide (0.90 g, 1.7 mmol) and DIPEA (0.70 g, 3.0 mmol) in DMAC (10 mL) was added (4aR,7aS)-hexahydro-2H-[1,4]dioxino[2,3-c]pyrrole (0.55 g, 2.2 mmol) at 25° C. The reaction mixture was heated to 45° C. and stirred for 5.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a brownish yellow solid (0.10 g, 10.2%). The compound was characterized by the following spectroscopic data: MS (ESI, pos.ion) m/z: 580.6 [M+1]$^+$; and $^1$H NMR (400 MHz, DMSO-d$_6$) δ: 10.34 (s, 1H), 8.70 (s, 1H), 8.46 (s, 2H), 8.32 (s, 1H), 8.18 (s, 1H), 8.03 (d, J=1.6 Hz, 1H), 7.74-7.69 (m, 2H), 7.45-7.38 (m, 2H), 7.09-7.06 (m, 1H), 6.60 (d, J=12.0 Hz, 1H), 5.75 (s, 2H), 3.78 (t, J=6.2 Hz, 4H), 3.26 (t, J=4.4 Hz, 2H), 3.20-3.12 (m, 2H), 2.27-2.20 (m, 4H).

Example 27

(E)-N-(4-((1-(3-Fluorobenzyl)-1H-indazol-5-yl)amino)-7-methoxyquinazolin-6-yl)-4-((4aR,7aS)-tetra hydro-2H-[1,4]dioxin[2,3-c]pyrrol-6(3H)-yl)but-2-enamide

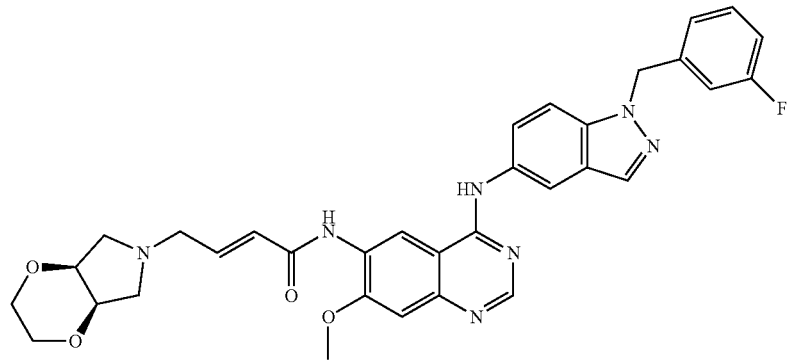 [SMILES: COc1cc2ncnc(Nc3ccc4c(cnn4Cc4cccc(F)c4)c3)c2cc1NC(=O)/C=C/CN1C[C@@H]2OCCO[C@@H]2C1]

Step 1) 7-fluoro-N-(1-(3-fluorobenzyl)-1H-indazol-5-yl)-6-nitroquinazolin-4-amine A solution of 4-chloro-7-fluoro-6-nitroquinazoline (8.00 g, 35.2 mmol) and 1-(3-fluorobenzyl)-1H-indazol 5-amine (9.22 g, 38.3 mmol) in isopropanol (150 mL) was heated to 80° C. and stirred for 3.0 hours. The reaction mixture was then cooled to 20° C., and a yellow solid precipitated out. The mixture was filtered. The filter cake was washed with isopropanol (20 mL) and dried under vacuum to give the title compound as a yellow solid (12.0 g, 78.9%). The compound was characterized by the following spectroscopic data: MS (ESI, pos.ion) m/z: 433.3 [M+1]$^+$.

Step 2) N-(1-(3-fluorobenzyl)-1H-indazol-5-yl)-7-methoxy-6-nitroquinazolin-4-amine To a solution of 7-fluoro-N-(1-(3-fluorobenzyl)-1H-indazol-5-yl)-6-nitroquinazolin-4-amine (10.00 g, 23.5 mmol) in anhydrous MeOH (300 mL) was added sodium methylate (7.30 g, 134.7 mmol) at 25° C. The reaction mixture was heated to 70° C. and stirred for 3.0 hours. Then the reaction mixture was cooled to 25° C. The resulting mixture was poured into water (2000 mL), and a lot of solid precipitated out. The mixture was filtered. The filter cake was dried under vacuum to give the title compound as a yellow solid (8.00 g, 77.8%). The compound was characterized by the following spectroscopic data: MS (ESI, pos.ion) m/z: 445.4 [M+1]$^+$.

Step 3) N$^4$-(1-(3-fluorobenzyl)-1H-indazol-5-yl)-7-methoxyquinazoline-4,6-diamine To a solution of N-(1-(3-fluorobenzyl)-1H-indazol-5-yl)-7-methoxy-6-nitroquinazolin-4-amine (7.00 g, 15.7 mmol) in EtOH (200 mL) were added iron powder (17.00 g, 304.0 mmol) and concentrated hydrochloric acid (5.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (40 mL) and filtered. The filter cake was dried under vacuum to give the title compound as a yellow solid (5.50 g, 84.6%). The compound was characterized by the following spectroscopic data: MS (ESI, pos.ion) m/z: 415.4 [M+1]$^+$.

Step 4) (E)-4-bromo-N-(4-((1-(3-fluorobenzyl)-1H-indazol-5-yl)amino)-7-methoxyquinazolin-6-yl)but-2-enamide To a solution of N$^4$-(1-(3-fluorobenzyl)-1H-indazol-5-yl)-7-methoxyquinazoline-4,6-diamine (0.90 g, 2.1 mmol) and TEA (0.60 g, 5.0 mmol) in anhydrous THF (10 mL) was added (E)-4-bromobut-2-enoyl chloride (0.35 g, 2.3 mmol) slowly at 0° C. The reaction mixture was then heated to 25° C. and stirred for 2.0 hours. The resulting mixture was poured into water (50 mL) and extracted with DCM (30 mL×3). The combined organic phases were dried over anhydrous Na$_2$SO$_4$, filtered and concentrated in vacuo. The residue was triturated with DCM (8 mL) and filtered. The filter cake was dried under vacuum to give the title compound as a brownish yellow solid (0.65 g, 53.2%). The compound was characterized by the following spectroscopic data: MS (ESI, pos.ion) m/z: 561.2 [M+1]$^+$.

Step 5) (E)-N-(4-((1-(3-fluorobenzyl)-1H-indazol-5-yl)amino)-7-methoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((1-(3-fluorobenzyl)-1H-indazol-5-yl)amino)-7-methoxyquinazolin-6-yl)but-2-enamide (0.50 g, 0.9 mmol) and DIPEA (0.70 g, 3.0 mmol) in DMAC (10 mL) was added (4aR,7aS)-hexahydro-2H-[1,4]dioxino[2,3-c]pyrrole (0.55 g, 2.2 mmol) at 25° C. The reaction mixture was heated to 45° C. and stirred for 5.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=10/1) to give the title compound as a brownish yellow solid (0.10 g, 18.5%). The compound was characterized by the following spectroscopic data: MS (ESI, pos.ion) m/z: 610.6 [M+1]$^+$; and $^1$H NMR (400 MHz, DMSO-d$_6$) δ: 10.37 (s, 1H), 9.42 (s, 1H), 8.75 (s, 2H), 8.45 (s, 1H), 8.21 (s, 1H), 8.10 (d, J=1.6 Hz, 1H), 7.84-7.72 (m, 2H), 7.55-7.38 (m, 2H), 7.09-7.06 (m, 1H), 6.60 (d, J=12.0 Hz, 1H), 5.76 (s, 2H), 3.82 (s, 3H), 3.78 (t, J=6.2 Hz, 4H), 3.26 (t, J=4.4 Hz, 2H), 3.20-3.12 (m, 2H), 2.25-2.28 (m, 4H).

Example 28

(E)-N-(7-Ethoxy-4-((1-(3-fluorobenzyl)-1H-indazol-5-yl)amino)quinazolin-6-yl)-4-((4aR,7aS)-tetrahydro-2H-[1,4]dioxino[2,3-c]pyrrol-6(3H)-yl)but-2-enamide

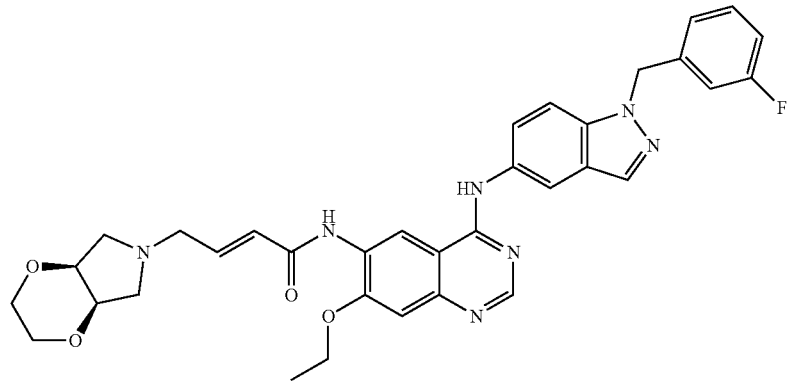 [SMILES: CCOc1cc2ncnc(Nc3ccc4c(cnn4Cc4cccc(F)c4)c3)c2cc1NC(=O)/C=C/CN1C[C@@H]2OCCO[C@@H]2C1]

Step 1) 7-ethoxy-N-(1-(3-fluorobenzyl)-1H-indazol-5-yl)-6-nitroquinazolin-4-amine To a solution of 7-fluoro-N-(1-(3-fluorobenzyl)-1H-indazol-5-yl)-6-nitroquinazolin-4-amine (10.00 g, 23.5 mmol) in anhydrous EtOH (300 mL) was added sodium ethylate (9.00 g, 132.3 mmol) at 25° C. The reaction mixture was heated to 70° C. and stirred for 3.0 hours. Then the reaction mixture was cooled to 25° C. The resulting mixture was poured into water (2000 mL), and a lot of solid precipitated out. The mixture was filtered and the filter cake was dried under vacuum to give the title compound as a yellow solid (8.20 g, 77.3%). The compound was characterized by the following spectroscopic data: MS (ESI, pos.ion) m/z: 459.4 [M+1]$^+$.

Step 2) 7-ethoxy-N$^4$-(1-(3-fluorobenzyl)-1H-indazol-5-yl)quinazoline-4,6-diamine To a solution of 7-ethoxy-N-(1-(3-fluorobenzyl)-1H-indazol-5-yl)-6-nitroquinazolin-4-amine (7.00 g, 15.2 mmol) in EtOH (200 mL) were added iron powder (17.00 g, 304.0 mmol) and concentrated hydrochloric acid (4.0 mL) at 25° C. The reaction mixture was heated to 90° C. and stirred for 3.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (40 mL) and filtered. The filter cake was dried under vacuum to give the title compound as a yellow solid (5.70 g, 87.6%). The compound was characterized by the following spectroscopic data: MS (ESI, pos.ion) m/z: 429.4 [M+1]$^+$.

Step 3) (E)-4-bromo-N-(7-ethoxy-4-((1-(3-fluorobenzyl)-1H-indazol-5-yl)amino)quinazolin-6-yl)but-2-enamide To a solution of 7-ethoxy-N$^4$-(1-(3-fluorobenzyl)-1H-indazol-5-yl)quinazoline-4,6-diamine (0.90 g, 2.1 mmol) and TEA (0.60 g, 5.0 mmol) in anhydrous THF (10 mL) was added (E)-4-bromobut-2-enoyl chloride (0.35 g, 2.3 mmol) slowly at 0° C. The reaction mixture was then heated to 25° C. and stirred for 2.0 hours. The resulting mixture was poured into water (50 mL) and extracted with DCM (30 mL×3). The combined organic phases were dried over anhydrous Na$_2$SO$_4$, filtered and concentrated in vacuo. The residue was triturated with DCM (8 mL) and filtered. The filter cake was dried under vacuum to give the title compound as a brownish yellow solid (0.67 g, 55.8%). The compound was characterized by the following spectroscopic data: MS (ESI, pos.ion) m/z: 574.2 [M+1]$^+$.

Step 4) (E)-N-(7-ethoxy-4-((1-(3-fluorobenzyl)-1H-indazol-5-yl)amino)quinazolin-6-yl)-4-((4aR,7aS) tetrahydro-2H-[1,4]dioxino[2,3-c]pyrrol-6(3H)-yl) but-2-enamide To a solution of (E)-4-bromo-N-(7-ethoxy-4-((1-(3-fluorobenzyl)-1H-indazol-5-yl)amino)quinazolin-6-yl)but-2-enamide (0.50 g, 0.9 mmol) and DIPEA (0.70 g, 3.0 mmol) in DMAC (10 mL) was added (4aR,7aS)-hexahydro-2H-[1,4]dioxino[2,3-c]pyrrole (0.55 g, 2.2 mmol) at 25° C. The reaction mixture was heated to 45° C. and stirred for 5.0 hours. Then the reaction mixture was cooled to 25° C. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=10/1) to give the title compound as a brownish yellow solid (0.09 g, 16.6%). The compound was characterized by the following spectroscopic data: MS (ESI, pos.ion) m/z: 624.6 [M+1]$^+$; and $^1$H NMR (400 MHz, DMSO-d$_6$) δ: 10.34 (s, 1H), 8.70 (s, 2H), 8.46 (s, 1H), 8.32 (s, 1H), 8.18 (s, 1H), 8.03 (d, J=1.6 Hz, 1H), 7.74-7.69 (m, 2H), 7.45-7.38 (m, 2H), 7.09-7.06 (m, 1H), 6.60-6.57 (d, J=12.0 Hz, 1H), 5.75 (s, 2H), 4.01 (q, J=8.4 Hz, 2H), 3.78 (t, J=6.2 Hz, 4H), 3.26 (t, J=4.4 Hz, 2H), 3.20-3.12 (m, 2H), 2.26-2.23 (m, 4H), 1.31 (t, J=1.6 Hz, 3H).

Example 29

(E)-N-(4-((3-Chloro-4-((3-fluorobenzyl)oxy)phenyl)amino)-7-methoxyquinazolin-6-yl)-4-((4aR,7aS)-tetrahydro-2H-[1,4]dioxino[2,3-c]pyrrol-6(3H)-yl)but-2-enamide

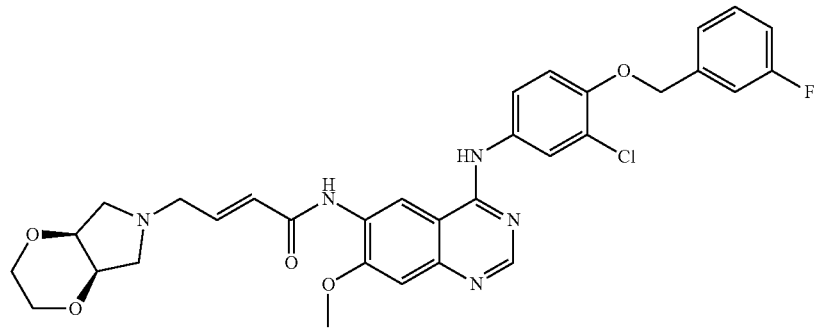 [SMILES: COc1cc2ncnc(Nc3ccc(OCc4cccc(F)c4)c(Cl)c3)c2cc1NC(=O)/C=C/CN1C[C@@H]2OCCO[C@@H]2C1]

Step 1) 4-chloro-7-fluoro-6-nitroquinazoline

To a solution of 7-fluoro-6-nitroquinazolin-4-ol (10.00 g, 48.0 mmol) and TEA (14.3 mL, 96.0 mmol) in toluene (200 mL) was added $POCl_3$ (4.0 mL, 45.0 mmol) slowly. The reaction mixture was then heated to 85° C. and stirred for 3.0 hours. The resulting mixture was cooled to 25° C., and then to the mixture was added toluene (200 mL). The separated organic phase was washed with saturated brine (100 mL), dried over anhydrous $Na_2SO_4$, filtered and concentrated in vacuo to give the title compound as a brown solid (10.0 g, 92.1%). The compound was characterized by the following spectroscopic data: MS (ESI, pos.ion) m/z: 228.0 $[M+H]^+$.

Step 2) N-(3-chloro-4-((3-fluorobenzyl)oxy)phenyl)-7-fluoro-6-nitroquinazolin-4-amine A solution of 4-chloro-7-fluoro-6-nitroquinazoline (10.00 g, 44.0 mmol) and 3-chloro-4-((3-fluorobenzyl)oxy)aniline (12.00 g, 46.5 mmol) in isopropanol (150 mL) was heated to 95° C. and stirred for 5.0 hours. The resulting mixture was cooled to 25° C., and a solid precipitated out. The mixture was filtered. The filter cake was washed with isopropanol (50 mL) and dried under vacuum to give the title compound as a yellow solid (14.0 g, 70.1%). The compound was characterized by the following spectroscopic data: MS (ESI, pos.ion) m/z: 443.0 $[M+H]^+$.

Step 3) N-(3-chloro-4-((3-fluorobenzyl)oxy)phenyl)-7-methoxy-6-nitroquinazolin-4-amine A mixture of N-(3-chloro-4-((3-fluorobenzyl)oxy)phenyl)-7-fluoro-6-nitroquinazolin-4-amine (5.00 g, 11.0 mmol) and sodium methylate (3.00 g, 55.0 mmol) in anhydrous MeOH (100 mL) was heated to 80° C. and stirred for 3.0 hours. The reaction mixture was then cooled to 25° C. The resulting mixture was poured into water (100 mL), and a yellow solid precipitated out. The mixture was filtered and the filter cake was dried under vacuum to give the title compound as a yellow solid (1.62 g, 39.1%). The compound was characterized by the following spectroscopic data: MS (ESI, pos.ion) m/z: 455.0 $[M+H]^+$.

Step 4) $N^4$-(3-chloro-4-((3-fluorobenzyl)oxy)phenyl)-7-methoxyquinazoline-4,6-diamine A mixture of N-(3-chloro-4-((3-fluorobenzyl)oxy)phenyl)-7-methoxy-6-nitroquinazolin-4-amine (1.60 g, 3.5 mmol) and Raney Ni (20 mg, 0.4 mmol) in anhydrous MeOH (16 mL) was stirred at 25° C. for 12.0 hours under $H_2$ atmosphere (1 MPa). The resulting mixture was filtered. The filter cake was washed with anhydrous MeOH (20 mL), and the filtrate was concentrated in vacuo to give the title compound as a yellow solid (1.16 g, 78.0%). The compound was characterized by the following spectroscopic data: MS (ESI, pos.ion) m/z: 425.0 $[M+H]^+$.

Step 5) (E)-4-bromo-N-(4-((3-chloro-4-((3-fluorobenzyl)oxy)phenyl)amino)-7-methoxyquinazolin-6-yl)but-2-enamide To a solution of $N^4$-(3-chloro-4-((3-fluorobenzyl)oxy)phenyl)-7-methoxyquinazoline-4,6-diamine (1.00 g, 2.4 mmol) and TEA (1.0 mL, 7.2 mmol) in anhydrous THF (20 mL) was added (E)-4-bromobut-2-enoyl chloride (0.44 g, 2.4 mmol) slowly. The reaction mixture was stirred at 25° C. for 3.0 hours, and then concentrated in vacuo. The residue was purified by silica gel column chromatography ($CH_2Cl_2$/MeOH (v/v)=50/1) to give the title compound as an orange solid (0.65 g, 48.0%). The compound was characterized by the following spectroscopic data: MS (ESI, pos.ion) m/z: 571.0 $[M+H]^+$.

Step 6) (E)-N-(4-((3-chloro-4-((3-fluorobenzyl)oxy)phenyl)amino)-7-methoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-((3-fluorobenzyl)oxy)phenyl)amino)-7-methoxyquinazolin-6-yl)but-2-enamide (0.60 g, 1.0 mmol) and (4aR,7aS)-hexahydro-2H-[1,4]dioxino[2,3-c]pyrrole hydrochloride (0.25 g, 1.5 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=10/1) to give the title compound as a white solid (0.32 g, 49.0%). The compound was characterized by the following spectroscopic data: MS (ESI, pos.ion) m/z: 620.0 [M+H]$^+$; and $^1$H NMR (600 MHz, DMSO-d$_6$) δ: 9.68 (s, 2H), 8.90 (s, 1H), 8.48 (s, 1H), 7.96 (d, J=2.4 Hz, 1H), 7.69 (dd, J$_1$=8.9 Hz, J$_2$=2.4 Hz, 1H), 7.46 (dd, J$_1$=14.0 Hz, J$_2$=7.8 Hz, 1H), 7.32 (t, J=9.6 Hz, 2H), 7.26-7.21 (m, 2H), 7.21-7.12 (m, 1H), 6.80 (dt, J$_1$=15.4 Hz, J$_2$=5.6 Hz, 1H), 6.58 (d, J=15.4 Hz, 1H), 5.24 (s, 2H), 4.01 (d, J=9.0 Hz, 2H), 3.71 (dd, J$_1$=11.2 Hz, J$_2$=6.0 Hz, 2H), 3.61-3.44 (m, 3H), 3.40 (s, 3H), 3.33 (d, J=4.2 Hz, 2H), 2.85 (dd, J$_1$=9.8 Hz, J$_2$=5.6 Hz, 2H), 2.50 (s, 1H).

Example 30

(E)-N-(4-((3-Chloro-4-((3-fluorobenzyl)oxy)phenyl)amino)-7-ethoxyquinazolin-6-yl)-4-((4aR,7aS)-tetrahydro-2H-[1,4]dioxino[2,3-c]pyrrol-6(3H)-yl)but-2-enamide

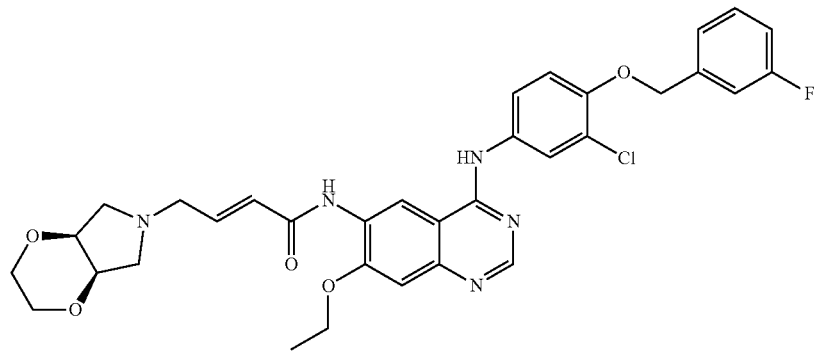 [SMILES: CCOc1cc2ncnc(Nc3ccc(OCc4cccc(F)c4)c(Cl)c3)c2cc1NC(=O)/C=C/CN1C[C@@H]2OCCO[C@@H]2C1]

Step 1) N-(3-chloro-4-((3-fluorobenzyl)oxy)phenyl)-7-ethoxy-6-nitroquinazolin-4-amine A solution of N-(3-chloro-4-((3-fluorobenzyl)oxy)phenyl)-7-fluoro-6-nitroquinazolin-4-amine (5.00 g, 11.0 mmol) and sodium ethylate (3.80 g, 55.0 mmol) in anhydrous EtOH (100 mL) was heated to 80° C. and stirred for 3.0 hours. The reaction mixture was then cooled to 25° C. The resulting mixture was poured into water (200 mL), and a yellow solid precipitated out. The mixture was filtered and the filter cake was dried under vacuum to give the title compound as a yellow solid (1.20 g, 30.0%). The compound was characterized by the following spectroscopic data: MS (ESI, pos.ion) m/z: 469.0 [M+H]$^+$.

Step 2) N$^4$-(3-chloro-4-((3-fluorobenzyl)oxy)phenyl)-7-ethoxyquinazoline-4,6-diamine A mixture of N-(3-chloro-4-((3-fluorobenzyl)oxy)phenyl)-7-ethoxy-6-nitroquinazolin-4-amine (1.00 g, 2.0 mmol) and Raney Ni (11 mg, 0.2 mmol) in anhydrous MeOH (20 mL) was stirred at 25° C. for 12.0 hours under H$_2$ atmosphere (1 MPa). The resulting mixture was filtered. The filter cake was washed with anhydrous MeOH (10 mL), and the filtrate was concentrated in vacuo to give the title compound as a red solid (0.98 g, 90.0%). The compound was characterized by the following spectroscopic data: MS (ESI, pos.ion) m/z: 439.0 [M+H]$^+$.

Step 3) (E)-4-bromo-N-(4-((3-chloro-4-((3-fluorobenzyl)oxy)phenyl)amino)-7-ethoxyquinazolin-6-yl) but-2-enamide To a solution of N$^4$-(3-chloro-4-((3-fluorobenzyl)oxy)phenyl)-7-ethoxyquinazoline-4,6-diamine (1.00 g, 2.3 mmol) and TEA (1.0 mL, 6.9 mmol) in anhydrous THF (7 mL) was added (E)-4-bromobut-2-enoyl chloride (0.42 g, 2.3 mmol) slowly. The reaction mixture was stirred at 25° C. for 0.5 hour, and then concentrated in vacuo. The residue was purified by silica gel column chromatography (CH$_2$Cl$_2$/MeOH (v/v)=50/1) to give the title compound as an orange solid (0.70 g, 51.1%). The compound was characterized by the following spectroscopic data: MS (ESI, pos.ion) m/z: 585.1 [M+H]$^+$.

Step 4) (E)-N-(4-((3-chloro-4-((3-fluorobenzyl)oxy)phenyl)amino)-7-ethoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-((3-fluorobenzyl)oxy)phenyl)amino)-7-ethoxyquinazolin-6-yl)but-2-enamide (0.67 g, 1.0 mmol) and (4aR,7aS)-hexahydro-2H-[1,4]dioxino[2,3-c]pyrrole hydrochloride (0.25 g, 1.5 mmol) in DMAC (10 mL) was added DIPEA (0.5 mL, 3.0 mmol). The reaction mixture was heated to 45° C. and stirred for 7.0 hours. Then the reaction mixture was cooled to 25° C. The resulting mixture was extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a white solid (0.11 g, 40.0%). The compound was characterized by the following spectroscopic data: MS (ESI, pos.ion) m/z: 634.0 [M+H]$^+$; and $^1$H NMR (600 MHz, DMSO-d$_6$) δ: 9.66 (s, 2H), 8.89 (s, 1H), 8.42 (s, 1H), 7.86 (d, J=2.4 Hz, 1H), 7.76 (d, J=2.4 Hz, 1H), 7.69 (dd, J$_1$=8.9 Hz, J$_2$=2.4 Hz, 1H), 7.45 (dd, J$_1$=14.0 Hz, J$_2$=7.8 Hz, 1H), 7.32 (t, J=9.2 Hz, 2H), 7.26-7.21 (m, 2H), 7.21-7.12 (m, 1H), 6.76 (t, J=5.6 Hz, 1H), 6.56 (d, J=16.4 Hz, 1H), 5.21 (s, 2H), 4.01 (d, J=9.0 Hz, 2H), 3.71 (dd, J$_1$=11.2 Hz, J$_2$=6.0 Hz, 2H), 3.61-3.44 (m, 3H), 3.40 (q, J=6.2 Hz, 2H), 3.33 (d, J=4.6 Hz, 2H), 2.85 (dd, J$_1$=9.8 Hz, J$_2$=5.6 Hz, 2H), 2.50 (s, 1H), 1.33 (t, J=1.8 Hz, 3H).

Example 31

(E)-N-(4-((3,4-Dichloro-2-fluorophenyl)amino)-7-methoxyquinazolin-6-yl)-4-((4aR,7aS)-tetrahydro-2H-[1,4]dioxino[2,3-c]pyrrol-6(3H)-yl)but-2-enamide

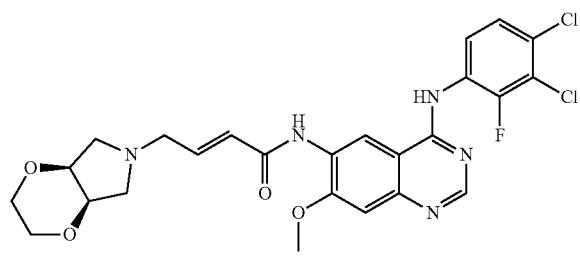 [SMILES: COc1cc2ncnc(Nc3ccc(Cl)c(Cl)c3F)c2cc1NC(=O)/C=C/CN1C[C@@H]2OCCO[C@@H]2C1]

Step 1) N-(3,4-dichloro-2-fluorophenyl)-7-fluoro-6-nitroquinazolin-4-amine

A solution of 4-chloro-7-fluoro-6-nitroquinazoline (10.00 g, 44.0 mmol) and 3,4-dichloro-2-fluoroaniline (8.40 g, 46.5 mmol) in isopropanol (150 mL) was heated to 70° C. and stirred for 5.0 hours. The reaction mixture was then cooled to 25° C., and a yellow solid precipitated out. The mixture was filtered. The filtered cake was washed with isopropanol (50 mL) and dried under vacuum to give the title compound as a yellow solid (11.4 g, 70.0%). The compound was characterized by the following spectroscopic data: MS (ESI, pos.ion) m/z: 371.0 [M+H]$^+$.

Step 2) N-(3,4-dichloro-2-fluorophenyl)-7-methoxy-6-nitroquinazolin-4-amine

A solution of N-(3,4-dichloro-2-fluorophenyl)-7-fluoro-6-nitroquinazolin-4-amine (5.00 g, 13.5 mmol) and sodium methylate (3.50 g, 67.7 mmol) in anhydrous MeOH (70 mL) was heated to 80° C. and stirred for 5.0 hours. The reaction mixture was then cooled to 25° C. The resulting mixture was poured into water (300 mL), and a yellow solid precipitated out. The mixture was filtered, and the filter cake was dried under vacuum to give the title compound as a yellow solid (2.10 g, 39.1%). The compound was characterized by the following spectroscopic data: MS (ESI, pos.ion) m/z: 383.0 [M+H]$^+$.

Step 3) N$^4$-(3,4-dichloro-2-fluorophenyl)-7-methoxyquinazoline-4,6-diamine A mixture of N-(3,4-dichloro-2-fluorophenyl)-7-methoxy-6-nitroquinazolin-4-amine (2.00 g, 5.2 mmol) and Raney Ni (0.03 g, 0.5 mmol) in anhydrous MeOH (40 mL) was stirred at 25° C. for 12.0 hours under H$_2$ atmosphere (1 MPa). The resulting mixture was filtered. The filter cake was washed with anhydrous MeOH (20 mL), and the filtrate was concentrated in vacuo to give the title compound as a yellow solid (1.50 g, 78.0%). The compound was characterized by the following spectroscopic data: MS (ESI, pos.ion) m/z: 353.0 [M+H]$^+$.

Step 4) (E)-4-bromo-N-(4-((3,4-dichloro-2-fluorophenyl)amino)-7-methoxyquinazolin-6-yl)but-2-enamide To a solution of N$^4$-(3,4-dichloro-2-fluorophenyl)-7-methoxyquinazoline-4,6-diamine (1.00 g, 2.8 mmol) and TEA (1.2 mL, 8.4 mmol) in anhydrous THF (15 mL) was added (E)-4-bromobut-2-enoyl chloride (0.51 g, 2.8 mmol) slowly at 0° C. The reaction mixture was then stirred at 0° C. for 2.0 hours. The resulting mixture was quenched with MeOH (3 mL), and then concentrated in vacuo. The residue was purified by silica gel column chromatography (CH$_2$Cl$_2$/MeOH (v/v)=50/1) to give the title compound as an orange solid (0.67 g, 48.0%). The compound was characterized by the following spectroscopic data: MS (ESI, pos.ion) m/z: 499.0 [M+H]$^+$.

Step 5) (E)-N-(4-((3,4-dichloro-2-fluorophenyl)amino)-7-methoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3,4-dichloro-2-fluorophenyl)amino)-7-methoxyquinazolin-6-yl)but-2-enamide (0.60 g, 1.2 mmol) and (4aR,7aS)-hexahydro-2H-[1,4]dioxino[2,3-c]pyrrole hydrochloride (0.30 g, 1.8 mmol) in DMAC (10 mL) was added DIPEA (0.5 mL, 3.0 mmol). The reaction mixture was heated to 45° C. and stirred for 7.0 hours. Then the reaction mixture was cooled to 25° C., and extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a white solid (0.23 g, 21.1%). The compound was characterized by the following spectroscopic data: MS (ESI, pos.ion) m/z: 548.0 [M+H]$^+$; and $^1$H NMR (600 MHz, CDCl$_3$) δ: 9.11 (s, 1H), 8.69-8.58 (m, 1H), 8.27-8.05 (m, 3H), 7.86 (s, 2H), 6.22 (d, J=15.4 Hz, 1H), 4.05-3.92 (m, 5H), 3.84 (td, J$_1$=6.2 Hz, J$_2$=2.6 Hz, 3H), 3.58 (td, J$_1$=6.6 Hz, J$_2$=2.6 Hz, 2H), 3.41 (dd, J$_1$=5.4 Hz, J$_2$=1.4 Hz, 2H), 2.97 (dd, J$_1$=10.4 Hz, J$_2$=3.8 Hz, 2H), 2.86 (dd, J$_1$=10.2 Hz, J$_2$=6.0 Hz, 2H), 1.72 (s, 12H), 1.28-1.21 (m, 1H).

Example 32

(E)-N-(4-((3,4-Dichloro-2-fluorophenyl)amino)-7-ethoxyquinazolin-6-yl)-4-((4aR,7aS)-tetrahydro-2H-[1,4]dioxino[2,3-c]pyrrol-6(3H)-yl)but-2-enamide

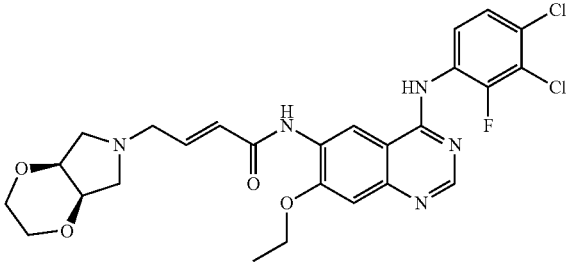 [SMILES: CCOc1cc2ncnc(Nc3ccc(Cl)c(Cl)c3F)c2cc1NC(=O)/C=C/CN1C[C@@H]2OCCO[C@@H]2C1]

Step 1) N-(3,4-dichloro-2-fluorophenyl)-7-ethoxy-6-nitroquinazolin-4-amine

A solution of N-(3,4-dichloro-2-fluorophenyl)-7-fluoro-6-nitroquinazolin-4-amine (5.00 g, 13.5 mmol) and sodium ethylate (4.70 g, 67.7 mmol) in anhydrous EtOH (100 mL) was heated to 80° C. and stirred for 5.0 hours. The reaction mixture was then cooled to 25° C. The resulting mixture was poured into water (300 mL), and a yellow solid precipitated out. The mixture was filtered and the filter cake was dried under vacuum to give the title compound as a yellow solid (1.20 g, 30.1%). The compound was characterized by the following spectroscopic data: MS (ESI, pos.ion) m/z: 397.0 [M+H]⁺.

Step 2) N⁴-(3,4-dichloro-2-fluorophenyl)-7-ethoxy-quinazoline-4,6-diamine

A mixture of N-(3,4-dichloro-2-fluorophenyl)-7-ethoxy-6-nitroquinazolin-4-amine (1.00 g, 2.6 mmol) and Raney Ni (11 mg, 0.2 mmol) in anhydrous MeOH (20 mL) was stirred at 25° C. for 12.0 hours under H₂ atmosphere (1 MPa). The resulting mixture was filtered. The filter cake was washed with anhydrous MeOH (10 mL), and the filtrate was concentrated in vacuo to give the title compound as a red solid (0.91 g, 90.1%). The compound was characterized by the following spectroscopic data: MS (ESI, pos.ion) m/z: 367.0 [M+H]⁺.

Step 3) (E)-4-bromo-N-(4-((3,4-dichloro-2-fluorophenyl)amino)-7-ethoxyquinazolin-6-yl)but-2-enamide To a solution of N⁴-(3,4-dichloro-2-fluorophenyl)-7-ethoxyquinazoline-4,6-diamine (1.00 g, 2.3 mmol) and TEA (1.0 mL, 6.9 mmol) in anhydrous THF (10 mL) was added (E)-4-bromobut-2-enoyl chloride (0.42 g, 2.3 mmol) slowly at 0° C. The reaction mixture was heated to 25° C. and stirred for 1.5 hours. Then to the mixture was added anhydrous MeOH (3 mL). The resulting mixture was concentrated in vacuo. The residue was purified by silica gel column chromatography (CH₂Cl₂/MeOH (v/v)=50/1) to give the title compound as an orange solid (0.70 g, 51.0%). The compound was characterized by the following spectroscopic data: MS (ESI, pos.ion) m/z: 513.0 [M+H]⁺.

Step 4) (E)-N-(4-((3,4-dichloro-2-fluorophenyl)amino)-7-ethoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3,4-dichloro-2-fluorophenyl)amino)-7-ethoxyquinazolin-6-yl)but-2-enamide (0.67 g, 1.0 mmol) and (4aR,7aS)-hexahydro-2H-[1,4]dioxino[2,3-c]pyrrole hydrochloride (0.25 g, 1.5 mmol) in DMAC (10 mL) was added DIPEA (0.5 mL, 3.0 mmol). The reaction mixture was heated to 45° C. and stirred for 12.0 hours. Then the reaction mixture was cooled to 25° C. The resulting mixture was poured into water (40 mL) and extracted with DCM (30 mL×4). The combined organic phases were dried over anhydrous Na₂SO₄, filtered and concentrated in vacuo. The residue was purified by silica gel column chromatography (CH₂Cl₂/MeOH (v/v)=25/1) to give the title compound as a white solid (0.12 g, 40.0%). The compound was characterized by the following spectroscopic data: MS (ESI, pos.ion) m/z: 562.0 [M+H]⁺; and ¹H NMR (600 MHz, CDCl₃) δ: 9.12 (s, 1H), 8.62 (s, 1H), 8.19 (dd, J₁=38.2 Hz, J₂=30.4 Hz, 2H), 7.78 (s, 1H), 7.26 (d, J=9.6 Hz, 3H), 7.03 (dt, J₁=15.0 Hz, J₂=5.4 Hz, 2H), 6.22 (d, J=15.2 Hz, 1H), 4.33-4.11 (m, 1H), 3.84-3.58 (m, 2H), 3.41 (d, J=4.8 Hz, 1H), 2.92-2.89 (m, 3H), 1.78 (s, 3H), 1.56 (t, J=6.8 Hz, 2H), 1.34-1.29 (m, 5H).

Example 33

(E)-N-(4-((3,4-Dichloro-2-fluorophenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide

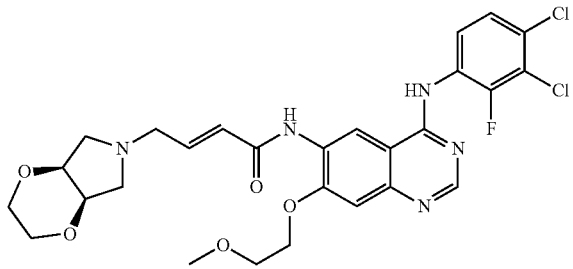 [SMILES: COCCOc1cc2ncnc(Nc3ccc(Cl)c(Cl)c3F)c2cc1NC(=O)/C=C/CN1C[C@@H]2OCCO[C@@H]2C1]

Step 1) N-(3,4-dichloro-2-fluorophenyl)-7-(2-methoxyethoxy)-6-nitroquinazolin-4-amine A solution of N-(3,4-dichloro-2-fluorophenyl)-7-fluoro-6-nitroquinazolin-4-amine (5.00 g, 11.0 mmol) and sodium 2-methoxyethanolate (5.30 g, 55.0 mmol) in 2-methoxyethanol (100 mL) was heated to 80° C. and stirred for 3.0 hours. The reaction mixture was then cooled to 25° C. The resulting mixture was poured into water (200 mL), and a yellow solid precipitated out. The mixture was filtered and the filter cake was dried under vacuum to give the title compound as a yellow solid (1.62 g, 39.0%). The compound was characterized by the following spectroscopic data: MS (ESI, pos.ion) m/z: 427.0 [M+H]⁺.

Step 2) N⁴-(3,4-dichloro-2-fluorophenyl)-7-(2-methoxyethoxy)quinazoline-4,6-diamine A mixture of N-(3,4-dichloro-2-fluorophenyl)-7-(2-methoxyethoxy)-6-nitroquinazolin-4-amine (1.60 g, 3.5 mmol) and Raney Ni (20 mg, 0.4 mmol) in anhydrous MeOH (30 mL) was stirred at 25° C. for 12.0 hours under H₂ atmosphere (1 MPa). The resulting mixture was filtered. The filter cake was washed with anhydrous MeOH (15 mL), and the filtrate was concentrated in vacuo to give the title compound as a yellow solid (1.16 g, 78.0%). The compound was characterized by the following spectroscopic data: MS (ESI, pos.ion) m/z: 397.0 [M+H]⁺.

Step 3) (E)-4-bromo-N-(4-((3,4-dichloro-2-fluorophenyl)amino)-7-(2-methoxyethoxy)quinazolin-6-yl)but-2-enamide To a solution of N⁴-(3,4-dichloro-2-fluorophenyl)-7-(2-methoxyethoxy)quinazoline-4,6-diamine (1.00 g, 2.4 mmol) and TEA (1.0 mL, 7.2 mmol) in anhydrous THF (10 mL) was added (E)-4-bromobut-2-enoyl chloride (0.44 g, 2.4 mmol) slowly at 0° C. The reaction mixture was heated to 25° C. and stirred for 1.5 hours. Then to the reaction mixture was added anhydrous EtOH (3 mL). The resulting mixture was concentrated in vacuo. The residue was purified by silica gel column chromatography (CH₂Cl₂/MeOH (v/v)=50/1) to give the title compound as an orange solid (0.65 g, 48.0%). The compound was characterized by the following spectroscopic data: MS (ESI, pos.ion) m/z: 543.0 [M+H]+.

Step 4) (E)-N-(4-((3,4-dichloro-2-fluorophenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3,4-dichloro-2-fluorophenyl)amino)-7-(2-methoxyethoxy)quinazolin-6-yl)but-2-enamide (0.54 g, 1.0 mmol) and (4aR,7aS)-hexahydro-2H-[1,4]dioxino[2,3-c]pyrrole hydrochloride (0.25 g, 1.5 mmol) in DMAC (10 mL) was added DIPEA (0.5 mL, 3.0 mmol). The reaction mixture was heated to 45° C. and stirred for 12.0 hours. Then the reaction mixture was cooled to 25° C. The resulting mixture was poured into water (40 mL) and extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=25/1) to give the title compound as a white solid (0.18 g, 30.4%). The compound was characterized by the following spectroscopic data: MS (ESI, pos.ion) m/z: 592.0 [M+H]+; and $^1$H NMR (600 MHz, CDCl$_3$) δ: 9.15 (s, 1H), 8.58 (d, J=18.6 Hz, 2H), 8.22 (s, 1H), 7.85 (s, 1H), 7.36-7.26 (m, 2H), 7.02 (d, J=15.2 Hz, 1H), 6.33 (s, 2H), 5.31 (dd, J$_1$=18.0 Hz, J$_2$=14.2 Hz, 1H), 4.39-4.29 (m, 2H), 4.22-4.06 (m, 2H), 3.91-3.76 (m, 3H), 3.63-3.55 (m, 2H), 3.51-3.32 (m, 4H), 3.06-2.81 (m, 4H), 1.23 (s, 3H).

Example 34

(E)-N-(4-((3,4-Dichloro-2-fluorophenyl)amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide

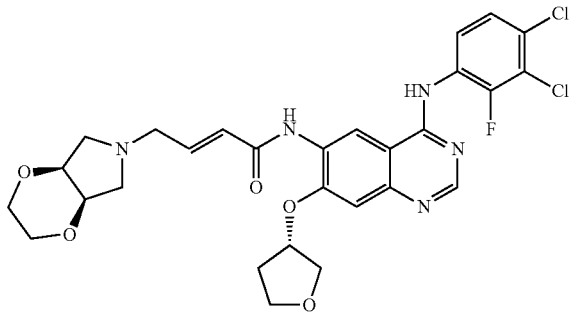 [SMILES: O=C(/C=C/CN1C[C@@H]2OCCO[C@@H]2C1)Nc1cc2c(Nc3ccc(Cl)c(Cl)c3F)ncnc2cc1O[C@H]1CCOC1]

Step 1) (S)—N-(3,4-dichloro-2-fluorophenyl)-6-nitro-7-((tetrahydrofuran-3-yl)oxy)quinazolin-4-amine To a solution of N-(3,4-dichloro-2-fluorophenyl)-7-fluoro-6-nitroquinazolin-4-amine (5.00 g, 13.4 mmol) in DMF (80 mL) was added potassium trimethylsilanolate (2.59 g, 20.2 mmol). After the mixture was stirred at 25° C. for 30 minutes, to the mixture was added (S)-tetrahydrofuran-3-ol (2.59 g, 20.2 mmol) at 25° C. The reaction mixture was heated to 40° C. and stirred for 5.0 hours. Then the reaction mixture was cooled to 25° C. The resulting mixture was poured into water (200 mL), and then adjusted to pH 6 with concentrated hydrochloric acid. A yellow solid precipitated out. The mixture was filtered and the filter cake was dried under vacuum to give the title compound as a yellow solid (5.00 g, 84.7%). The compound was characterized by the following spectroscopic data: MS (ESI, pos.ion) m/z: 439.2 [M+1]+.

Step 2) (S)—N$^4$-(3,4-dichloro-2-fluorophenyl)-7-((tetrahydrofuran-3-yl)oxy)quinazoline-4,6-diamine To a solution of (S)—N-(3,4-dichloro-2-fluorophenyl)-6-nitro-7-((tetrahydrofuran-3-yl)oxy)quinazolin-4-amine (4.20 g, 9.6 mmol) in MeOH (80 mL) was added a catalyst of Raney Ni (20 mg, 0.4 mmol) under N$_2$ atmosphere. Then the mixture was purged with H$_2$ three times. The reaction mixture was stirred at 25° C. for 36.0 hours, and then filtered. The filtrate was concentrated in vacuo to give the title compound as a yellow solid (1.20 g, 30.7%). The compound was characterized by the following spectroscopic data: MS (ESI, pos.ion) m/z: 409.2 [M+1]+.

Step 3) (S,E)-4-bromo-N-(4-((3,4-dichloro-2-fluorophenyl)amino)-7-((tetrahydrofuran-3-yl)oxy)quinazolin-6-yl)but-2-enamide To a solution of (S)—N$^4$-(3,4-dichloro-2-fluorophenyl)-7-((tetrahydrofuran-3-yl)oxy)quinazoline-4,6-diamine (0.52 g, 1.3 mmol) in THF (50 mL) were added TEA (192 mg, 1.9 mmol) and (E)-4-bromobut-2-enoyl chloride (279 mg, 1.5 mmol) at 0° C. After the mixture was stirred at 0° C. for 3.0 hours, to the mixture was added anhydrous EtOH (3.0 mL). The resulting mixture was concentrated in vacuo. The residue was purified by silica gel column chromatography (CH$_2$Cl$_2$/MeOH (v/v)=50/1) to give the title compound as a yellow solid (0.57 g, 89.1%). The compound was characterized by the following spectroscopic data: MS (ESI, pos.ion) m/z: 555.1 [M+1]+.

Step 4) (E)-N-(4-((3,4-dichloro-2-fluorophenyl)amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide To a solution of (S,E)-4-bromo-N-(4-((3,4-dichloro-2-fluorophenyl)amino)-7-((tetrahydrofuran-3-yl)oxy) quinazolin-6-yl)but-2-enamide (1.00 g, 2.0 mmol) in DMAC (50 mL) were added DIPEA (1.26 g, 9.8 mmol) and (4aR,7aS)-hexahydro-2H-[1,4]dioxino[2,3-c]pyrrole (0.38 g, 2.9 mmol) at 25° C. The reaction mixture was heated to 45° C. and stirred for 12.0 hours. Then the reaction mixture was cooled to 25° C. The resulting mixture was poured into water (40 mL) and extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=25/1) to give the title compound as a yellow solid (0.10 g, 6.74%). The compound was characterized by the following spectroscopic data: MS (ESI, pos.ion) m/z: 604.2 [M+1]+; and $^1$H NMR (600 MHz, DMSO-d$_6$) δ: 9.99 (s, 1H), 9.50 (s, 1H), 9.03 (s, 1H), 8.48 (s, 1H), 7.72-7.50 (m, 1H), 7.30 (s, 1H), 6.98-6.61 (m, 2H), 5.81 (s, 1H), 5.37 (d, J=4.6 Hz, 1H), 4.16-3.93 (m, 2H), 3.90-3.66 (m, 2H), 3.54 (d, J=5.4 Hz, 2H), 2.93-2.73 (m, 2H), 2.48-1.97 (m, 3H), 1.44-1.21 (m, 3H).

Example 35

(E)-N-(4-((3-Chloro-2,4-difluorophenyl)amino)-7-methoxyquinazolin-6-yl)-4-((4aR,7aS)-tetrahydro-2H-[1,4]dioxino[2,3-c]pyrrol-6(3H)-yl)but-2-enamide

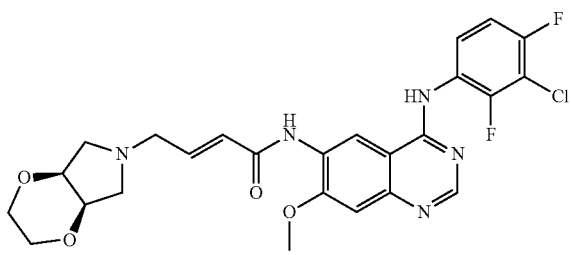 [SMILES: COc1cc2ncnc(Nc3ccc(F)c(Cl)c3F)c2cc1NC(=O)/C=C/CN1C[C@@H]2OCCO[C@@H]2C1]

Step 1) N-(3-chloro-2,4-difluorophenyl)-7-fluoro-6-nitroquinazolin-4-amine

A solution of 4-chloro-7-fluoro-6-nitroquinazoline (10.00 g, 44.0 mmol) and 3-chloro-2,4-difluoroaniline (8.40 g, 51.5 mmol) in isopropanol (150 mL) was heated to 70° C. and stirred for 5.0 hours. The reaction mixture was then cooled to 25° C., and a yellow solid precipitated out. The mixture was filtered. The filtered cake was washed with isopropanol (50 mL) and dried under vacuum to give the title compound as a yellow solid (10.8 g, 69.2%). The compound was characterized by the following spectroscopic data: MS (ESI, pos.ion) m/z: 354.1 [M+H]$^+$.

Step 2) N-(3-chloro-2,4-difluorophenyl)-7-methoxy-6-nitroquinazolin-4-amine

A solution of N-(3-chloro-2,4-difluorophenyl)-7-fluoro-6-nitroquinazolin-4-amine (5.00 g, 14.2 mmol) and sodium methylate (3.50 g, 67.7 mmol) in anhydrous MeOH (70 mL) was heated to 80° C. and stirred for 5.0 hours. The reaction mixture was then cooled to 25° C. The resulting mixture was poured into water (300 mL), and a yellow solid precipitated out. The mixture was filtered, and the filter cake was dried under vacuum to give the title compound as a yellow solid (3.10 g, 60.7%). The compound was characterized by the following spectroscopic data: MS (ESI, pos.ion) m/z: 366.1 [M+H]$^+$.

Step 3) N$^4$-(3-chloro-2,4-difluorophenyl)-7-methoxyquinazoline-4,6-diamine A mixture of N-(3-chloro-2,4-difluorophenyl)-7-methoxy-6-nitroquinazolin-4-amine (2.00 g, 5.4 mmol) and Raney Ni (0.03 g, 0.5 mmol) in anhydrous MeOH (40 mL) was stirred at 25° C. for 12.0 hours under H$_2$ atmosphere (1 MPa). The resulting mixture was filtered. The filter cake was washed with anhydrous MeOH (20 mL), and the filtrate was concentrated in vacuo to give the title compound as a yellow solid (1.10 g, 60.7%). The compound was characterized by the following spectroscopic data: MS (ESI, pos.ion) m/z: 337.0 [M+H]$^+$.

Step 4) (E)-4-bromo-N-(4-((3-chloro-2,4-difluorophenyl)amino)-7-methoxyquinazolin-6-yl)but-2-enamide To a solution of N$^4$-(3-chloro-2,4-difluorophenyl)-7-methoxyquinazoline-4,6-diamine (1.00 g, 2.9 mmol) in THF (15 mL) were added TEA (0.37 g, 3.7 mmol) and a solution of (E)-4-bromobut-2-enoyl chloride (0.45 g, 2.5 mmol) in THF (5 mL) under N$_2$ atmosphere at 0° C. The reaction mixture was then stirred at 0° C. for 3.0 hours. The resulting mixture was poured into water (50 mL) and extracted with DCM (30 mL×4). The combined organic phases were washed with saturated brine (50 mL), dried over anhydrous Na$_2$SO$_4$, filtered and concentrated in vacuo. The residue was purified by silica gel column chromatography (CH$_2$Cl$_2$/MeOH (v/v)=50/1) to give the title compound as a yellow solid (0.80 g, 67.5%). The compound was characterized by the following spectroscopic data: MS (ESI, pos.ion) m/z: 483.1 [M+1]$^+$.

Step 5) (E)-N-(4-((3-chloro-2,4-difluorophenyl)amino)-7-methoxyquinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-2,4-difluorophenyl)amino)-7-methoxyquinazolin-6-yl)but-2-enamide (0.80 g, 1.6 mmol) in DMAC (8 mL) were added (4aR,7aS)-hexahydro-2H-[1,4]dioxino[2,3-c]pyrrole (0.32 g, 2.5 mmol) and DIPEA (0.64 g, 4.9 mmol) at 25° C. The reaction mixture was heated to 45° C. and stirred for 6.0 hours. Then the reaction mixture was cooled to 25° C. The resulting mixture was poured into water (40 mL) and extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=25/1) to give the title compound as a white solid (0.38 g, 43.9%). The compound was characterized by the following spectroscopic data: MS (ESI, pos.ion) m/z: 532.1 [M+1]$^+$; and $^1$H NMR (600 MHz, CDCl$_3$) δ: 9.15 (s, 1H), 8.65 (s, 1H), 8.34-8.02 (m, 2H), 7.29 (d, J=9.4, 2H), 7.10-6.98 (m, 2H), 6.42 (d, J=15.4 Hz, 2H), 4.23 (s, 2H), 4.08 (s, 3H), 3.88 (dd, J$_1$=11.4 Hz, J$_2$=5.8 Hz, 2H), 3.64 (dd, J$_1$=11.4 Hz, J$_2$=5.2 Hz, 2H), 3.14 (t, J=15.4 Hz, 2H).

Example 36

(E)-N-(4-((3-Ethynylphenyl)amino)-7-methoxyquinazolin-6-yl)-4-((4aR,7aS)-tetrahydro-2H-[1,4]dioxino[2,3-c]pyrrol-6(3H)-yl)but-2-enamide

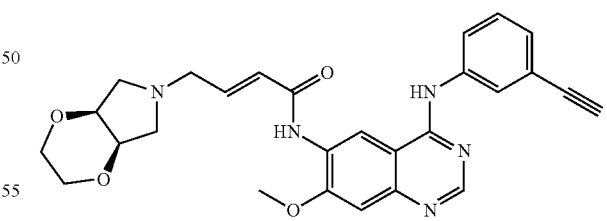

Step 1) 4-chloro-7-fluoro-6-nitroquinazoline

To a solution of 7-fluoro-6-nitroquinazolin-4-ol (50.00 g, 239.1 mmol) in toluene (1000 mL) were added TEA (72.10 g, 478.2 mmol) and POCl$_3$ (44.30 g, 286.9 mmol) at 25° C. The reaction mixture was heated to 85° C. and stirred for 2.5 hours. Then the reaction mixture was cooled to 25° C. To the resulting mixture was added toluene (500 mL). The separated toluene phase was concentrated in vacuo, and the residue was dried under vacuum to give the title compound as a yellow solid (48.0 g, 88.2%). The compound was characterized by the following spectroscopic data: MS (ESI, pos.ion) m/z: 228.5 [M+H]$^+$.

Step 2) N-(3-ethynylphenyl)-7-fluoro-6-nitroquinazolin-4-amine

To a solution of 4-chloro-7-fluoro-6-nitroquinazoline (48.00 g, 210.9 mmol) in isopropanol (500 mL) was added 3-ethynylaniline (24.70 g, 210.9 mmol) at 25° C. The reaction mixture was heated to 70° C. and stirred for 6.0 hours. Then the reaction mixture was cooled to 25° C. A yellow solid precipitated out. The mixture was filtered and the filter cake was dried under vacuum to give the title compound as a yellow solid (52.0 g, 63.9%). The compound was characterized by the following spectroscopic data: MS (ESI, pos.ion) m/z: 309.2 [M+H]$^+$.

Step 3) N-(3-ethynylphenyl)-7-methoxy-6-nitroquinazolin-4-amine

To a solution of N-(3-ethynylphenyl)-7-fluoro-6-nitroquinazolin-4-amine (10.00 g, 16.2 mmol) in MeOH (150 mL) was added sodium methylate (4.34 g, 81.1 mmol) at 25° C. The reaction mixture was heated to 65° C. and stirred for 1.0 hour. Then the reaction mixture was cooled to 25° C. The resulting mixture was poured into water (1000 mL), and then adjusted to pH 6 with concentrated hydrochloric acid. A solid precipitated out. The mixture was filtered and the filtered cake was dried under vacuum to give the title compound as a gray solid (2.75 g, 47.6%). The compound was characterized by the following spectroscopic data: MS (ESI, pos.ion) m/z: 321.3 [M+H]$^+$.

Step 4) N$^4$-(3-ethynylphenyl)-7-methoxyquinazoline-4,6-diamine

To a mixture of iron powder (15.00 g, 267.9 mmol) in MeOH (100 mL) were added concentrated hydrochloric acid (5.0 mL) and water (2.0 mL) at 25° C. The mixture was heated to 65° C. and stirred for 1.0 hour. Then to the mixture was added N-(3-ethynylphenyl)-7-methoxy-6-nitroquinazolin-4-amine (4.08 g, 84.3 mmol). The reaction mixture was heated to 75° C. and stirred for 7.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo to give the title compound as a yellow solid (1.75 g, 96.5%). The compound was characterized by the following spectroscopic data: MS (ESI, pos.ion) m/z: 291.2 [M+H]$^+$.

Step 5) (E)-ethyl 4-((4aR,7aS)-tetrahydro-2H-[1,4]dioxino[2,3-c]pyrrol-6(3H)-yl)but-2-enoate To a solution of (4aR,7aS)-hexahydro-2H-[1,4]dioxino[2,3-c]pyrrole hydrochloride (30.00 g, 181.1 mmol) in DCM (300 mL) were added DIPEA (63.2 mL, 362.5 mmol) and ethyl 4-bromocrotonate (41.94 g, 217.3 mmol) at 0° C. The reaction mixture was stirred at 0° C. for 2.0 hours. Then to the resulting mixture were added DCM (300 mL) and saturated brine (100 mL). The separated organic phase was washed with saturated brine (100 mL×3), dried over anhydrous Na$_2$SO$_4$, filtered and concentrated in vacuo to give the title compound as yellow oil (35.1 g, 80.0%). The compound was characterized by the following spectroscopic data: MS (ESI, pos.ion) m/z: 242.2 [M+1]$^+$.

Step 6) (E)-4-((4aR,7aS)-tetrahydro-2H-[1,4]dioxino[2,3-c]pyrrol-6(3H)-yl)but-2-enoic acid To a mixture of (E)-ethyl 4-((4aR,7aS)-tetrahydro-2H-[1,4]dioxino[2,3-c]pyrrol-6(3H)-yl)but-2-enoate (25.00 g, 103.6 mmol) in water (250 mL) was added aqueous potassium hydroxide solution (13 mL, 50% wt) at 0° C. The reaction mixture was then stirred at 0° C. for 3.0 hours. The resulting mixture was adjusted to pH 6 with aqueous hydrochloric acid solution (1 M), and then concentrated in vacuo. The residue was dried under vacuum to give a yellow solid (15.4 g), which was used in the next step without further purification. The compound was characterized by the following spectroscopic data: MS (ESI, pos.ion) m/z: 214.1 [M+1]$^+$.

Step 7) (E)-4-((4aR,7aS)-tetrahydro-2H-[1,4]dioxino[2,3-c]pyrrol-6(3H)-yl)but-2-enoyl chloride To a solution of (E)-4-((4aR,7aS)-tetrahydro-2H-[1,4]dioxino[2,3-c]pyrrol-6(3H)-yl)but-2-enoic acid (0.60 g, 3.0 mmol) in DCM (20 mL) was added oxalyl chloride (6.0 mL, 7.0 mmol) dropwise. The reaction mixture was stirred at 25° C. for 2.0 hours, and then concentrated in vacuo. The residue was stored in a refrigerator for the next step.

Step 8) (E)-N-(4-((3-ethynylphenyl)amino)-7-methoxyquinazolin-6-yl)-4-((4aR,7aS)-tetrahydro-2H-[1,4]dioxino[2,3-c]pyrrol-6(3H)-yl)but-2-enamide To a mixture of N$^4$-(3-ethynylphenyl)-7-methoxyquinazoline-4,6-diamine (0.40 g, 1.0 mmol) and sodium carbonate (0.58 g, 5.0 mmol) in THF (60 mL) was added a solution of (E)-4-((4aR,7aS)-tetrahydro-2H-[1,4]dioxino[2,3-c]pyrrol-6(3H)-yl)but-2-enoyl chloride (0.69 g, 3.0 mmol) in DCM (10 mL) dropwise at −5° C. The reaction mixture was then heated to 0° C. and stirred for 3.0 hours. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a light yellow solid (0.075 g, 10.0%). The compound was characterized by the following spectroscopic data: MS (ESI, pos.ion) m/z: 486.2 [M+1]$^+$; and $^1$H NMR (600 MHz, CDCl$_3$) δ: 9.08 (s, 1H), 8.67 (s, 1H), 8.45 (s, 1H), 7.97 (d, J=12.0 Hz, 1H), 7.79 (s, 1H), 7.09-7.05 (m, 3H), 6.97-6.95 (m, 1H), 6.32 (d, J=12.0 Hz, 1H), 4.30 (t, J=6.0 Hz, 2H), 4.15 (d, J=6.0 Hz, 1H), 3.64-3.60 (m, 1H), 3.43 (s, 1H), 3.40 (d, J=2.4 Hz, 2H), 3.33 (s, 3H), 2.96 (d, J=6.0 Hz, 1H), 2.90-2.88 (m, 3H), 2.03 (s, 1H), 1.28-1.05 (m, 2H).

Example 37

(E)-N-(4-((3-Ethynylphenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide

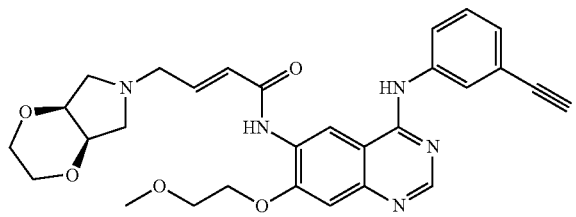 [SMILES: C#Cc1cccc(Nc2ncnc3cc(OCCOC)c(NC(=O)/C=C/CN4C[C@@H]5OCCO[C@@H]5C4)cc23)c1]

Step 1) N-(3-ethynylphenyl)-7-(2-methoxyethoxy)-6-nitroquinazolin-4-amine

To a solution of N-(3-ethynylphenyl)-7-fluoro-6-nitroquinazolin-4-amine (3.50 g, 11.0 mmol) in 2-methoxyethanol (52.5 mL) was added a solution of sodium 2-methoxyethanolate in 2-methoxyethanol (28.0 mL, 57.0 mmol, 20% wt) at 25° C. The reaction mixture was heated to 70° C. and stirred for 4.0 hours. Then the reaction mixture was cooled to 25° C. The resulting mixture was poured into water (100 mL), and a yellow solid precipitated out. The mixture was filtered and the filtrate cake was dried under vacuum to give the title compound as a yellow solid (2.45 g, 60.0%). The compound was characterized by the following spectroscopic data: MS (ESI, pos.ion) m/z: 365.3 [M+1]$^+$.

Step 2) N$^4$-(3-ethynylphenyl)-7-(2-methoxyethoxy)quinazoline-4,6-diamine

To a mixture of iron powder (6.10 g, 110.0 mmol) in 95% ethanol (60 mL) was added aqueous hydrochloric acid (3.0 mL, 36.0 mmol, 37% wt) at 25° C. After the mixture was heated to 90° C. and stirred for 1.0 hour, to the mixture was added N-(3-ethynylphenyl)-7-(2-methoxyethoxy)-6-nitroquinazolin-4-amine (2.00 g, 5.5 mmol). The reaction mixture was stirred at 90° C. for a further 3.5 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo. The residue was triturated with EtOH (20 mL) and filtered. The filter cake was dried under vacuum to give the title compound as a dark brown solid (1.00 g, 54.5%). The compound was characterized by the following spectroscopic data: MS (ESI, pos.ion) m/z: 335.3 [M+1]$^+$.

Step 3) (E)-N-(4-((3-ethynylphenyl)amino)-7-(2-methoxyethoxy)quinazolin-6-yl)-4-((4aR,7aS)-tetrahydro-2H-[1,4]dioxino[2,3-c]pyrrol-6(3H)-yl)but-2-enamide To a mixture of N$^4$-(3-ethynylphenyl)-7-(2-methoxyethoxy)quinazoline-4,6-diamine (0.40 g, 1.0 mmol) and sodium carbonate (0.53 g, 5.0 mmol) in THF (100 mL) was added a solution of (E)-4-((4aR,7aS)-tetrahydro-2H-[1,4]dioxino[2,3-c]pyrrol-6(3H)-yl)but-2-enoyl chloride (0.69 g, 3.0 mmol) in DCM (10 mL) dropwise at −7° C. The reaction mixture was then heated to 0° C. and stirred for 2.5 hours. The resulting mixture was poured into water (70 mL) and extracted with DCM (40 mL×3). The combined organic phases were dried over anhydrous Na$_2$SO$_4$, filtered and concentrated in vacuo. The residue was purified by silica gel column chromatography (CH$_2$Cl$_2$/MeOH (v/v)=20/1) to give the title compound as a light yellow solid (0.30 g, 50.0%). The compound was characterized by the following spectroscopic data: MS (ESI, pos.ion) m/z: 530.5 [M+1]$^+$; and $^1$H NMR (600 MHz, CDCl$_3$) δ: 9.12 (s, 1H), 8.67 (s, 1H), 8.45 (s, 1H), 7.99 (d, J=12.0 Hz, 1H), 7.79 (s, 1H), 7.06-7.03 (m, 3H), 6.97-6.95 (m, 1H), 6.30 (d, J=12.0 Hz, 1H), 4.37 (t, J=6.0 Hz, 1H), 4.15 (d, J=6.0 Hz, 1H), 3.88-3.79 (m, 4H), 3.64-3.60 (m, 1H), 3.43 (s, 1H), 3.40 (d, J=2.4 Hz, 2H), 3.33 (s, 3H), 2.99 (d, J=6.0 Hz, 1H), 2.90-2.88 (m, 3H), 2.03 (s, 1H), 1.28-1.05 (m, 2H).

Example 38

(E)-N-(7-Ethoxy-4-((3-ethynylphenyl)amino)quinazolin-6-yl)-4-((4aR,7aS)-tetrahydro-2H-[1,4]dioxino[2,3-c]pyrrol-6(3H)-yl)but-2-enamide

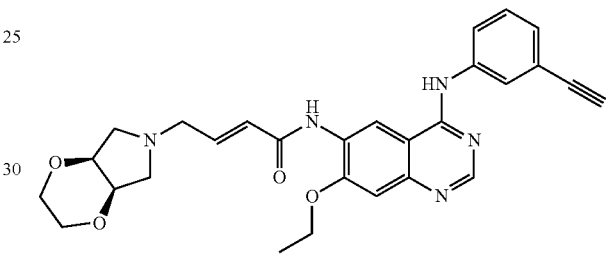

Step 1) 7-ethoxy-N-(3-ethynylphenyl)-6-nitroquinazolin-4-amine

To a solution of N-(3-ethynylphenyl)-7-fluoro-6-nitroquinazolin-4-amine (7.00 g, 17.0 mmol) in EtOH (100 mL) was added sodium ethylate (5.79 g, 85.1 mmol) at 25° C. The reaction mixture was heated to 90° C. and stirred for 1.0 hour. Then the reaction mixture was cooled to 25° C. The resulting mixture was poured into water (600 mL), and then adjusted to pH 6 with concentrated hydrochloric acid. A solid precipitated out. The mixture was filtered and the filter cake was dried under vacuum to give the title compound as a yellow solid (3.80 g, 60.0%). The compound was characterized by the following spectroscopic data: MS (ESI, pos.ion) m/z: 335.3 [M+1]$^+$.

Step 2) 7-ethoxy-N$^4$-(3-ethynylphenyl)quinazoline-4,6-diamine

To a mixture of iron powder (15.00 g, 267.8 mmol) in EtOH (100 mL) was added concentrated hydrochloric acid (5.0 mL) at 25° C. After the mixture was heated to 90° C. and stirred for 1 hour, to the mixture was added 7-ethoxy-N-(3-ethynylphenyl)-6-nitroquinazolin-4-amine (4.00 g, 12.0 mmol). The reaction mixture was stirred at 90° C. for further 7.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo to give the title compound as a gray solid (2.63 g, 72.3%). The compound was characterized by the following spectroscopic data: MS (ESI, pos.ion) m/z: 305.3 [M+1]$^+$;

Step 3) (E)-4-bromo-N-(7-ethoxy-4-((3-ethynylphenyl)amino)quinazolin-6-yl)but-2-enamide To a solution of 7-ethoxy-N⁴-(3-ethynylphenyl)quinazoline-4,6-diamine (0.50 g, 1.6 mmol) in THF (30 mL) were added TEA (0.30 g, 3.0 mmol) and (E)-4-bromobut-2-enoyl chloride (0.35 g, 1.9 mmol) at 0° C. The reaction mixture was then stirred at 0° C. for 3.0 hours. The resulting mixture was poured into water (30 mL) and extracted with DCM (50 mL×3). The combined organic phases were dried over anhydrous $Na_2SO_4$, filtered and concentrated in vacuo. The residue was purified by silica gel column chromatography ($CH_2Cl_2$/MeOH (v/v)=50/1) to give the title compound as a yellow solid (0.10 g, 10.0%). The compound was characterized by the following spectroscopic data: MS (ESI, pos.ion) m/z: 451.2 [M+1]⁺.

Step 4) (E)-N-(7-ethoxy-4-((3-ethynylphenyl)amino)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(7-ethoxy-4-((3-ethynylphenyl)amino)quinazolin-6-yl)but-2-enamide (0.10 g, 0.2 mmol) in DMAC (15 mL) were added DIPEA (0.09 g, 0.7 mmol) and (4aR,7aS)-hexahydro-2H-[1,4]dioxino[2,3-c]pyrrole (0.04 g, 0.3 mmol) at 25° C. The reaction mixture was heated to 35° C. and stirred for 12.0 hours. Then the reaction mixture was cooled to 25° C. The resulting mixture was poured into water (30 mL) and extracted with DCM (50 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a gray solid (0.018 g, 20.0%). The compound was characterized by the following spectroscopic data: MS (ESI, pos.ion) m/z: 500.2 [M+1]⁺; and ¹H NMR (600 MHz, DMSO-$d_6$) δ: 9.82 (s, 1H), 9.66 (s, 1H), 8.99 (s, 1H), 8.58 (s, 1H), 8.06 (s, 1H), 7.94 (d, J=8.2 Hz, 1H), 7.44 (t, J=7.8 Hz, 1H), 7.31 (d, J=8.1 Hz, 1H), 7.25 (d, J=7.6 Hz, 1H), 6.90-6.82 (m, 1H), 6.68 (s, 2H), 4.35 (dd, $J_1$=13.2 Hz, $J_2$=6.8 Hz, 1H), 4.25 (s, 1H), 4.11 (s, 2H), 3.78 (d, J=5.4 Hz, 3H), 3.55 (dd, $J_1$=13.4 Hz, $J_2$=7.8 Hz, 6H), 2.89 (d, J=5.8 Hz, 2H), 1.52 (t, J=7.0 Hz, 3H), 1.30 (d, J=15.2 Hz, 3H).

Example 39

(E)-N-(4-((3-Ethynylphenyl)amino)-7-(((S)-tetrahydrofuran-3-yl)oxy)quinazolin-6-yl)-4-((4aR,7aS)-tetrahydro-2H-[1,4]dioxin[2,3-c]pyrrol-6(3H)-yl)but-2-enamide

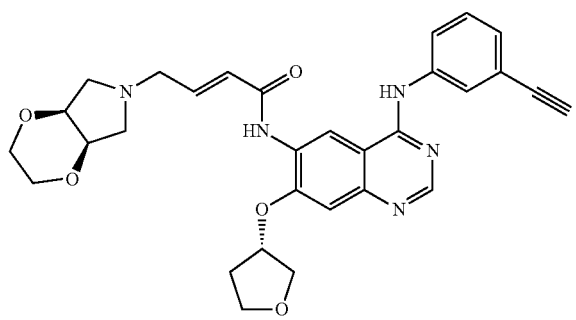 [SMILES: C#Cc1cccc(Nc2ncnc3cc(O[C@H]4CCOC4)c(NC(=O)/C=C/CN4C[C@@H]5OCCO[C@@H]5C4)cc23)c1]

Step 1) (S)—N-(3-ethynylphenyl)-6-nitro-7-((tetrahydrofuran-3-yl)oxy)quinazolin-4-amine To a solution of (S)-tetrahydrofuran-3-ol (3.43 g, 39.0 mmol) in THF (100 mL) was added sodium hydride (1.87 g, 46.0 mmol, 60% dispersion in mineral oil) at 0° C. After the mixture was heated to 25° C. and stirred for 2.0 hours, to the mixture was added N-(3-ethynylphenyl)-7-fluoro-6-nitroquinazolin-4-amine (10.00 g, 32.0 mmol). The reaction mixture was heated to 60° C. and stirred for 6.0 hours. Then the reaction mixture was cooled to 25° C. The resulting mixture was quenched with water (1 mL), and then concentrated in vacuo. The residue was purified by silica gel column chromatography ($CH_2Cl_2$/MeOH (v/v)=100/1) to give the title compound as a yellow solid (7.10 g, 58.1%). The compound was characterized by the following spectroscopic data: MS (ESI, pos.ion) m/z: 377.1 [M+1]⁺.

Step 2) (S)—N⁴-(3-ethynylphenyl)-7-((tetrahydrofuran-3-yl)oxy)quinazoline-4,6-diamine To a mixture of iron powder (15.00 g, 267.8 mmol) in EtOH (100 mL) was added concentrated hydrochloric acid (5.0 mL) at 25° C. After the mixture was heated to 90° C. and stirred for 1.0 hour, to the mixture was added (S)—N-(3-ethynylphenyl)-6-nitro-7-((tetrahydrofuran-3-yl)oxy)quinazolin-4-amine (4.00 g, 10.6 mmol). The reaction mixture was stirred at 90° C. for a further 5.0 hours. Then heating was stopped, and the resulting mixture was adjusted to pH 11 with aqueous sodium hydroxide solution (1 M) while the mixture was still at a temperature of about 60±10° C. The pH-adjusted resulting mixture was then immediately filtered hot to remove iron mud. The filtrate was concentrated in vacuo to give the title compound as a gray solid (2.50 g, 67.9%). The compound was characterized by the following spectroscopic data: MS (ESI, pos.ion) m/z: 347.1 [M+1]⁺.

Step 3) (E)-N-(4-((3-ethynylphenyl)amino)-7-(((S)-tetrahydrofuran-3-yl)oxy)quinazolin-6-yl)-4-((4aR,7aS)-tetrahydro-2H-[1,4]dioxino[2,3-c]pyrrol-6(3H)-yl)but-2-enamide To a mixture of (S)—N⁴-(3-ethynylphenyl)-7-((tetrahydrofuran-3-yl)oxy)quinazoline-4,6-diamine (0.40 g, 1.0 mmol) and sodium carbonate (0.53 g, 5.0 mmol) in THF (100 mL) was added a solution of (E)-4-((4aR,7aS)-tetrahydro-2H-[1,4]dioxino[2,3-c]pyrrol-6(3H)-yl)but-2-enoyl chloride (0.69 g, 3.0 mmol) in DCM (10 mL) dropwise at −5° C. The reaction mixture was then heated to 0° C. and stirred for 3.0 hours. The resulting mixture was poured into water (70 mL) and extracted with DCM (40 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as a light yellow solid (0.25 g, 40.0%). The compound was characterized by the following spectroscopic data: MS (ESI, pos.ion) m/z: 542.6 [M+1]⁺; and ¹H NMR (400 MHz, DMSO-$d_6$) δ: 9.08 (s, 1H), 8.82 (d, J=4.4 Hz, 1H), 8.70 (s, 1H), 7.86 (dd, $J_1$=6.4 Hz, $J_2$=2.8 Hz, 1H), 7.68-7.59 (m, 2H), 7.09 (t, J=8.8 Hz, 1H), 6.77-6.69 (m, 1H), 6.34 (d, J=16.2 Hz, 1H), 4.12-4.02 (m, 4H), 4.00-3.89 (m, 1H), 3.76-3.68 (m, 6H), 3.43 (s, 1H), 3.28 (t, J=4.4 Hz, 2H), 3.25 (dd, $J_1$=7.8 Hz, $J_2$=2.6 Hz, 2H), 2.22-2.12 (m, 4H).

Example 40

(E)-N-(4-((3-Chloro-4-fluorophenyl)amino)-7-((tetrahydrofuran-3-yl)ethynyl)quinazolin-6-yl)-4-((4aR,7aS)-tetrahydro-2H-[1,4]dioxino[2,3-c]pyrrol-6(3H)-yl)but-2-enamide

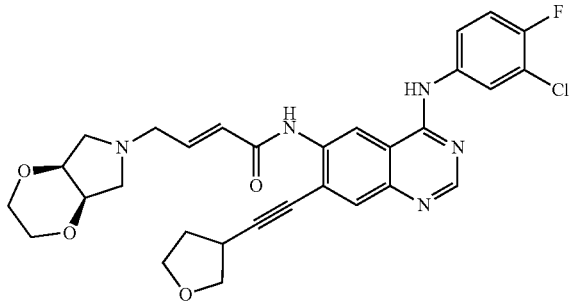 [SMILES: O=C(/C=C/CN1C[C@@H]2OCCO[C@@H]2C1)Nc1cc2c(Nc3ccc(F)c(Cl)c3)ncnc2cc1C#CC1CCOC1]

Step 1) 7-bromo-4-chloro-6-nitroquinazoline

To a solution of 7-bromo-6-nitroquinazolin-4-ol (10.00 g, 37.0 mmol) and TEA (11.0 mL, 74.0 mmol) in toluene (200 mL) was added POCl$_3$ (4.0 mL, 44.0 mmol). The reaction mixture was heated to 85° C. and stirred for 3.0 hours. Then the reaction mixture was cooled to 25° C., and to the mixture was added toluene (800 mL). The toluene phase was washed with saturated brine (150 mL), dried over anhydrous Na$_2$SO$_4$, filtered and concentrated in vacuo to give the title compound as a brown solid (10.0 g, 94.0%). The compound was characterized by the following spectroscopic data: MS (ESI, pos.ion) m/z: 288.0 [M+H]$^+$.

Step 2) 7-bromo-N-(3-chloro-4-fluorophenyl)-6-nitroquinazolin-4-amine

A solution of 7-bromo-4-chloro-6-nitroquinazoline (10.00 g, 35.0 mmol) and 3-chloro-4-fluoroaniline (5.40 g, 37.0 mmol) in isopropanol (200 mL) was heated to 70° C. and stirred for 3.0 hours. The reaction mixture was then cooled to 25° C. and filtered. The filter cake was washed with isopropanol (50 mL) and dried under vacuum to give the title compound as a yellow solid (9.60 g, 70.0%). The compound was characterized by the following spectroscopic data: MS (ESI, pos.ion) m/z: 397.0 [M+H]$^+$.

Step 3) 7-bromo-N$^4$-(3-chloro-4-fluorophenyl)quinazoline-4,6-diamine

A mixture of 7-bromo-N-(3-chloro-4-fluorophenyl)-6-nitroquinazolin-4-amine (8.00 g, 20.0 mmol) and Raney Ni (0.10 g, 2.0 mmol) in anhydrous MeOH (200 mL) was stirred at 25° C. for 12.0 hours under H$_2$ atmosphere (1 MPa). After completion of the reaction, the reaction mixture was filtered. The filter cake was washed with anhydrous MeOH (100 mL) and the filtrate was concentrated in vacuo to give the title compound as a yellow solid (5.70 g, 78.1%). The compound was characterized by the following spectroscopic data: MS (ESI, pos.ion) m/z: 367.0 [M+H]$^+$.

Step 4) N$^4$-(3-chloro-4-fluorophenyl)-7-((tetrahydrofuran-3-yl)ethynyl)quinazoline-4,6-diamine To a mixture of 3-ethynyltetrahydrofuran (1.30 g, 14.0 mmol), CuI (5.70 g, 3.0 mmol), Pd(dppf)Cl$_2$ (1.00 g, 1.4 mmol) and 7-bromo-N$^4$-(3-chloro-4-fluorophenyl)quinazoline-4,6-diamine (5.00 g, 13.7 mmol) in DMF (15 mL) was added TEA (6.0 mL, 40.0 mmol) dropwise. The reaction mixture was sealed in a tube and stirred at 70° C. for 14.0 hours. Then the reaction mixture was cooled to 25° C., and diluted with EtOAc (40 mL). The resulting mixture was filtered, and the filtrate was washed with saturated brine (15 mL). The organic phase was dried over anhydrous Na$_2$SO$_4$, filtered and concentrated in vacuo. The residue was purified by silica gel column chromatography (CH$_2$Cl$_2$/MeOH (v/v) =100/1) to give the title compound as a light yellow solid (4.70 g, 90.0%). The compound was characterized by the following spectroscopic data: MS (ESI, pos.ion) m/z: 383.0 [M+H]$^+$.

Step 5) (E)-4-bromo-N-(4-((3-chloro-4-fluorophenyl)amino)-7-((tetrahydrofuran-3-yl)ethynyl)quinazolin-6-yl)but-2-enamide To a solution of N$^4$-(3-chloro-4-fluorophenyl)-7-((tetrahydrofuran-3-yl)ethynyl)quinazoline-4,6-diamine (2.00 g, 5.3 mmol) and TEA (2.5 mL, 16.0 mmol) in anhydrous THF (20 mL) was added (E)-4-bromobut-2-enoyl chloride (1.16 g, 6.3 mmol) slowly. The reaction mixture was stirred at 25° C. for 2.0 hours, and then concentrated in vacuo. The residue was purified by silica gel column chromatography (CH$_2$Cl$_2$/MeOH (v/v)=50/1) to give the title compound as an orange solid (1.47 g, 51.0%). The compound was characterized by the following spectroscopic data: MS (ESI, pos.ion) m/z: 529.0 [M+H]$^+$.

Step 6) (E)-N-(4-((3-chloro-4-fluorophenyl)amino)-7-((tetrahydrofuran-3-yl)ethynyl)quinazolin-6-yl)-4-((4aR,7aS)-tetrahydro-2H-[1,4]dioxino[2,3-c]pyrrol-6(3H)-yl)but-2-enamide To a solution of (E)-4-bromo-N-(4-((3-chloro-4-fluorophenyl)amino)-7-((tetrahydrofuran-3-yl)ethynyl) quinazolin-6-yl)but-2-enamide (1.00 g, 1.9 mmol) and (4aR,7aS)-hexahydro-2H-[1,4]dioxino[2,3-c]pyrrole hydrochloride (0.34 g, 2.3 mmol) in DMAC (15 mL) was added DIPEA (0.5 mL, 3.0 mmol). The reaction mixture was heated to 45° C. and stirred for 12.0 hours. Then the reaction mixture was cooled to 25° C. The resulting mixture was poured into water (40 mL) and extracted with DCM (30 mL×4). The combined organic phases were dried over anhydrous Na$_2$SO$_4$, filtered and concentrated in vacuo. The residue was purified by silica gel column chromatography (CH$_2$Cl$_2$/MeOH (v/v)=25/1) to give the title compound as a white solid (0.42 g, 39.0%). The compound was characterized by the following spectroscopic data: MS (ESI, pos.ion) m/z: 578.0 [M+H]$^+$; and $^1$H NMR (400 MHz, CDCl$_3$) δ: 10.15 (s, 1H), 8.62 (s, 1H), 7.88 (d, J=0.8 Hz, 1H), 7.06 (d, J=8.6 Hz, 1H), 7.09-7.01 (m, 1H), 6.70 (s, 1H), 6.35-6.29 (m, 2H), 5.65 (d, J=12.0 Hz, 1H), 4.01-3.89 (m, 5H), 3.70 (s, 2H), 3.66-3.32 (m, 8H), 2.70-2.50 (m, 4H).

Examples 41-76

The compounds of examples 41-76 were prepared by the procedures described in example 1, example 5 or example 7.

| Example No. | Structures | MS [M + H]+ |
|---|---|---|
| 41 | 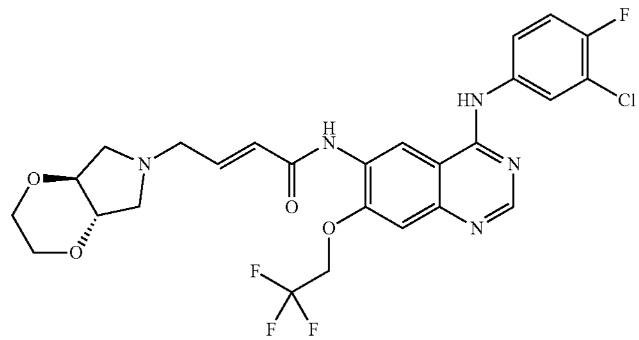 [SMILES: O=C(/C=C/CN1C[C@@H]2OCCO[C@H]2C1)Nc1cc2c(Nc3ccc(F)c(Cl)c3)ncnc2cc1OCC(F)(F)F] | 582.1 |
| 42 | 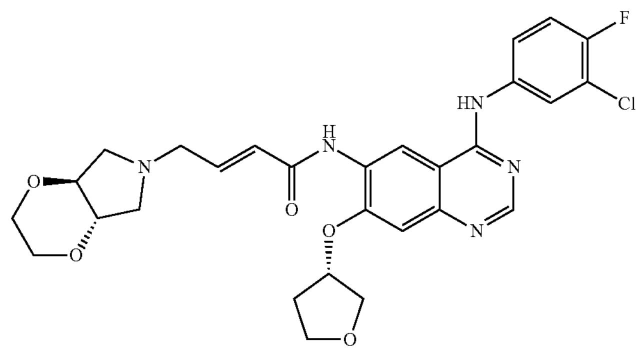 [SMILES: O=C(/C=C/CN1C[C@@H]2OCCO[C@H]2C1)Nc1cc2c(Nc3ccc(F)c(Cl)c3)ncnc2cc1O[C@H]1CCOC1] | 570.2 |
| 43 | 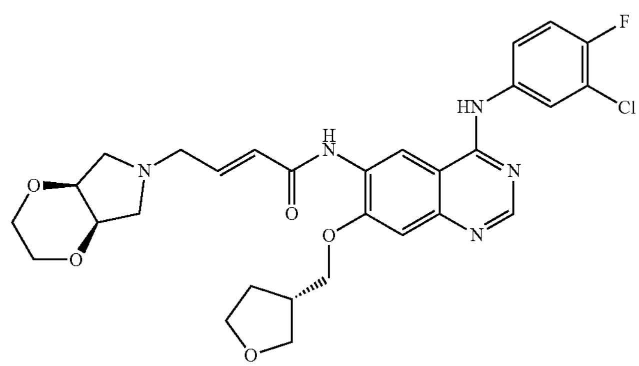 [SMILES: O=C(/C=C/CN1C[C@@H]2OCCO[C@@H]2C1)Nc1cc2c(Nc3ccc(F)c(Cl)c3)ncnc2cc1OC[C@H]1CCOC1] | 584.2 |
| 44 | 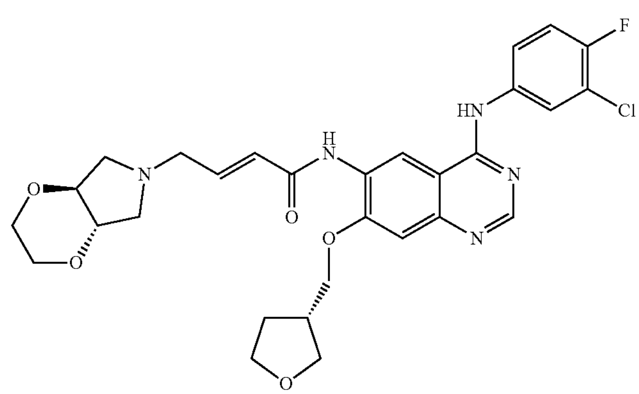 [SMILES: O=C(/C=C/CN1C[C@@H]2OCCO[C@H]2C1)Nc1cc2c(Nc3ccc(F)c(Cl)c3)ncnc2cc1OC[C@H]1CCOC1] | 584.2 |

-continued

| Example No. | Structures | MS [M + H]+ |
|---|---|---|
| 45 | 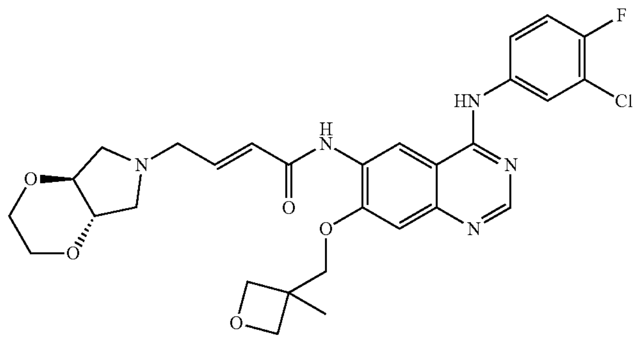 [SMILES: CC1(COc2cc3ncnc(Nc4ccc(F)c(Cl)c4)c3cc2NC(=O)/C=C/CN2C[C@@H]3OCCO[C@H]3C2)COC1] | 584.2 |
| 46 | 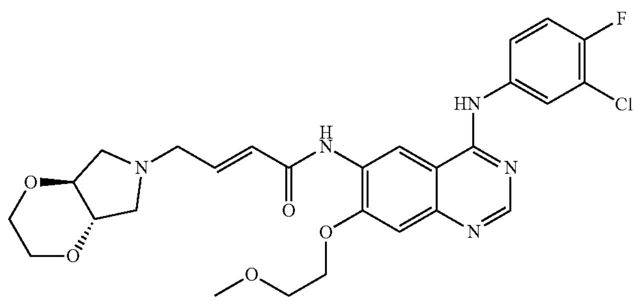 [SMILES: COCCOc1cc2ncnc(Nc3ccc(F)c(Cl)c3)c2cc1NC(=O)/C=C/CN1C[C@@H]2OCCO[C@H]2C1] | 558.2 |
| 47 | 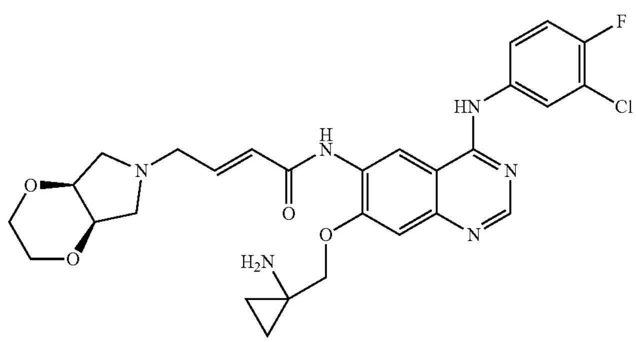 [SMILES: NC1(COc2cc3ncnc(Nc4ccc(F)c(Cl)c4)c3cc2NC(=O)/C=C/CN2C[C@@H]3OCCO[C@@H]3C2)CC1] | 569.2 |
| 48 | 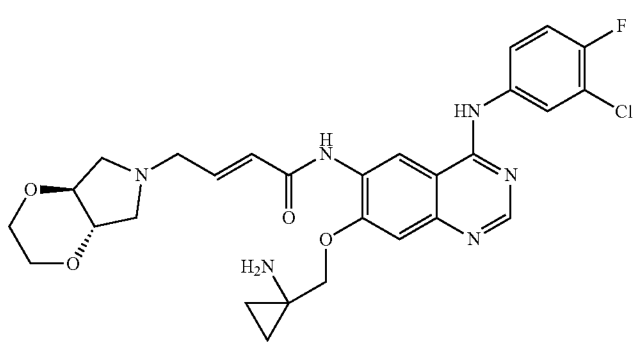 [SMILES: NC1(COc2cc3ncnc(Nc4ccc(F)c(Cl)c4)c3cc2NC(=O)/C=C/CN2C[C@@H]3OCCO[C@H]3C2)CC1] | 569.2 |

-continued
| Example No. | Structures | MS [M + H]+ |
|---|---|---|
| 49 | 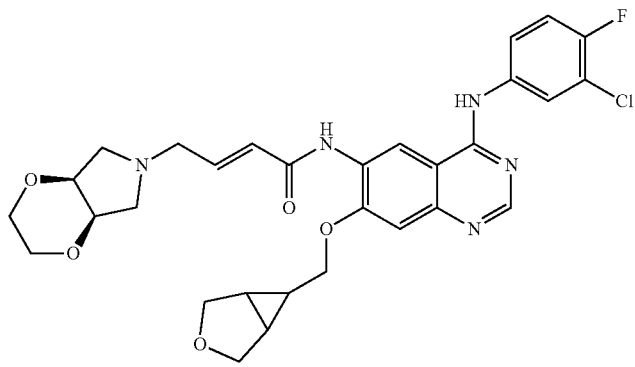 [SMILES: O=C(/C=C/CN1C[C@@H]2OCCO[C@@H]2C1)Nc1cc2c(Nc3ccc(F)c(Cl)c3)ncnc2cc1OCC1C2COCC21] | 596.2 |
| 50 | 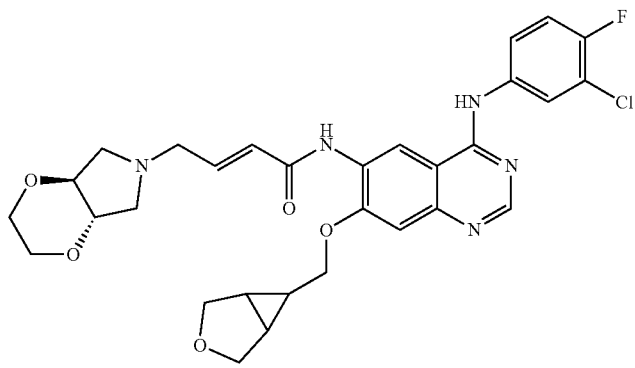 [SMILES: O=C(/C=C/CN1C[C@@H]2OCCO[C@H]2C1)Nc1cc2c(Nc3ccc(F)c(Cl)c3)ncnc2cc1OCC1C2COCC21] | 596.2 |
| 51 | 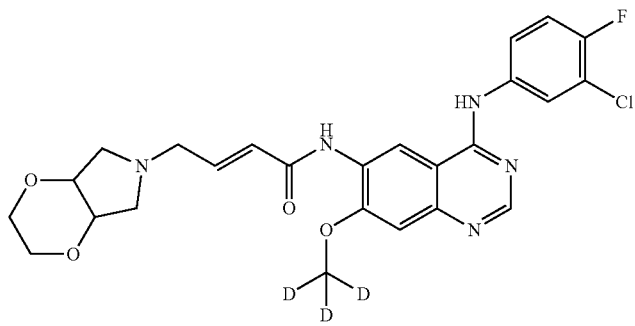 [SMILES: [2H]C([2H])([2H])Oc1cc2ncnc(Nc3ccc(F)c(Cl)c3)c2cc1NC(=O)/C=C/CN1CC2OCCOC2C1] | 517.1 |
| 52 | 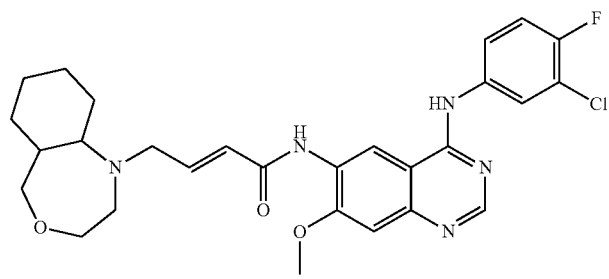 [SMILES: COc1cc2ncnc(Nc3ccc(F)c(Cl)c3)c2cc1NC(=O)/C=C/CN1CCOCC2CCCCC21] | 540.2 |

-continued
| Example No. | Structures | MS [M + H]+ |
|---|---|---|
| 53 | 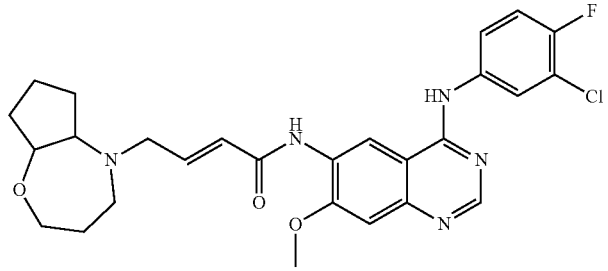 [SMILES: COc1cc2ncnc(Nc3ccc(F)c(Cl)c3)c2cc1NC(=O)/C=C/CN1CCCOC2CCCC21] | 526.1 |
| 54 | 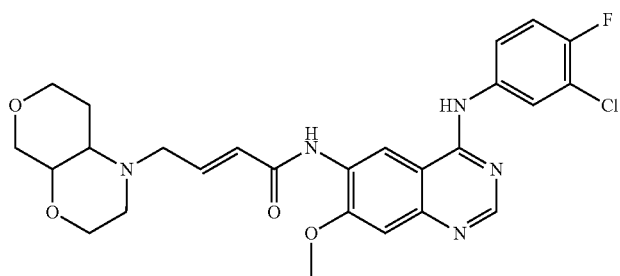 [SMILES: COc1cc2ncnc(Nc3ccc(F)c(Cl)c3)c2cc1NC(=O)/C=C/CN1CCOC2COCCC21] | 527.1 |
| 55 | 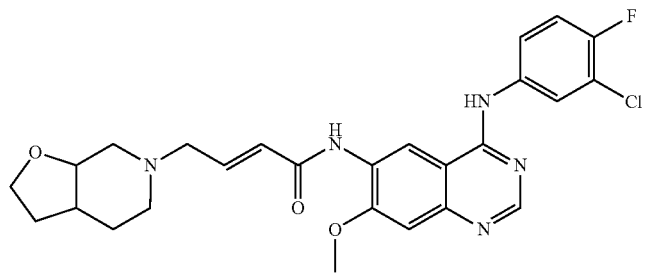 [SMILES: COc1cc2ncnc(Nc3ccc(F)c(Cl)c3)c2cc1NC(=O)/C=C/CN1CCC2CCOC2C1] | 512.1 |
| 56 | 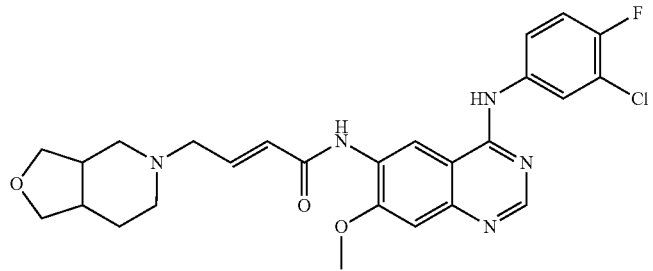 [SMILES: COc1cc2ncnc(Nc3ccc(F)c(Cl)c3)c2cc1NC(=O)/C=C/CN1CCC2COCC2C1] | 512.1 |
| 57 | 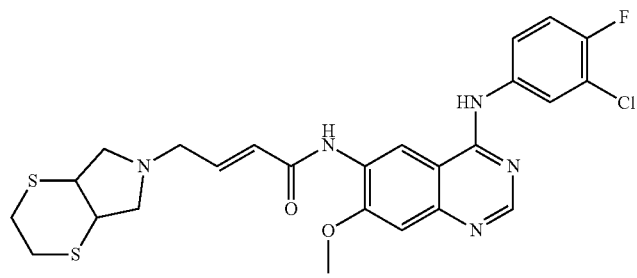 | 546.1 |

-continued

| Example No. | Structures | MS [M + H]+ |
|---|---|---|
| 58 | 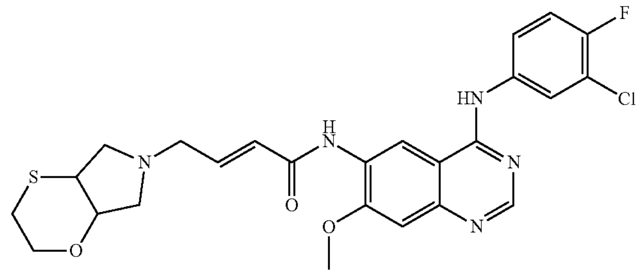 [SMILES: COc1cc2ncnc(Nc3ccc(F)c(Cl)c3)c2cc1NC(=O)/C=C/CN1CC2OCCSC2C1] | 530.2 |
| 59 | 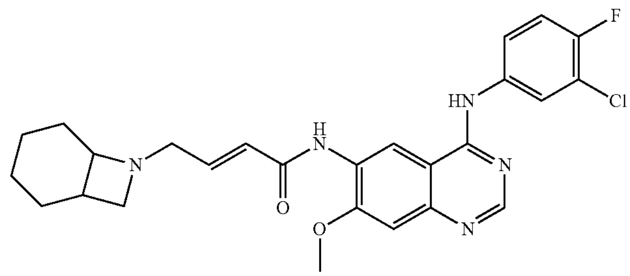 [SMILES: COc1cc2ncnc(Nc3ccc(F)c(Cl)c3)c2cc1NC(=O)/C=C/CN1CC2CCCCC21] | 496.2 |
| 60 | 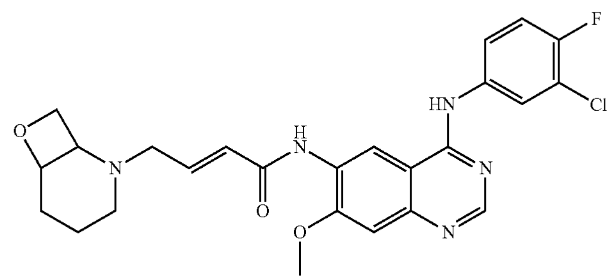 [SMILES: COc1cc2ncnc(Nc3ccc(F)c(Cl)c3)c2cc1NC(=O)/C=C/CN1CCCC2OCC21] | 498.2 |
| 61 | 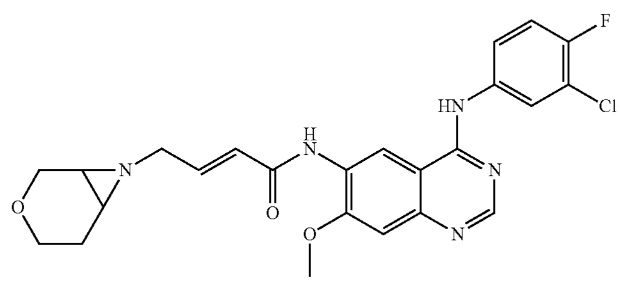 [SMILES: COc1cc2ncnc(Nc3ccc(F)c(Cl)c3)c2cc1NC(=O)/C=C/CN1C2CCOCC21] | 484.1 |
| 62 | 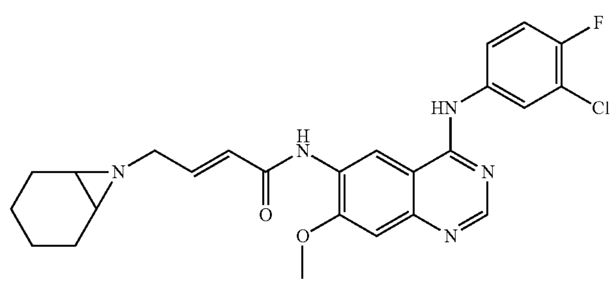 [SMILES: COc1cc2ncnc(Nc3ccc(F)c(Cl)c3)c2cc1NC(=O)/C=C/CN1C2CCCCC21] | 482.2 |

-continued

| Example No. | Structures | MS [M + H]+ |
|---|---|---|
| 63 | 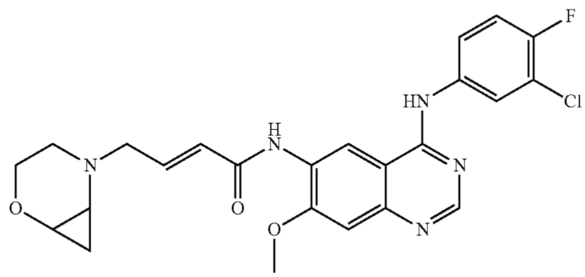 [SMILES: COc1cc2ncnc(Nc3ccc(F)c(Cl)c3)c2cc1NC(=O)/C=C/CN1CCOC2CC21] | 484.1 |
| 64 | 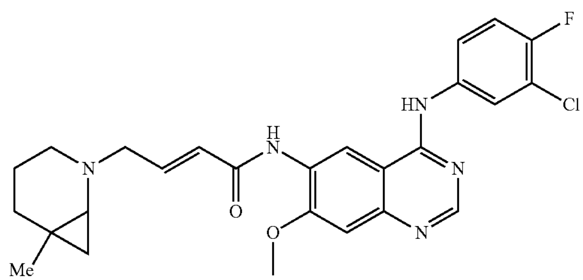 [SMILES: COc1cc2ncnc(Nc3ccc(F)c(Cl)c3)c2cc1NC(=O)/C=C/CN1CCCC2(C)CC12] | 496.2 |
| 65 | 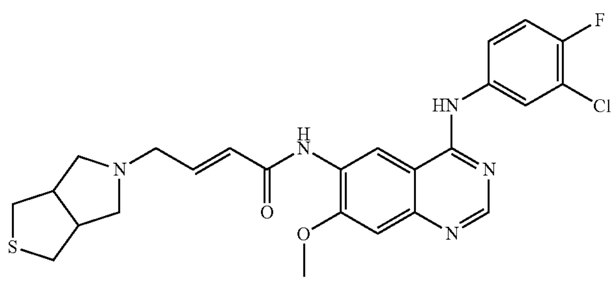 [SMILES: COc1cc2ncnc(Nc3ccc(F)c(Cl)c3)c2cc1NC(=O)/C=C/CN1CC2CSCC2C1] | 514.1 |
| 66 | 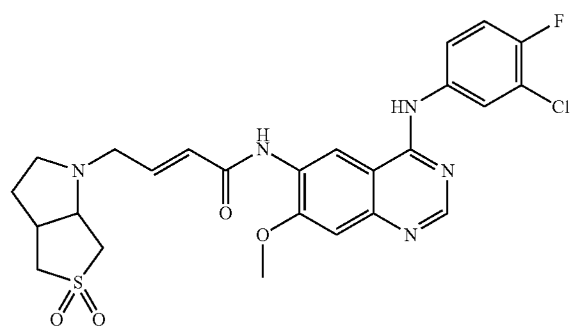 [SMILES: COc1cc2ncnc(Nc3ccc(F)c(Cl)c3)c2cc1NC(=O)/C=C/CN1CCC2CS(=O)(=O)CC21] | 546.1 |
| 67 | 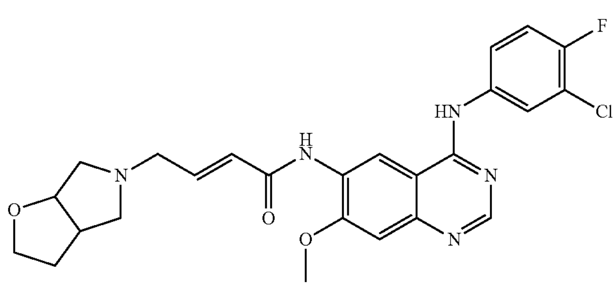 [SMILES: COc1cc2ncnc(Nc3ccc(F)c(Cl)c3)c2cc1NC(=O)/C=C/CN1CC2CCOC2C1] | 498.2 |

-continued

| Example No. | Structures | MS [M + H]+ |
|---|---|---|
| 68 | 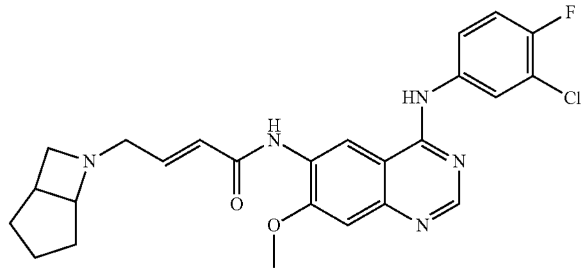 [SMILES: COc1cc2ncnc(Nc3ccc(F)c(Cl)c3)c2cc1NC(=O)/C=C/CN1CC2CCCC21] | 482.2 |
| 69 | 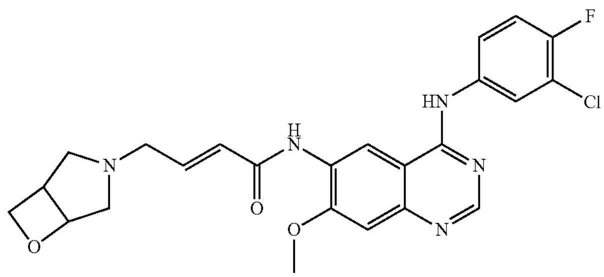 [SMILES: COc1cc2ncnc(Nc3ccc(F)c(Cl)c3)c2cc1NC(=O)/C=C/CN1CC2COC2C1] | 484.1 |
| 70 | 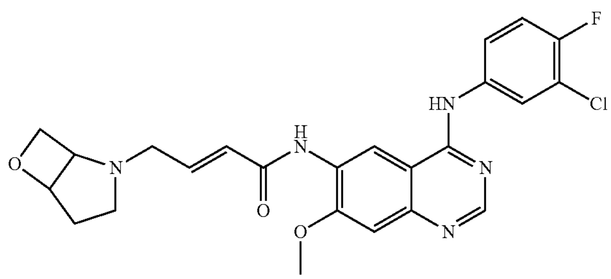 [SMILES: COc1cc2ncnc(Nc3ccc(F)c(Cl)c3)c2cc1NC(=O)/C=C/CN1CCC2OCC21] | 484.1 |
| 71 | 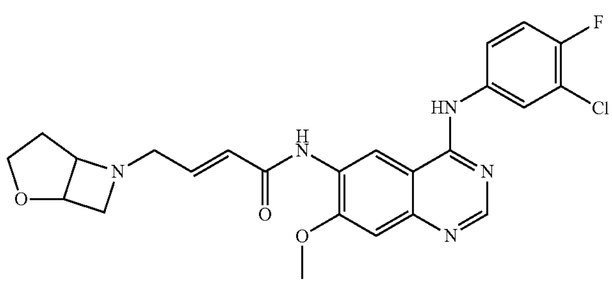 [SMILES: COc1cc2ncnc(Nc3ccc(F)c(Cl)c3)c2cc1NC(=O)/C=C/CN1CC2OCCC21] | 484.1 |
| 72 | 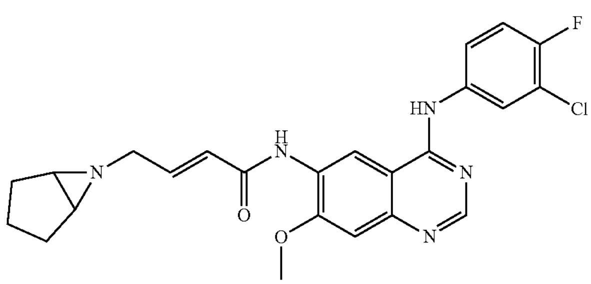 [SMILES: COc1cc2ncnc(Nc3ccc(F)c(Cl)c3)c2cc1NC(=O)/C=C/CN1C2CCCC21] | 468.2 |

-continued
| Example No. | Structures | MS [M + H]+ |
|---|---|---|
| 73 | 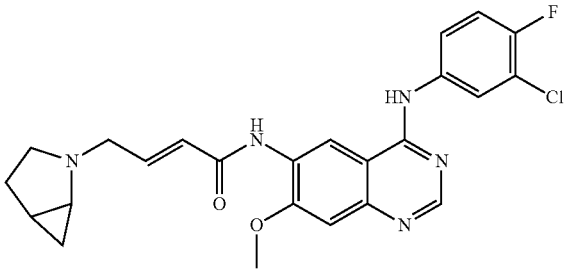 [SMILES: COc1cc2ncnc(Nc3ccc(F)c(Cl)c3)c2cc1NC(=O)/C=C/CN1CCC2CC21] | 468.2 |
| 74 | 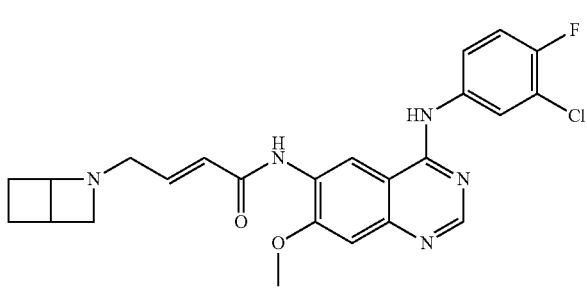 [SMILES: COc1cc2ncnc(Nc3ccc(F)c(Cl)c3)c2cc1NC(=O)/C=C/CN1CC2CCC21] | 468.1 |
| 75 | 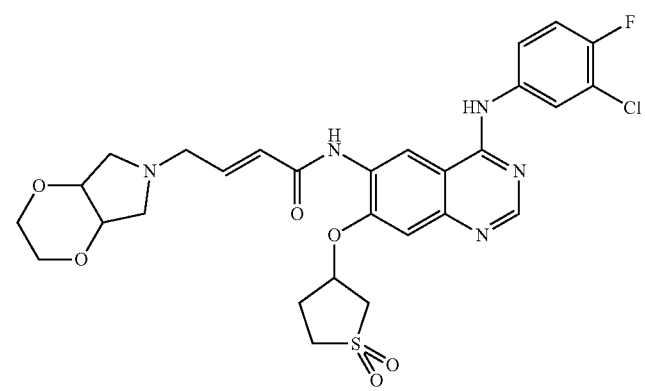 [SMILES: O=C(/C=C/CN1CC2OCCOC2C1)Nc1cc2c(Nc3ccc(F)c(Cl)c3)ncnc2cc1OC1CCS(=O)(=O)C1] | 618.2 |
| 76 | 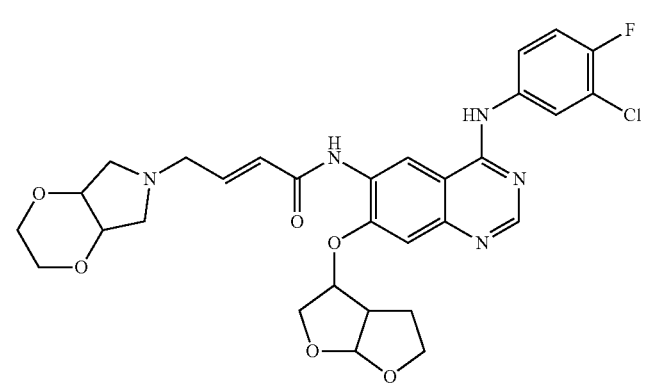 [SMILES: O=C(/C=C/CN1CC2OCCOC2C1)Nc1cc2c(Nc3ccc(F)c(Cl)c3)ncnc2cc1OC1COC2OCCC12] | 612.2 |

Examples 77-90
The compounds of examples 77-90 were prepared according to example 5 and example 9.
| Example No. | Structures | MS [M + H]+ |
|---|---|---|
| 77 | 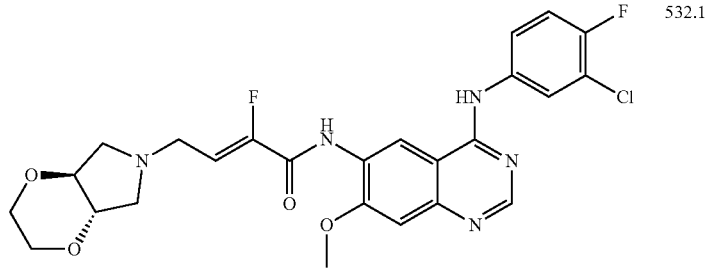 | 532.1 |
|  |  | 532.1 |
| 78 | 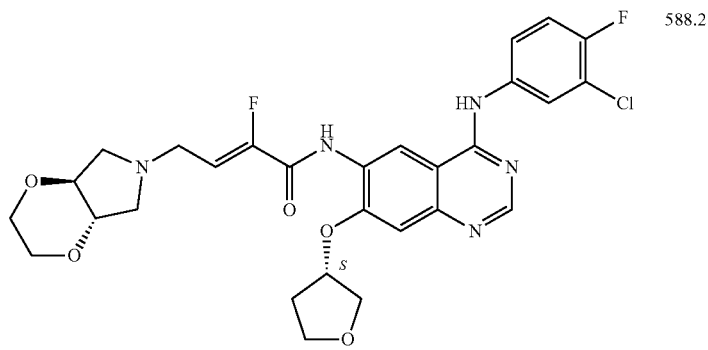 | 588.2 |
|  | 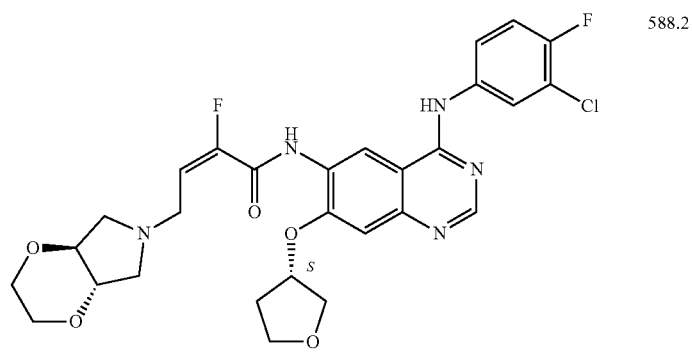 | 588.2 |

| Example No. | Structures | MS [M + H]+ |
|---|---|---|
| 79 | 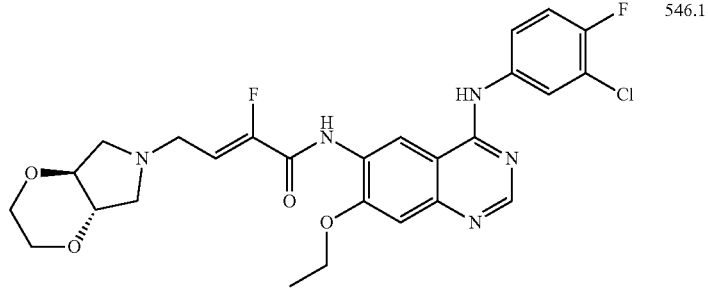 | 546.1 |
|  | 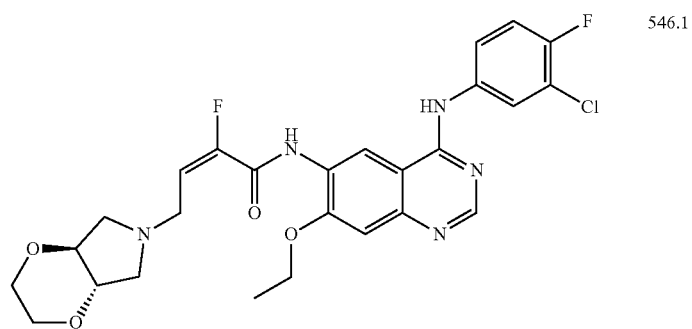 | 546.1 |
| 80 | 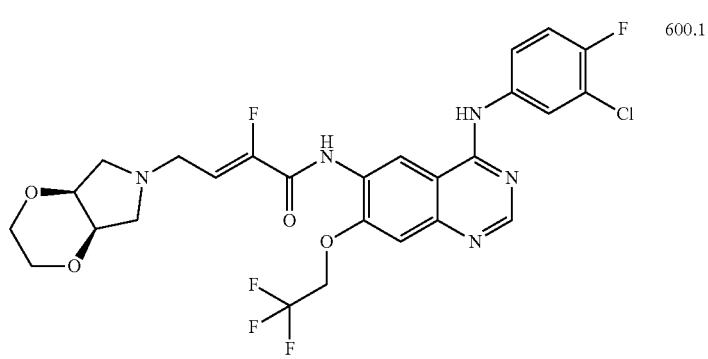 | 600.1 |
|  | 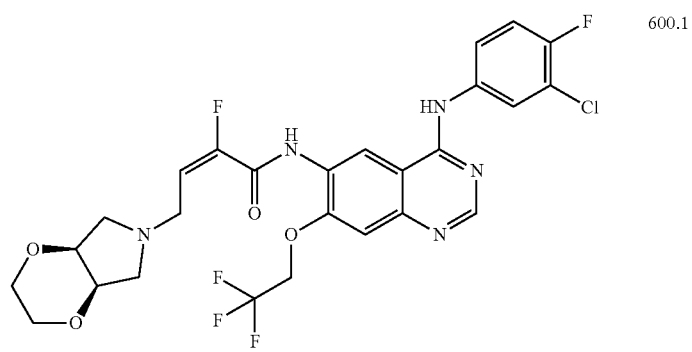 | 600.1 |

-continued
| Example No. | Structures | MS [M + H]+ |
|---|---|---|
| 81 | 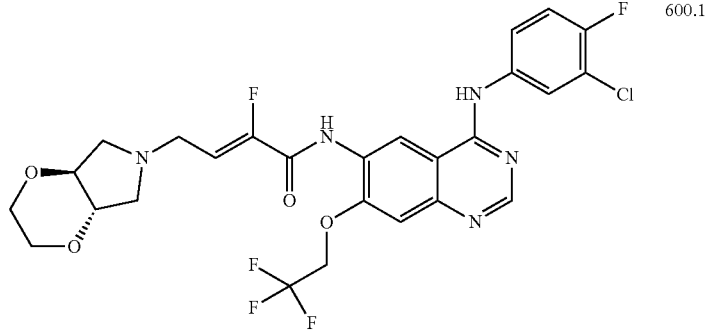 | 600.1 |
|  | 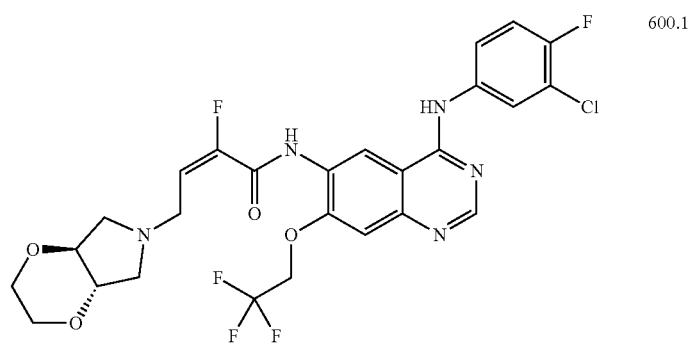 | 600.1 |
| 82 | 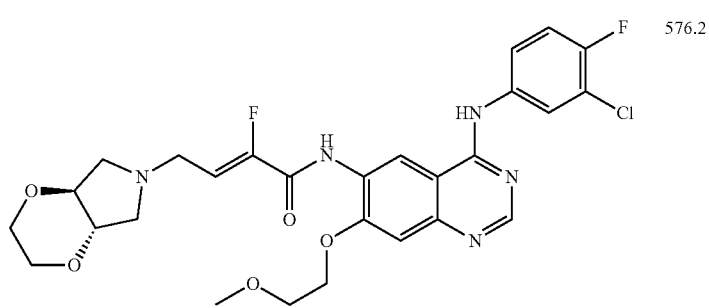 | 576.2 |
|  | 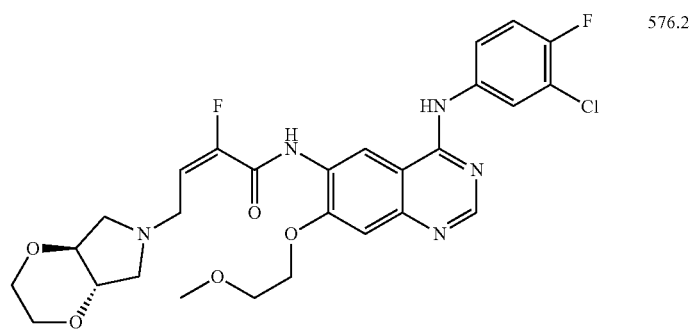 | 576.2 |

-continued
| Example No. | Structures | MS [M + H]+ |
|---|---|---|
| 83 | 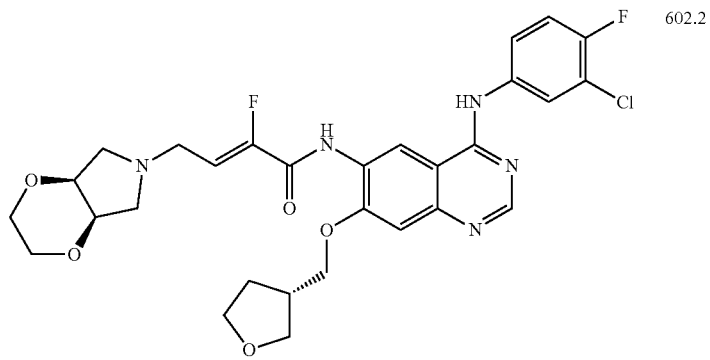 | 602.2 |
|  | 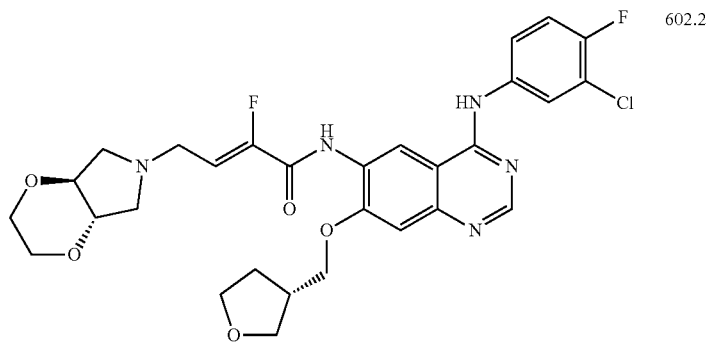 | 602.2 |
| 84 | 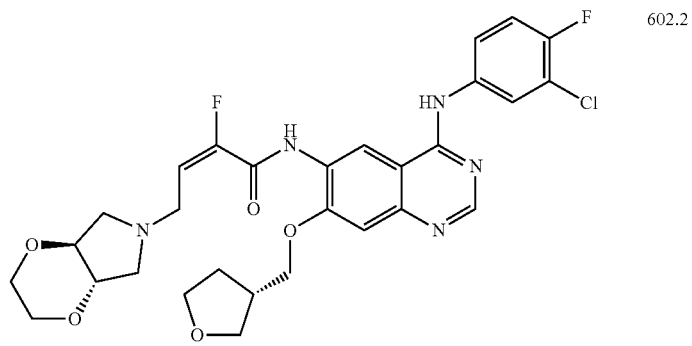 | 602.2 |
|  |  | 602.2 |

| Example No. | Structures | MS [M + H]+ |
|---|---|---|
| 85 | 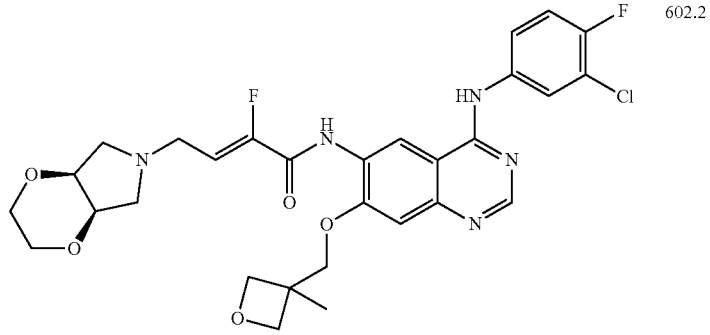 | 602.2 |
|  |  | 602.2 |
| 86 | 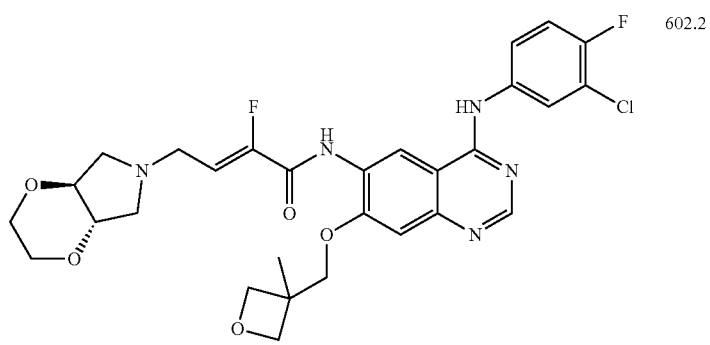 | 602.2 |
|  | 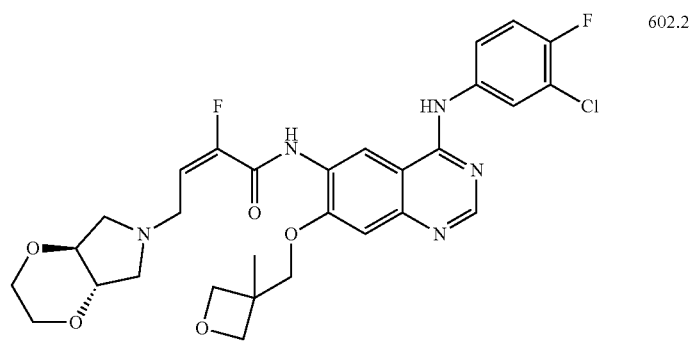 | 602.2 |

| Example No. | Structures | MS [M + H]+ |
|---|---|---|
| 87 | 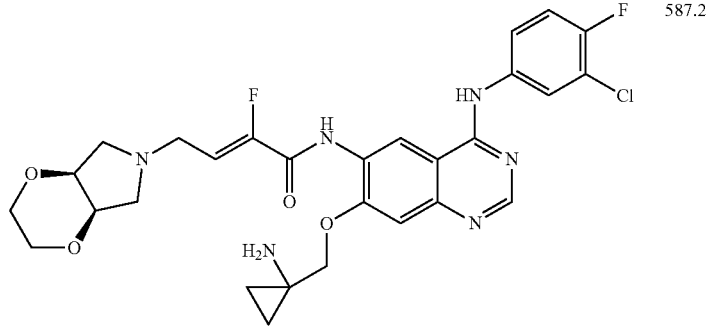 | 587.2 |
|  |  | 587.2 |
| 88 | 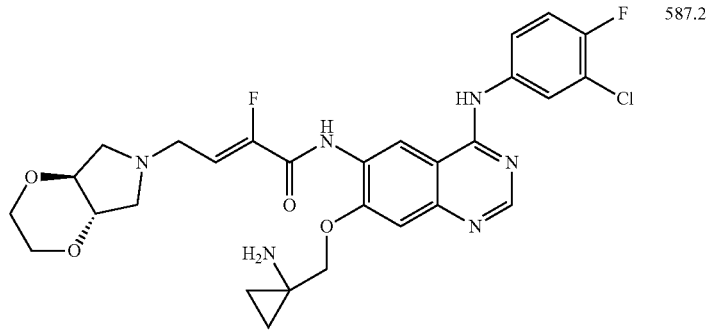 | 587.2 |
|  | 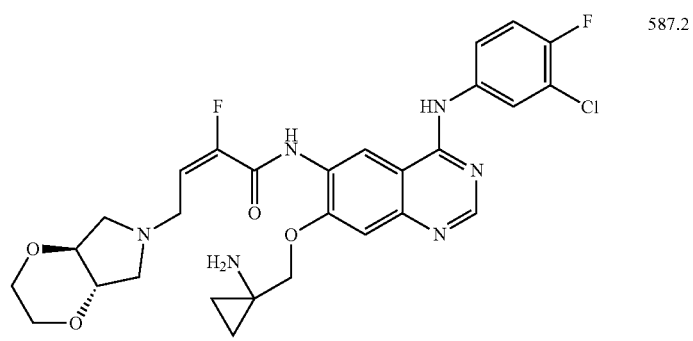 | 587.2 |

| Example No. | Structures | MS [M + H]+ |
|---|---|---|
| 89 | 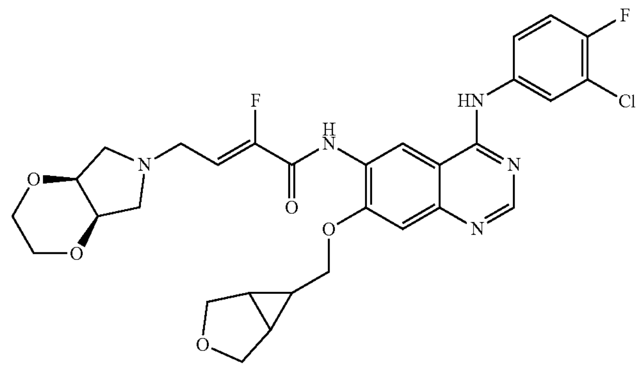 [SMILES: O=C(Nc1cc2c(Nc3ccc(F)c(Cl)c3)ncnc2cc1OCC1C2COCC21)/C(F)=C/CN1C[C@@H]2OCCO[C@@H]2C1] | 614.2 |
| | | 614.2 |
| 90 | 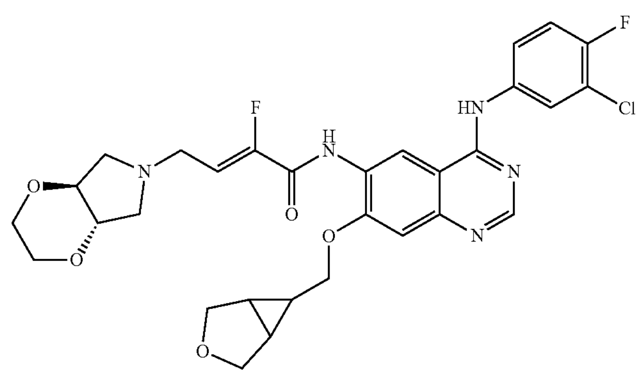 [SMILES: O=C(Nc1cc2c(Nc3ccc(F)c(Cl)c3)ncnc2cc1OCC1C2COCC21)/C(F)=C/CN1C[C@@H]2OCCO[C@H]2C1] | 614.2 |
| | | 614.2 |

Examples 91-96

The compound of example 91 was prepared by the procedures described in example 21.

The compound of example 92 was prepared by the procedures described in example 29.

The compound of example 93 was prepared by the procedures described in example 26.

The compound of example 94 was prepared by the procedures described in example 27.

The compound of example 95 was prepared by the procedures described in example 22.

The compound of example 96 was prepared by the procedures described in example 23.

| Example No. | Structures | MS [M + H]⁺ |
|---|---|---|
| 91 | 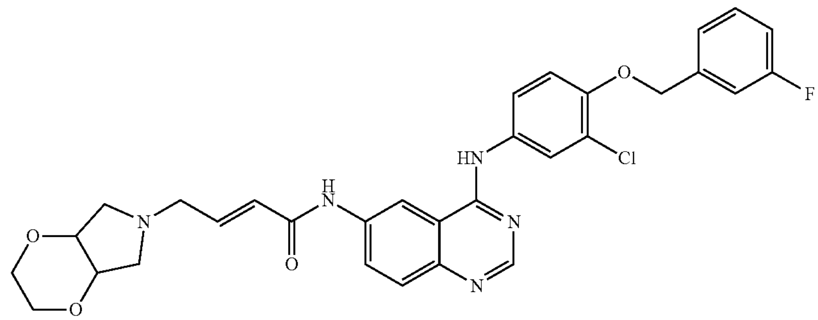 [SMILES: O=C(/C=C/CN1CC2OCCOC2C1)Nc1ccc2ncnc(Nc3ccc(OCc4cccc(F)c4)c(Cl)c3)c2c1] | 590.1 |
| 92 | 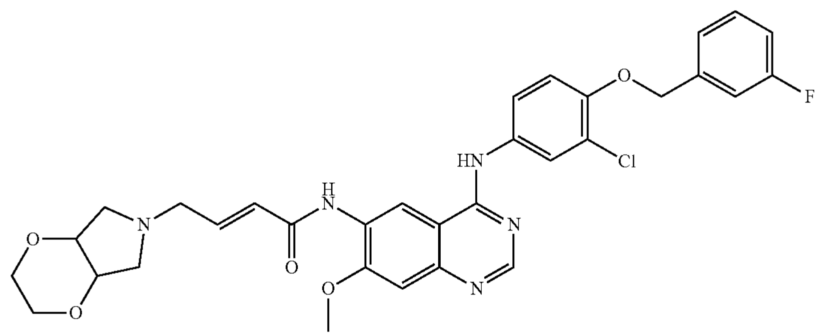 [SMILES: COc1cc2ncnc(Nc3ccc(OCc4cccc(F)c4)c(Cl)c3)c2cc1NC(=O)/C=C/CN1CC2OCCOC2C1] | 620.2 |
| 93 | 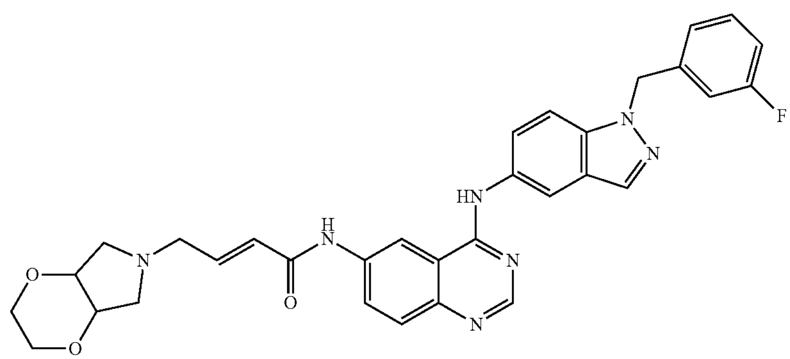 [SMILES: O=C(/C=C/CN1CC2OCCOC2C1)Nc1ccc2ncnc(Nc3ccc4c(cnn4Cc4cccc(F)c4)c3)c2c1] | 580.2 |
| 94 | 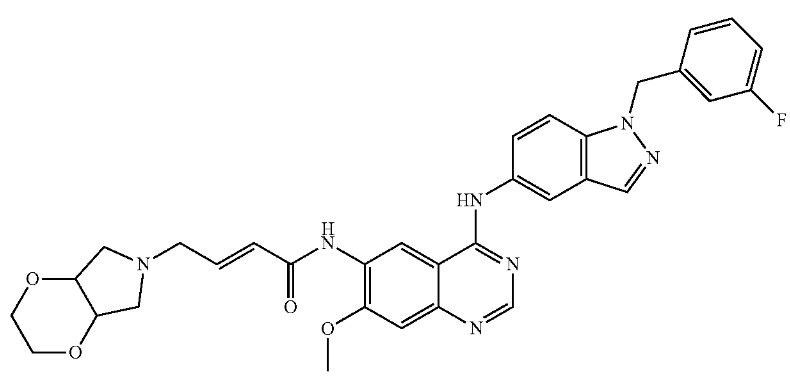 [SMILES: COc1cc2ncnc(Nc3ccc4c(cnn4Cc4cccc(F)c4)c3)c2cc1NC(=O)/C=C/CN1CC2OCCOC2C1] | 610.3 |

| Example No. | Structures | MS [M + H]+ |
|---|---|---|
| 95 | 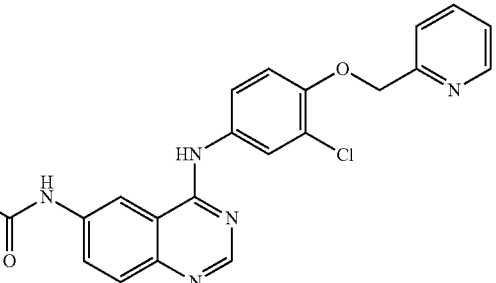 | 573.1 |
| 96 | 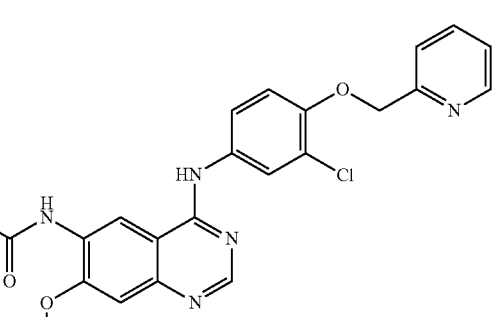 | 603.2 |
Examples 97-107
The compounds of example 97-107 were prepared by the procedures described in example 40.
| Example No. | Structures | MS [M + H]+ |
|---|---|---|
| 97 | 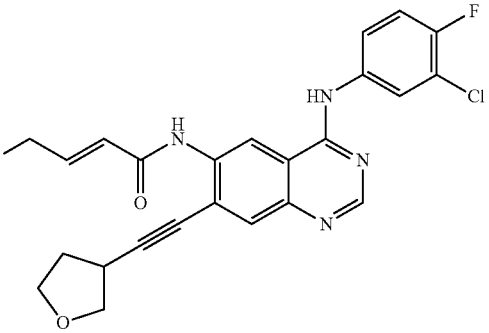 | 578.2 |
| 98 | 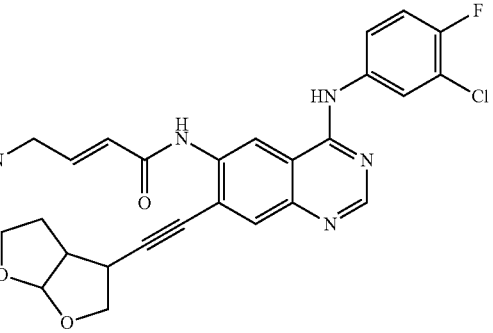 | 620.3 |

| Example No. | Structures | MS [M + H]+ |
|---|---|---|
| 99 | 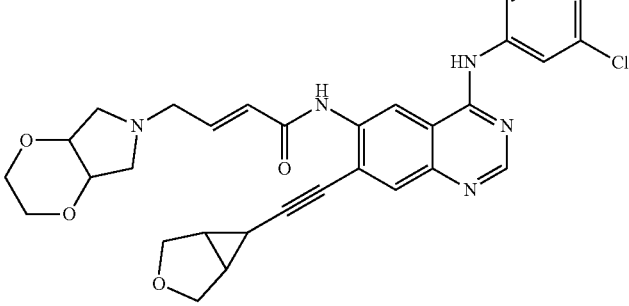 | 590.2 |
| 100 | 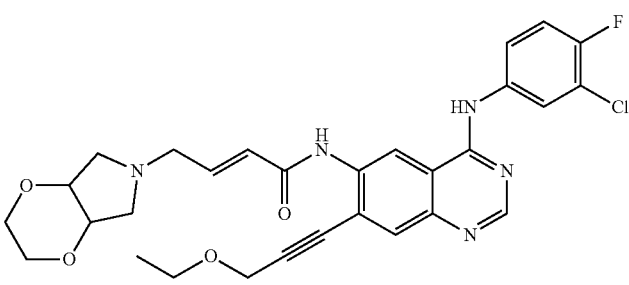 [SMILES: CCOCC#Cc1cc2ncnc(Nc3ccc(F)c(Cl)c3)c2cc1NC(=O)/C=C/CN1CC2OCCOC2C1] | 566.1 |
| 101 | 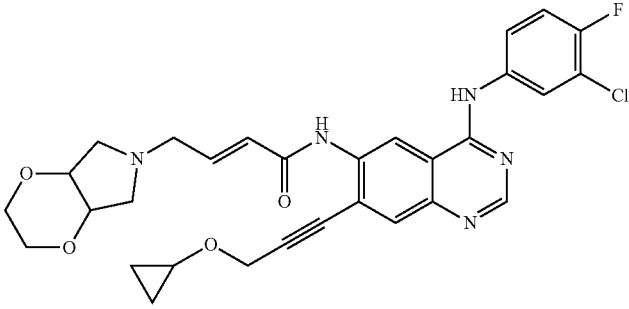 [SMILES: O=C(/C=C/CN1CC2OCCOC2C1)Nc1cc2c(Nc3ccc(F)c(Cl)c3)ncnc2cc1C#CCOC1CC1] | 578.1 |
| 102 | 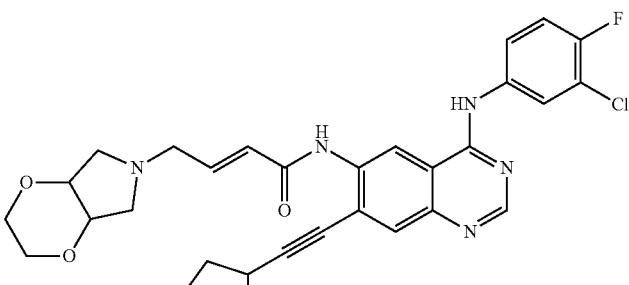 | 591.2 |

-continued

| Example No. | Structures | MS [M + H]+ |
|---|---|---|
| 103 | 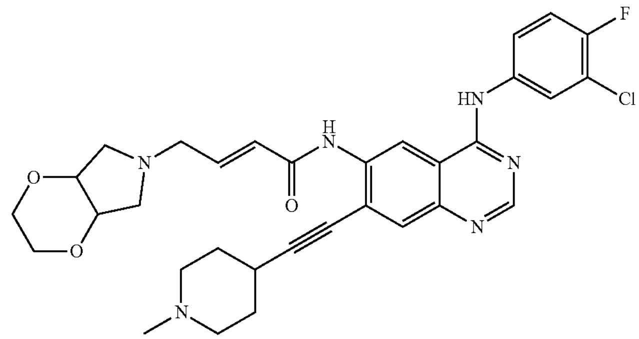 [SMILES: CN1CCC(C#Cc2cc3ncnc(Nc4ccc(F)c(Cl)c4)c3cc2NC(=O)/C=C/CN2CC3OCCOC3C2)CC1] | 605.2 |
| 104 | 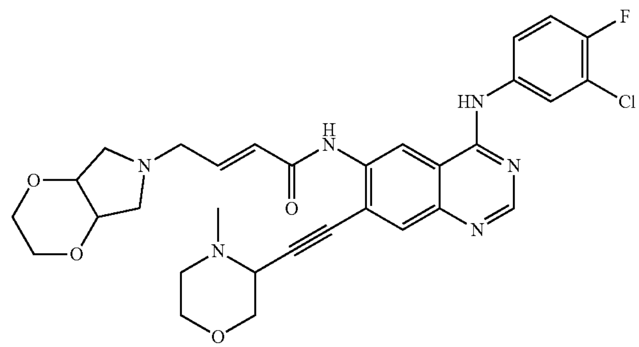 [SMILES: CN1CCOCC1C#Cc1cc2ncnc(Nc3ccc(F)c(Cl)c3)c2cc1NC(=O)/C=C/CN1CC2OCCOC2C1] | 607.1 |
| 105 | 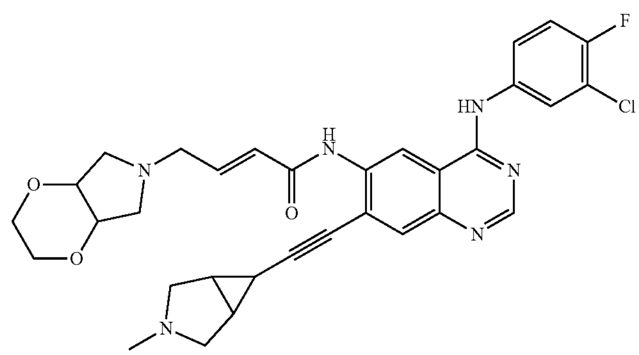 [SMILES: CN1CC2C(C#Cc3cc4ncnc(Nc5ccc(F)c(Cl)c5)c4cc3NC(=O)/C=C/CN3CC4OCCOC4C3)C2C1] | 603.1 |
| 106 | 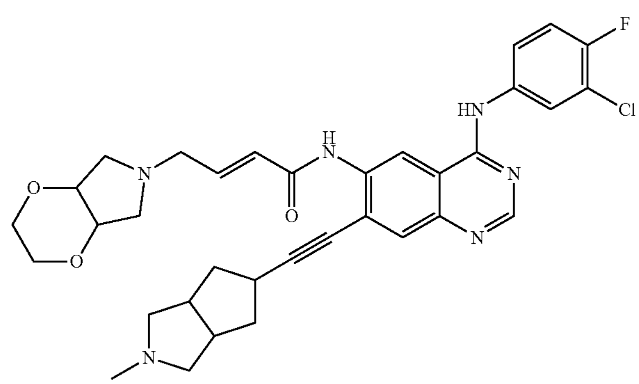 [SMILES: CN1CC2CC(C#Cc3cc4ncnc(Nc5ccc(F)c(Cl)c5)c4cc3NC(=O)/C=C/CN3CC4OCCOC4C3)CC2C1] | 631.2 |

-continued

| Example No. | Structures | MS [M + H]+ |
|---|---|---|
| 107 | 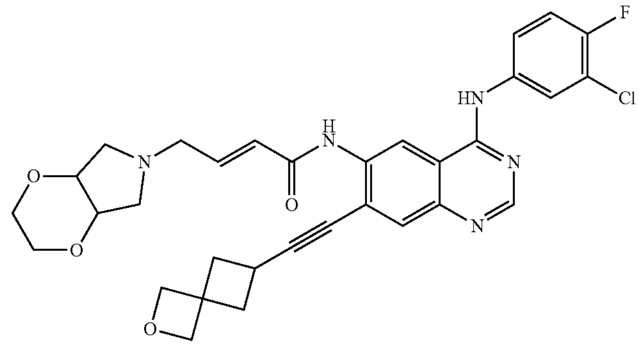 [SMILES: O=C(/C=C/CN1CC2OCCOC2C1)Nc1cc2c(Nc3ccc(F)c(Cl)c3)ncnc2cc1C#CC1CC2(COC2)C1] | 604.2 |

Biological Activity Testing

Example 108

The chemical names, structures and preparation methods of the compounds disclosed herein are as described in their preparation examples.

Test Method

Materials used include HEPES (4-(2-hydroxyethyl)-1-piperazineethanesulfonic acid), Brij-35 (dodecyl polyglycol ether), DTT (dithiothreitol), EDTA (ethylenediamine tetraacetic acid), EGFR (human epidermal growth factor receptor), HER2 (human epidermal growth factor receptor 2), EGFR T790M (human epidermal growth factor receptor T790M mutation), Peptide FAM-P22 (fluorescein-labeled peptide 22), ATP (adenosine triphosphate), DMSO (dimethyl sulfoxide), 96-well plate, 384-well plate, staurosporine, Coating Reagent #3 and so on, all of which are commercially available.

1. Preparation of Kinase Base Buffer and Stop Buffer

1× Kinase buffer without $MnCl_2$ was prepared from 50 mM HEPES, pH 7.5, 0.0015% Brij-35, 10 mM $MgCl_2$, and 2 mM DTT. Stop buffer was prepared from 100 mM HEPES, pH 7.5, 0.015% Brij-35, 0.2% Coating Reagent #3, and 50 mM EDTA.

2. Preparation of the Compounds for Testing Kinases

Preparation of the compounds was performed according to the following procedures: (1) the compound to be tested was diluted to the concentration of 500 μM with 100% DMSO which is 50× of the final desired highest inhibitor concentration, and 100 μL of the diluted compound solution was transferred to a well in a 96-well plate; (2) the compound was gradiently diluted by transferring 20 μL original solution to 60 μL of 100% DMSO in the next well and so forth for a total of 10 concentrations; (3) DMSO (100 μL, 100%) was added to two empty wells as a no-compound control and a no-enzyme control in the same 96-well plate, and the plate was marked as source plate; (4) intermediate plate was prepared by transferring 10 μL of each compound from source plate to a new 96-well plate as the intermediate plate, and to each well of the intermediate plate was added 90 μL of 1× Kinase base buffer, then the intermediate plate was mixed for 10 min on shaker; and (5) assay plate was prepared by transferring 5 μL of each well from the 96-well intermediate plate to a 384-well plate in duplicates.

3. Kinase Reaction

Kinase reaction was performed according to the following procedures: (1) 2.5× kinase solution was prepared by adding kinase into 1× kinase base buffer; (2) 2.5× peptide solution was prepared by adding FAM-labeled peptide and ATP into 1× kinase base buffer; (3) 2.5× kinase solution (10 μL) was added to each well of the 384-well assay plate containing 5 μL of compound in 10% DMSO and then the assay plate was incubated at room temperature for 10 minutes; (4) 2.5× peptide solution (10 μL) was added to each well of the 384-well assay plate; and (5) stop buffer (25 μL) was added to stop the kinase reaction after incubation at 28° C. for a specified period of time.

4. Data Measurement

Multifunctional microplate reader (BMG LABTECH, PHER Astar FS) with a 320 nM excitation wavelength was used to read and collected the data of by absorbing light at 665 nM and 620 nM, which was converted from the rate of 665 signal/620 signal.

5. Curve Fitting

Conversion data were copied, and then converted to inhibition values with the following formula: percent inhibition=(max−conversion)/(max−min)*100 where "max" stands for the DMSO control value, "conversion" stands for the sample value and "mM" stands for the no-kinase control value. The data were fitted in XLfit to obtain $IC_{50}$ values.

6. Results as Shown in Table 2

TABLE 2

In vitro kinase inhibitory activity of the compounds disclosed herein

| Example No. | Kinase inhibitory activity $IC_{50}$ (nM) | | |
|---|---|---|---|
| | EGFR | HER-2 | EGFR T790M |
| 1 | 3.2 | 14 | 8.3 |
| 2 | 4.3 | 31 | 16 |
| 3 | 6.4 | 8.1 | 6.2 |
| 5 | 3.6 | 11.7 | 6.8 |
| 6 | 1.8 | 10.4 | 8.7 |
| 7 | 15.4 | 44 | 22.6 |
| 20 | 4.8 | 15.8 | 12.5 |
| 21 | 15 | 3.5 | 317.2 |
| 22 | 22 | 1.9 | 47.3 |
| 23 | 60.4 | 1.8 | 8.5 |
| 24 | 18.4 | 1.7 | 4.2 |
| 25 | 8.6 | 2.5 | 5.9 |
| 26 | 14 | 1.6 | 89.3 |
| 27 | 7.9 | 2.2 | 22.9 |

TABLE 2-continued

In vitro kinase inhibitory activity
of the compounds disclosed herein

| Example No. | Kinase inhibitory activity IC$_{50}$ (nM) | | |
|---|---|---|---|
| | EGFR | HER-2 | EGFR T790M |
| 28 | 40.1 | 1.6 | 14.5 |
| 29 | 22.6 | 3.7 | 87.3 |
| 30 | 31.9 | 6.6 | 132.8 |
| 31 | 2.1 | 9.1 | 6.4 |
| 32 | 1.2 | 7 | 4 |
| 33 | 1.5 | 9.6 | 5 |
| 34 | 3.3 | 20.3 | 7 |
| 35 | 0.9 | 17.8 | 20 |

The results, shown in Table 2, demonstrated that the compounds disclosed herein showed high inhibitory activity on EGFR, HER2 and EGFR T790M kinase.

Example 109

The chemical names, structures and preparation methods of the compounds disclosed herein are as described in their preparation examples.

Test Method

Materials used include Propranolol (internal standard), methyl alcohol, ammonium acetate, K$_2$EDTA (potassium ethylenediaminetetraacetate), methane acid, acetonitrile, MTBE (methyl tert-butyl ether), Cremophor EL (polyoxyethylated castor oil), KolliphorHS 15 (polyethylene glycol 12-hydroxystearate), DMSO (dimethylsulfoxide), PEG400 (polyethylene glycol 400) and SD rat (male, 180-220 g, 7-8 weeks old, purchased from Hunan Slack King of Laboratory Animal Co., Ltd.), all of which are commercially available.

1. Sample Preparation

Each test compound prepared in above examples was completely dissolved in a mixture of 5% DMSO, 5% KolliphorHS 15 and 90% saline.

2. Animal Experiment Design

| Sample to be tested | Compounds prepared in above examples | | |
|---|---|---|---|
| Animal groups | IV | n = 3 2 mg/kg | Collecting blood at time points of 0.083, 0.25, 0.5, 1, 2, 4, 6, 8 and 24 h after drug administration (the time point of drug administration is set as 0 h) |
| | PO | n = 3 5 mg/kg | Collecting blood at time points of 0.25, 0.5, 1, 2, 4, 6, 8 and 24 h after drug administration (the time point of drug administration is set as 0 h) |
| Method of administration | I.V.: administration on hind leg; PO: gavage. | | |
| Blood sampling method | Collecting blood from caudal vein | | |
| Blood collection | 200~400 µL/point-in-time | | |
| Anticoagulation | K$_2$EDTA | | |
| Plasma preparation | All the samples were processed to separate plasma within 60 min by centrifugation at 10000 rpm for 2 minutes at 4° C. The sample was stored at −80° C. under test. | | |
| Fasting conditions | Animals were deprived of food, but not of drinking water, for 15 hours before experiments. Eating was allowed 4 hours after administration. | | |

| Sample to be tested | Compounds prepared in above examples |
|---|---|
| Vehicle of stock solution | Test sample: 20% DMSO; internal standard: Propranolol aqueous solution (100 ng/mL) |
| Data processing | WinNonlin 6.1 software for calculating the pharmacokinetic parameters |

3. Dosage Table of Administration

| Group | Sex | Number of animals | Dosage of administration | Concentration of drugs | Dose volume |
|---|---|---|---|---|---|
| I.V. | male | 3 | 2 mg/kg | 1 mg/mL | 2 mL/kg |
| PO | male | 3 | 5 mg/kg | 1 mg/mL | 5 mL/kg |

4. Preparation of Solution

Preparation of solution was performed according to the following procedures.

(1) The test sample stock solution was prepared by dissolving an accurately weighed test sample in DMSO followed by dilution to the concentration of 1 mg/mL with acetonitrile. The stock solution was stored under the condition of −20° C. for later use.

(2) Internal standard solution was prepared by diluting a certain amount of the Propranolol stock solution in the concentration of 1 mg/mL to 100 ng/mL with water.

5. Sample Analysis

Samples treated with liquid-liquid extraction and chromatographic separation were analyzed by triple quadrupole tandem mass spectrometer in multiple reaction monitoring (MRM) mode for quantitative analysis.

6. Pretreatment of Plasma Sample

Pretreatment of plasma sample was performed according to the following procedures: (1) plasma sample (30 µL) was precisely measured, and internal standard (250 µL) was then added to the plasma sample which was then mixed by vortexing; (2) the sample was extracted once with 1 mL of MTBE and then centrifuged at 13000 rpm for 2 minutes at 4° C.; (3) supernatant (800 µL) was aspirated and dried with 96 holes nitrogen gas blowing; (4) the residue was dissolved with 150 µL of a mixture of methanol and water (v/v=1/1) and then mixed by vortexing; and (5) sampling: sample quantity was 8 µL.

7. Preparation of Standard Sample

Preparation of standard sample was performed according to the following procedures: (1) a pre-determined amount of the compound stock solution was precisely measured, and then was diluted to standard series of solution with acetonitrile; (2) each of the standard solution (20 µL) prepared above was precisely measured and to each was added 180 µL of blank plasma; (3) each sample was mixed by vortexing to obtain series of standard samples in which the plasma concentration was 3, 5, 10, 30, 100, 300, 1000, 3000, 5000 or 10000 ng/mL; and (4) standard curve was established.

8. Analytical Method

The content of each test compound in rat plasma after administration was determined by LC/MS/MS.

9. Data Processing

Noncompartmental analysis to calculate pharmacokinetic parameters was performed with WinNonlin 6.1 software.

10. Results as Shown in Table 3

TABLE 3

Pharmacokinetic activity of the compounds disclosed herein

| Example No. | Dosing | Rat PK | | | | | |
|---|---|---|---|---|---|---|---|
| | | $T_{1/2}$ (h) | $AUC_{last}$ (ng·h/mL) | $C_{max}$ (ng/ml) | $V_{ss}$ (L/kg) | CL_F (L/h/kg) | F (%) |
| 20 | iv(2 g/kg) | 2.22 | 1447.28 | 867.93 | 3.71 | 1.29 | 83.19 |
|    | po(5 g/kg) | 3.60 | 3187.36 | 336.07 | / | / | |
| 23 | iv(2 g/kg) | 3.06 | 7559.3 | 2773.33 | 0.88 | 0.27 | 73.50 |
|    | po(5 g/kg) | 2.77 | 13892.70 | 1926.67 | / | / | |
| 24 | iv(2 g/kg) | 3.59 | 10545.68 | 2926.67 | 0.79 | 0.19 | 87.10 |
|    | po(5 g/kg) | 3.49 | 22935.00 | 2770.00 | / | / | |
| 25 | iv(2 g/kg) | 1.42 | 4528.14 | 4110.00 | 0.65 | 0.44 | 5.94 |
|    | po(5 g/kg) | 4.42 | 474.22 | 72.97 | / | / | |
| 27 | iv(2 g/kg) | 1.97 | 1187.66 | 922.93 | 3.65 | 1.62 | 10.84 |
|    | po(5 g/kg) | 2.33 | 303.15 | 67.80 | / | / | |
| 28 | iv(2 g/kg) | 1.99 | 692.28 | 450.30 | 6.66 | 2.74 | 41.51 |
|    | po(5 g/kg) | 1.41 | 720.82 | 146.87 | / | / | |
| 31 | iv(2 g/kg) | 3.66 | 2985.20 | 1205.60 | 2.58 | 0.67 | 93.48 |
|    | po(5 g/kg) | 3.16 | 6984.95 | 793.90 | / | / | |
| 32 | iv(2 g/kg) | 2.95 | 2169.42 | 1004.17 | 2.97 | 0.87 | 108.49 |
|    | po(5 g/kg) | 2.97 | 6223.60 | 748.23 | / | / | |
| 33 | iv(2 g/kg) | 1.29 | 1250.70 | 890.30 | 2.77 | 1.60 | 44.49 |
|    | po(5 g/kg) | 1.27 | 1372.60 | 346.50 | / | / | |
| 34 | iv(2 g/kg) | 1.15 | 950.95 | 645.33 | 3.18 | 2.13 | 68.73 |
|    | po(5 g/kg) | 1.40 | 1552.25 | 377.67 | / | / | |

The results in Table 3 demonstrated that the compounds disclosed herein had a good in vivo metabolism, good absorption and exposure, and high bioavailability of more than 30%, and some preferred compounds achieved a bioavailability of 60%-80%.

Reference throughout this specification to "an embodiment," "some embodiments," "explanatory embodiment", "an example," "a specific example," or "some examples," means that a particular feature, structure, material or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments or examples and the features of them described above if they are not conflict with each other.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A compound having Formula (I):

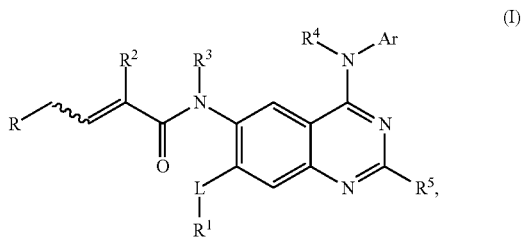

or a stereoisomer, a geometric isomer, a tautomer, a hydrate, a solvate, or a pharmaceutically acceptable salt thereof, wherein R is

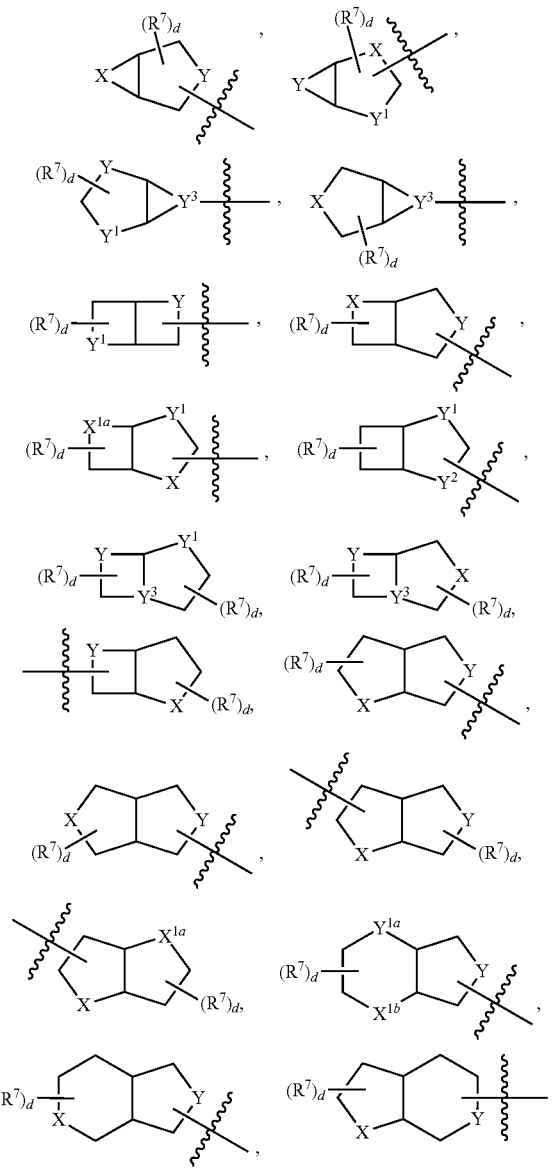

-continued

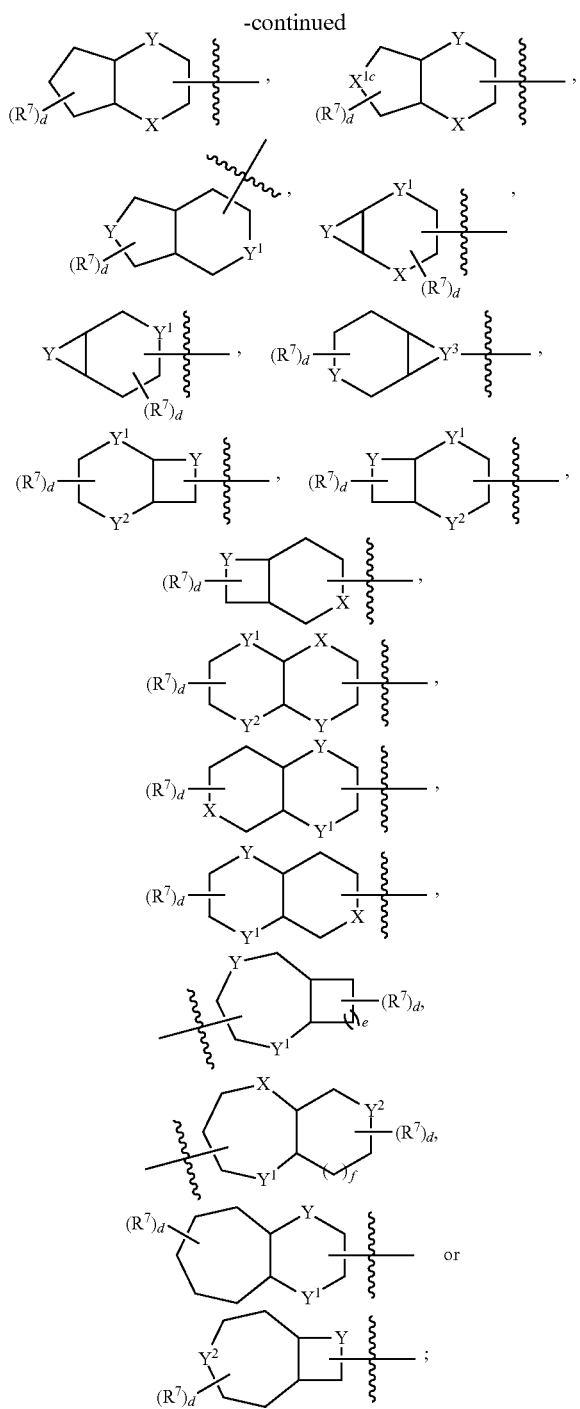

wherein each X and $X^{1a}$ is independently O, S, S(=O), S(=O)$_2$ or NR$^a$;
$X^{1b}$ is O, S, S(=O), or S(=O)$_2$;
$X^{1c}$ is S, S(=O) or S(=O)$_2$;
each Y, Y$^1$, and Y$^2$ is independently O, S, S(=O), S(=O)$_2$, NR$^a$ or CR$^b$R$^{b'}$;
$Y^{1a}$ is O, S, S(=O), S(=O)$_2$, or CR$^b$R$^{b'}$;
each Y$^3$ is independently CR$^{b''}$ or N;
wherein each R$^a$ is independently H, D or C$_{1-3}$ alkyl;
each R$^b$, R$^{b'}$ and R$^{b''}$ is independently H, D, F, Cl, Br, I, —OH, —NO$_2$, —NH$_2$, —CN, C$_{1-3}$ alkyl, C$_{1-3}$ alkoxy or C$_{1-3}$ alkylamino;

each R$^7$ is independently H, D, F, Cl, Br, I, —OH, —SH, —NO$_2$, —NH$_2$, —CN, —COOH, C$_{1-6}$ alkyl, C$_{1-6}$ heteroalkyl, C$_{1-6}$ alkylamino, C$_{1-6}$ alkoxy, C$_{2-6}$ alkenyl, C$_{2-6}$ alkynyl, C$_{3-8}$ cycloalkyl, C$_{2-10}$ heterocyclyl, C$_{6-10}$ aryl, C$_{6-10}$ aryl-C$_{1-6}$-alkyl, C$_{6-10}$ aryloxy, C$_{6-10}$ aryl-C$_{1-6}$-alkoxy or C$_{1-9}$ heteroaryl;
each d is independently 0, 1, 2, 3, 4 or 5;
e is 0, 1, 2, or 3;
f is 0 or 1;
L is a bond, O or S;
R$^1$ is H, D, F, Cl, Br, I, —OH, —NO$_2$, —NH$_2$, —CN, C$_{1-6}$ alkyl, C$_{1-6}$ haloalkyl, C$_{1-6}$ alkoxy-C$_{1-6}$-alkyl, C$_{2-6}$ alkenyl, C$_{2-6}$ alkynyl, C$_{1-6}$ alkylamino-C$_{1-6}$-alkyl, C$_{3-8}$ cycloalkyl, C$_{3-8}$ cycloalkyl-C$_{16}$-alkyl, C$_{3-8}$ cycloalkyl-C$_{2-6}$-alkenyl, C$_{3-8}$ cycloalkyl-C$_{2-6}$-alkynyl, C$_{3-8}$ cycloalkyloxy-C$_{2-6}$-alkynyl, C$_{2-10}$ heterocyclyl, C$_{2-10}$ heterocyclyl-C$_{1-6}$-alkyl, C$_{2-10}$ heterocyclyl-C$_{2-6}$-alkenyl, C$_{2-10}$ heterocyclyl-C$_{2-6}$-alkynyl, C$_{5-12}$ fused bicyclyl, C$_{5-12}$ fused bicyclyl-C$_{1-6}$-alkyl, C$_{5-12}$ fused bicyclyl-C$_{2-6}$-alkenyl, C$_{5-12}$ fused bicyclyl-C$_{2-6}$-alkynyl, C$_{5-12}$ fused heterobicyclyl, C$_{5-12}$ fused heterobicyclyl-C$_{1-6}$-alkyl, C$_{5-12}$ fused heterobicyclyl-C$_{2-6}$-alkenyl, C$_{5-12}$ fused heterobicyclyl-C$_{2-6}$-alkynyl, C$_{5-12}$ spiro bicyclyl, C$_{5-12}$ spiro bicyclyl-C$_{1-6}$-alkyl, C$_{5-12}$ spiro bicyclyl-C$_{2-6}$-alkenyl, C$_{5-12}$ spiro bicyclyl-C$_{2-6}$-alkynyl, C$_{5-12}$ spiro heterobicyclyl, C$_{5-12}$ spiro heterobicyclyl-C$_{1-6}$-alkyl, C$_{5-12}$ spiro heterobicyclyl-C$_{2-6}$-alkenyl, C$_{5-12}$ spiro heterobicyclyl-C$_{2-6}$-alkynyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl;
R$^2$ is H, F, Cl, Br, I, —NH$_2$, —NO$_2$, —CN or C$_{1-6}$ alkyl;
each of R$^3$ and R$^4$ is independently H, D or C$_{1-4}$ alkyl;
R$^5$ is H;
Ar is

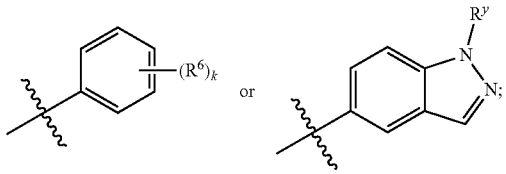

wherein each R$^6$ is independently H, D, F, Cl, Br, I, C$_{2-6}$ alkynyl, C$_{6-10}$ aryl-C$_{1-6}$-alkoxy, or C$_{1-9}$ heteroaryl-C$_{1-6}$-alkoxy;
k is 0, 1, 2, 3, 4 or 5; and
R$^y$ is H or C$_{6-10}$ aryl-C$_{1-6}$-alkyl,
wherein optionally each of alkyl, alkoxy, alkoxyalkyl, alkylamino, alkylaminoalkyl, heteroalkyl, alkenyl, alkynyl, cycloalkyl, cycloalkylalkyl, cycloalkylalkenyl, cycloalkylalkynyl, cycloalkyloxyalkynyl, heterocyclyl, heterocyclylalkyl, heterocyclylalkenyl, heterocyclylalkynyl, fused bicyclyl, fused bicyclylalkyl, fused bicyclylalkenyl, fused bicyclylalkynyl, fused heterobicyclyl, fused heterobicyclylalkyl, fused heterobicyclylalkenyl, fused heterobicyclylalkynyl, spiro bicyclyl, spiro bicyclylalkyl, spiro bicyclylalkenyl, spiro bicyclylalkynyl, spiro heterobicyclyl, spiro heterobicyclylalkyl, spiro heterobicyclylalkenyl, spiro heterobicyclylalkynyl, aryl, aryloxy, arylalkyl, arylalkoxy, arylamino, heteroaryl, heteroarylalkyl, heteroarylalkoxy, heteroaryloxy, alkylthio, alkylcarbonyl, alkylacylamino, alkylsulfonyl, haloalkyl and alkylsulfinyl is independently substituted with one or more substituents independently selected from D, F, Cl, Br, I, —OH, —NO$_2$, —NH$_2$, —CN, —COOH, C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl, and wherein optionally each of C$_{1-3}$ alkyl, C$_{1-3}$ alkoxy, C$_{1-3}$ alkylamino, C$_{1-3}$ alkylthio, C$_{6-10}$ aryl, C$_{6-10}$ aryloxy, C$_{6-10}$ arylamino, C$_{1-9}$ heteroaryl, C$_{1-9}$ heteroaryloxy, C$_{3-8}$ cycloalkyl, C$_{3-8}$ cycloalkyloxy, C$_{2-10}$ heterocyclyl and C$_{5-12}$ fused heterobicyclyl is independently substituted with one or more substituents independently selected from D, F, Cl, Br, I, —OH, —NO$_2$, —NH$_2$, —CN, —COOH, C$_{1-3}$ alkyl, deuterated C$_{1-3}$ alkyl, C$_{1-3}$ haloalkyl and hydroxy-substituted C$_{1-3}$ alkyl.

2. The compound according to claim 1, wherein R is

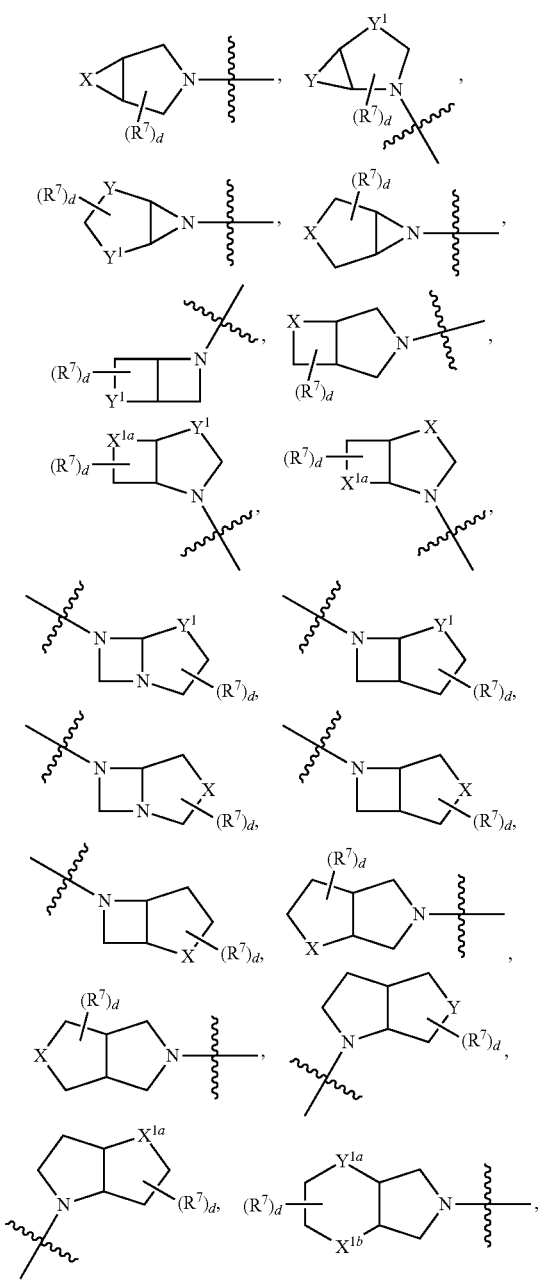

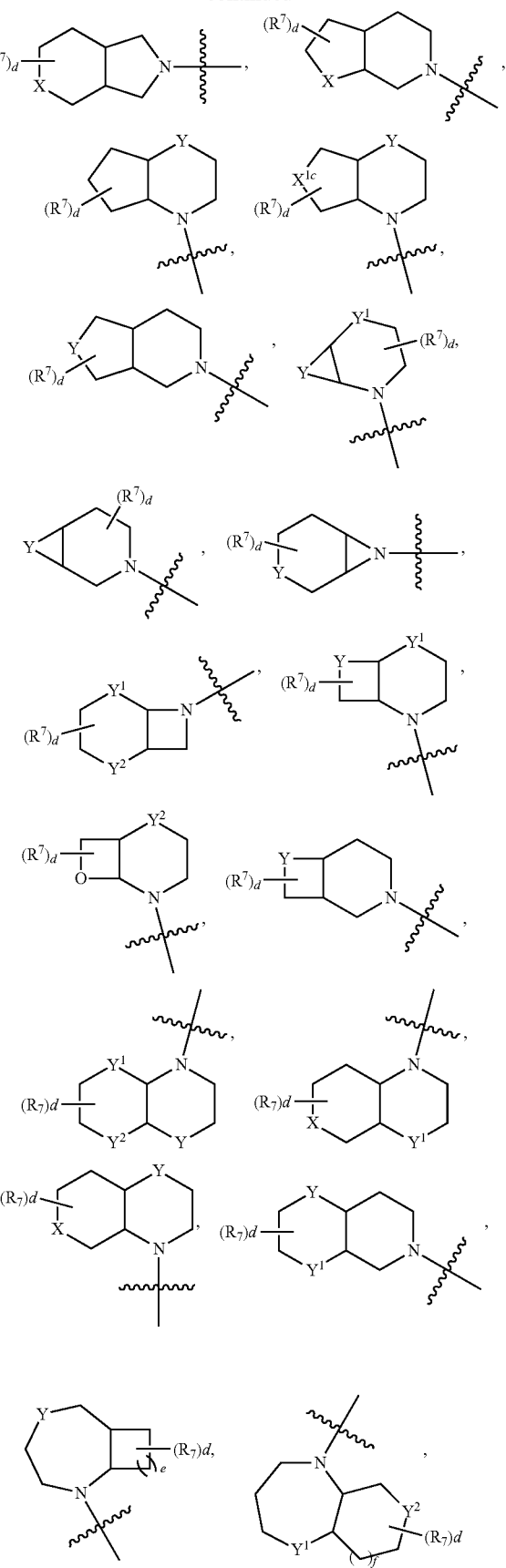

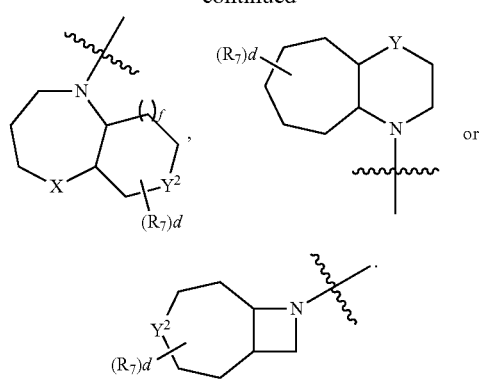
3. The compound according to claim 2, wherein R is
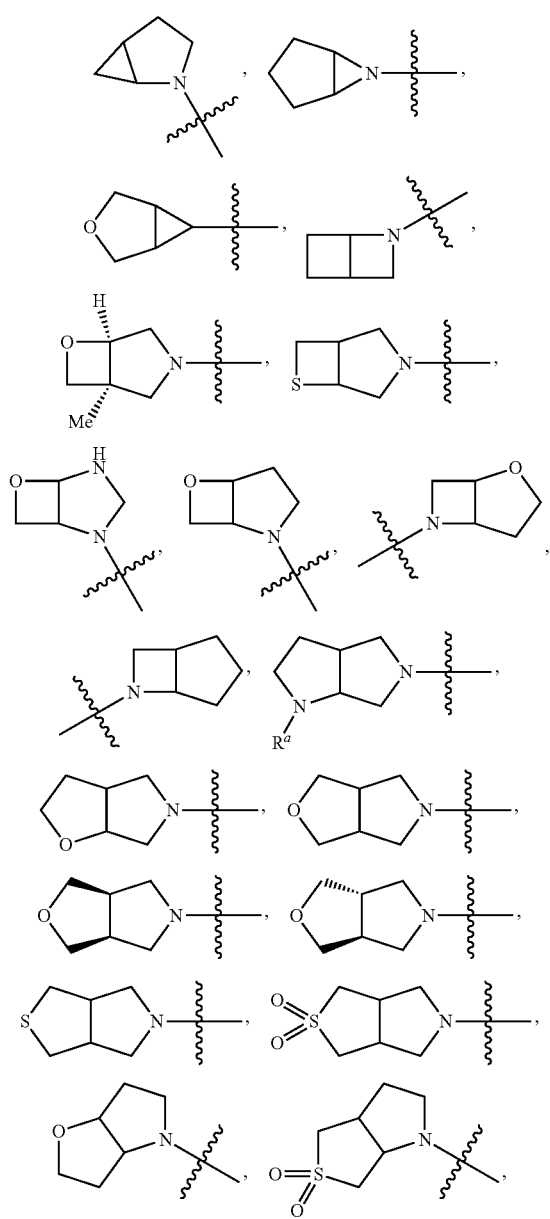
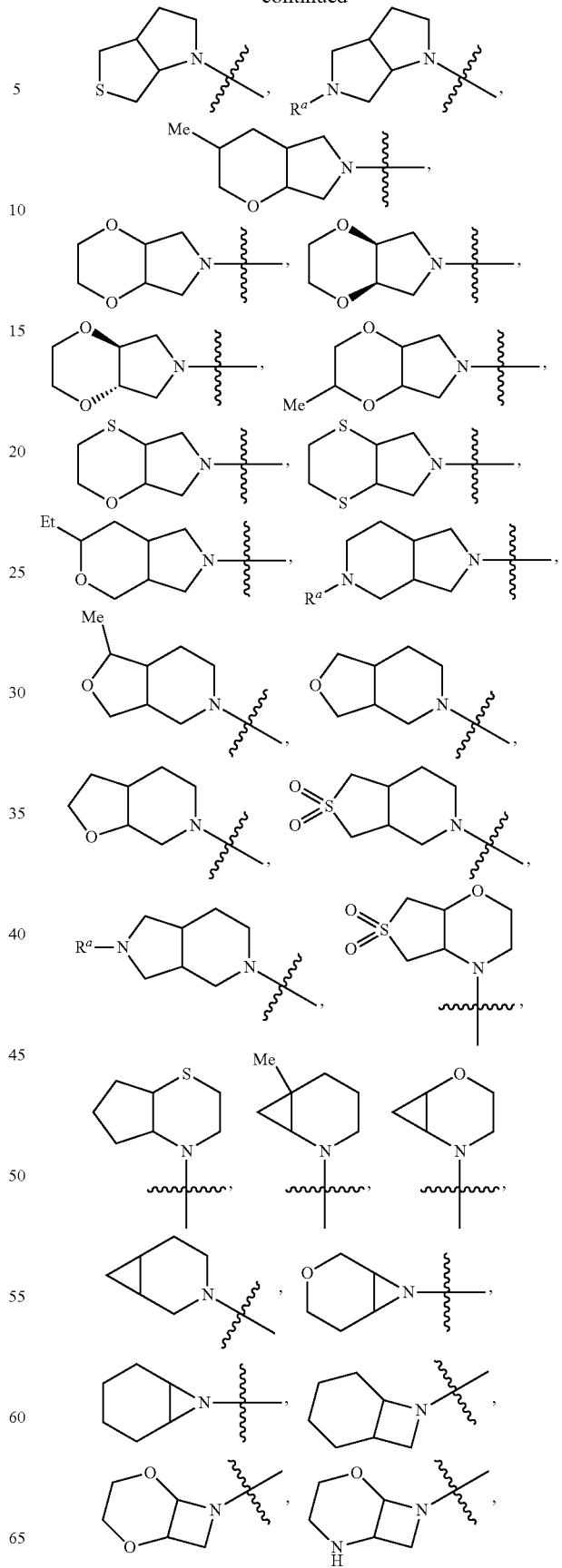

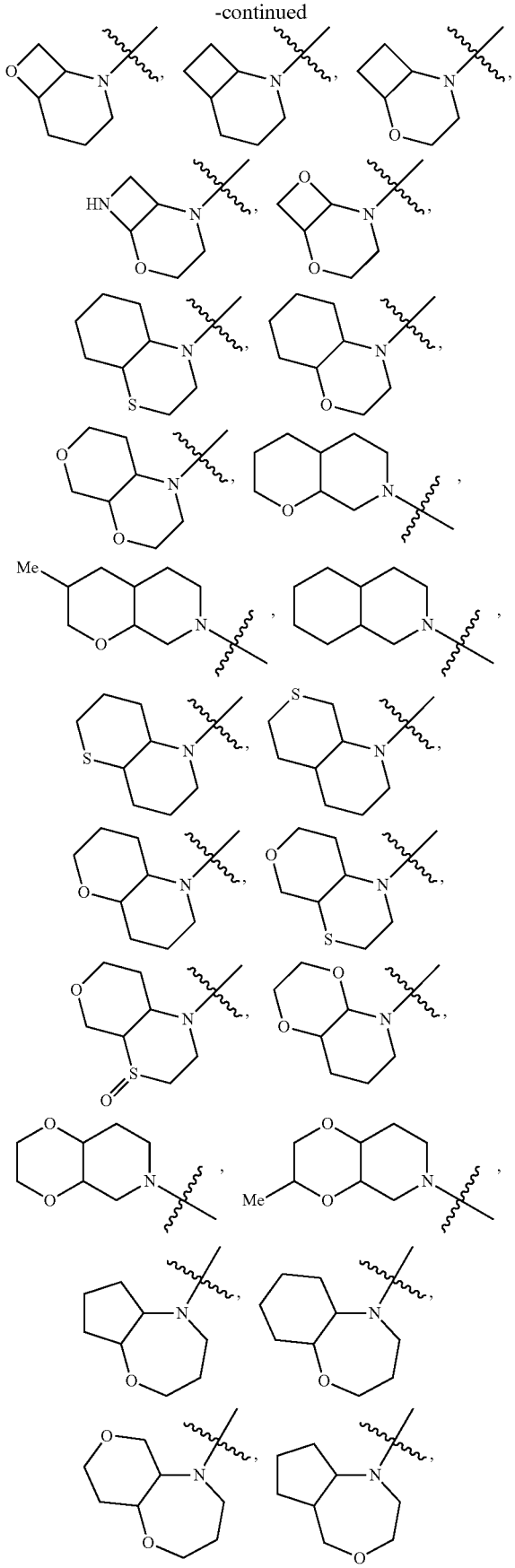

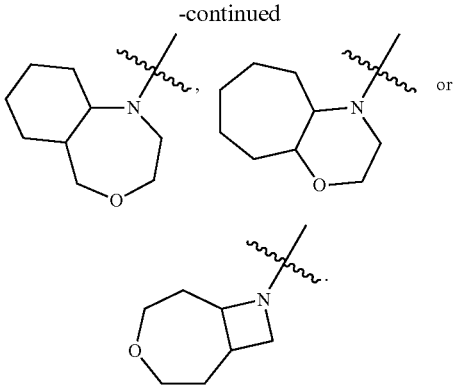

4. The compound according to claim 1, wherein $R^1$ is H, D, F, Cl, Br, I, —OH, —NO$_2$, —NH$_2$, —CN, $C_{1-6}$ alkyl, $C_{2-6}$ alkynyl or $C_{1-6}$ alkoxy-$C_{1-6}$-alkyl, and wherein optionally each of $C_{1-6}$ alkyl, $C_{2-6}$ alkynyl and $C_{1-6}$ alkoxy-$C_{1-6}$-alkyl is independently substituted with one or more substituents independently selected from D, F, Cl, Br, I, —OH, —NO$_2$, —NH$_2$, —CN, —COOH, $C_{1-3}$ alkyl, $C_{1-3}$ haloalkyl, $C_{1-3}$ alkylamino, $C_{1-3}$ alkoxy, $C_{6-10}$ aryl, $C_{1-9}$ heteroaryl, $C_{3-8}$ cycloalkyl, $C_{3-8}$ cycloalkyloxy and $C_{2-10}$ heterocyclyl, or $R^1$ is

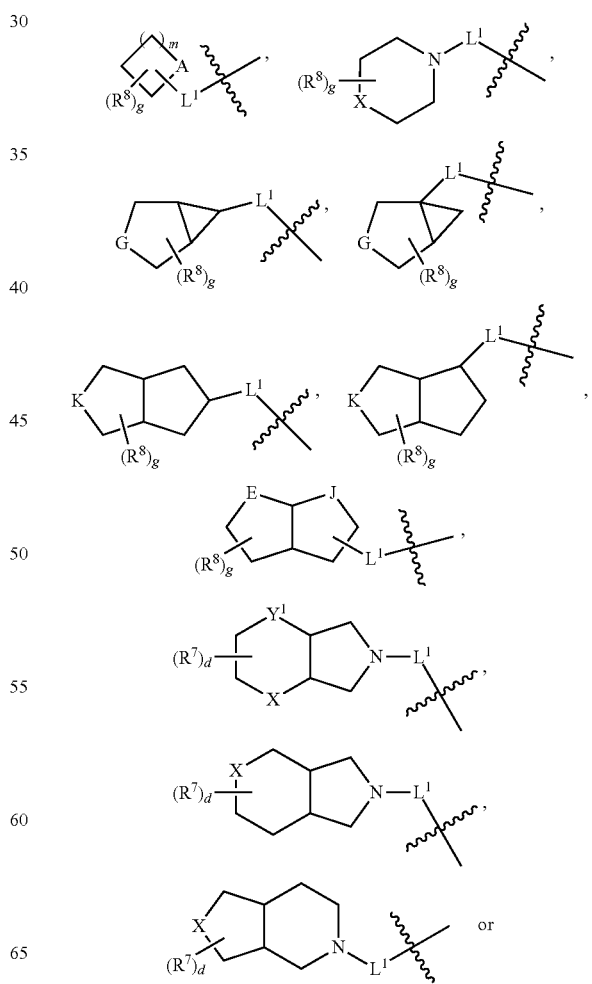

-continued

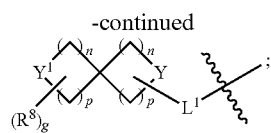

wherein each A, G, E and J is independently $CR^bR^{b'}$, $NR^a$, O, S, S(=O) or S(=O)$_2$;

each K is independently $NR^a$, O, S, S(=O) or S(=O)$_2$;

each L is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —NO$_2$, —NH$_2$, —CN, —COOH and $C_{1-3}$ alkyl;

each $R^8$ is independently H, D, F, Cl, Br, I, —OH, —SH, —NO$_2$, —NH$_2$, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —NO$_2$, —NH$_2$, —CN, —COOH, $C_{1-3}$ alkyl and $C_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2; and each p is independently 1 or 2.

5. The compound according to claim 4, wherein $R^1$ is H, D, F, Cl, Br, I, —OH, —NO$_2$, —NH$_2$, —CN, $C_{1-3}$ alkyl, $C_{2-3}$ alkynyl or $C_{1-3}$ alkoxy-$C_{1-3}$-alkyl, and wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —NO$_2$, —NH$_2$, —CN, —COOH, $C_{1-3}$ alkyl, $C_{1-3}$ haloalkyl, $C_{1-3}$ alkylamino, $C_{1-3}$ alkoxy and $C_{3-8}$ cycloalkyloxy, or $R^1$ is

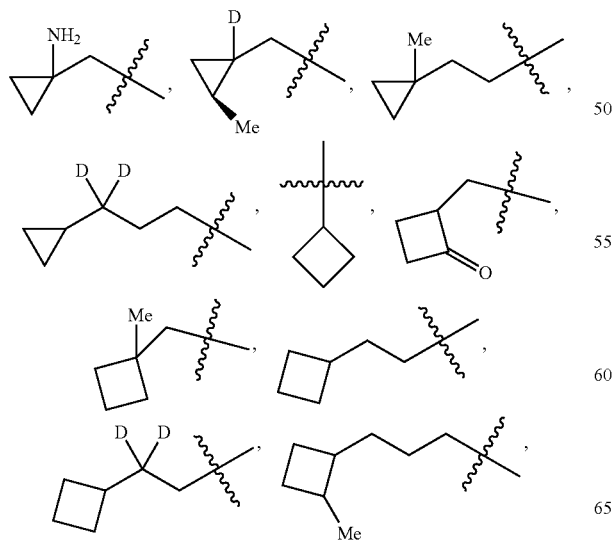

-continued

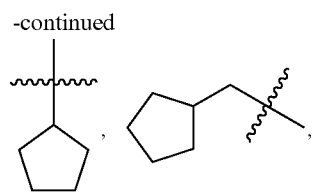

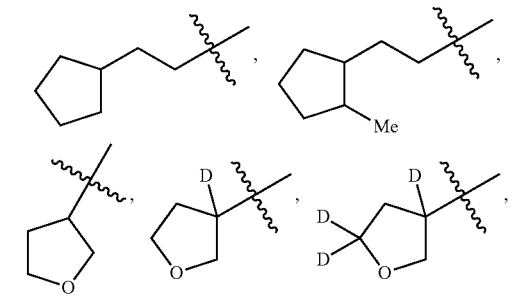

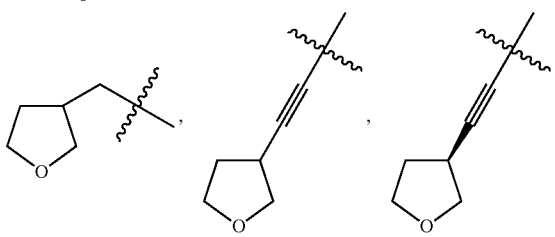

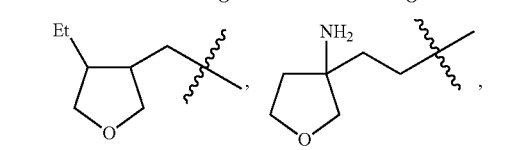

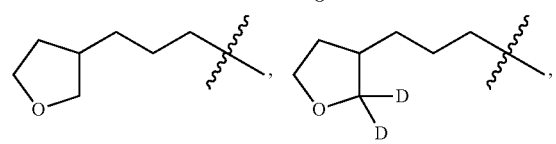

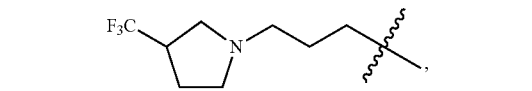

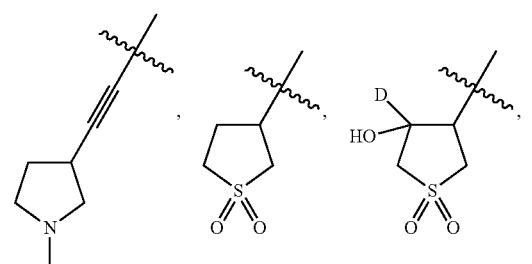

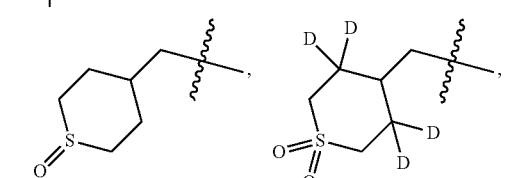

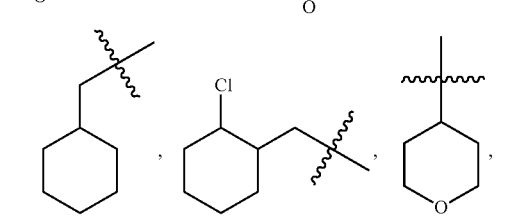

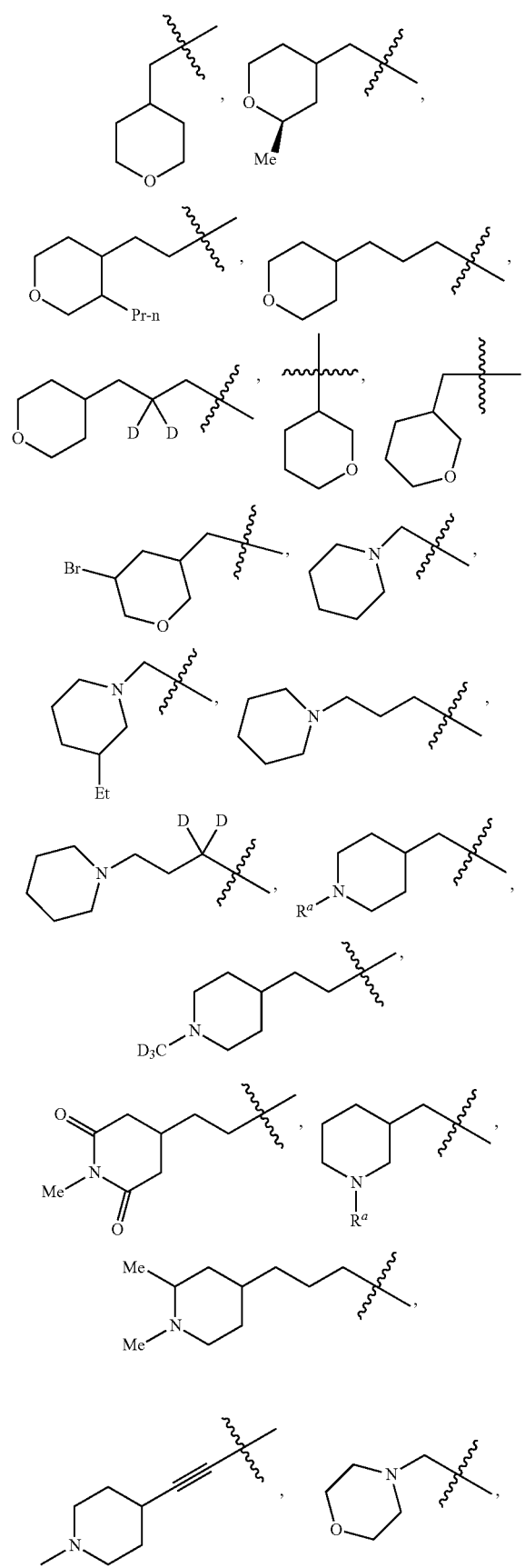
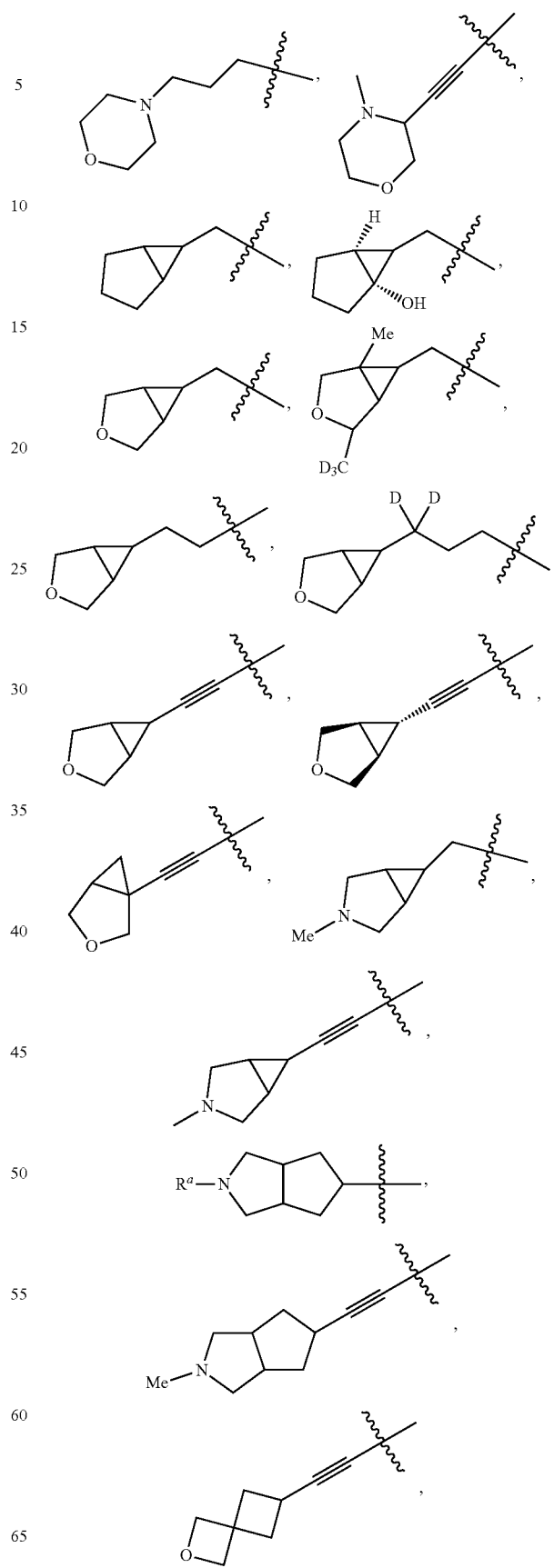

231
-continued

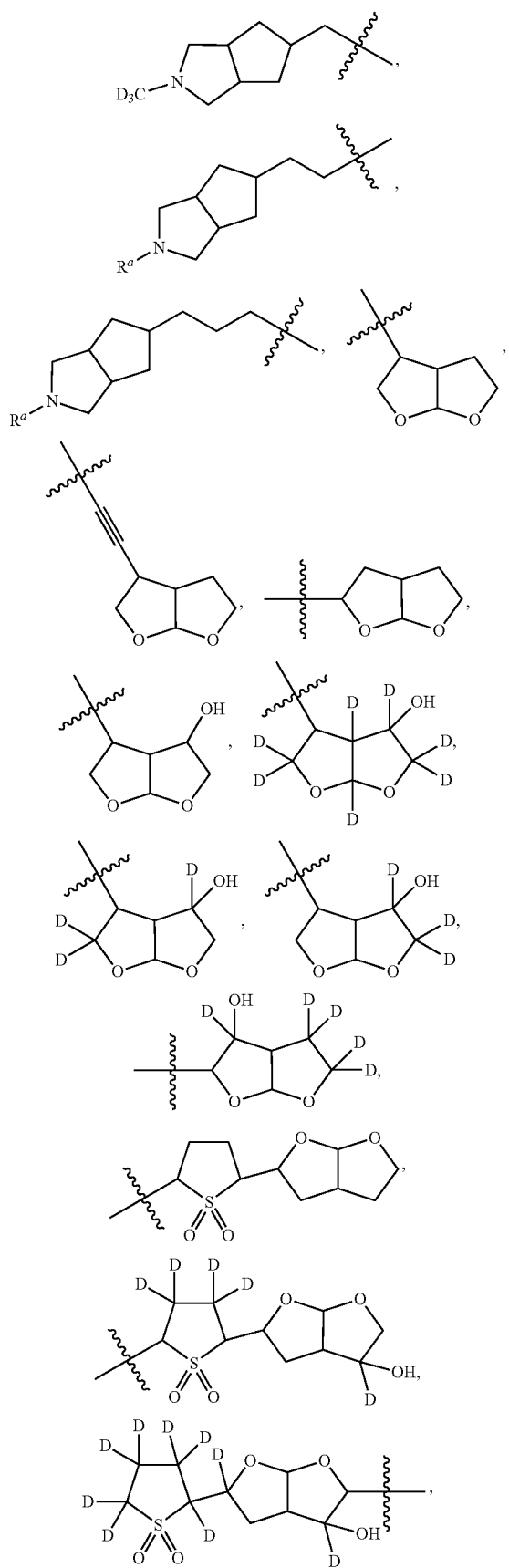

232
-continued

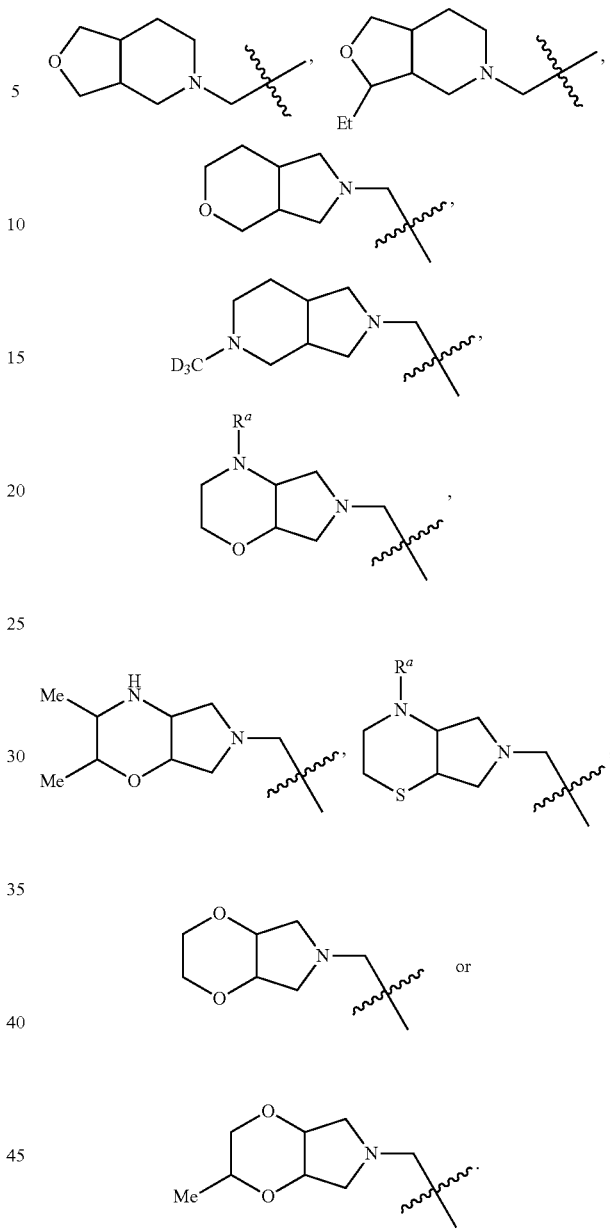

6. The compound according to claim 1, wherein $R^1$ is H, D, F, Cl, Br, I, —OH, —NO$_2$, —NH$_2$, —CN, C$_{1-6}$ alkyl,) The compound according to claim 1, wherein each $R^6$ is independently H, D, F, Cl, Br, I, C$_{2-4}$ alkynyl, C$_{6-10}$ aryl-C$_{1-3}$-alkoxy, or C$_{2-5}$ heteroaryl-C$_{1-3}$-alkoxy; and $R^y$ is H or C$_{6-10}$ aryl-C$_{1-3}$-alkyl, wherein optionally each of C$_{2-4}$ alkynyl, C$_{6-10}$ aryl-C$_{1-3}$-alkyl, C$_{6-10}$ aryl-C$_{1-3}$-alkoxy, and C$_{2-5}$ heteroaryl-C$_{1-3}$-alkoxy is independently substituted with one or more substituents independently selected from D, F, Cl, Br, I, —OH, —NO$_2$, —NH$_2$, —CN, —COOH, C$_{1-3}$ alkyl, C$_{1-3}$ haloalkyl, C$_{1-3}$ alkylamino, C$_{1-3}$ alkoxy, and C$_{3-8}$ cycloalkyloxy.

7. The compound according to claim 1, wherein $R^1$ is H, D, F, Cl, Br, I, —OH, —NO$_2$, —NH$_2$, —CN, C$_{1-6}$ alkyl,) The compound according to claim 1 having Formula (Ia):

233

(Ia)

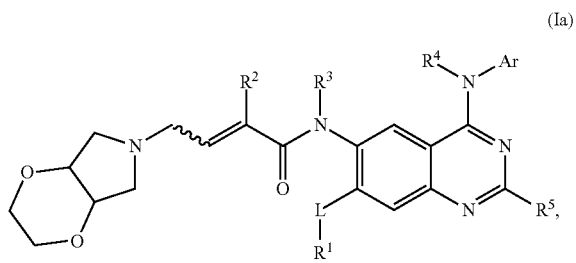

wherein R¹ is H, D, F, Cl, Br, I, —OH, —NO₂, —NH₂, —CN, $C_{1-6}$ alkyl, $C_{2-6}$ alkynyl or $C_{1-6}$ alkoxy-$C_{1-6}$-alkyl, wherein optionally each of $C_{1-6}$ alkyl, $C_{2-6}$ alkynyl and $C_{1-6}$ alkoxy-$C_{1-6}$-alkyl is independently substituted with one or more substituents independently selected from D, F, Cl, Br, I, —OH, —NO₂, —NH₂, —CN, —COOH, $C_{1-3}$ alkyl, $C_{1-3}$ haloalkyl, $C_{1-3}$ alkylamino, $C_{1-3}$ alkoxy, $C_{6-10}$ aryl, $C_{1-9}$ heteroaryl, $C_{3-8}$ cycloalkyl, $C_{3-8}$ cycloalkyloxy and $C_{2-10}$ heterocyclyl, or R¹ is

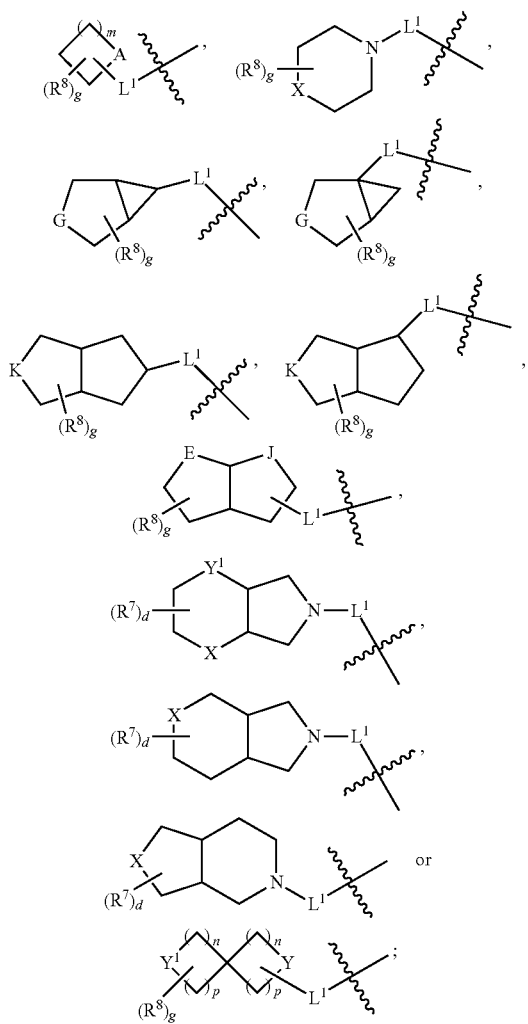

wherein each A, G E and J is independently $CR^bR^{b'}$, $NR^a$, O, S, S(=O) or S(=O)₂;
each K is independently $NR^a$, O, S, S(=O) or S(=O)₂;

234 each L¹ is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —NO₂, —NH₂, —CN, —COOH and $C_{1-3}$ alkyl;
each R⁸ is independently H, D, F, Cl, Br, I, —OH, —SH, —NO₂, —NH₂, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —NO₂, —NH₂, —CN, —COOH, $C_{1-3}$ alkyl and $C_{1-3}$ haloalkyl;
each g is independently 0, 1, 2, 3, 4, 5, 6, 7, 8, 9, 10, 11, 12 or 13;
m is 0, 1, 2, 3 or 4;
each n is independently 0, 1 or 2;
each p is independently 1 or 2;
Ar is

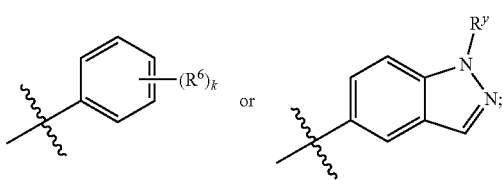

wherein each R⁶ is independently H, D, F, Cl, Br, I, $C_{2-4}$ alkynyl, $C_{6-10}$ aryl-$C_{1-3}$-alkoxy, or $C_{2-5}$ heteroaryl-$C_{1-3}$-alkoxy, and wherein optionally each of $C_{2-4}$ alkynyl, —$C_{6-10}$ aryl-$C_{1-3}$-alkoxy, and $C_{2-5}$ heteroaryl-$C_{1-3}$-alkoxy is independently substituted with one or more substituents independently selected from D, F, Cl, Br, I, —OH, —NO₂, —NH₂, —CN, —COOH, $C_{1-3}$ alkyl, $C_{1-3}$ haloalkyl, $C_{1-3}$ alkylamino and $C_{1-3}$ alkoxy;
k is 0, 1,2,3, 4 or 5; and
$R^y$ is H or $C_{6-10}$ aryl-$C_{1-6}$-alkyl, wherein $C_{6-10}$ aryl-$C_{1-6}$-alkyl is benzyl and optionally substituted with one or more substituents independently selected from F, Cl, Br or I.

8. The compound according to claim 7, wherein R¹ is H, D, $C_{1-3}$ alkyl, $C_{2-3}$ alkynyl or $C_{1-3}$ alkoxy-$C_{1-3}$-alkyl, and wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —NO₂, —NH₂, —CN, —COOH, $C_{1-3}$ alkoxy and $C_{3-8}$ cycloalkyloxy, or R¹ is

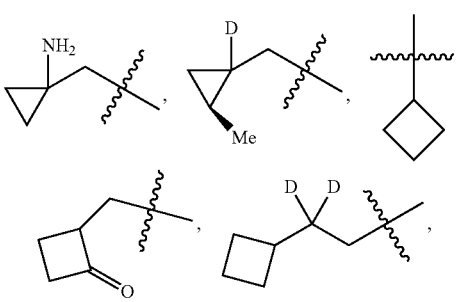

235
-continued
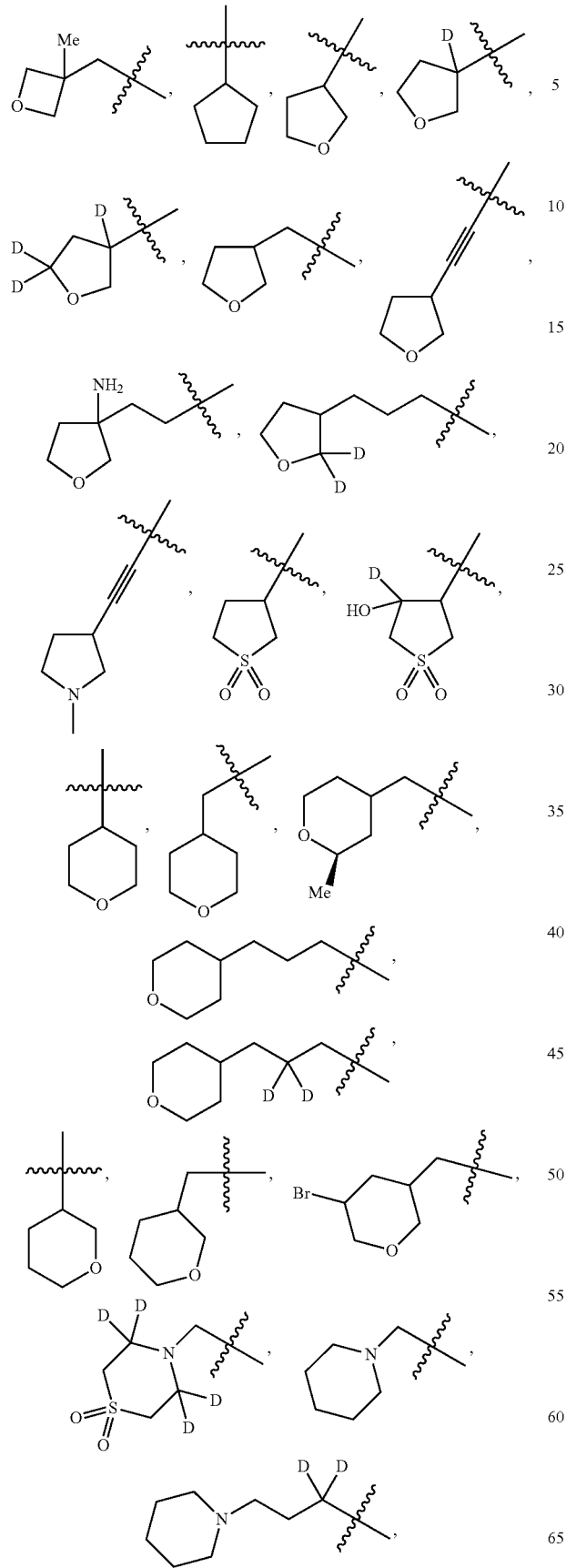
236
-continued
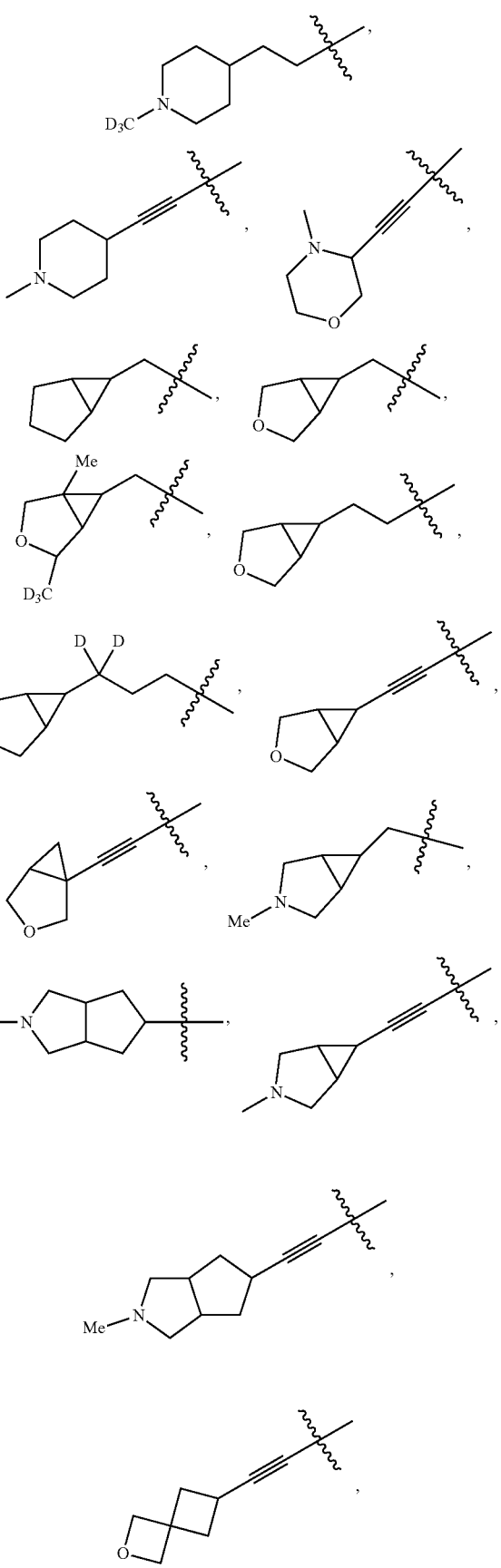

-continued

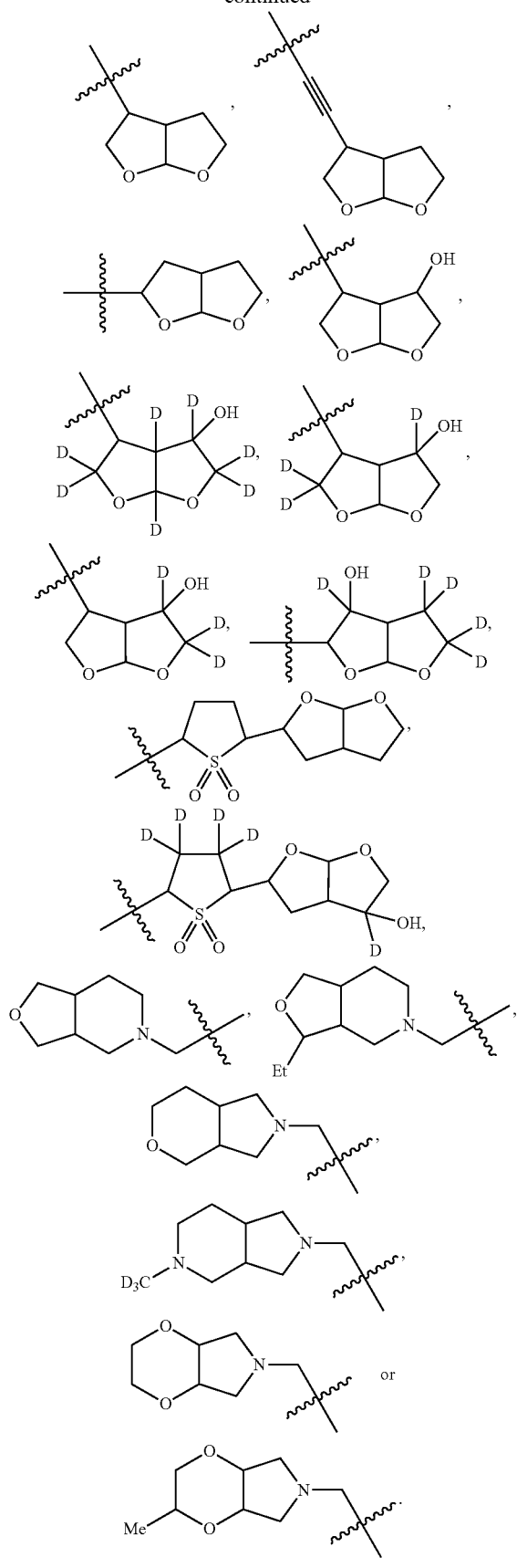

9. The compound according to claim 1, wherein $R^1$ is H, D, F, Cl, Br, I, —OH, —$NO_2$, —$NH_2$, —CN, $C_{1-6}$ alkyl,)
The compound according to claim 1 having Formula (Ib):

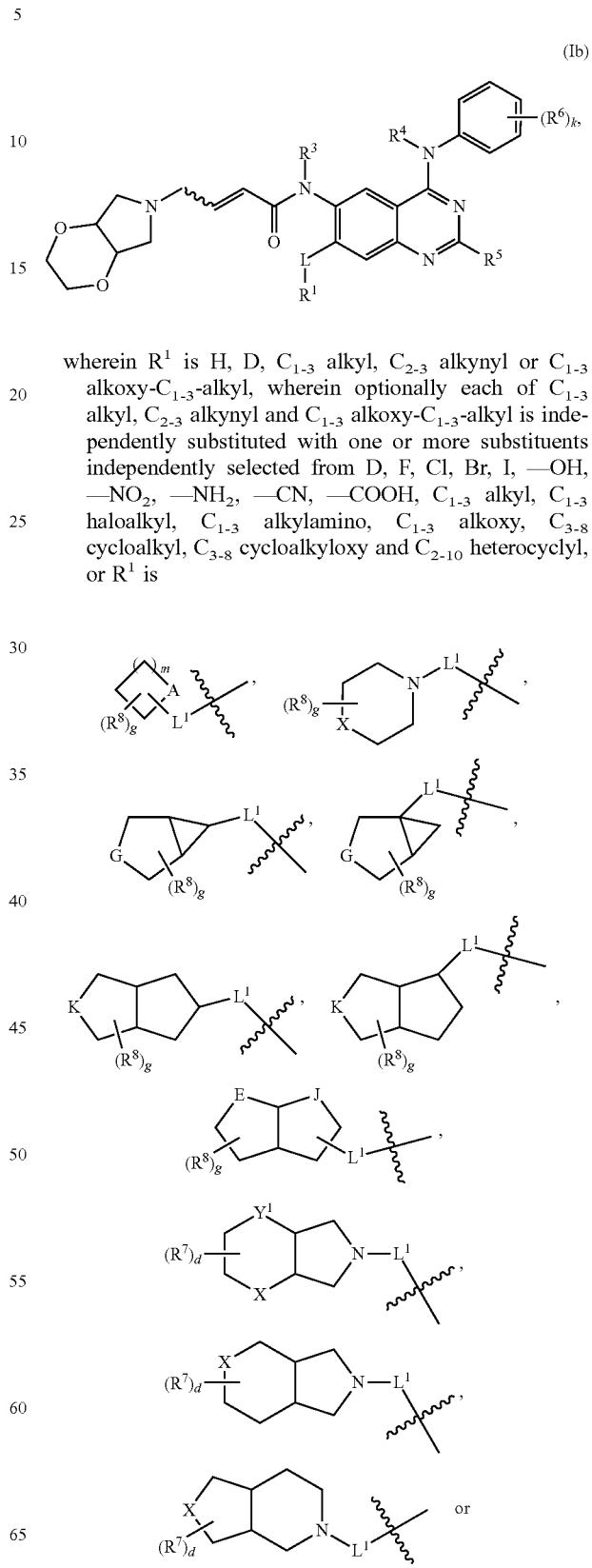

wherein $R^1$ is H, D, $C_{1-3}$ alkyl, $C_{2-3}$ alkynyl or $C_{1-3}$ alkoxy-$C_{1-3}$-alkyl, wherein optionally each of $C_{1-3}$ alkyl, $C_{2-3}$ alkynyl and $C_{1-3}$ alkoxy-$C_{1-3}$-alkyl is independently substituted with one or more substituents independently selected from D, F, Cl, Br, I, —OH, —$NO_2$, —$NH_2$, —CN, —COOH, $C_{1-3}$ alkyl, $C_{1-3}$ haloalkyl, $C_{1-3}$ alkylamino, $C_{1-3}$ alkoxy, $C_{3-8}$ cycloalkyl, $C_{3-8}$ cycloalkyloxy and $C_{2-10}$ heterocyclyl, or $R^1$ is

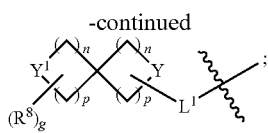

wherein each A, G, E and J is independently $CR^bR^{b'}$, $NR^a$, O, S, S(=O) or $S(=O)_2$;

each K is independently $NR^a$, O, S, S(=O) or $S(=O)_2$;

each $L^1$ is independently a bond, $C_{1-4}$ alkylene, $C_{2-4}$ alkenylene or $C_{2-4}$ alkynylene, wherein optionally each of $C_{1-4}$ alkylene, $C_{2-4}$ alkenylene and $C_{2-4}$ alkynylene is independently substituted with one or more substituents independently selected from D, F, Cl, Br, I, —OH, —$NO_2$, —$NH_2$, —CN, —COOH and $C_{1-3}$ alkyl;

each $R^8$ is independently H, D, F, Cl, Br, I, —OH, —SH, —$NO_2$, —$NH_2$, —CN, —COOH, $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl or $C_{5-12}$ fused heterobicyclyl, wherein optionally each of $C_{1-6}$ alkyl, $C_{1-6}$ heteroalkyl, $C_{1-6}$ alkylamino, $C_{1-6}$ alkoxy, $C_{2-6}$ alkenyl, $C_{2-6}$ alkynyl, $C_{3-8}$ cycloalkyl, $C_{2-10}$ heterocyclyl and $C_{5-12}$ fused heterobicyclyl is independently substituted with one or more substituents independently selected from D, F, Cl, Br, I, —OH, —SH, —$NO_2$, —$NH_2$, —CN, —COOH, $C_{1-3}$ alkyl and $C_{1-3}$ haloalkyl;

each g is independently 0, 1, 2, 3, 4, 5, 6, 7, 8, 9, 10, 11, 12 or 13;

m is 0, 1, 2, 3 or 4;

each n is independently 0, 1 or 2;

each p is independently 1 or 2;

each $R^6$ is independently H, D, F, Cl, Br, I, or $C_{2-4}$ alkynyl, or each $R^6$ is

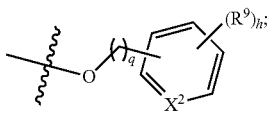

wherein $X^2$ is $CR^{10}$ or N, and wherein $R^{10}$ is H;

q is 1, 2 or 3;

each $R^9$ is independently H, D, F, Cl, Br, I, —OH, —$NO_2$, —$NH_2$, —CN, $C_{1-3}$ alkyl, $C_{2-4}$ alkynyl or $C_{1-3}$ alkoxy; and h is 0, 1, 2, 3, 4 or 5.

10. The compound according to claim 9, wherein $R^1$ is

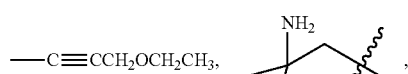

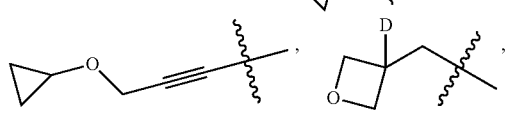

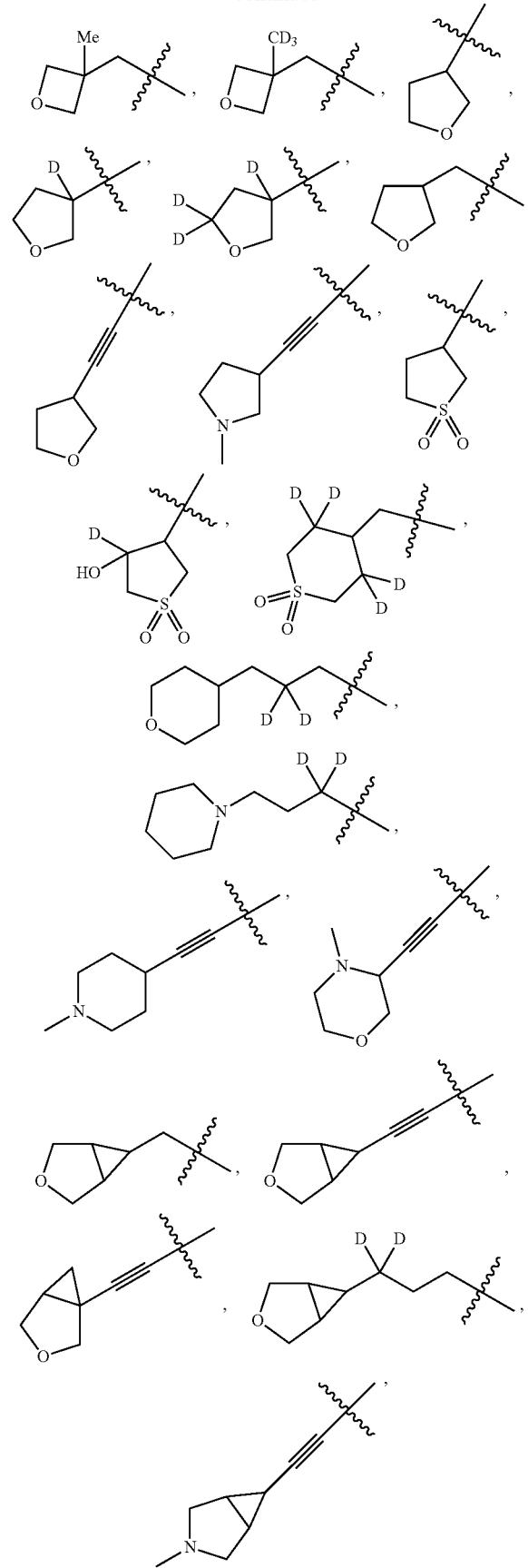

241
-continued
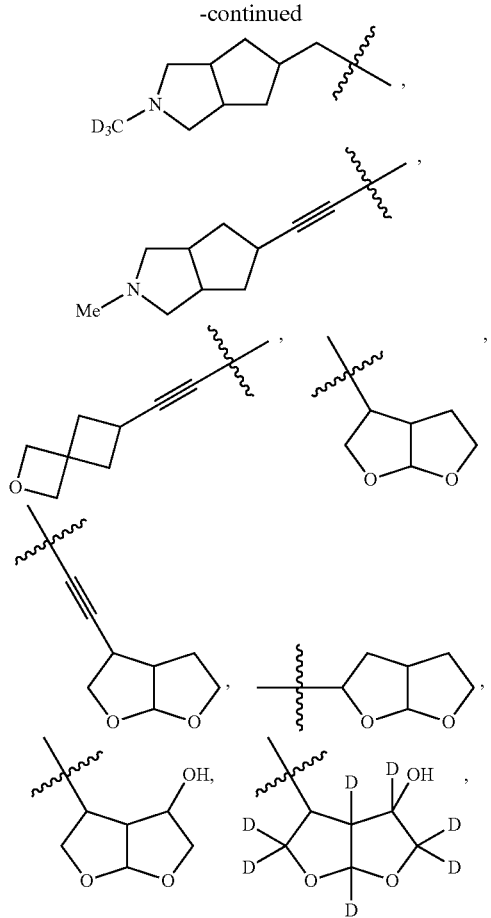
242
-continued
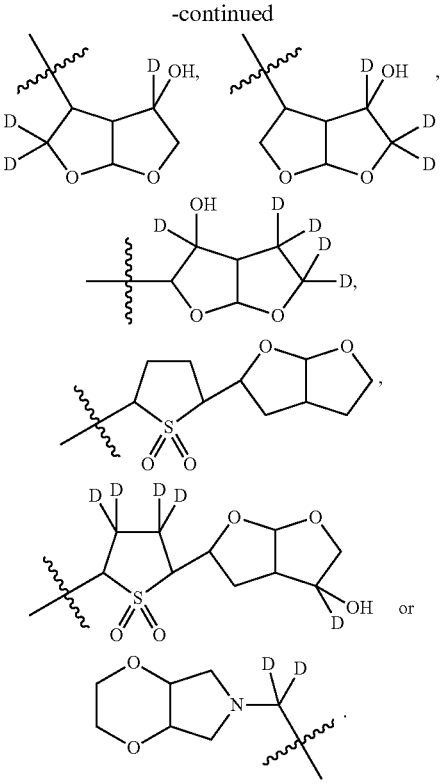
11. The compound according to claim 1 having one of the following structures:
(1)
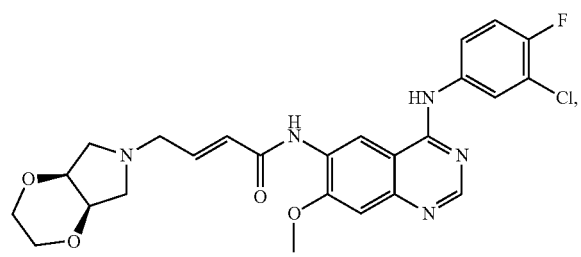
(2)
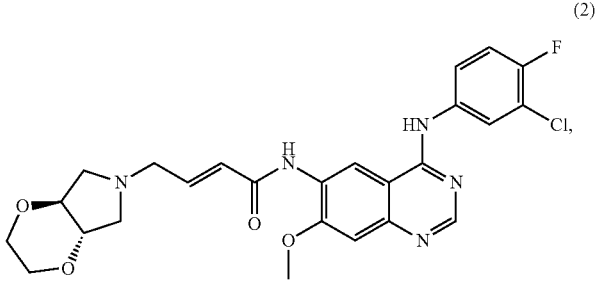
(3)
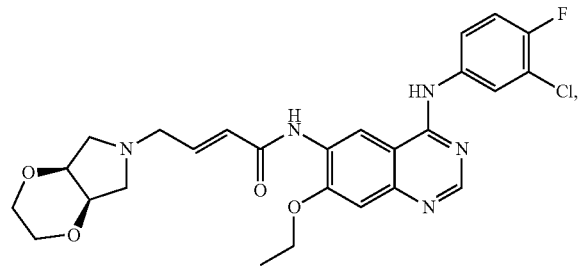
(4)
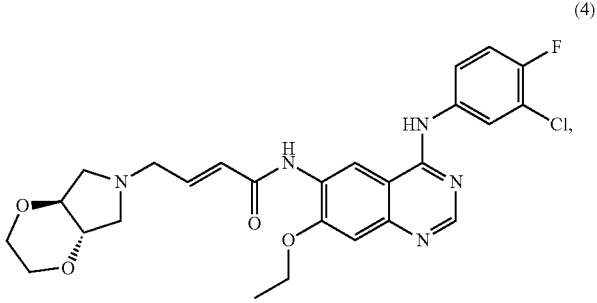

-continued
(5)
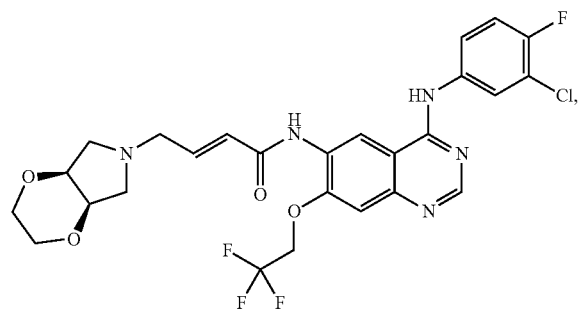
(6)
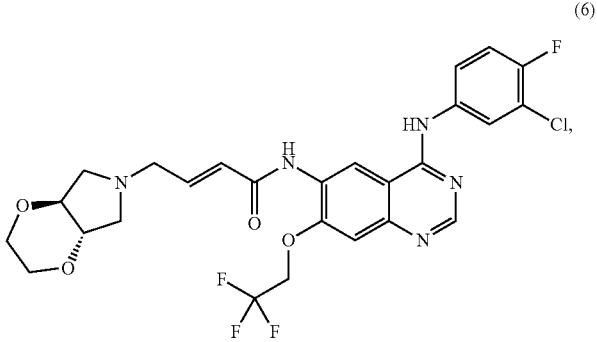
(7)
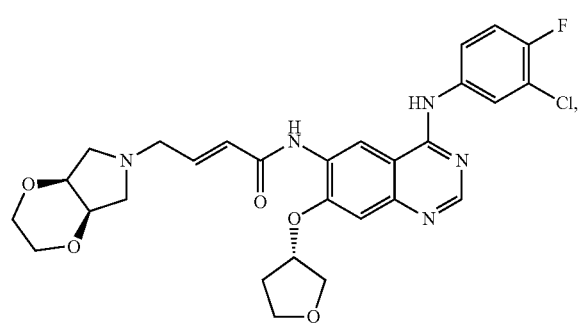
(8)
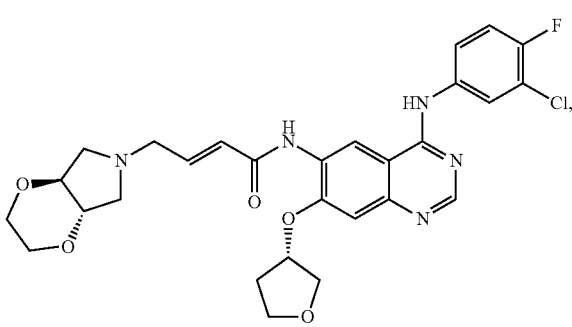
(9)
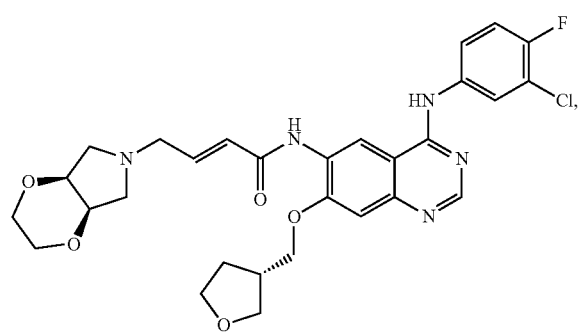
(10)
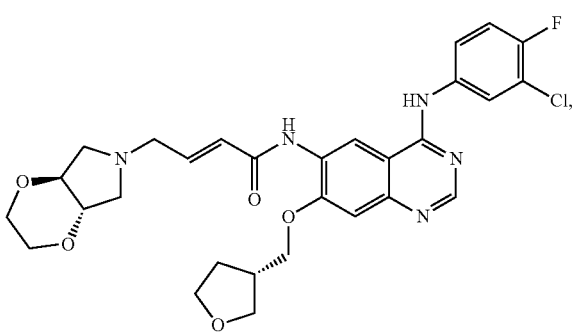
(11)
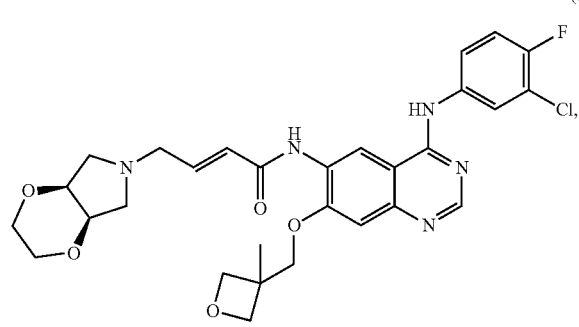
(12)
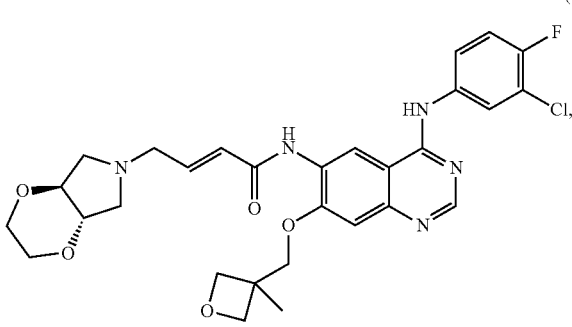
(13)
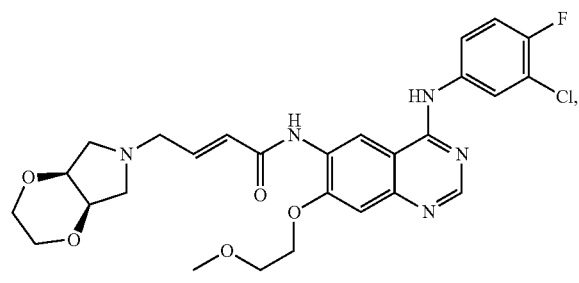
(14)
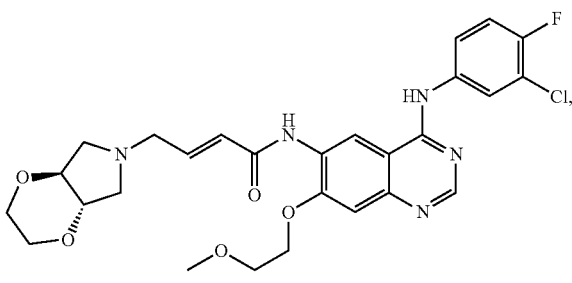

-continued
(15)
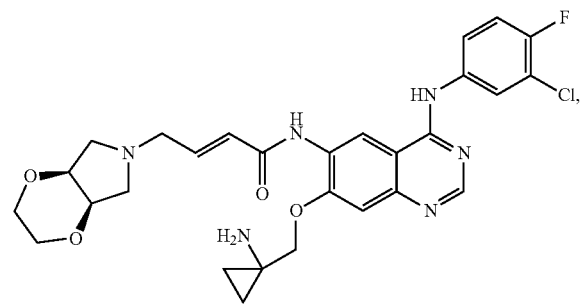
(16)
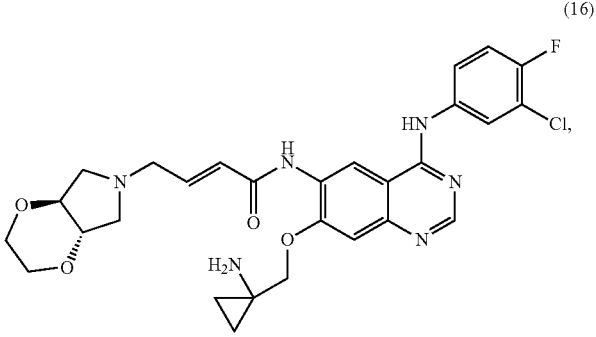
(17)
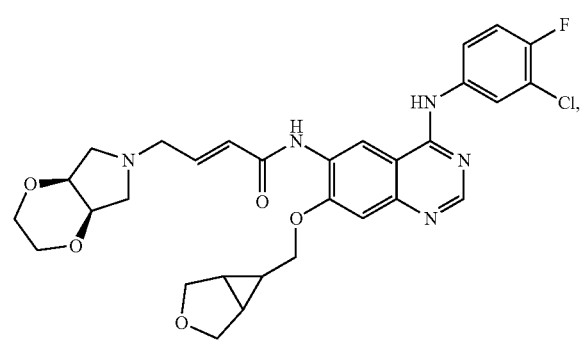
(18)
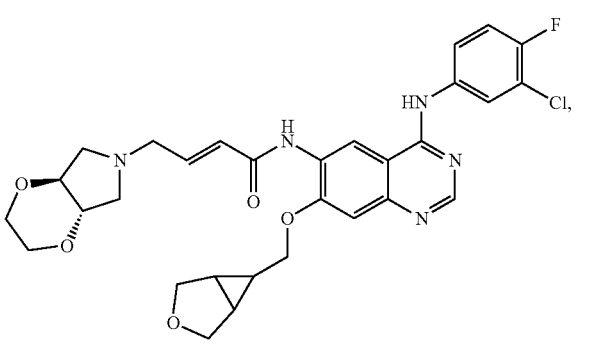
(19)
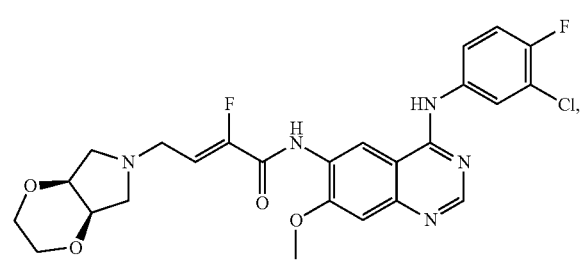
(20)
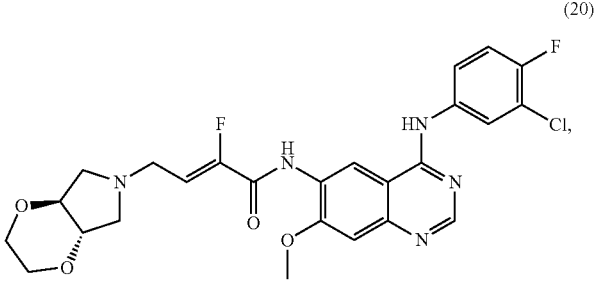
(21)
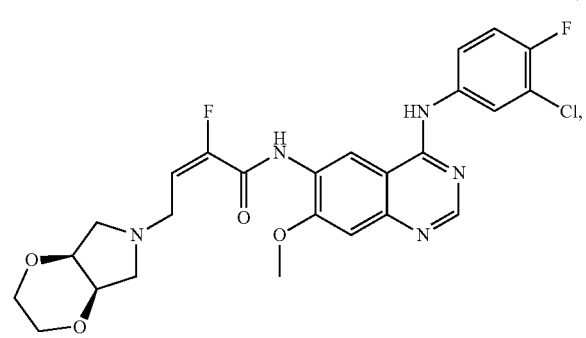
(22)
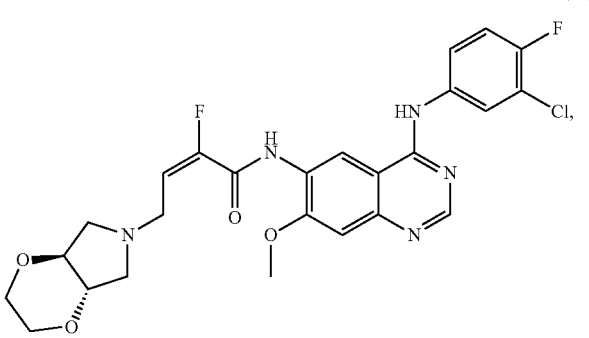
(23)
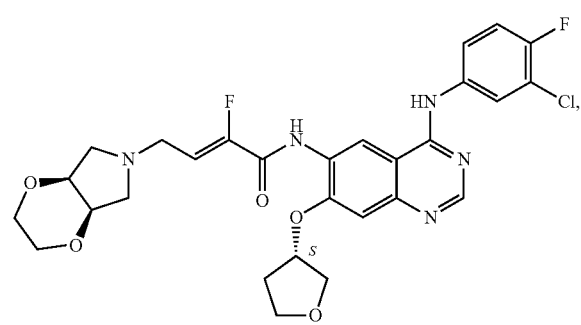
(24)
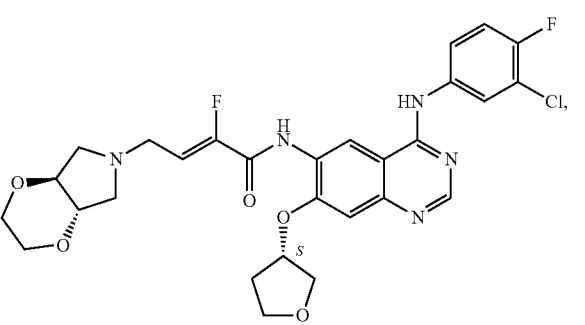

-continued
(25) 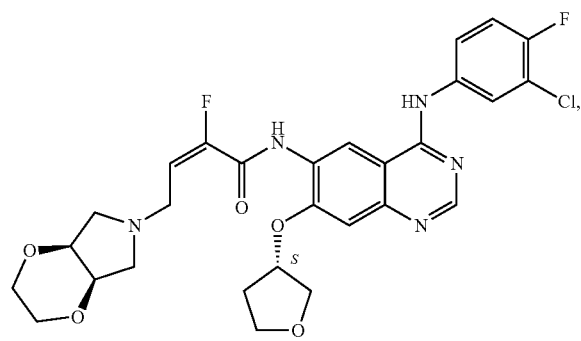
(26) 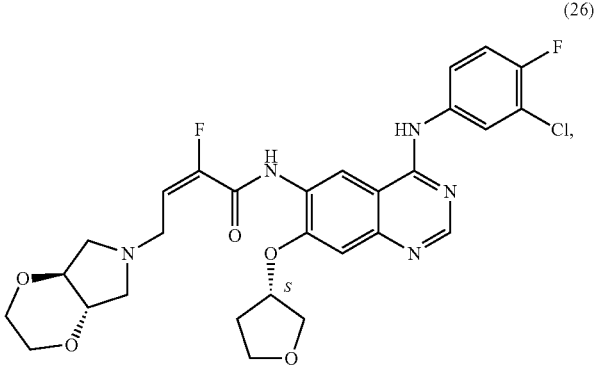
(27) 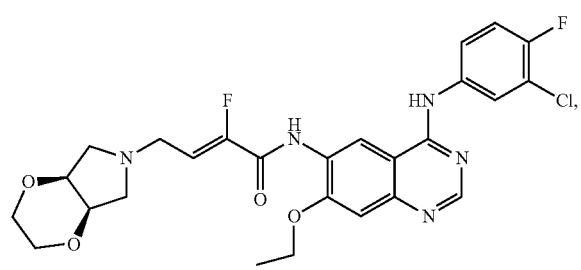
(28) 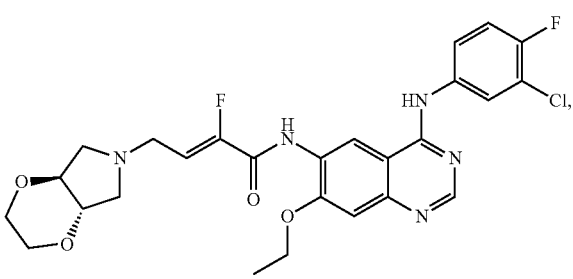
(29) 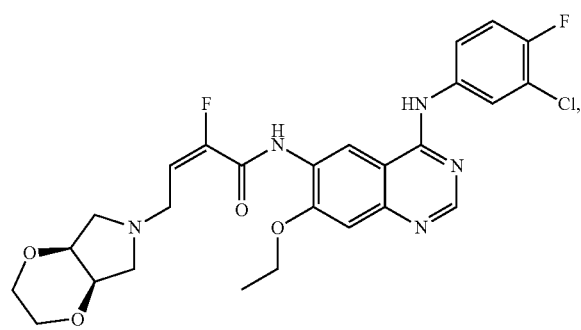
(30) 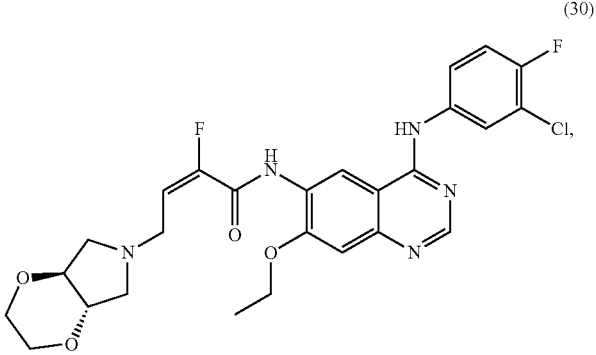
(31) 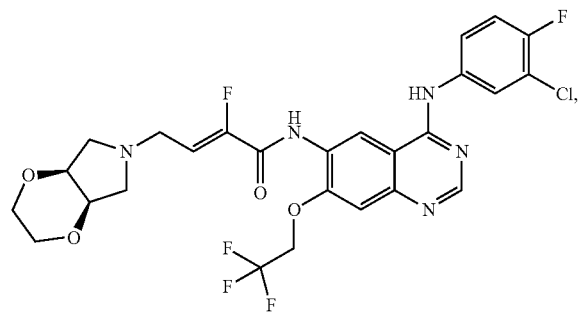
(32) 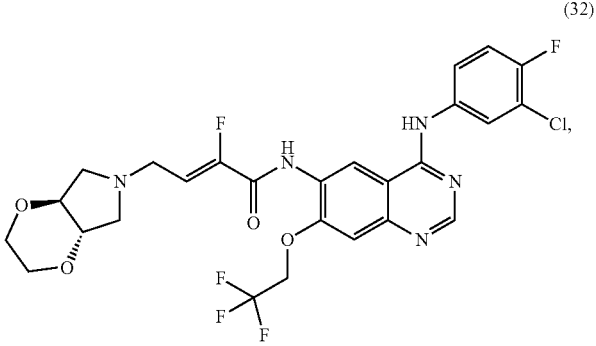

-continued
(33)
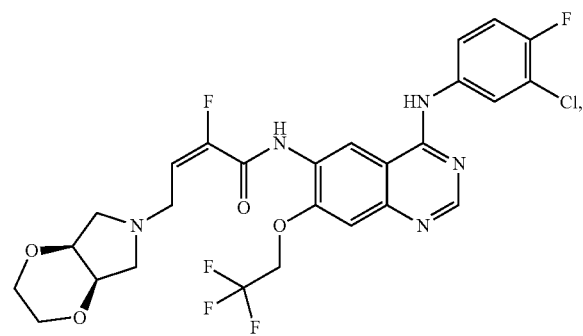
(34)
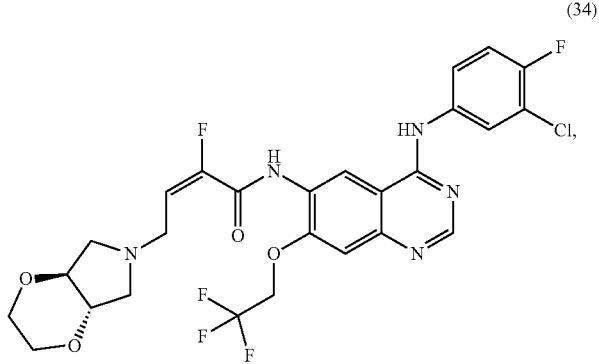
(35)
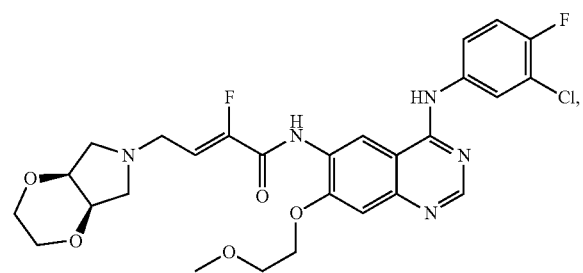
(36)
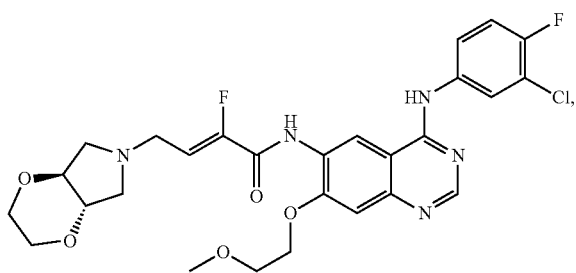
(37)
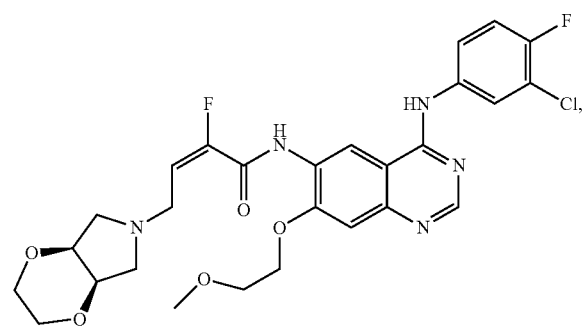
(38)
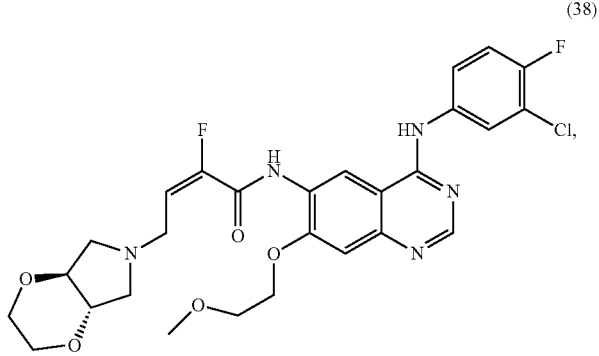
(39)
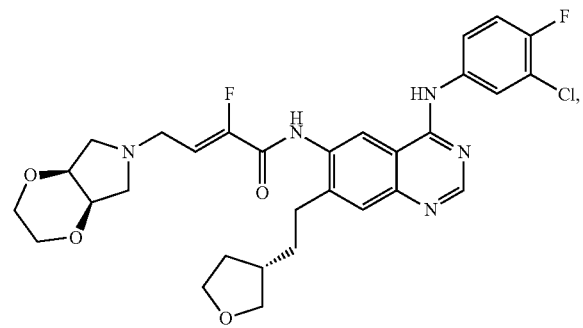
(40)
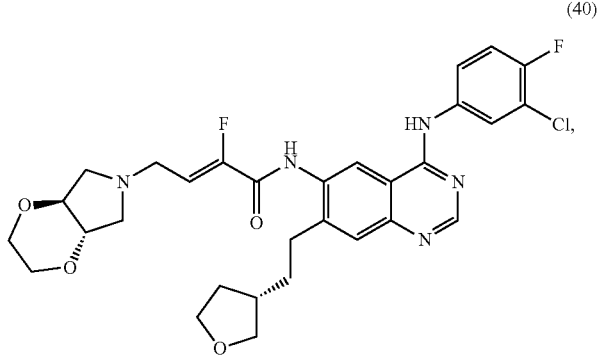

-continued
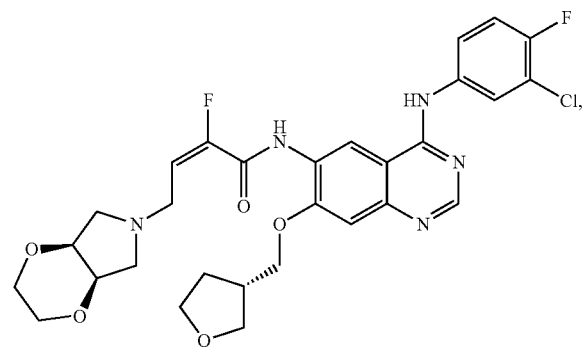
(41)
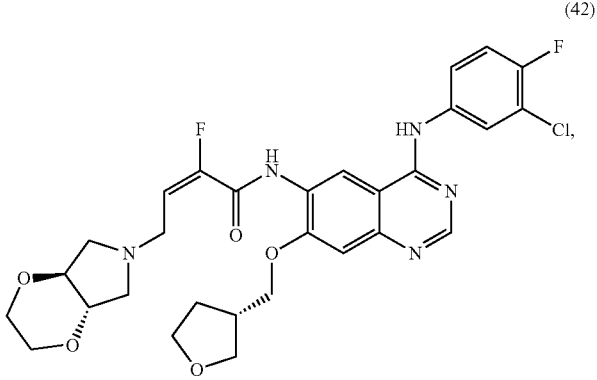
(42)
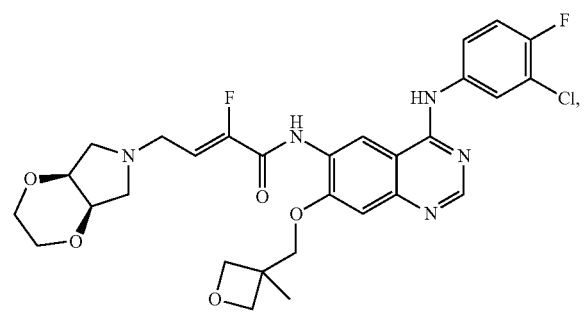
(43)
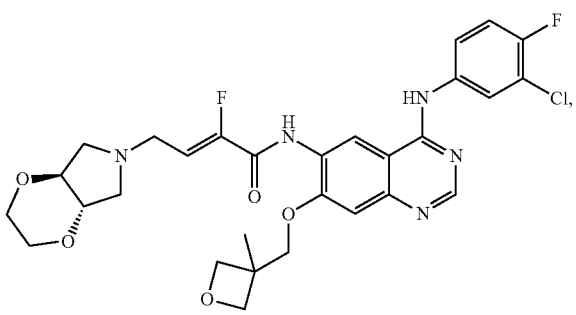
(44)
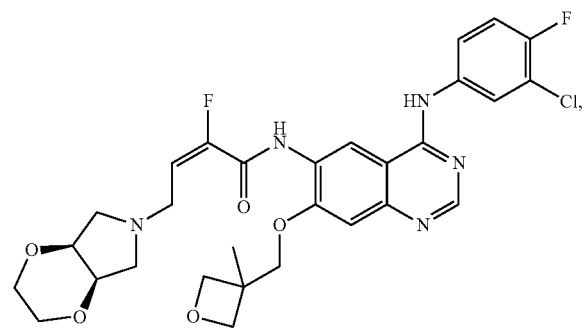
(45)
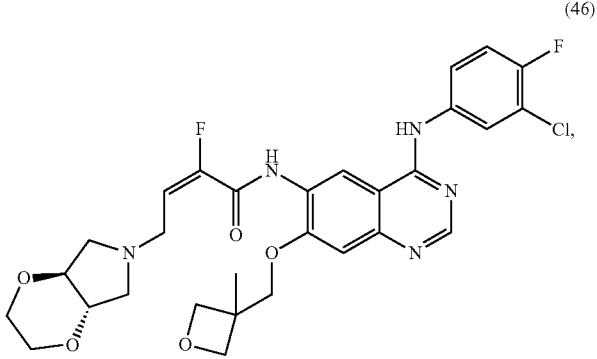
(46)
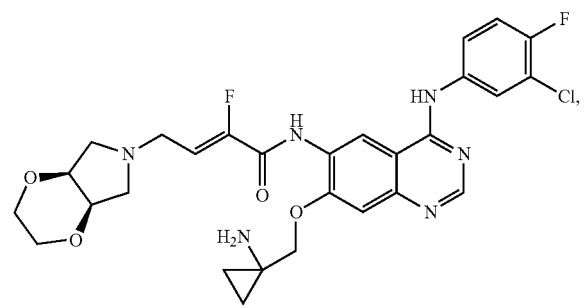
(47)
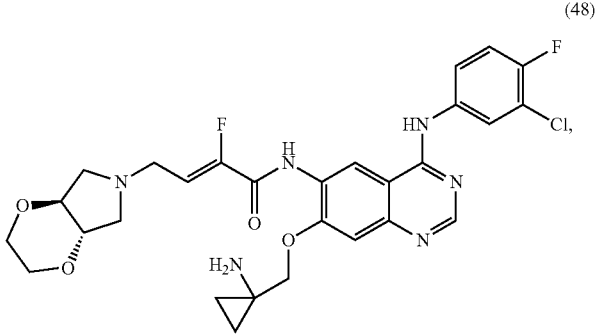
(48)

-continued
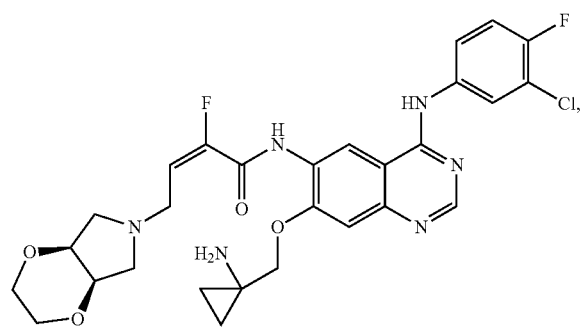
(49)
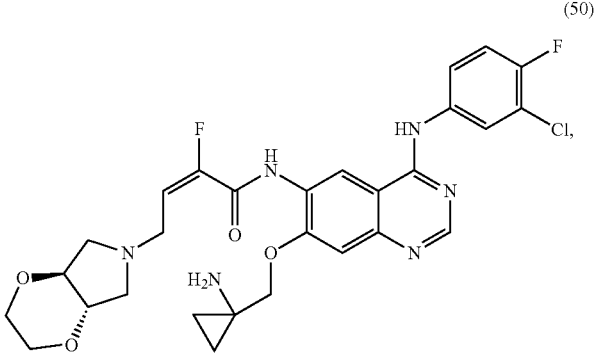
(50)
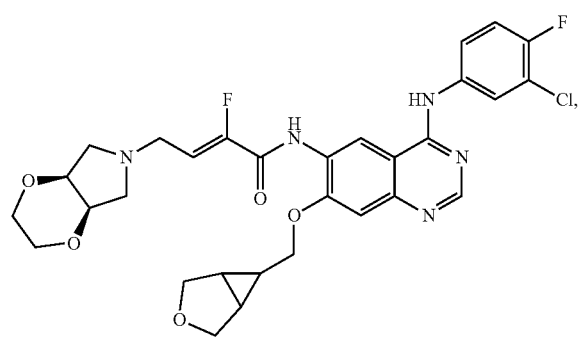
(51)
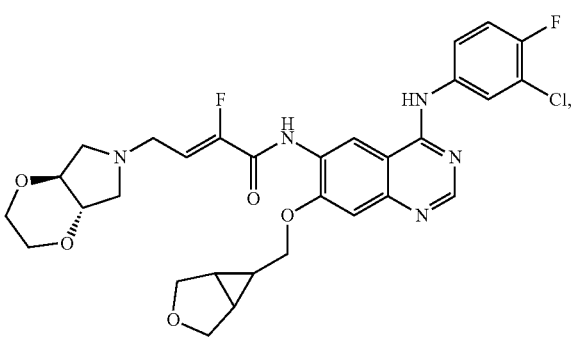
(52)
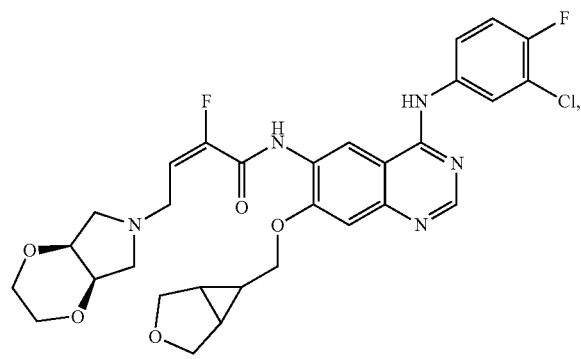
(53)
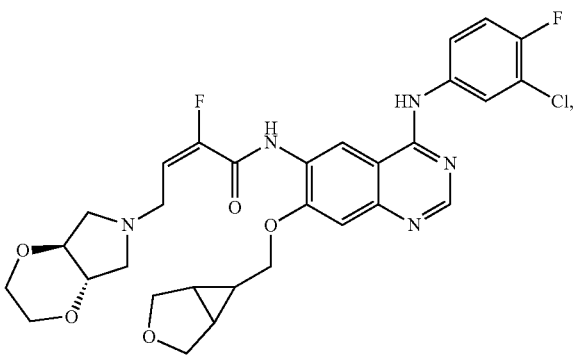
(54)
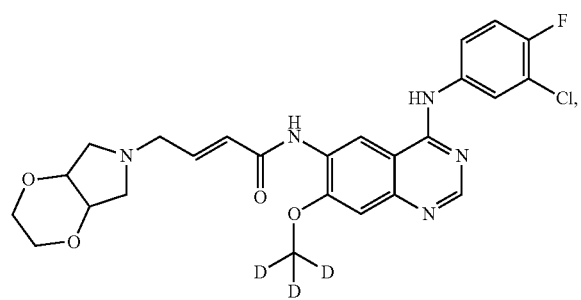
(55)

-continued
(56)
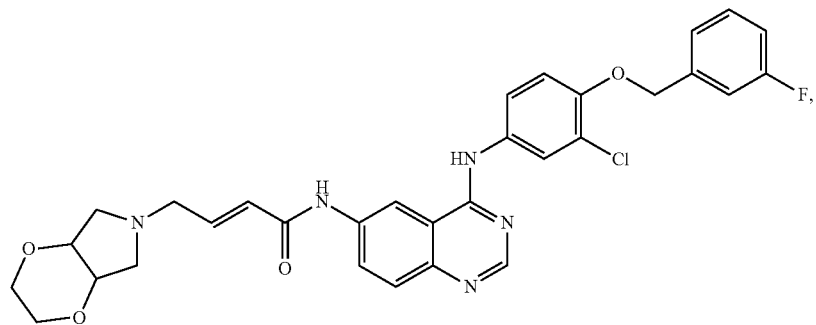
(57)
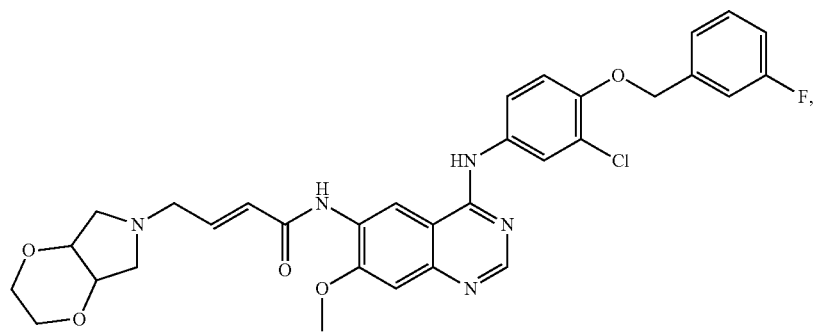
(58)
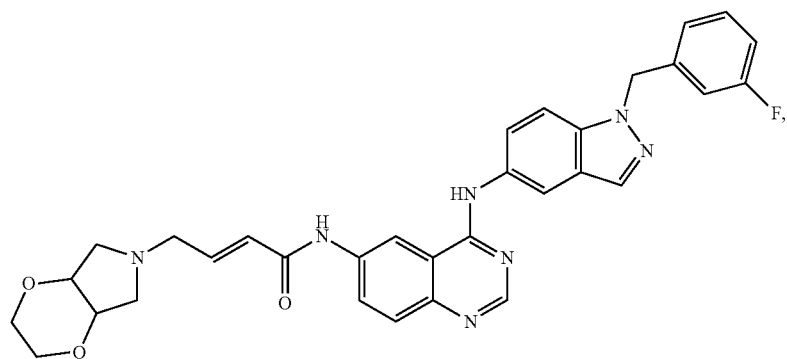
(59)
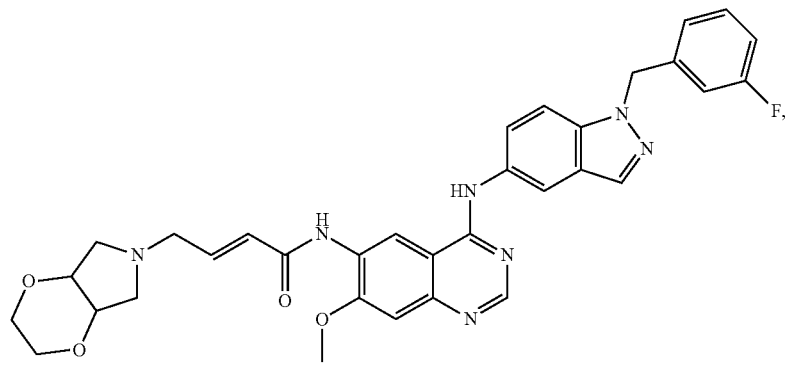

-continued
(60)
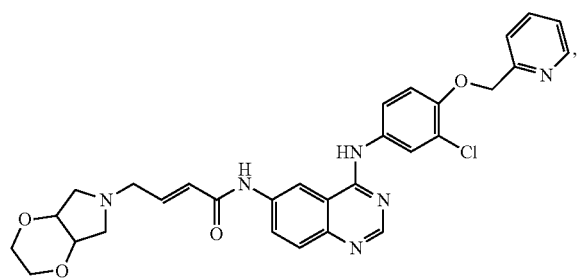
(61)
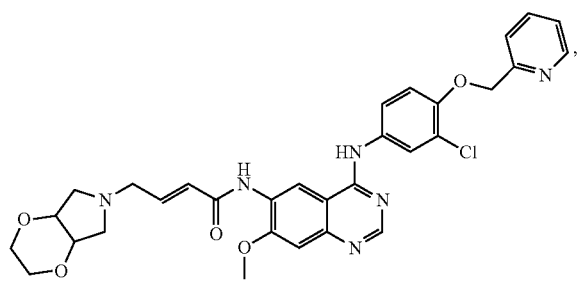
(62)
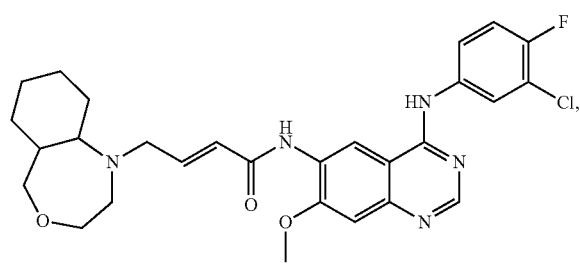
(63)
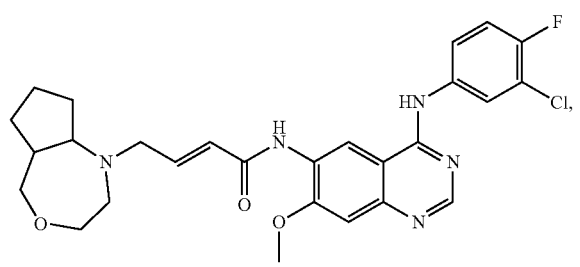
(64)
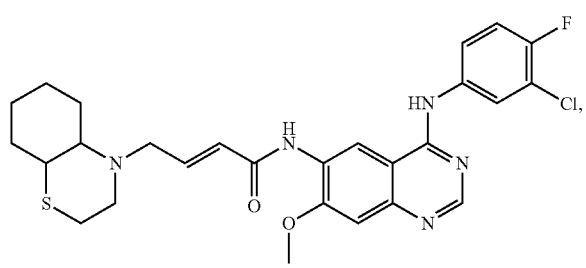
(65)
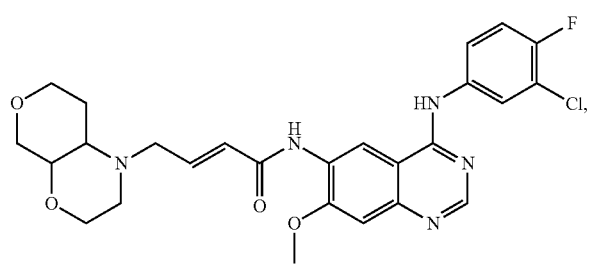
(66)
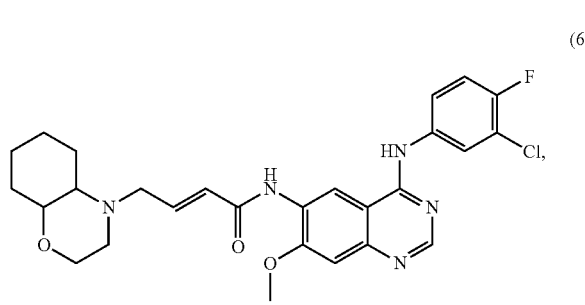
(67)
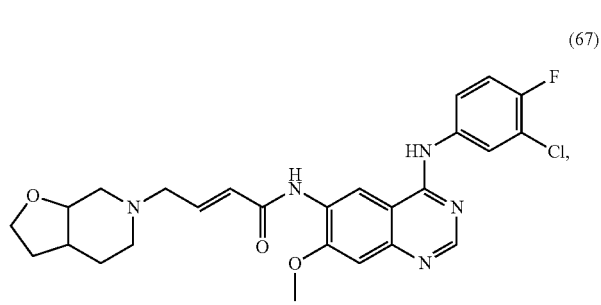
(68)
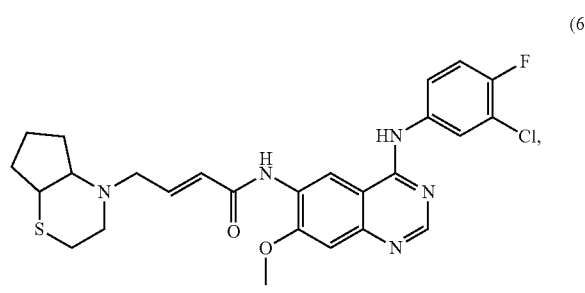
(69)
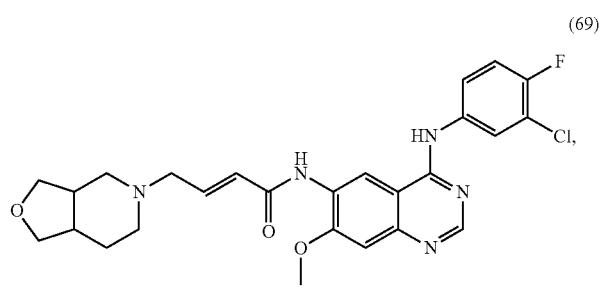

-continued
(70)
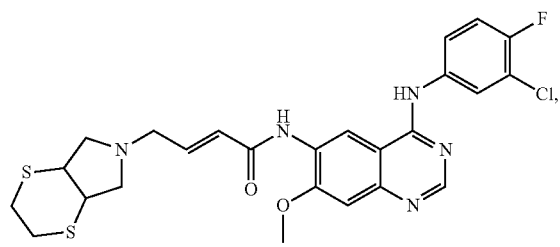
(71)
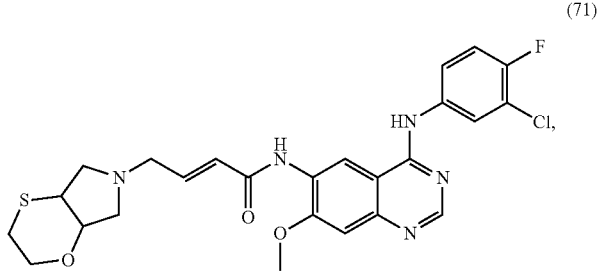
(72)
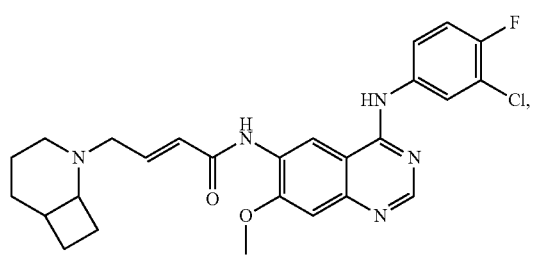
(73)
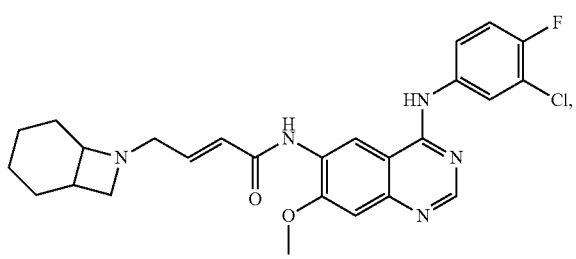
(74)
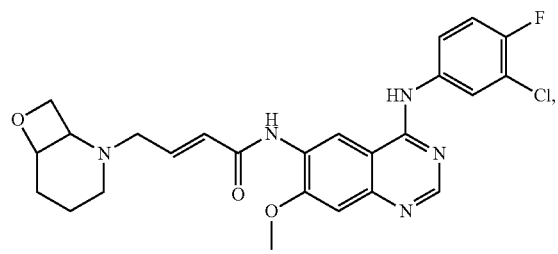
(75)
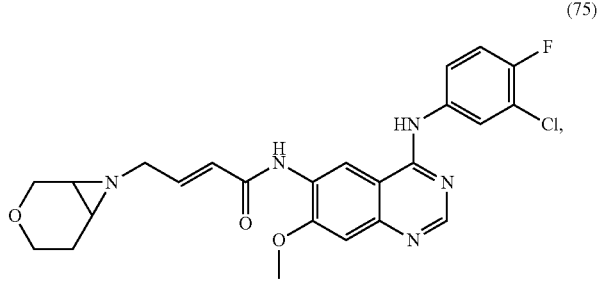
(76)
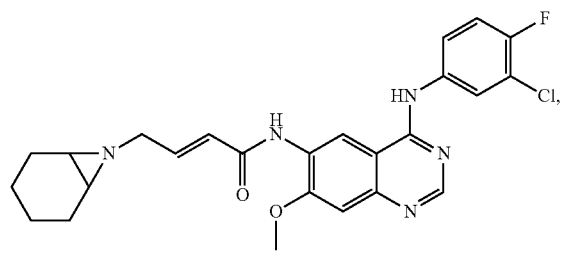
(77)
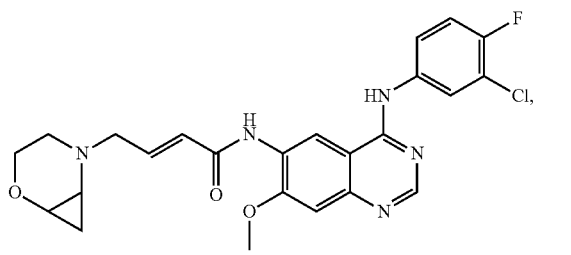
(78)
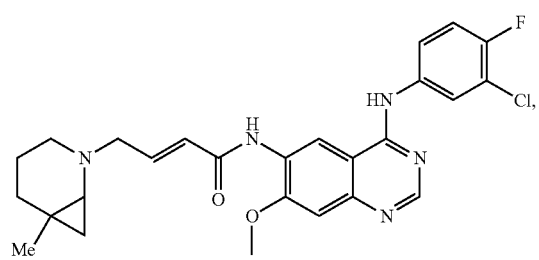
(79)
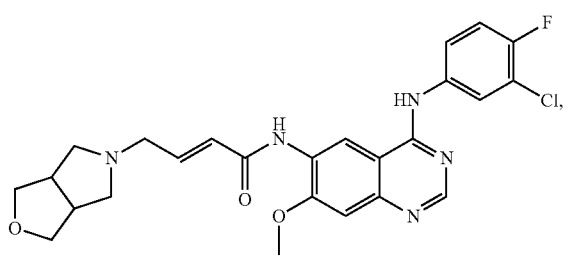
(80)
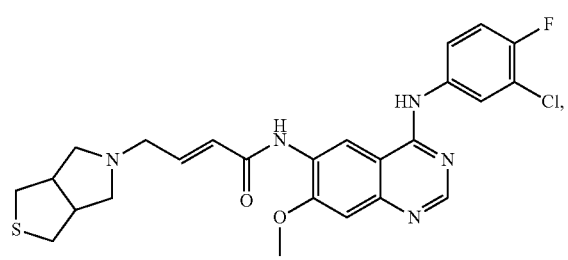
(81)

-continued
(82)
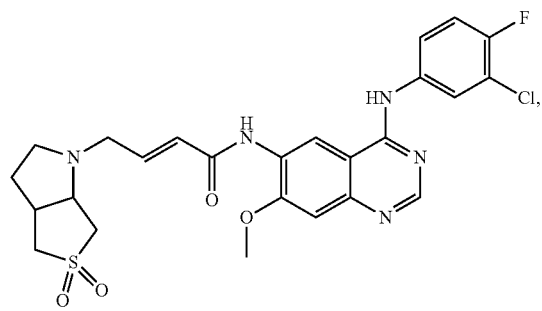
(83)
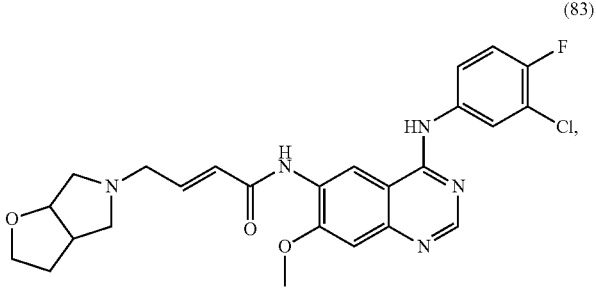
(84)
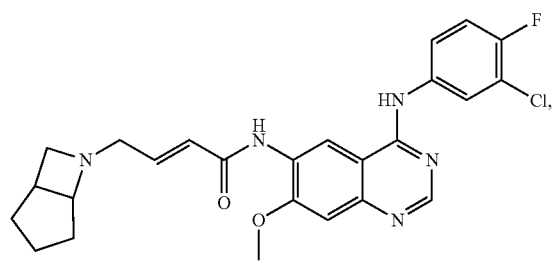
(85)
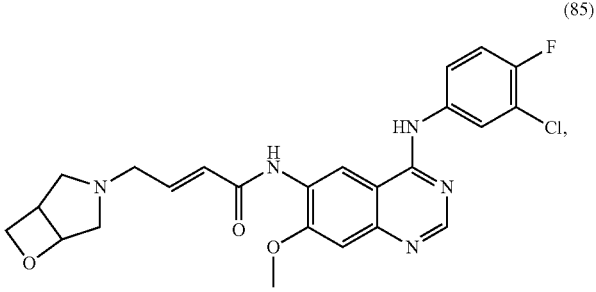
(86)
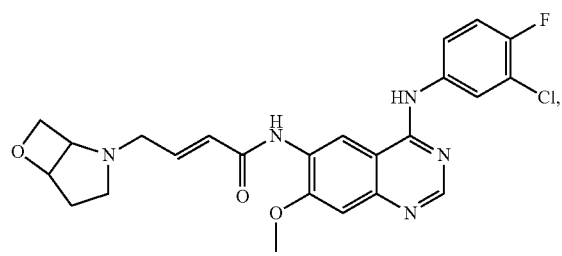
(87)
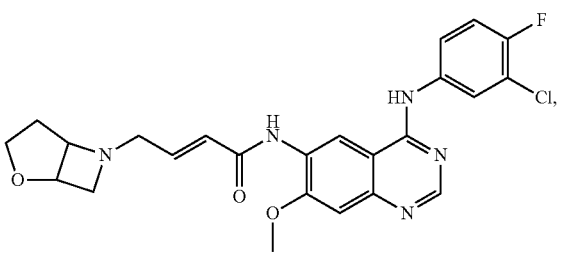
(88)
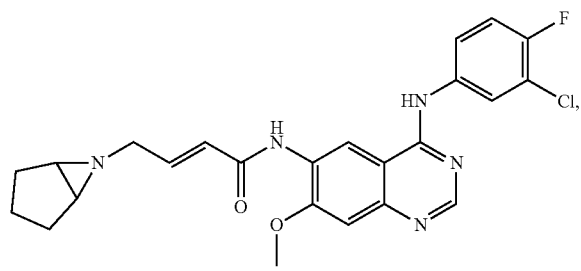
(89)
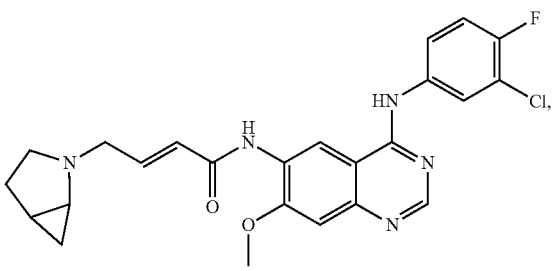
(90)
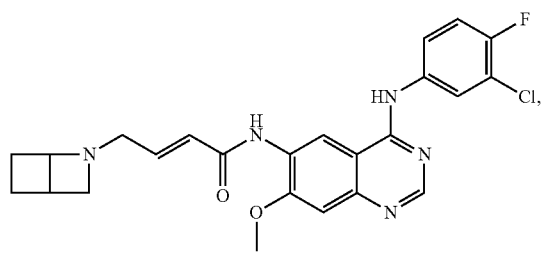
(91)
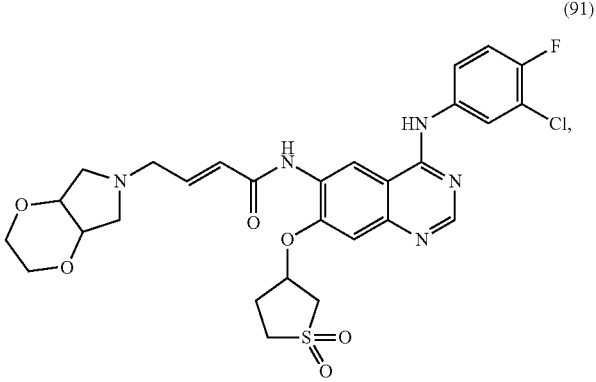

-continued
(92)
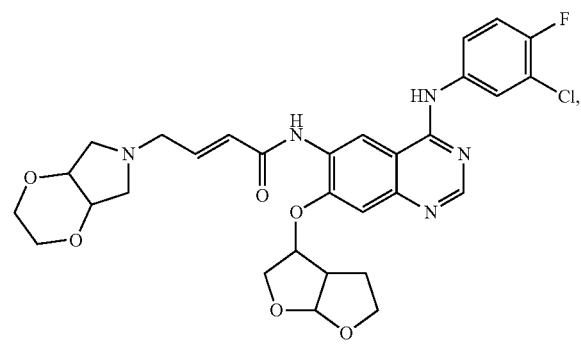
(93)
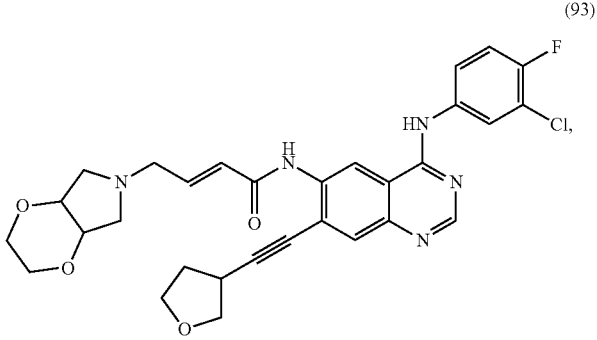
(94)
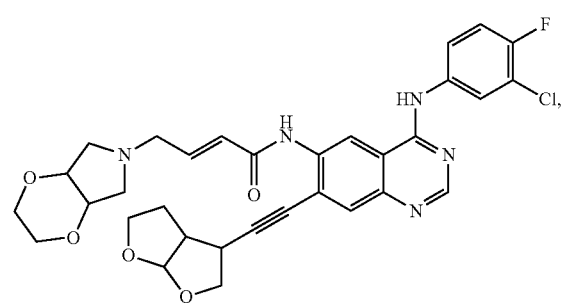
(95)
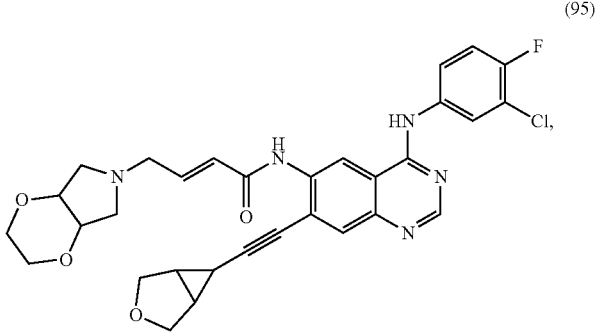
(96)
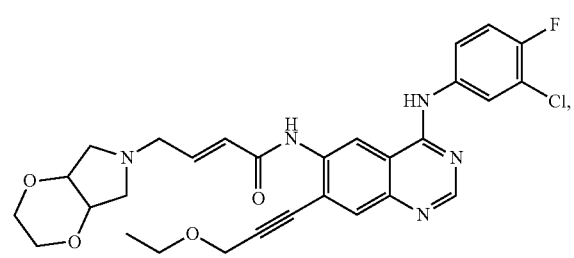
(97)
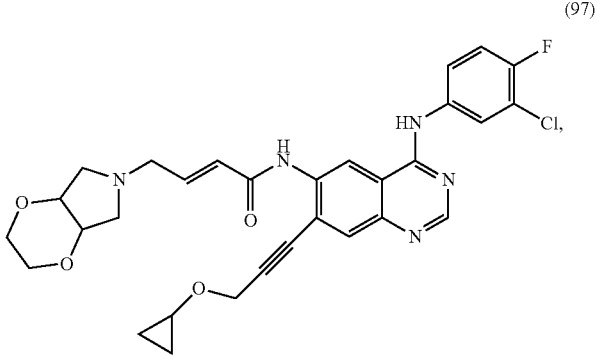
(98)
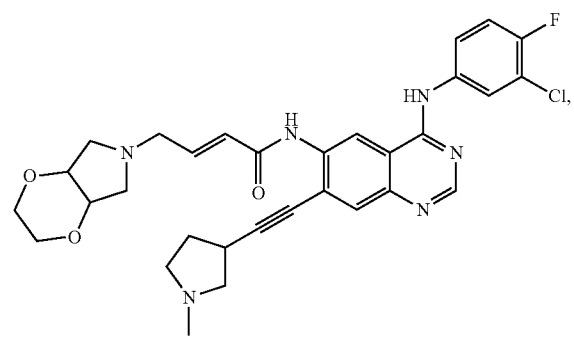
(99)
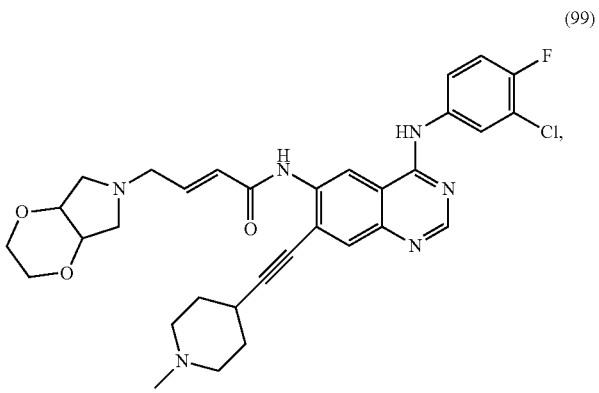

-continued
(100)
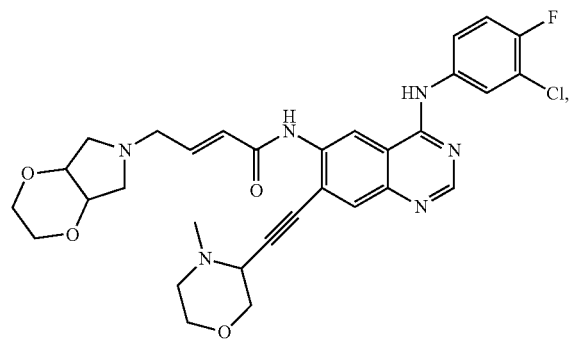
(101)
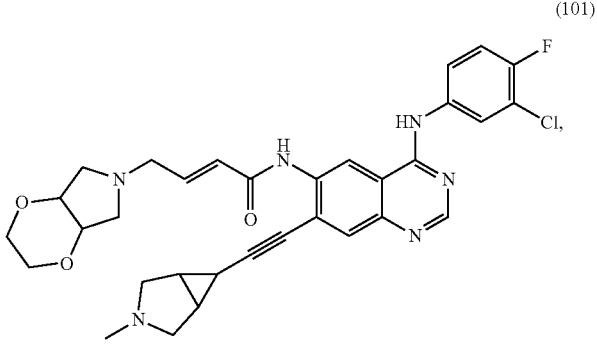
(102)
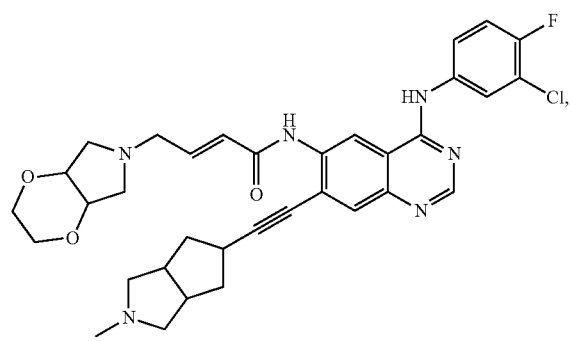
(103)
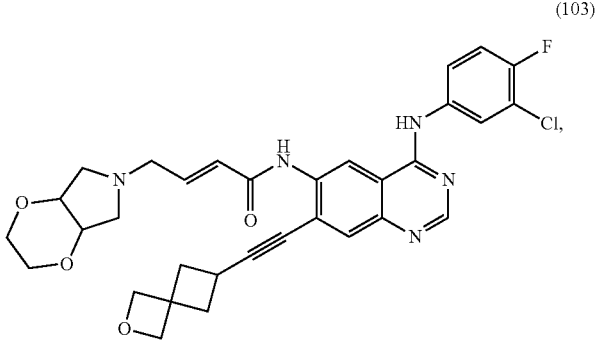
(104)
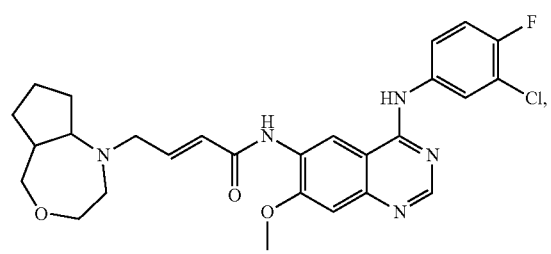
(105)
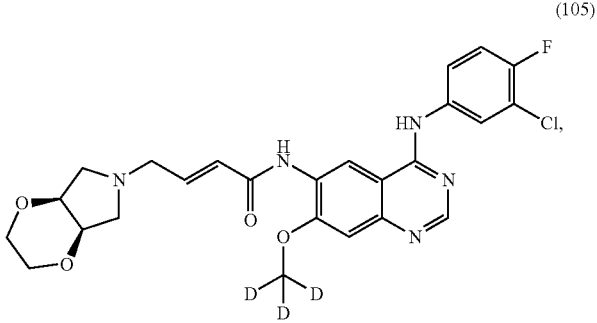
(106)
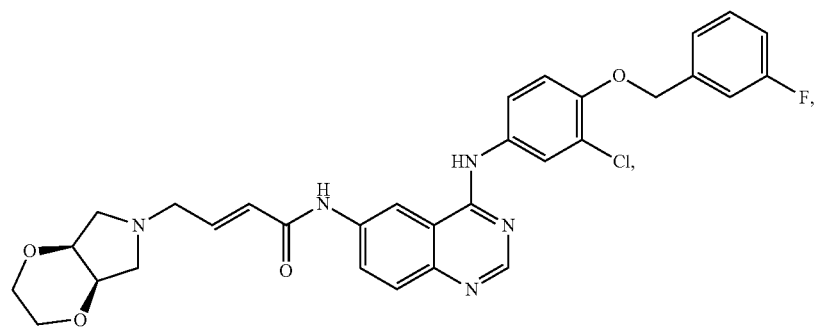

-continued
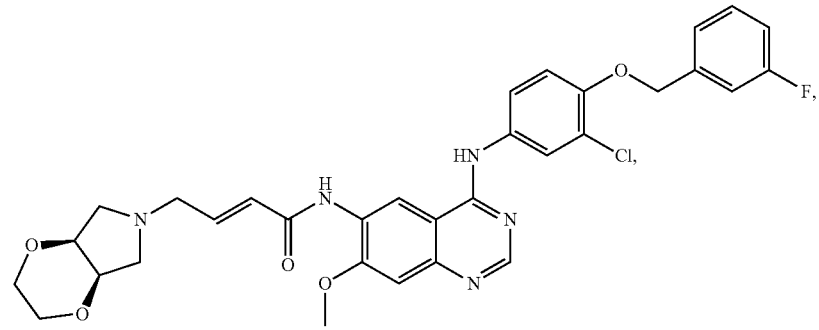
(107)
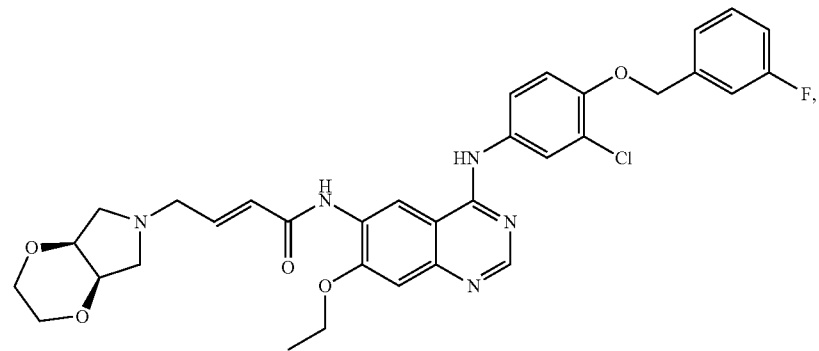
(108)
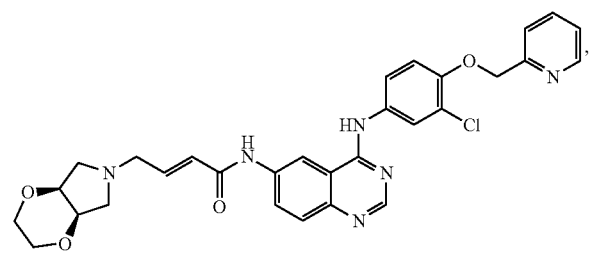
(109)
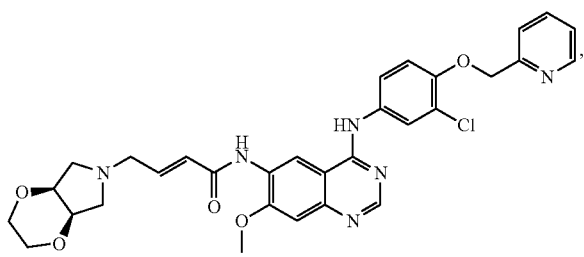
(110)
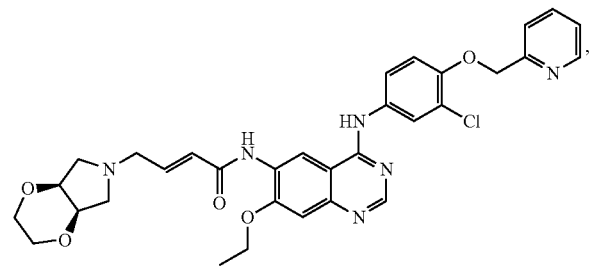
(111)
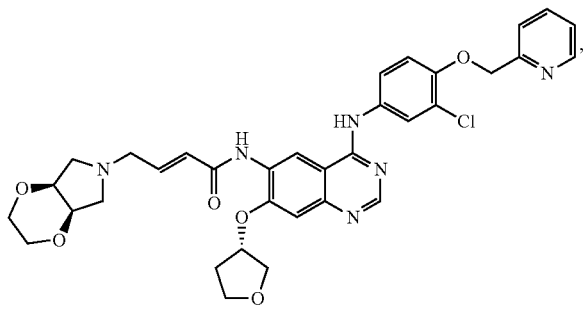
(112)

(113)
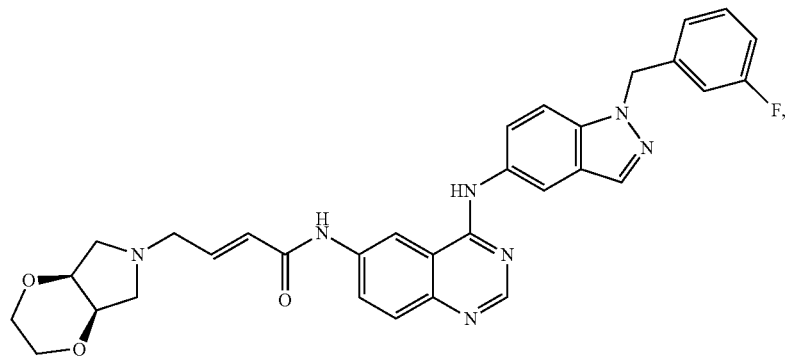
(114)
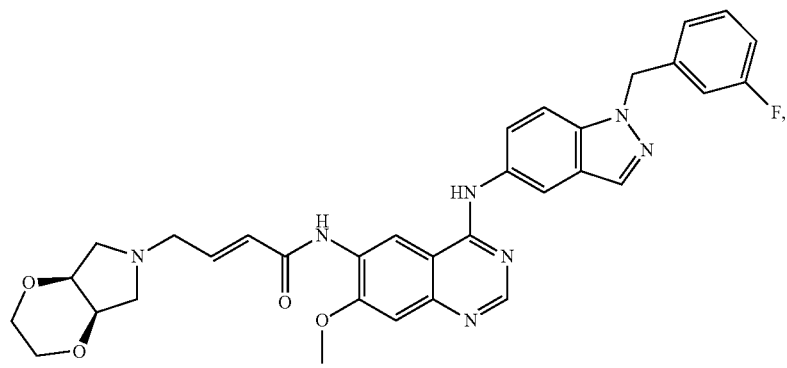
(115)
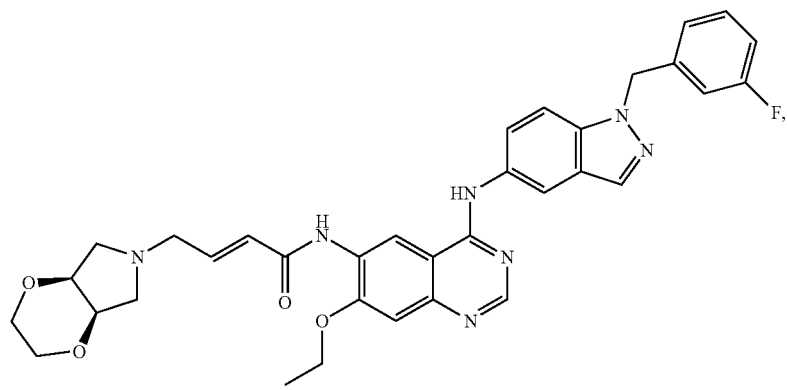
(116)
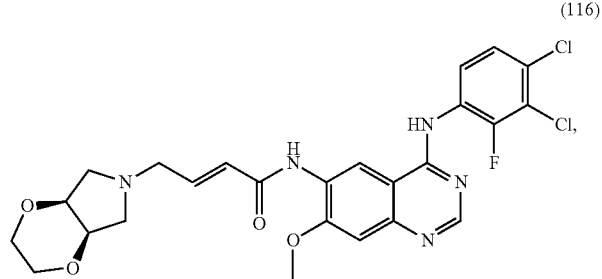
(117)
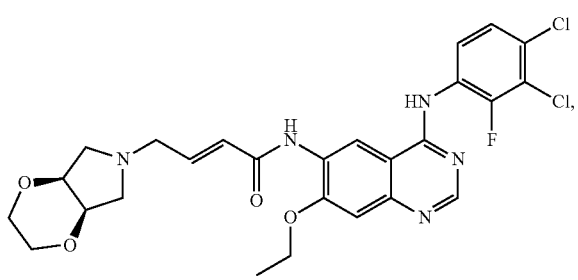

-continued (118) 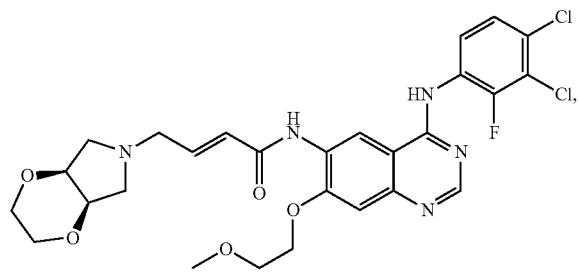

(119) 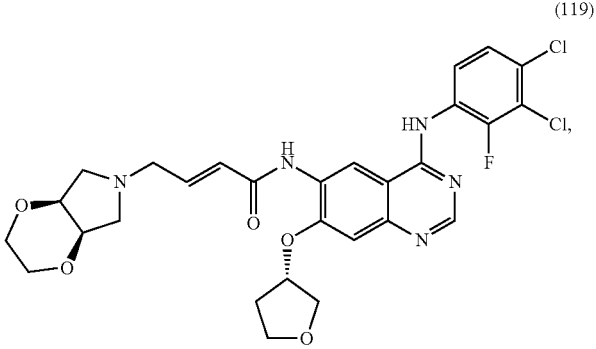

(120) 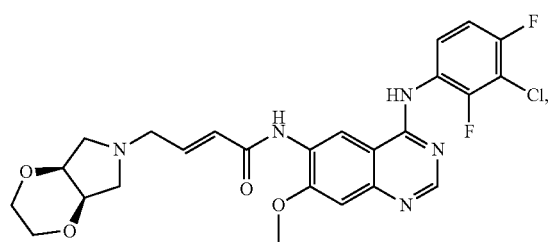

(121) 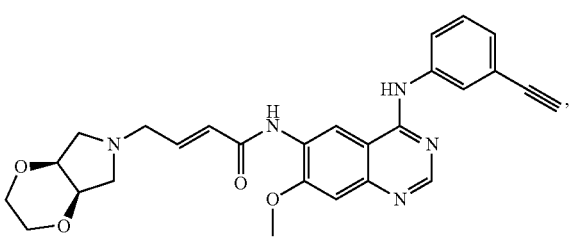

(122) 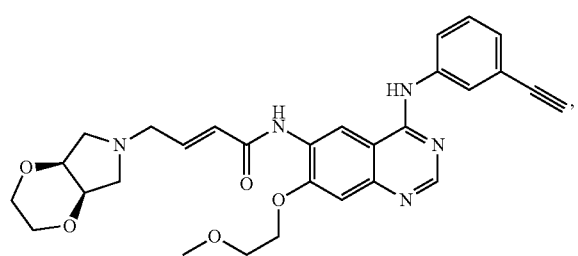

(123) 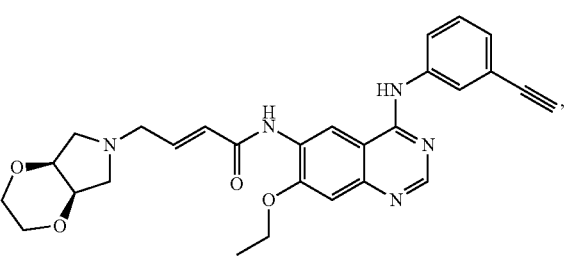

(124) 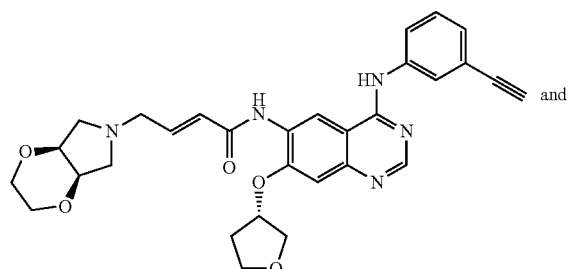 and (125) 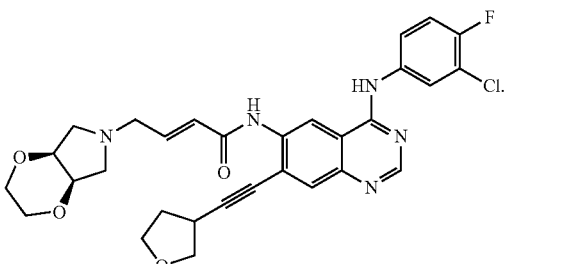

12. A pharmaceutical composition comprising the compound according to claim 1, wherein the pharmaceutical composition further comprising at least one of a pharmaceutically acceptable carrier, a pharmaceutically acceptable excipient, a pharmaceutically acceptable diluent, a pharmaceutically acceptable adjuvant and a pharmaceutically acceptable vehicle; or
wherein the pharmaceutical composition further comprising at least one additional therapeutic agent selected from a chemotherapeutic agent, an anti-proliferative agent, an agent for treating non-small cell lung cancer and an agent for treating epidermal carcinoma.

13. A method of managing, treating or lessening the severity of a proliferative disorder, atherosclerosis or lung fibrosis in a patient comprising administering to the patient a therapeutically effective amount of the compound according to claim 1.

14. The method according to claim 13, wherein the proliferative disorder is metastatic cancer, colon cancer, gastric adenocarcinoma, bladder cancer, breast cancer, kidney cancer, liver cancer, lung cancer, thyroid cancer, head and neck cancer, prostate cancer, pancreatic cancer, central nervous system cancer, glioblastoma or a myeloproliferative disorder.

15. A method of modulating protein kinase activity with the compound according to any one of claim 1, wherein the protein kinase is receptor tyrosine kinase.

16. The method according to claim 15, wherein the receptor tyrosine kinase is at least one of EGFR and HER-2.

17. A method of managing, treating or lessening the severity of a proliferative disorder, atherosclerosis or lung fibrosis in a patient comprising administering to the patient a therapeutically effective amount of the pharmaceutical composition according to claim 12.

18. The method according to claim 17, wherein the proliferative disorder is metastatic cancer, colon cancer, gastric adenocarcinoma, bladder cancer, breast cancer, kidney cancer, liver cancer, lung cancer, thyroid cancer, head and neck cancer, prostate cancer, pancreatic cancer, central nervous system cancer, glioblastoma or a myeloproliferative disorder.

19. A method of modulating protein kinase activity with the pharmaceutical composition according to claim 12, wherein the protein kinase is receptor tyrosine kinase.

20. The method according to claim 19, wherein the receptor tyrosine kinase is at least one of EGFR and HER-2.

* * * * *